United States Patent
Harris et al.

(10) Patent No.: US 11,446,032 B2
(45) Date of Patent: Sep. 20, 2022

(54) COMPRESSIBLE NON-FIBROUS ADJUNCTS

(71) Applicant: Ethicon LLC, Guaynabo, PR (US)

(72) Inventors: Jason L. Harris, Lebanon, OH (US); Michael J. Vendely, Lebanon, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/009,748

(22) Filed: Sep. 1, 2020

(65) Prior Publication Data

US 2021/0077107 A1  Mar. 18, 2021

Related U.S. Application Data

(60) Provisional application No. 63/053,863, filed on Jul. 20, 2020, provisional application No. 62/913,227, (Continued)

(51) Int. Cl.
*A61B 17/072* (2006.01)
*A61B 17/068* (2006.01)
(Continued)

(52) U.S. Cl.
CPC ...... *A61B 17/07292* (2013.01); *A61B 17/064* (2013.01); *A61B 17/0686* (2013.01);
(Continued)

(58) Field of Classification Search
CPC .............. A61B 17/068; A61B 17/0684; A61B 17/0686; A61B 17/07207;
(Continued)

(56) References Cited

U.S. PATENT DOCUMENTS 3,213,058 A  10/1965 Boyle et al.
3,707,056 A  12/1972 Cole et al.
(Continued)

FOREIGN PATENT DOCUMENTS

EP  0449431 A2  10/1991
EP  0594148 A1  4/1994
(Continued)

OTHER PUBLICATIONS

Extended European Search Report for European Application No. 20196541.5, dated Nov. 25, 2020, 10 pages.
(Continued)

*Primary Examiner* — Stephen F. Gerrity
*Assistant Examiner* — Linda J Hodge
(74) *Attorney, Agent, or Firm* — Mintz Levin Cohn Ferris Glovsky and Popeo, P.C.

(57) ABSTRACT

Stapling assemblies for use with a surgical stapler are provided. In one exemplary embodiment, the stapling assembly includes a cartridge having a plurality of staples disposed therein and a non-fibrous adjunct formed of at least one fused bioabsorbable polymer and configured to be releasably retained on the cartridge. Adjunct systems for use with a surgical stapler are also provided. Surgical end effectors using the stapling assemblies are also provided. Methods for manufacturing stapling assemblies and using the same are also provided.

24 Claims, 78 Drawing Sheets

Related U.S. Application Data filed on Oct. 10, 2019, provisional application No. 62/900,708, filed on Sep. 16, 2019.

(51) Int. Cl.
*A61B 17/064* (2006.01)
*A61L 17/10* (2006.01)

(52) U.S. Cl.
CPC ............ *A61B 17/072* (2013.01); *A61L 17/10* (2013.01); *A61B 2017/07228* (2013.01); *A61B 2017/07235* (2013.01); *A61B 2017/07257* (2013.01); *A61B 2017/07271* (2013.01); *A61B 2017/07278* (2013.01); *A61B 2017/07285* (2013.01)

(58) Field of Classification Search
CPC .... A61B 17/07292; A61B 2017/07271; A61B 17/0725; A61B 17/07242
See application file for complete search history.

(56) References Cited

U.S. PATENT DOCUMENTS

| | | | |
|---|---|---|---|
| D297,764 S | 9/1988 | Spreckelmeier et al. | |
| 4,818,437 A | 4/1989 | Wiley | |
| 4,892,244 A | 1/1990 | Fox et al. | |
| 5,236,637 A | 8/1993 | Hull | |
| RE34,519 E | 1/1994 | Fox et al. | |
| 5,391,072 A | 2/1995 | Lawton et al. | |
| 5,468,253 A | 11/1995 | Bezwada et al. | |
| 5,529,473 A | 6/1996 | Lawton et al. | |
| 5,542,594 A | 8/1996 | McKean et al. | |
| 5,711,960 A | 1/1998 | Shikinami | |
| 6,916,867 B2 | 7/2005 | Gugumus | |
| 7,157,586 B2 | 1/2007 | Wood et al. | |
| 7,195,640 B2 | 3/2007 | Falotico et al. | |
| 7,438,846 B2 | 10/2008 | John | |
| 7,641,091 B2 | 1/2010 | Olson et al. | |
| 7,695,643 B2 | 4/2010 | Fritzsche et al. | |
| 7,718,709 B2* | 5/2010 | Ishikawa .............. A23D 7/0053 |
| | | | 516/75 |
| 7,892,474 B2 | 2/2011 | Shkolnik et al. | |
| 8,062,330 B2 | 11/2011 | Prommersberger et al. | |
| 8,110,135 B2 | 2/2012 | El-siblani | |
| 8,590,762 B2 | 11/2013 | Hess et al. | |
| 8,814,025 B2 | 8/2014 | Miller et al. | |
| 9,205,601 B2 | 12/2015 | Desimone et al. | |
| 9,211,120 B2 | 12/2015 | Scheib et al. | |
| 9,211,678 B2 | 12/2015 | Desimone et al. | |
| 9,216,546 B2 | 12/2015 | Desimone et al. | |
| 9,307,965 B2 | 4/2016 | Ming et al. | |
| 9,332,984 B2 | 5/2016 | Meaner et al. | |
| 9,453,142 B2 | 9/2016 | Rolland et al. | |
| 9,700,311 B2 | 7/2017 | Shelton, IV et al. | |
| 9,770,241 B2 | 9/2017 | Rousseau et al. | |
| 9,873,790 B1 | 1/2018 | Andjelic et al. | |
| 9,924,944 B2 | 3/2018 | Shelton, IV et al. | |
| 9,999,408 B2 | 6/2018 | Boudreaux et al. | |
| 10,004,496 B2* | 6/2018 | Shelton, IV ....... A61B 17/0644 |
| 10,028,744 B2 | 7/2018 | Shelton, IV et al. | |
| 10,052,104 B2 | 8/2018 | Shelton, IV et al. | |
| D831,209 S | 10/2018 | Huitema et al. | |
| 10,085,745 B2 | 10/2018 | Dalessandro et al. | |
| 10,111,661 B2 | 10/2018 | Widenhouse et al. | |
| D836,198 S | 12/2018 | Harris et al. | |
| 10,149,753 B2 | 12/2018 | Chen et al. | |
| 10,166,026 B2 | 1/2019 | Shelton, IV et al. | |
| 10,172,616 B2 | 1/2019 | Murray et al. | |
| 10,271,849 B2 | 4/2019 | Vendely et al. | |
| 10,285,692 B2 | 5/2019 | Widenhouse et al. | |
| 10,335,150 B2 | 7/2019 | Shelton, IV | |
| 10,349,939 B2 | 7/2019 | Shelton et al. | |
| D882,782 S | 4/2020 | Shelton et al. | |
| D885,574 S | 5/2020 | Shelton et al. | |
| 10,779,817 B2 | 9/2020 | Shelton, IV et al. | |
| 10,799,237 B2 | 10/2020 | Shelton, IV et al. | |
| 10,835,216 B2 | 11/2020 | Stevenson et al. | |
| 10,835,246 B2 | 11/2020 | Shelton, IV et al. | |
| 2004/0260315 A1 | 12/2004 | Dell et al. | |
| 2006/0013863 A1 | 1/2006 | Shalaby et al. | |
| 2006/0271104 A1 | 11/2006 | Viola et al. | |
| 2007/0131732 A1* | 6/2007 | Holsten ............ A61B 17/32053 |
| | | | 227/179.1 |
| 2009/0048423 A1 | 2/2009 | Stopek | |
| 2009/0090763 A1 | 4/2009 | Zemlok et al. | |
| 2009/0093550 A1 | 4/2009 | Rolfes et al. | |
| 2011/0125284 A1 | 5/2011 | Gabbrielli et al. | |
| 2011/0276125 A1 | 11/2011 | Walker et al. | |
| 2012/0080336 A1 | 4/2012 | Shelton et al. | |
| 2012/0080344 A1 | 4/2012 | Shelton, IV | |
| 2012/0080493 A1 | 4/2012 | Shelton et al. | |
| 2012/0241491 A1 | 9/2012 | Aldridge et al. | |
| 2012/0241497 A1 | 9/2012 | Mandakolathur Vasudevan et al. | |
| 2012/0241502 A1 | 9/2012 | Aldridge et al. | |
| 2012/0241505 A1 | 9/2012 | Alexander et al. | |
| 2012/0253298 A1 | 10/2012 | Henderson et al. | |
| 2012/0318842 A1 | 12/2012 | Anim et al. | |
| 2013/0068816 A1 | 3/2013 | Mandakolathur Vasudevan et al. | |
| 2013/0075449 A1 | 3/2013 | Schmid et al. | |
| 2013/0161374 A1 | 6/2013 | Swayze et al. | |
| 2013/0161375 A1 | 6/2013 | Huitema et al. | |
| 2013/0253661 A1 | 9/2013 | D'agostino et al. | |
| 2013/0256365 A1 | 10/2013 | Shelton, IV et al. | |
| 2013/0256375 A1 | 10/2013 | Shelton et al. | |
| 2013/0292862 A1 | 11/2013 | Joyce | |
| 2013/0295081 A1 | 11/2013 | Guelcher et al. | |
| 2013/0295212 A1 | 11/2013 | Chen et al. | |
| 2013/0317526 A1 | 11/2013 | Mortarino | |
| 2014/0155916 A1 | 6/2014 | Hodgkinson et al. | |
| 2014/0166721 A1 | 6/2014 | Stevenson et al. | |
| 2014/0166726 A1* | 6/2014 | Schellin ........... A61B 17/07207 |
| | | | 227/178.1 |
| 2014/0224857 A1 | 8/2014 | Schmid | |
| 2014/0252674 A1 | 9/2014 | Hundley et al. | |
| 2014/0291379 A1* | 10/2014 | Schellin ............... A61B 17/068 |
| | | | 227/176.1 |
| 2015/0034696 A1 | 2/2015 | Shelton et al. | |
| 2015/0133995 A1 | 5/2015 | Shelton et al. | |
| 2015/0134077 A1 | 5/2015 | Shelton, IV et al. | |
| 2015/0136831 A1 | 5/2015 | Baxter, III et al. | |
| 2015/0245841 A1 | 9/2015 | Linder et al. | |
| 2015/0250475 A1 | 9/2015 | Ek | |
| 2015/0297222 A1 | 10/2015 | Huitema et al. | |
| 2015/0297236 A1 | 10/2015 | Harris et al. | |
| 2015/0313594 A1 | 11/2015 | Shelton et al. | |
| 2015/0331402 A1 | 11/2015 | Lin et al. | |
| 2015/0351754 A1* | 12/2015 | Harris .............. A61B 17/07207 |
| | | | 606/219 |
| 2015/0351758 A1* | 12/2015 | Shelton, IV ....... A61B 17/0644 |
| | | | 606/219 |
| 2015/0351858 A9 | 12/2015 | Kubiak et al. | |
| 2015/0360419 A1 | 12/2015 | Willis et al. | |
| 2016/0000430 A1 | 1/2016 | Ming et al. | |
| 2016/0034696 A1 | 2/2016 | Jooste et al. | |
| 2016/0066914 A1 | 3/2016 | Baber et al. | |
| 2016/0100933 A1 | 4/2016 | Linder et al. | |
| 2016/0106426 A1 | 4/2016 | Shelton et al. | |
| 2016/0106427 A1 | 4/2016 | Shelton et al. | |
| 2016/0174974 A1 | 6/2016 | Schmid et al. | |
| 2016/0213395 A1 | 7/2016 | Anim | |
| 2016/0249919 A1 | 9/2016 | Savage et al. | |
| 2016/0278765 A1 | 9/2016 | Shelton et al. | |
| 2016/0288376 A1 | 10/2016 | Sun et al. | |
| 2016/0345976 A1 | 12/2016 | González et al. | |
| 2017/0056000 A1 | 3/2017 | Nalagatla et al. | |
| 2017/0086829 A1 | 3/2017 | Vendely et al. | |
| 2017/0086837 A1 | 3/2017 | Vendely et al. | |
| 2017/0086841 A1* | 3/2017 | Vendely ................... B32B 3/20 |
| 2017/0129167 A1 | 5/2017 | Castanon | |
| 2017/0129169 A1 | 5/2017 | Batchelder et al. | |
| 2017/0231633 A1 | 8/2017 | Marczyk et al. | |
| 2017/0355815 A1 | 12/2017 | Becker et al. | |
| 2018/0103952 A1 | 4/2018 | Aronhalt et al. | |

(56) References Cited

U.S. PATENT DOCUMENTS

| | | |
|---|---|---|
| 2018/0126630 A1 | 5/2018 | Panzer et al. |
| 2018/0132845 A1 | 5/2018 | Schmid et al. |
| 2018/0147327 A1 | 5/2018 | Joyce |
| 2018/0208735 A1 | 7/2018 | Nash et al. |
| 2018/0235615 A1* | 8/2018 | Landgrebe ........... A61B 17/072 |
| 2018/0235616 A1 | 8/2018 | Shelton, IV et al. |
| 2018/0235624 A1 | 8/2018 | Shelton, IV et al. |
| 2018/0235626 A1 | 8/2018 | Shelton, IV et al. |
| 2018/0243976 A1 | 8/2018 | Feller |
| 2018/0290374 A1 | 10/2018 | Willis et al. |
| 2018/0361510 A1 | 12/2018 | Stamp et al. |
| 2019/0059889 A1 | 2/2019 | Shelton et al. |
| 2019/0133578 A1 | 5/2019 | Kriksunov et al. |
| 2019/0240385 A1 | 8/2019 | Hartwell et al. |
| 2019/0254654 A1 | 8/2019 | Shelton et al. |
| 2019/0254655 A1 | 8/2019 | Shelton et al. |
| 2019/0254656 A1 | 8/2019 | Shelton et al. |
| 2019/0254657 A1 | 8/2019 | Shelton et al. |
| 2019/0254658 A1 | 8/2019 | Shelton et al. |
| 2019/0254659 A1 | 8/2019 | Harris et al. |
| 2019/0254660 A1 | 8/2019 | Shelton et al. |
| 2019/0254661 A1 | 8/2019 | Shelton et al. |
| 2019/0254664 A1 | 8/2019 | Vendely et al. |
| 2019/0254665 A1 | 8/2019 | Vendely et al. |
| 2019/0254666 A1 | 8/2019 | Vendely et al. |
| 2019/0254667 A1 | 8/2019 | Vendely et al. |
| 2019/0254668 A1 | 8/2019 | Vendely et al. |
| 2019/0254669 A1 | 8/2019 | Shelton et al. |
| 2019/0254670 A1 | 8/2019 | Shelton et al. |
| 2019/0269400 A1 | 9/2019 | Mandakolathur Vasudevan et al. |
| 2019/0269817 A1 | 9/2019 | Williams et al. |
| 2020/0000469 A1 | 1/2020 | Shelton et al. |
| 2020/0190278 A1 | 6/2020 | Gardner et al. |
| 2021/0077094 A1 | 3/2021 | Harris et al. |
| 2021/0077095 A1 | 3/2021 | Harris et al. |
| 2021/0077096 A1 | 3/2021 | Harris et al. |
| 2021/0077097 A1 | 3/2021 | Harris et al. |
| 2021/0077098 A1 | 3/2021 | Harris et al. |
| 2021/0077103 A1 | 3/2021 | Harris et al. |
| 2021/0077104 A1 | 3/2021 | Harris et al. |
| 2021/0077105 A1 | 3/2021 | Harris et al. |
| 2021/0077106 A1 | 3/2021 | Harris et al. |
| 2021/0077108 A1 | 3/2021 | Harris et al. |
| 2021/0077109 A1 | 3/2021 | Harris et al. |
| 2022/0079579 A1 | 3/2022 | Shelton, IV et al. |

FOREIGN PATENT DOCUMENTS

| | | |
|---|---|---|
| EP | 1815804 A2 | 8/2007 |
| EP | 2090248 A2 | 8/2009 |
| EP | 2764824 A1 | 8/2014 |
| EP | 2764827 A2 | 8/2014 |
| EP | 2783640 A2 | 10/2014 |
| EP | 2954857 A1 | 12/2015 |
| EP | 3087931 A2 | 11/2016 |
| EP | 3132811 A1 | 2/2017 |
| EP | 3132812 A1 | 2/2017 |
| EP | 3135222 A1 | 3/2017 |
| EP | 3135317 A1 | 3/2017 |
| EP | 3135318 A1 | 3/2017 |
| EP | 3150134 A1 | 4/2017 |
| EP | 3150137 A1 | 4/2017 |
| EP | 3150138 A2 | 4/2017 |
| EP | 3150142 A2 | 4/2017 |
| EP | 3150144 A1 | 4/2017 |
| EP | 3162388 A1 | 5/2017 |
| EP | 3363382 A1 | 8/2018 |
| EP | 3363386 A1 | 8/2018 |
| RU | 2629239 C2 | 8/2017 |
| WO | 2006088946 A2 | 8/2006 |
| WO | 2017058599 A1 | 4/2017 |

OTHER PUBLICATIONS

European Search Report and Written Opinion for EP Application No. 19158219 dated Apr. 9, 2019, 10 pages.

European Search Report and Written Opinion for EP Application No. 19158301 dated Mar. 27, 2019, 7 pages.

European Search Report and Written Opinion for EP Application No. 19158186 dated Jul. 5, 2019, 9 pages.

European Search Report and Written Opinion for EP Application No. 19158306 dated May 8, 2019,19 pages.

International Search Report and Written Opinion for PCT/IB2019/050402, dated Apr. 30, 2019, 14 pages.

International Search Report and Written Opinion for PCT/IB2019/050408, dated Jun. 5, 2019, 12 pages.

International Preliminary Report on Patentability issued in International Patent Application No. PCT/IB2019/050500, dated Aug. 27, 2020, 12 pages.

International Preliminary Report on Patentability issued in International Patent Application No. PCT/IB2019/050363, dated Aug. 27, 2020, 8 pages.

International Preliminary Report on Patentability issued in International Patent Application No. PCT/IB2019/050400, dated Aug. 27, 2020, 8 pages.

International Preliminary Report on Patentability issued in International Patent Application No. PCT/IB2019/050402, dated Aug. 27, 2020, 10 pages.

International Search Report and Written Opinion for PCT/IB2019/050500, dated May 17, 2019, 16 pages.

International Preliminary Report on Patentability issued in International Patent Application No. PCT/IB2019/050403, dated Aug. 27, 2020,22 pages.

International Preliminary Report on Patentability issued in International Patent Application No. PCT/IB2019/050404, dated Aug. 27, 2020, 9 pages.

International Preliminary Report on Patentability issued in International Patent Application No. PCT/IB2019/050406, dated Aug. 27, 2020, 8 pages.

International Preliminary Report on Patentability issued in International Patent Application No. PCT/IB2019/050407, dated Aug. 27, 2020, 12 pages.

International Preliminary Report on Patentability issued in International Patent Application No. PCT/IB2019/050408, dated Aug. 27, 2020, 8 pages.

International Search Report and Written Opinion for PCT/IB2019/050363, dated Jul. 15, 2019, 11 pages.

Partial European Search Report and Written Opinion for EP Application No. 19158223 dated Apr. 25, 2019, 10 pages.

Partial European Search Report and Written Opinion for EP Application 19158306 dated May 8, 2019, 21 pages.

Baker et al. (2004) "The Science of Stapling and Leaks", Obesity Surgery, 14;1290-1298.

Januszkiewicz et al. (2016) "Layerless Fabrication with Continuous Liquid Interface Production", Proceedings of the National Academy of Sciences,113(42); 11703-11708.

U.S. Appl. No. 15/689,198 entitled "Endocutter Control System", filed Aug. 29, 2017, 60 pages.

Tumbleston et al. (2015) "Continuous Liquid Interface Production of 3D Objects", Science, 347(6228);1349-1352.

Wismans et al.(2009) "Characterization of Polymeric Foams", Eindhoven University of Technology, 35 pages.

Ye et al.(2008) "Development of the Warp Knitted Spacer Fabrics for Cushion Applications", Journal of Industrial Textiles, 37(3);213-223.

Yo et al.(2006) "Buttressing of the Staple Line in Gastrointestinal Anastomoses: Overview of New Technology Designed to Reduce Perioperative Complications", Digestive Surgery, 23;283-291.

Elomaa et al.(2011) "Preparation of Poly(e-caprolactone)-based Tissue Engineering Scaffolds", Acta Biomaterialia, 7;3850-3856.

Melchels et al.(2010) "Effects of The Architecture of Tissue Engineering Scaffolds On Cell Seeding and Culturing", Acta Biomater., 6(11):4208-4217.

Extended European Search Report and Written Opinion for EP Application No. 20196533.2, dated Oct. 30, 2020, 10 pages.

(56) References Cited

OTHER PUBLICATIONS

U.S. Appl. No. 17/009,740, filed Sep. 1, 2020, Compressible Non-Fibrous Adjuncts.
U.S. Appl. No. 17/009,742, filed Sep. 1, 2020, Compressible Non-Fibrous Adjuncts.
U.S. Appl. No. 17/009,743, filed Sep. 1, 2020, Compressible Non-Fibrous Adjuncts.
U.S. Appl. No. 17/009,744, filed Sep. 1, 2020, Compressible Non-Fibrous Adjuncts.
U.S. Appl. No. 17/009,745, filed Sep. 1, 2020, Compressible Non-Fibrous Adjuncts.
U.S. Appl. No. 17/009,746, filed Sep. 1, 2020, Compressible Non-Fibrous Adjuncts.
U.S. Appl. No. 17/009,750, filed Sep. 1, 2020, Compressible Non-Fibrous Adjuncts.
U.S. Appl. No. 17/009,755, filed Sep. 1, 2020, Compressible Non-Fibrous Adjuncts.
U.S. Appl. No. 17/009,766, filed Sep. 1, 2020, Compressible Non-Fibrous Adjuncts.
U.S. Appl. No. 17/009,768, filed Sep. 1, 2020, Compressible Non-Fibrous Adjuncts.
U.S. Appl. No. 17/009,769, filed Sep. 1, 2020, Compressible Non-Fibrous Adjuncts.
U.S. Appl. No. 29/748,933, filed Sep 1, 2020 Stapling Cartridge Assembly with Compressible Adjunct.
U.S. Appl. No. 15/901,087, filed Feb. 21, 2018, Three Dimensional Adjuncts.
U.S. Appl. No. 15/901,259, filed Feb. 21, 2018, Three Dimensional Adjuncts.
U.S. Appl. No. 15/901,713, filed Feb. 21, 2018, Three Dimensional Adjuncts.
U.S. Appl. No. 15/901,723, filed Feb. 21, 2018, Three Dimensional Adjuncts.
U.S. Appl. No. 15/901,731, filed Feb. 21, 2018, Three Dimensional Adjuncts.
U.S. Appl. No. 15/901,746, filed Feb. 21, 2018, Three Dimensional Adjuncts.
U.S. Appl. No. 15/901,753, filed Feb. 21, 2018, Three Dimensional Adjuncts.
U.S. Appl. No. 15/901,758, filed Feb. 21, 2018, Three Dimensional Adjuncts.
U.S. Appl. No. 15/901,767, filed Feb. 21, 2018, Three Dimensional Adjuncts.
U.S. Appl. No. 29/638,769, filed Feb. 21, 2018, Three Dimensional Adjuncts.
U.S. Appl. No. 29/708,336, filed Oct. 4, 2019, Three Dimensional Adjuncts.
U.S. Appl. No. 29/768,286, filed Jan. 28, 2021, Three Dimensional Adjuncts.
U.S. Appl. No. 17/532,133, filed Nov. 22, 2021, Three Dimensional Adjuncts.
Extended European Search Report issued in European Application No. 20196517.5, dated Apr. 23, 2021, 13 pages.
Extended European Search Report issued in European Application No. 20196519.1, dated Apr. 20, 2021, 20 pages.
Almeida Henrique De A. (2013) "Smart Design of Scaffolds Obtained by Biofabrication for Tissue Engineering Applications", 24 pages.
Schwarz Hermann (2019) "Schwarz Minimal Surface", Wikipedia, 4 pages.
Wikipedia (2013) "Gyroid", Wikipedia Retrieved from URL https://en.wikipedia.org/w/index.php?title=Gyroid&oldid=914209926, 4 pages.
Array (2022) "Definition by Merriam-Webster", URL https://www.merriam-webster.com/dictionary/array as retrieved on Feb. 4, 2022, 15 pages.

\* cited by examiner

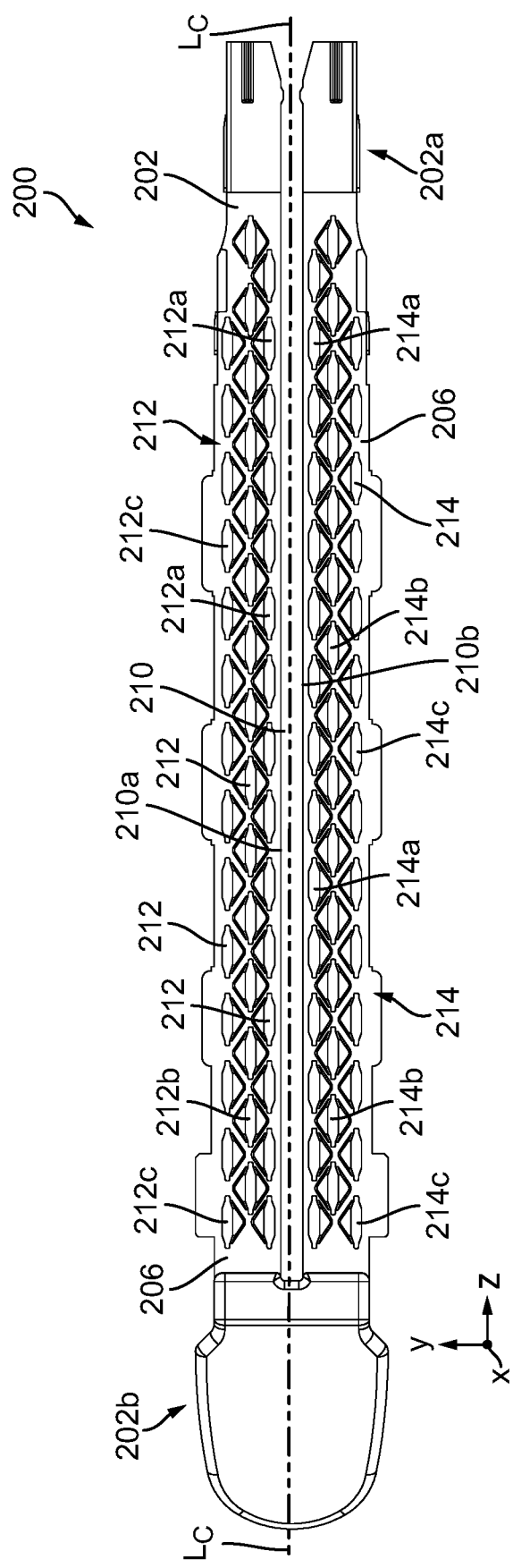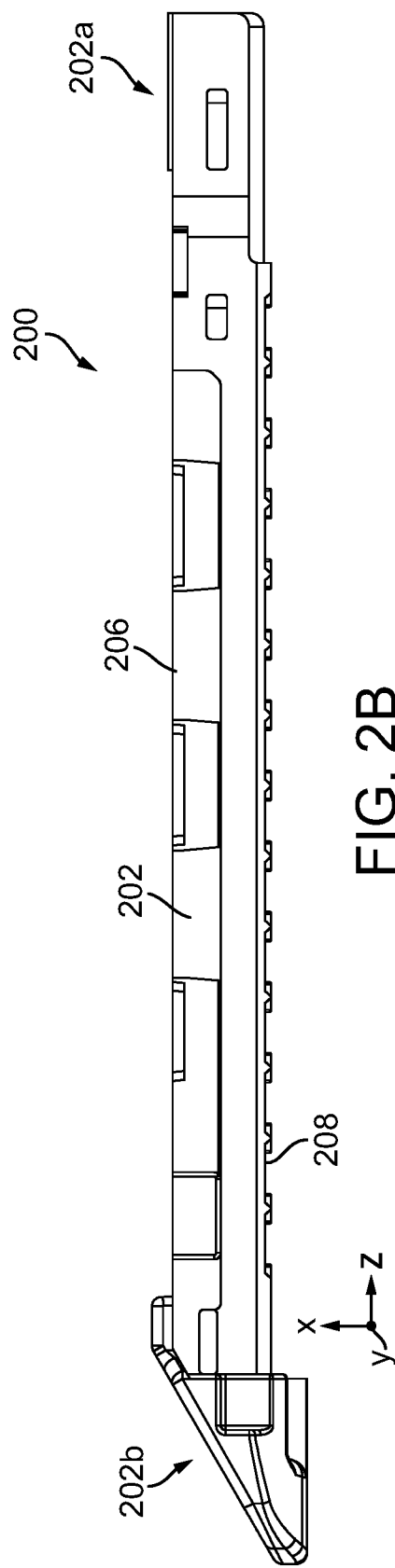
FIG. 2A
FIG. 2B

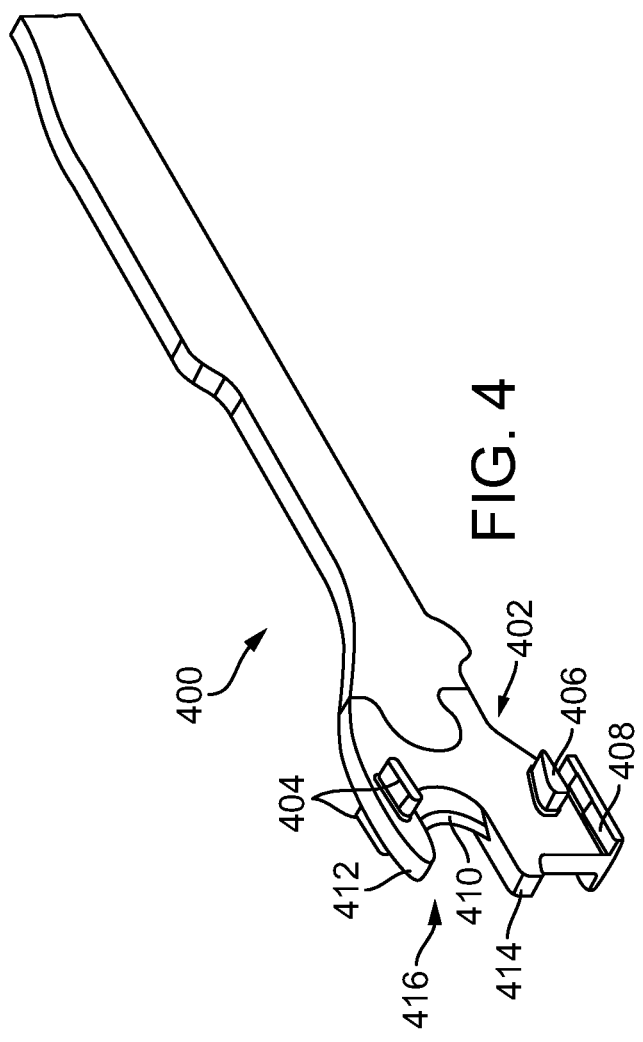
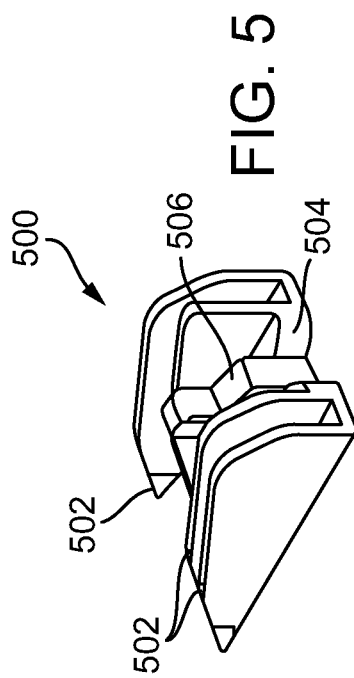
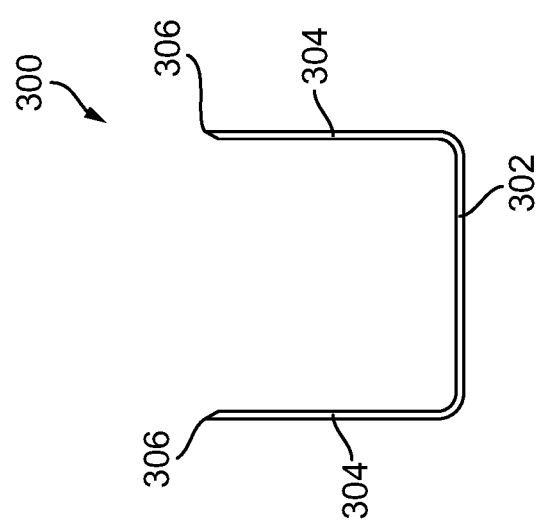

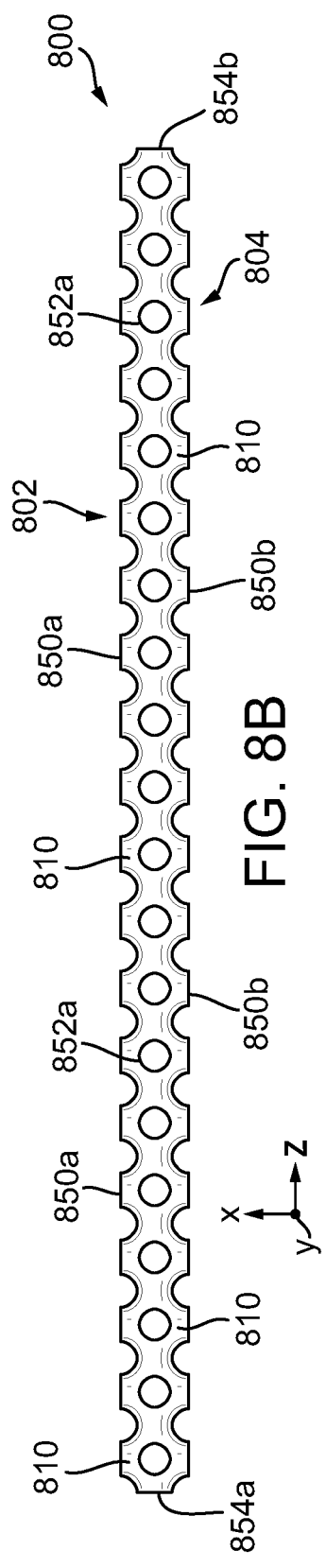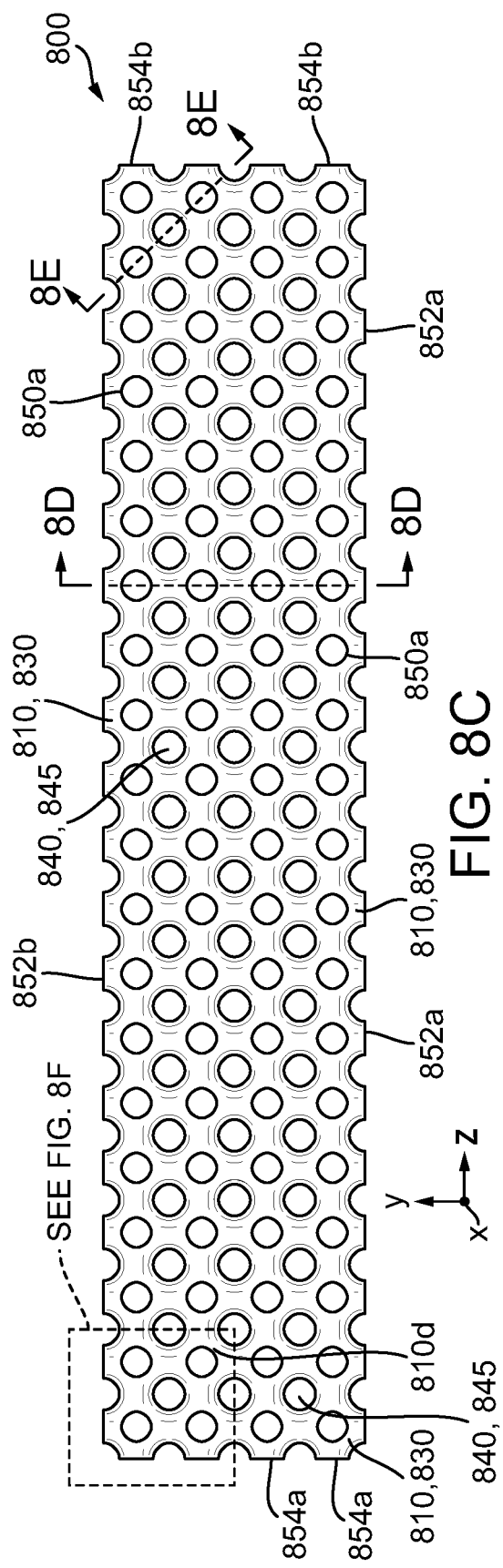

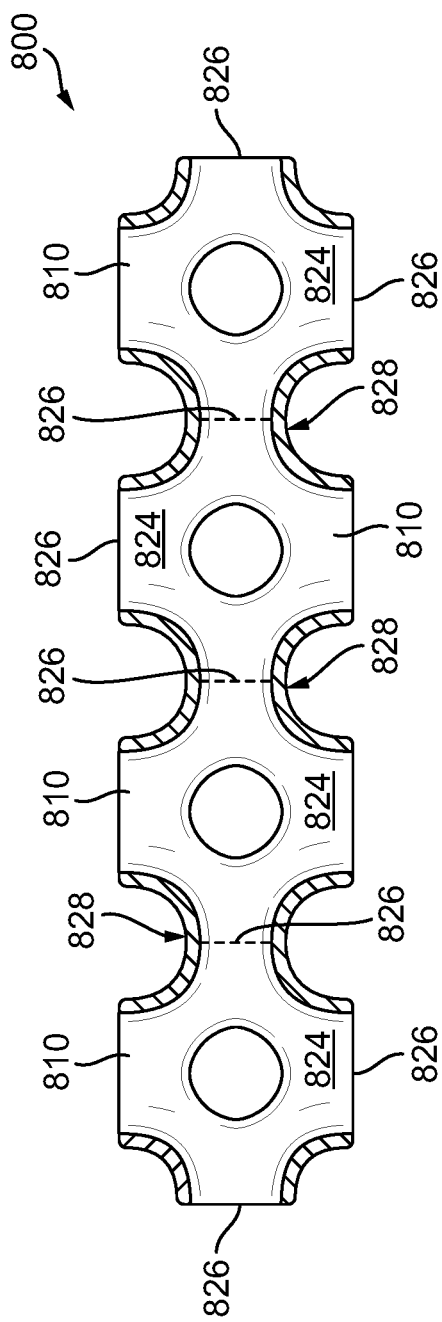
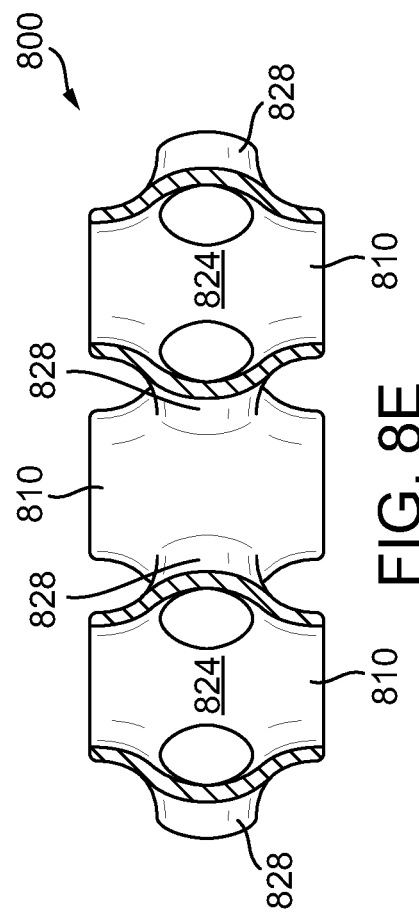
FIG. 8D
FIG. 8E

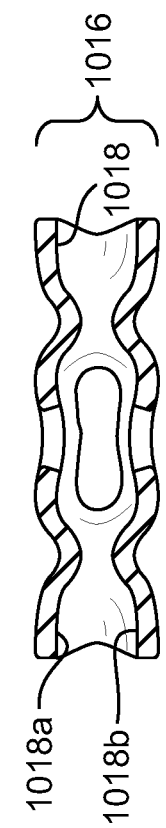
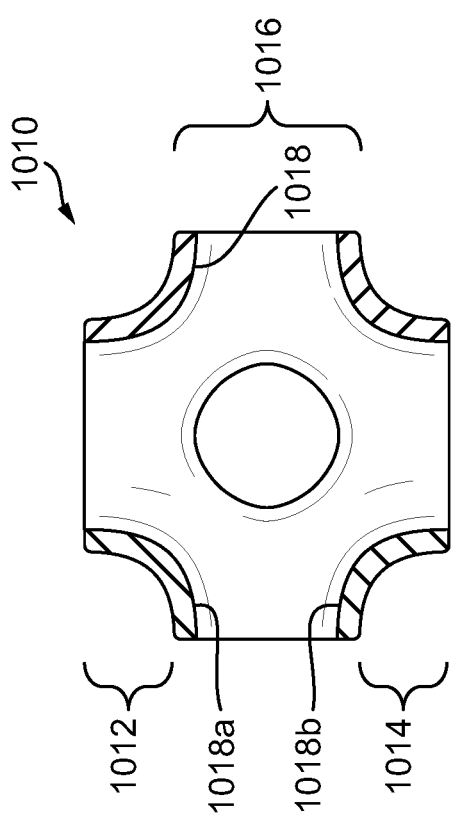
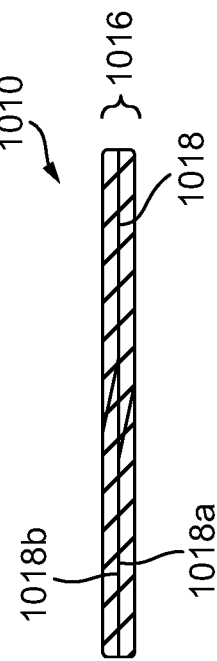
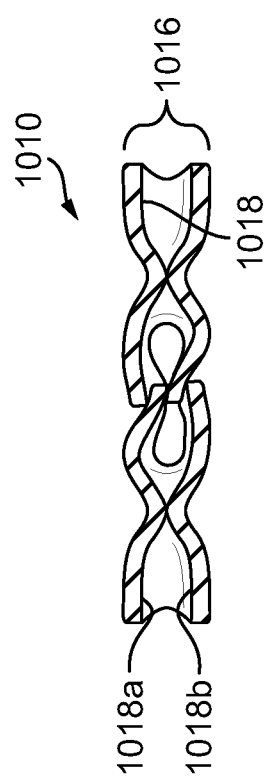
FIG. 10A
FIG. 10B
FIG. 10C
FIG. 10D

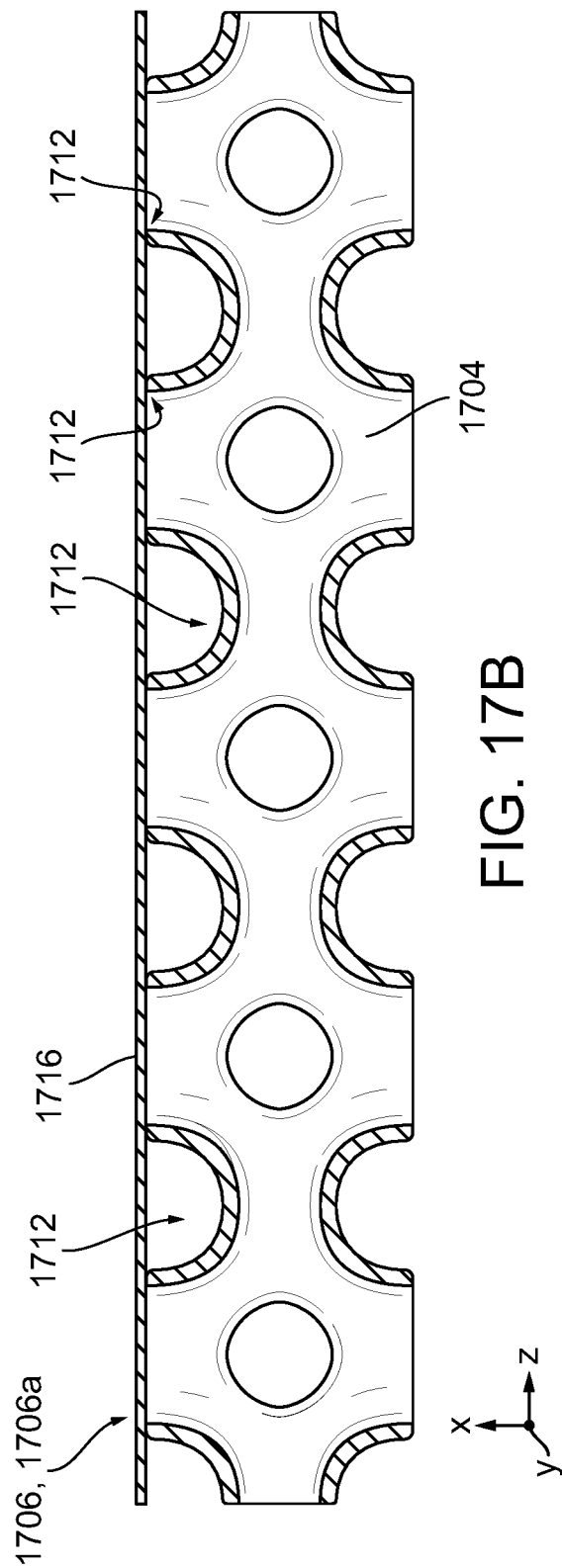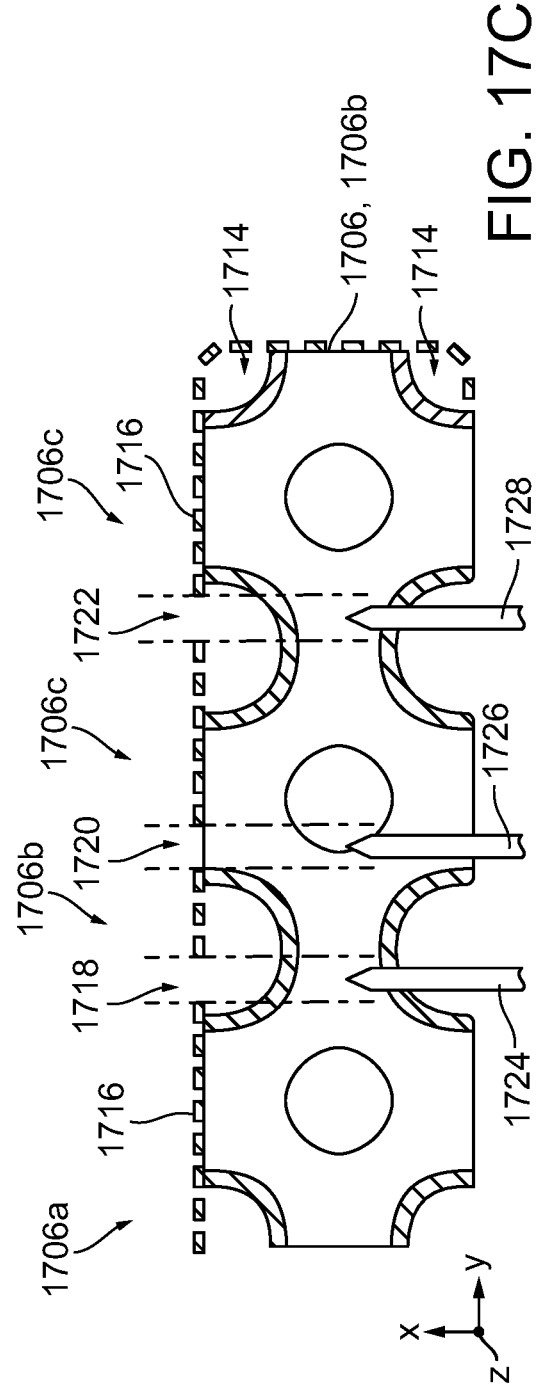

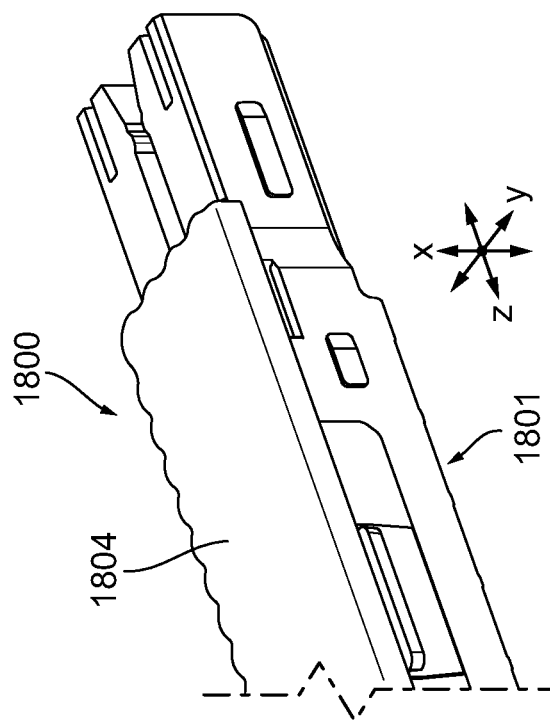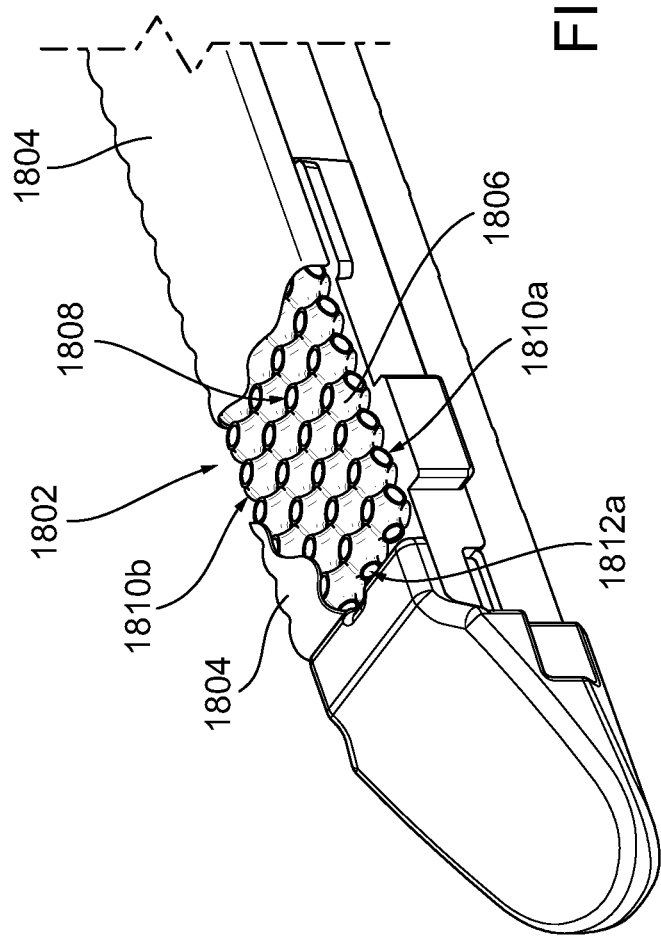
FIG. 18

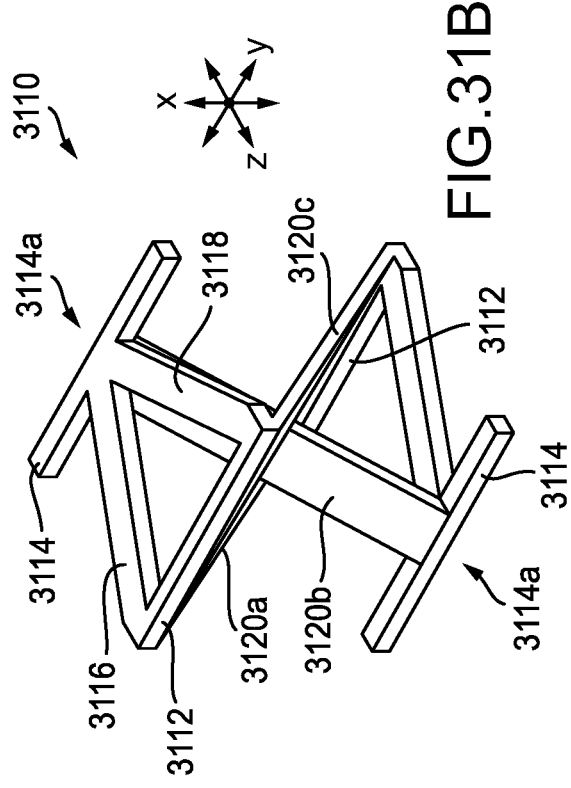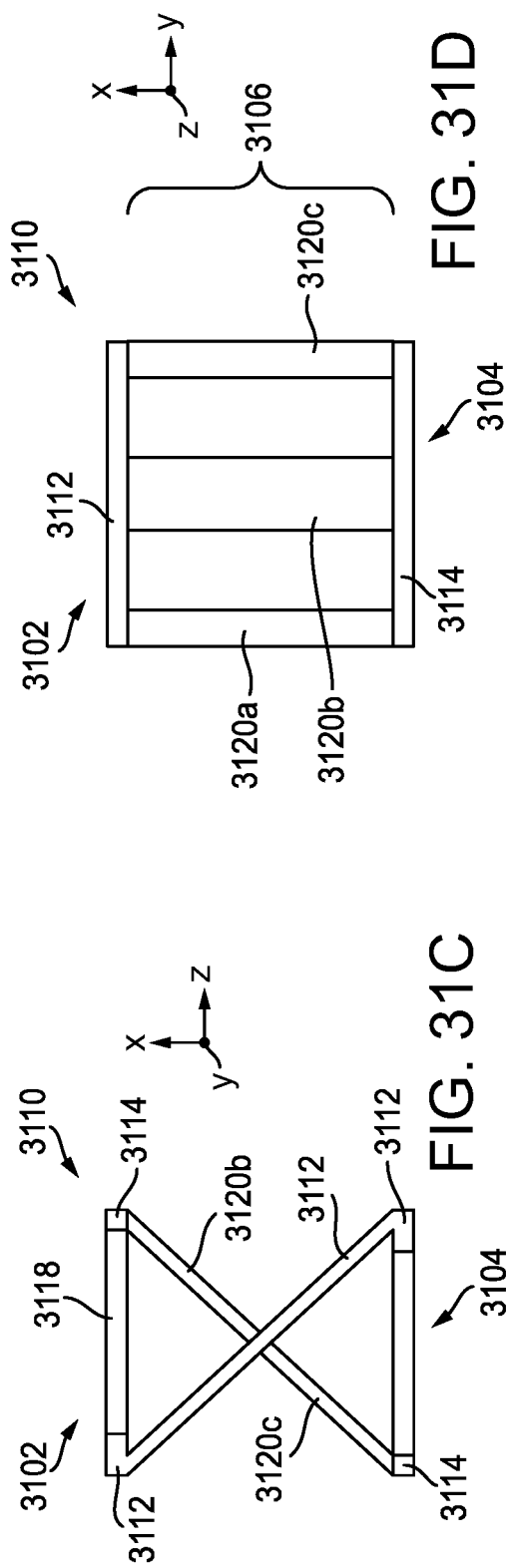

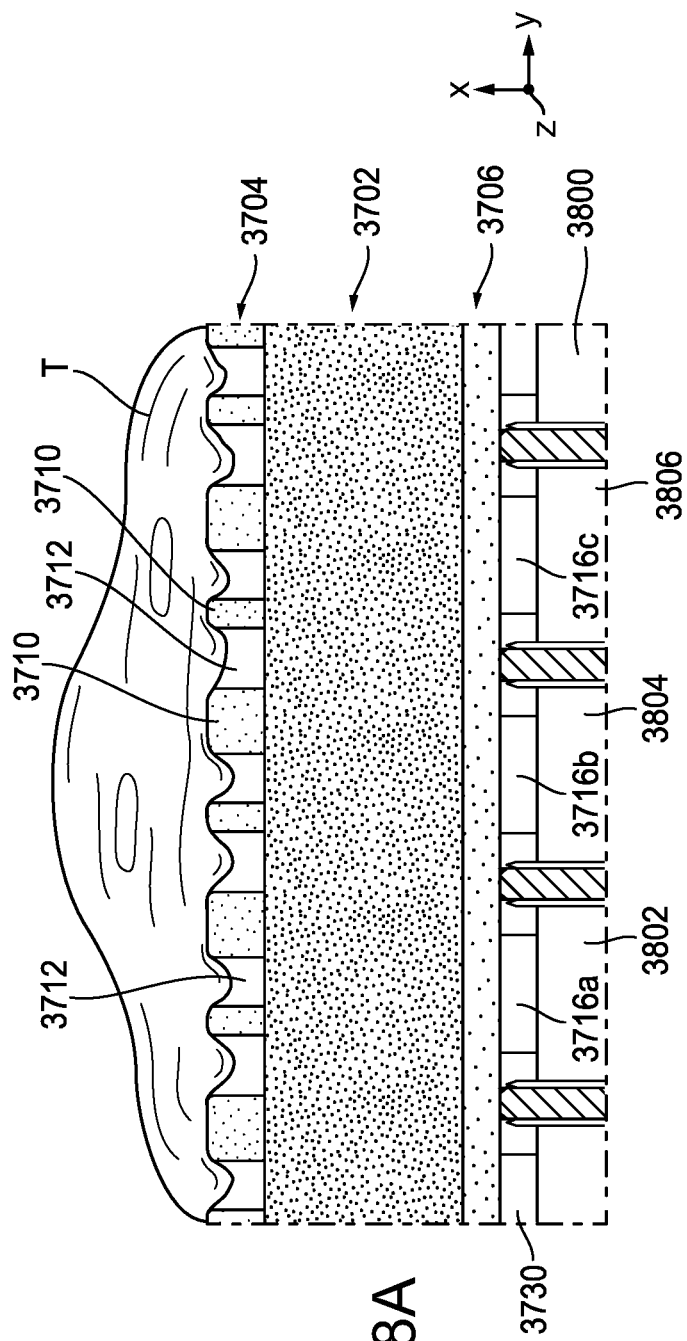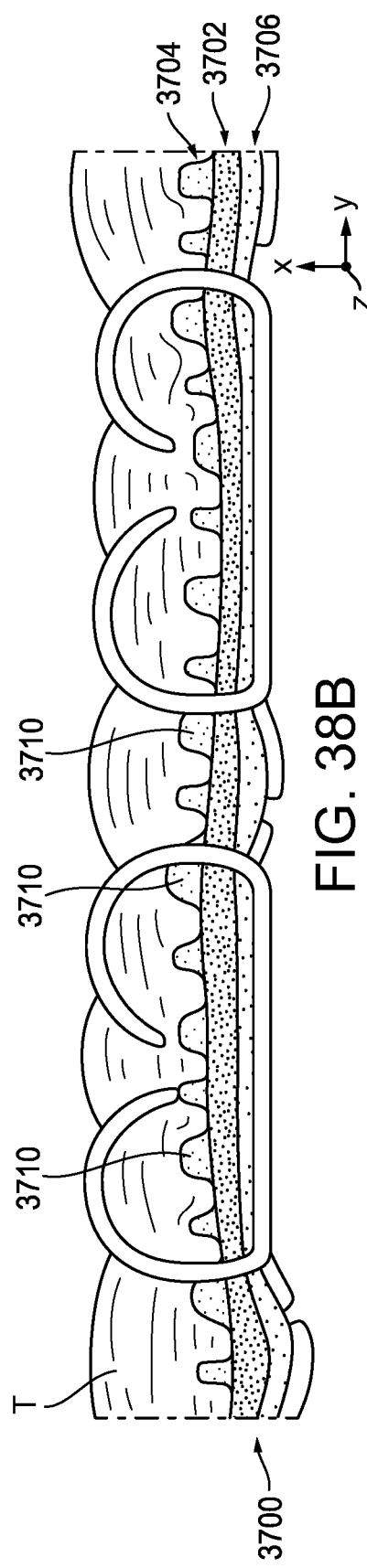

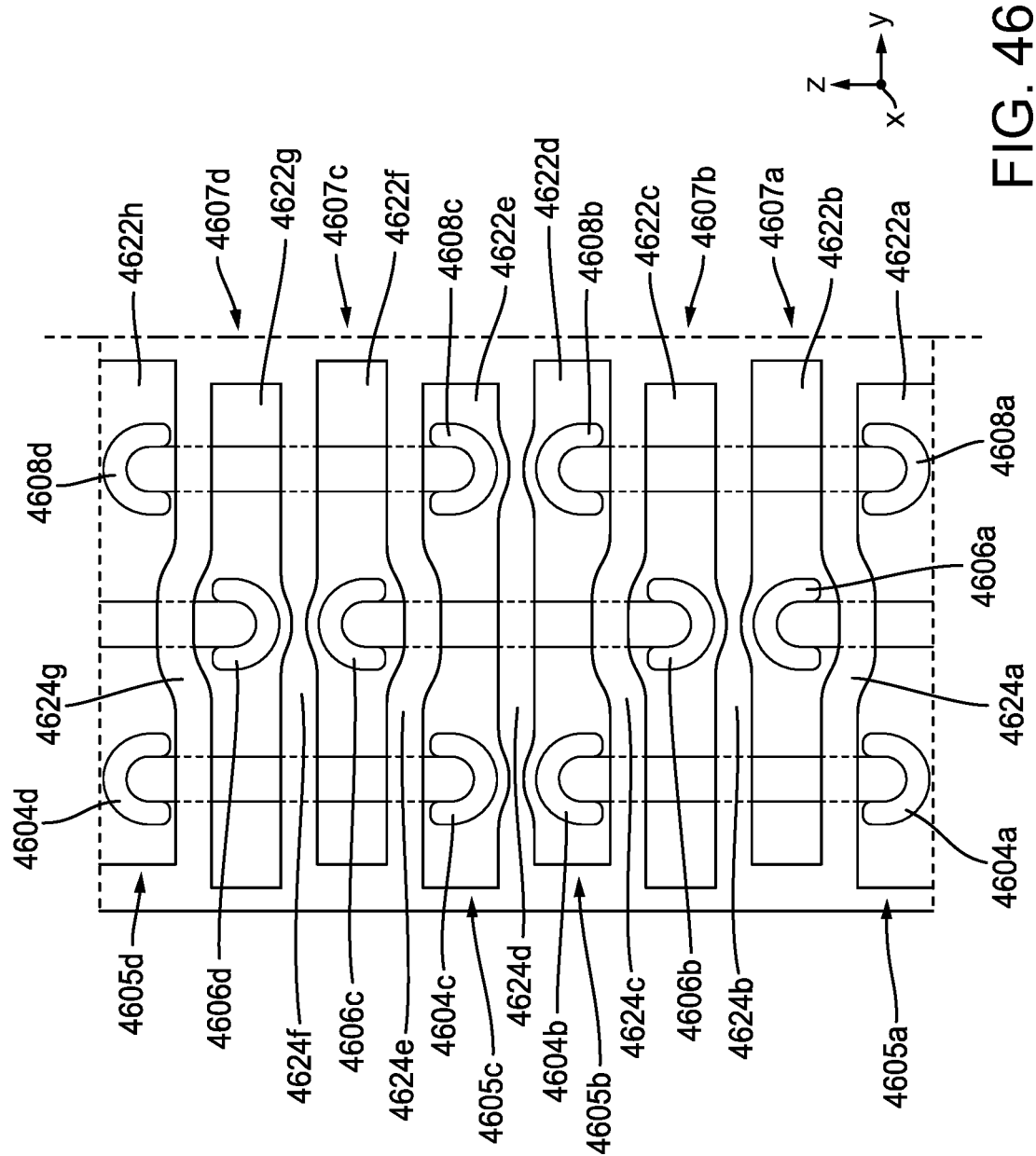

COMPRESSIBLE NON-FIBROUS ADJUNCTS

CROSS-REFERENCE TO RELATED APPLICATIONS

This application claims priority to U.S. Provisional Patent Application No. 62/900,708, filed Sep. 16, 2019, and entitled "Bioabsorbable Resin for Additive Manufacturing," U.S. Provisional Patent Application No. 62/913,227, filed Oct. 10, 2019, and entitled "Bioabsorbable Resin for Additive Manufacturing," and U.S. Provisional Patent Application No. 63/053,863, filed on Jul. 20, 2020, and entitled "Compressible 3D Printed Scaffolds," the disclosures of which are incorporated herein by reference in their entireties.

FIELD

Compressible non-fibrous adjuncts and methods of manufacturing and using the same are provided.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Some surgical staplers require a surgeon to select the appropriate staples having the appropriate staple height for the tissue being stapled. For example, a surgeon could select tall staples for use with thick tissue and short staples for use with thin tissue. In some instances, however, the tissue being stapled does not have a consistent thickness and, thus the staples cannot achieve the desired fired configuration at each staple site. As a result, a desirable seal at or near all of the stapled sites cannot be formed, thereby allowing blood, air, gastrointestinal fluids, and other fluids to seep through the unsealed sites.

Further, staples, as recessed channel as other objects and materials that can be implanted in conjunction with procedures like stapling, generally lack some characteristics of the tissue in which they are implanted. For example, staples and other objects and materials can lack the natural flexibility of the tissue in which they are implanted, and therefore are unable to withstand the varying intra-tissue pressures at the implantation site. This can lead to undesirable tissue tearing, and consequently leakage, at or near the staple site.

Accordingly, there remains a need for improved instruments and methods that address current issues with surgical staplers.

SUMMARY

Surgical end effectors for use with a surgical stapler are provided. In one exemplary embodiment, a surgical end effector includes a cartridge and an anvil movable relative to the cartridge between open and closed positions, the cartridge having a plurality of staples disposed therein, the plurality of staples being configured to be deployed into tissue, and a non-fibrous adjunct formed of at least one fused bioabsorbable polymer and configured to be releasably retained on the cartridge such that the adjunct can be attached to tissue by the plurality of staples in the cartridge, the adjunct having a first end, a second end, and a longitudinal axis extending therebetween. The adjunct includes a cartridge-contacting surface, a tissue-contacting surface that is opposite the cartridge-contacting surface, wherein at least a portion of the tissue-contacting surface is curved, and an internal structure extending between the cartridge-contacting surface and the tissue-contacting surface, the internal structure being formed of a first lattice and a second lattice that is interposed between the first lattice and the cartridge, the first lattice having a first compressive strength and the second lattice having a second compressive strength that is greater than the first compressive strength. The adjunct has a uncompressed thickness that at least partially varies in a lateral direction relative to the longitudinal axis of the adjunct to thereby create a variable tissue gap between the anvil and the adjunct when the adjunct is releasably retained on the cartridge and the anvil is in a closed position without tissue therebetween, in which the adjunct, when in a tissue deployed state, applies a generally uniform pressure to the tissue stapled thereto for a predetermined period of time.

In some embodiments, when in a tissue deployed state, the adjunct can have a compressed generally uniform thickness.

In some embodiments, when in a tissue deployed state, the adjunct can have a compressed thickness that at least partially varies in the lateral direction.

The adjunct can have a variety of configurations. For example, in some embodiments, the adjunct can be configured to be releasably retained on a surface of the cartridge that faces the anvil, in which the surface of the cartridge can be planar and the plurality of staples can be generally uniform. In other embodiments, the adjunct can be configured to be releasably retained on a surface of the cartridge that faces the anvil, in which the surface can be non-planar and the plurality of staples can include a first plurality of staples having a first height and a second plurality of staples having a second height that is greater than the first undeformed height. In some embodiments, the adjunct can have a first thickness measured at a center of the adjunct and a second thickness measured at a terminal lateral-facing edge of the adjunct, in which the second thickness can be less than the first thickness. In other embodiments, the center of the adjunct can have a first stiffness and the terminal lateral-facing edge of the adjunct can have a second stiffness that is greater than the first stiffness. In certain embodiments, the uncompressed thickness of the adjunct can decrease in the lateral direction from the first thickness to the second thickness while the tissue gap increases in the same direction.

The plurality of staples can have a variety of configurations. For example, in some embodiments, the plurality of staples can be arranged in a plurality of staples rows, in which the plurality of staples rows can include an inner-most staple row of the first plurality of staples and an outer-most staple row of the second plurality of staples. In other embodiments, the outer-most staple row can overlap with only the second lattice. In certain embodiments, the plurality of staples can include a third plurality of staples having a third height that is between the first and second heights, in which the plurality of staple rows can include an intermediate staple row of the third plurality of staples that is positioned between the inner-most staple row and the outer-most staple row.

The first lattice can have a variety of configurations. For example, in some embodiments, the first lattice can extend from a first top surface to a first bottom surface, in which the top surface can define at least a portion of the tissue-contacting surface of the adjunct. In other embodiments, the first top surface can have a convex configuration. In certain embodiments, the first lattice can include a first plurality of unit cells, in which each unit cell can be a triply periodic minimal surface structure or can be defined by a plurality of planar interconnected struts.

The second lattice can have a variety of configurations. For example, in some embodiments, the second lattice can extend from a second top surface to a second bottom surface, in which the second top surface can define at least a portion of the tissue-contacting surface of the adjunct. In other embodiments, the second top surface can have a concave configuration. In some embodiments, the second lattice can include a second plurality of unit cells, in which each unit cell can be a triply periodic minimal surface structure or can be defined by a plurality of planar interconnected struts.

In another exemplary embodiment, a surgical end effector includes a cartridge and an anvil movable relative to the cartridge between open and closed positions, the cartridge having a plurality of staples disposed therein, the plurality of staples being configured to be deployed into tissue, and a non-fibrous adjunct formed of at least one fused bioabsorbable polymer and configured to be releasably retained on at least a portion of the top surface of the cartridge such that the adjunct can be attached to tissue by the plurality of staples in the cartridge, the adjunct having a cartridge-contacting surface and a tissue-contacting surface that is opposite the cartridge-contacting surface. The adjunct includes a first lattice structure having first compressive strength, the first lattice extending from a first top surface and a first bottom surface that opposes the first top surface, wherein the first bottom surface defines the cartridge-contacting surface, a second lattice structure disposed on at least the first top surface of the first lattice structure, the second lattice structure having a second compressive strength that is less than the first compressive strength, the second lattice extending from a second top surface and a second bottom surface that is opposite the second top surface, in which the second top surface defines at least a portion of the tissue-contacting surface. The adjunct has proximal and distal ends and a longitudinal axis extending therebetween, in which the adjunct has a variable compression strength along a length that extends along the longitudinal axis such that the adjunct, when in a tissue deployed state, applies a generally uniform pressure to the tissue stapled thereto for a predetermined period of time.

In some embodiments, the adjunct can have an uncompressed thickness that at least partially varies along the length of the adjunct to thereby create a variable tissue gap between the anvil and the adjunct when the adjunct is releasably retained on the cartridge and the anvil is in a closed position without tissue therebetween.

The first and second lattice structures can have a variety of configurations. For example, in some embodiments, the first lattice structure and the second lattice structure can differ from each other in at least one of unit cells, density, and shape. In other embodiments, the first lattice structure can have an uncompressed thickness that at least partially varies along the length of the adjunct. In certain embodiments, the second lattice structure can have an uncompressed thickness that at least partially varies along the length of the adjunct. In other embodiments, the first lattice structure can include a first plurality of unit cells, in which each unit cell is a triply periodic minimal surface structure or defined by a plurality of interconnected struts interconnected. In certain embodiments, the second lattice structure can include a second plurality of unit cells, in which each unit cell can be a triply periodic minimal surface structure or can be defined by a plurality of interconnected struts.

BRIEF DESCRIPTION OF THE DRAWINGS

This invention will be more fully understood from the following detailed description taken in conjunction with the accompanying drawings, in which:

FIG. 2A is a top view of a staple cartridge for use with the surgical stapling and severing instrument of FIG. 1;

FIG. 2B is a side view of the staple cartridge of FIG. 2A;

FIG. 3 is a side view of a staple in an unfired (pre-deployed) configuration that can be disposed within the staple cartridge of the surgical cartridge assembly of FIG. 4;

FIG. 4 is a perspective view of a knife and firing bar ("E-beam") of the surgical stapling and severing instrument of FIG. 1;

FIG. 5 is a perspective view of a wedge sled of a staple cartridge of the surgical stapling and severing instrument of FIG. 1;

FIG. 8B is a side view of the adjunct of FIG. 8A;

FIG. 8C is a top view of the adjunct of FIG. 8A;

FIG. 8D is a cross-sectional view of the adjunct of FIG. 8C taken at line 8D-8D;

FIG. 8E is a cross-sectional view of the adjunct of FIG. 8C taken at line 8E-8E;

FIG. 10A is a schematic illustration of an exemplary unit cell in a precompressed state;

FIG. 10B is a schematic illustration of the unit cell of FIG. 10A in a first compressed state;

FIG. 10C is a schematic illustration of the unit cell of FIG. 10A in a second compressed state;

FIG. 10D is a schematic illustration of the unit cell of FIG. 10A in a densified state;

FIG. 17B is a cross-sectional view of the adjunct of FIG. 17A taken at line 17B-17B;

FIG. 17C is a cross-sectional view of the adjunct of FIG. 17A taken at line 17C-17C;

FIG. 18 is a perspective view of another exemplary embodiment of a compressible non-fibrous adjunct disposed on a staple cartridge;

FIG. 31B is a perspective view of a single unit cell of the adjunct of FIG. 31A;

FIG. 31C is a side view of the unit cell of FIG. 31B;

FIG. 31D is an alternate side view of the unit cell of FIGS. 31B-31C;

FIG. 38A is a schematic illustration of the portion of the stapling assembly of FIG. 37B, showing tissue disposed onto the adjunct;

FIG. 38B is a partial-schematic illustrating the adjunct of FIG. 37A in a tissue deployed condition;

FIG. 46B is a top down view of the portion of the stapling assembly of FIG. 46A;

FIG. 55 is a schematic illustration of the stress-strain curves of the adjunct of FIG. 54 at each of the three staple;

FIG. 56 is a graph showing a stress-strain curve of an exemplary compressible non-fibrous adjunct (Adjunct 1) of Example 9 and 10;

FIG. 57 is a graph showing stress-strain curves of four exemplary compressible non-fibrous adjuncts (Adjuncts 2-5) of Example 9 and 10; and FIG. 58 is a graph showing stress-strain curves of six exemplary embodiments of compressible non-fibrous adjuncts of Example 11.

DETAILED DESCRIPTION

Figure 1:
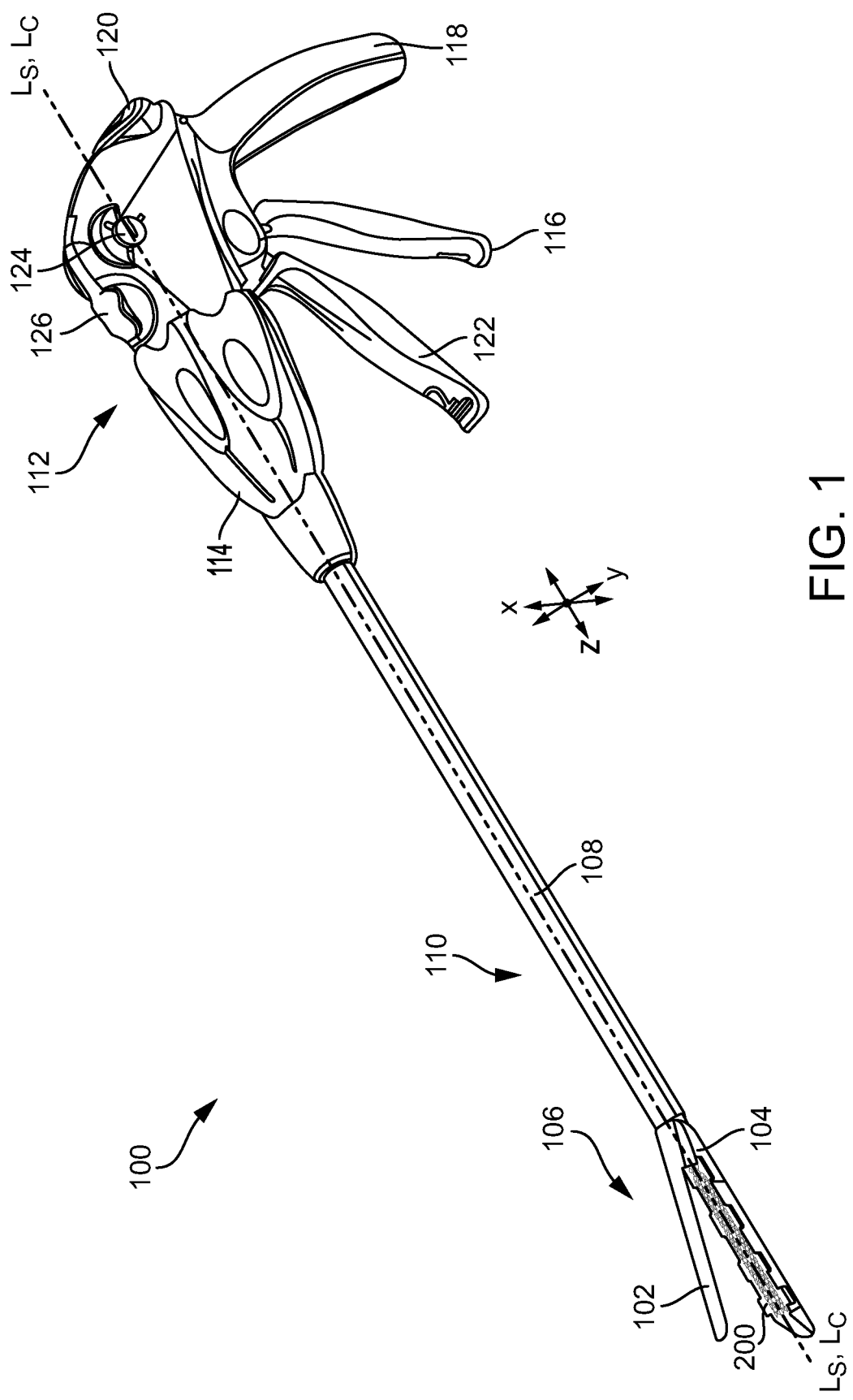
FIG. 1 is a perspective view of one exemplary embodiment of a conventional surgical stapling and severing instrument.

Certain exemplary embodiments will now be described to provide an overall understanding of the principles of the structure, function, manufacture, and use of the adjuncts, systems, and methods disclosed herein. One or more examples of these embodiments are illustrated in the accompanying drawings. Those skilled in the art will understand that the adjuncts, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Surgical stapling assemblies and methods for manufacturing and using the same are provided. In general, a surgical stapling assembly can include a staple cartridge having staples disposed therein and a compressible, bioabsorbable non-fibrous adjunct configured to be releasably retained on the staple cartridge. In some embodiments, the non-fibrous adjunct can be formed from a matrix that includes at least one fused bioabsorbable polymer, and thus it can be three-dimensionally printed. In other embodiments, the non-fibrous adjunct can be partially or wholly formed via any suitable non-additive manufacturing processes, such as injection molding, foaming, and forming processes as understood by a person skilled in the art. As discussed herein, the various adjuncts provided can be configured to compensate for variations in tissue properties, such as variations in tissue thickness, and/or to promote tissue ingrowth when the adjuncts are stapled to tissue. For example, the adjuncts can be configured such that, while under an applied stress in a range of about 30 kPa to 90 kPa, the adjunct undergoes a strain in a range of about 0.1 (10% deformation) to 0.9 (90 percent deformation). That is, the adjuncts described herein can be configured to deform from about 10% to 90% when the adjunct is under an amount of stress that is between and/or including about 30 kPa to 90 kPa, e.g., when the adjunct is in a tissue-deployed state.

An exemplary stapling assembly can include a variety of features to facilitate application of a surgical staple, as described herein and illustrated in the drawings. However, a person skilled in the art will appreciate that the stapling assembly can include only some of these features and/or it can include a variety of other features known in the art. The stapling assemblies described herein are merely intended to represent certain exemplary embodiments. Moreover, while the adjuncts are described in connection with surgical staple cartridge assemblies, the adjuncts can be used in connection with staple reloads that are not cartridge based or any type of surgical instrument.

FIG. 1 illustrates an exemplary surgical stapling and severing device 100 suitable for use with an implantable adjunct. The illustrated surgical stapling and severing device 100 includes a staple applying assembly 106 or end effector having an anvil 102 that is pivotably coupled to an elongate staple channel 104. As a result, the staple applying assembly 106 can move between an open position, as shown in FIG. 1, and a closed position in which the anvil 102 is positioned adjacent to the elongate staple channel 104 to engage tissue therebetween. The staple applying assembly 106 can be attached at its proximal end to an elongate shaft 108 forming an implement portion 110. When the staple applying assembly 106 is closed, or at least substantially closed, (e.g., the anvil 102 moves from the open position in FIG. 1 toward the elongate staple channel) the implement portion 110 can present a sufficiently small cross-section suitable for inserting the staple applying assembly 106 through a trocar. While the device 100 is configured to staple and sever tissue, surgical devices configured to staple but not sever tissue are also contemplated herein.

In various instances, the staple applying assembly 106 can be manipulated by a handle 112 connected to the elongate shaft 108. The handle 112 can include user controls such as a rotation knob 114 that rotates the elongate shaft 108 and the staple applying assembly 106 about a longitudinal axis of the elongate shaft 108, and a closure trigger 116 which can pivot relative to a pistol grip 118 to close the staple applying assembly 106. A closure release button 120 can be outwardly presented on the handle 112 when the closure trigger 116 is clamped such that the closure release button 120 can be depressed to unclamp the closure trigger 116 and open the staple applying assembly 106, for example.

A firing trigger 122, which can pivot relative to the closure trigger 116, can cause the staple applying assembly 106 to simultaneously sever and staple tissue clamped therein. In various instances, multiple firing strokes can be employed using the firing trigger 122 to reduce the amount of force required to be applied by the surgeon's hand per stroke. In certain embodiments, the handle 112 can include one or more rotatable indicator wheels such as, for example, rotatable indicator wheel 124 which can indicate the firing progress. A manual firing release lever 126 can allow the firing system to be retracted before full firing travel has been completed, if desired, and, in addition, the firing release lever 126 can allow a surgeon, or other clinician, to retract the firing system in the event that the firing system binds and/or fails.

Additional details on the surgical stapling and severing device 100 and other surgical stapling and severing devices suitable for use with the present disclosure are described, for example, in U.S. Pat. No. 9,332,984 and in U.S. Patent Publication No. 2009/0090763, the disclosures of which are incorporated herein by reference in their entireties. Further, the surgical stapling and severing device need not include a handle, but instead can have a housing that is configured to couple to a surgical robot, for example, as described in U.S. Patent Publication No. 2019/0059889, the disclosure of which is incorporated herein by reference in its entirety.

As further shown in FIG. 1, a staple cartridge 200 can be utilized with the instrument 100. In use, the staple cartridge 200 is placed within and coupled to the elongate staple channel 104. While the staple cartridge 200 can have a variety of configurations, in this illustrated embodiment, the staple cartridge 200, which is shown in more detail in FIGS. 2A-2B, has a proximal end 202a and a distal end 202b with a longitudinal axis ($L_C$) extending therebetween. As a result, when the staple cartridge 200 is inserted into the elongate staple channel 104 (FIG. 1), the longitudinal axis ($L_C$) aligns with the longitudinal axis ($L_S$) of the elongate shaft 108. Further, the staple cartridge 200 includes a longitudinal slot 210 defined by two opposing walls 210a, 210b and configured to receive at least a portion of a firing member of a firing assembly, like firing assembly 400 in FIG. 4, as discussed further below. As shown, the longitudinal slot 202 extends from the proximal end 202a toward the distal end 202b of the staple cartridge 200. It is also contemplated herein that in other embodiments, the longitudinal slot 202 can be omitted.

The illustrated staple cartridge 200 includes staple cavities 212, 214 defined therein, in which each staple cavity 212, 214 is configured to removably house at least a portion of a staple (not shown). The number, shape, and position of the staple cavities can vary and can depend at least on the size and shape of the staples to be removably disposed therein. In this illustrated embodiment, the staple cavities are arranged in two sets of three longitudinal rows, in which the first set of staple cavities 212 is positioned on a first side of the longitudinal slot 210 and the second set of staple cavities 214 is positioned on a second side of the longitudinal slot 210. On each side of the longitudinal slot 210, and thus for each set of rows, a first longitudinal row of staple cavities 212a, 214a extends alongside the longitudinal slot 210, a second row of staple cavities 212b, 214b extends alongside the first row of staple cavities 212a, 214b, and a third row of staple cavities 212c, 214c extends alongside the second row of staple cavities 212b, 214b. For each set of rows, the first row of staple cavities 212a, 214b, the second row of staple cavities 212b, 214b, and the third row of staple cavities 214c, 214c are parallel to one another and the longitudinal slot 210. Further, as shown, for each set of rows, the second row of staple cavities 212b, 214b is staggered with respect to the first and third rows of staple cavities 212a, 212c, 214a, 214c. In other embodiments, the staple cavity rows in each set 212, 214 are not parallel to one another and/or the longitudinal slot 210.

The staples releasably stored in the staple cavities 212, 214 can have a variety of configurations. An exemplary staple 300 that can be releasably stored in each of the staple cavities 212, 214 is illustrated in FIG. 3 in its unfired (pre-deployed, unformed) configuration. The illustrated staple 300 includes a crown (base) 302 and two legs 304 extending from each end of the crown 302. In this embodiment, the crown 302 extends in a linear direction and the staple legs 304 have the same unformed height, whereas in other embodiments, the crown can be a step up crown, e.g., like crown 2804c, 2806c, 2808c in FIG. 28A, and/or the staple legs can have different unformed heights (see FIG. 29). Further, prior to the staples 300 being deployed, the staple crowns 302 can be supported by staple drivers that are positioned within the staple cartridge 200 and, concurrently, the staple legs 304 can be at least partially contained within the staple cavities 212, 214. Further, the staple legs 304 can extend beyond a top surface, like top surface 206, of the staple cartridge 200 when the staples 300 are in their unfired positions. In certain instances, as shown in FIG. 3, the tips 306 of the staple legs 304 can be pointed and sharp which can incise and penetrate tissue.

In use, staples 300 can be deformed from an unfired position into a fired position such that the staple legs 304 move through the staple cavities 212, 214, penetrate tissue positioned between the anvil 102 and the staple cartridge 200, and contact the anvil 102. As the staple legs 304 are deformed against the anvil 102, the legs 304 of each staple 300 can capture a portion of the tissue within each staple 300 and apply a compressive force to the tissue. Further, the legs 304 of each staple 300 can be deformed downwardly toward the crown 302 of the staple 300 to form a staple entrapment area in which the tissue can be captured therein. In various instances, the staple entrapment area can be defined between the inner surfaces of the deformed legs and the inner surface of the crown of the staple. The size of the entrapment area for a staple can depend on several factors such as the length of the legs, the diameter of the legs, the width of the crown, and/or the extent in which the legs are deformed, for example.

In some embodiments, all of the staples disposed within the staple cartridge 200 can have the same unfired (pre-deployed, unformed) configuration. In other embodiments, the staples can include at least two groups of staples each having a different unfired (pre-deployed, unformed) configuration, e.g., varying in height and/or shape, relative to one another, etc. For example, the staple cartridge 200 can include a first group of staples having a first height disposed within the first row of staple cavities 212a, 214a, a second group of staples having a second height disposed within the second row of staple cavities 212b, 214b, and a third group of staples having a third height disposed within the third row of staple cavities 212c, 214c. In some embodiments, the first, second, and third heights can be different, in which the third height is greater than the first height and the second height. In other embodiments, the first and second heights are the same, but the third height is different and greater than the first height and the second height. A person skilled in the art will appreciate that other combinations of staples are contemplated herein.

Further, the staples can include one or more external coatings, e.g., a sodium stearate lubricant and/or an antimicrobial agent(s). The antimicrobial agent(s) can be applied to the staples as its own coating or incorporated into another coating, such as a lubricant. Non-limiting examples of suitable antimicrobial agents include 5-Chloro-2-(2,4-dichlorophenoxy)phenol, chlorhexidine, silver formulations (e.g., nano-crystalline silver), lauric arginate ethyl ester (LAE), octenidine, polyhexamethylene biguanide (PHMB), taurolidine, lactic acid, citric acid, acetic acid, and their salts.

Referring back to FIGS. 2A-2B, the staple cartridge 200 extends from a top surface or deck surface 206 to a bottom surface 208, in which the top surface 206 is configured as a tissue-facing surface and the bottom surface 208 is configured as a channel-facing surface. As a result, when the staple cartridge 200 is inserted into the elongate staple channel 104, as shown in FIG. 1, the top surface 206 faces the anvil 102 and the bottom surface 208 (obstructed) faces the elongate staple channel 104.

In some embodiments, the top surface 206 can include surface features defined therein. For example, the surface features can be recessed channels defined within the top surface 206. As shown in more detail in FIG. 2C, a first recessed channel 216 surrounds each first staple cavity 212a, 214a. Each first recessed channel 216 is defined by a substantially triangular wall 216a having a vertex pointing proximally, a vertex pointing distally, and a vertex pointing laterally outwardly. Further, each first recessed channel 216 includes a first floor 206a which is at a first height from the top surface 206. A second recessed channel 218 surrounds each second staple cavity 212b, 214b. Each second recessed channel 218 is defined by a wall 218a which is substantially diamond-shaped comprising a vertex pointing proximally, a vertex pointing distally, a vertex pointing laterally inwardly, and a vertex pointing laterally outwardly relative to the longitudinal axis. Further, each second recessed channel 218 includes a second floor 206b which is a second height from the top surface 206. A third recessed channel 220 surrounds each third staple cavity 212c, 214c. Each third recessed channel 220 is defined by a substantially triangular wall 220a comprising a vertex pointing proximally, a vertex pointing distally, and a vertex pointing laterally inwardly relative to the longitudinal axis. Further, each third recessed channel 220 includes a third floor 206c which is a third height from the top surface 206. In some embodiments, the first height of the first recessed channels 216, the second height of the second recessed channels 218, and the third height of the third recessed channels 220 can have the same height. In other instances, the first height, the second height, and/or the third height can be different. Additional details on the surface features and other exemplary surface features can be found in U.S. Publication No. 2016/0106427, which is incorporated by reference herein in its entirety. Further, as will be discussed in more detail below, these recessed channels 216, 218, 220 can be used to interact with an adjunct, like adjunct 2600 in FIGS. 26A-26C, that the adjunct can be releasably retained to the top surface of cartridge prior to staple deployment.

With reference to FIGS. 4 and 5, a firing assembly such as, for example, firing assembly 400, can be utilized with a surgical stapling and severing device, like device 100 in FIG. 1. The firing assembly 400 can be configured to advance a wedge sled 500 having wedges 502 configured to deploy staples from the staple cartridge 200 into tissue captured between an anvil, like anvil 102 in FIG. 1, and a staple cartridge, like staple cartridge 200 in FIG. 1. Furthermore, an E-beam 402 at a distal portion of the firing assembly 400 may fire the staples from the staple cartridge. During firing, the E-beam 402 can also cause the anvil to pivot towards the staple cartridge, and thus move the staple applying assembly from the open position towards a closed position. The illustrated E-beam 402 includes a pair of top pins 404, a pair of middle pins 406, which may follow a portion 504 of the wedge sled 500, and a bottom pin or foot 408. The E-beam 402 can also include a sharp cutting edge 410 configured to sever the captured tissue as the firing assembly 400 is advanced distally, and thus towards the distal end of the staple cartridge. In addition, integrally formed and proximally projecting top guide 412 and middle guide 414 bracketing each vertical end of the cutting edge 410 may further define a tissue staging area 416 assisting in guiding tissue to the sharp cutting edge 410 prior to being severed. The middle guide 414 may also serve to engage and fire the staples within the staple cartridge by abutting a stepped central member 506 of the wedge sled 500 that effects staple formation by the staple applying assembly 106.

In use, the anvil 102 in FIG. 1 can be moved into a closed position by depressing the closure trigger in FIG. 1 to advance the E-beam 402 in FIG. 4. The anvil can position tissue against at least the top surface 206 of the staple cartridge 200 in FIGS. 2A-2C. Once the anvil has been suitably positioned, the staples 300 in FIG. 3 disposed within the staple cartridge can be deployed.

To deploy staples from the staple cartridge, as discussed above, the sled 500 in FIG. 5 can be moved from the proximal end toward a distal end of the cartridge body, and thus, of the staple cartridge. As the firing assembly 400 in FIG. 4 is advanced, the sled can contact and lift staple drivers within the staple cartridge upwardly within the staple cavities 212, 214. In at least one example, the sled and the staple drivers can each include one or more ramps, or inclined surfaces, which can co-operate to move the staple drivers upwardly from their unfired positions. As the staple drivers are lifted upwardly within their respective staple cavities, the staples are advanced upwardly such that the staples emerge from their staple cavities and penetrate into tissue. In various instances, the sled can move several staples upwardly at the same time as part of a firing sequence.

As indicated above, the stapling device can be used in combination with a compressible adjunct. A person skilled in the art will appreciate that, while adjuncts are shown and described below, the adjuncts disclosed herein can be used with other surgical instruments, and need not be coupled to a staple cartridge as described. Further, a person skilled in the art will also appreciate that the staple cartridges need not be replaceable.

As discussed above, with some surgical staplers, a surgeon is often required to select the appropriate staples having the appropriate staple height for tissue to be stapled. For example, a surgeon will utilize tall staples for use with thick tissue and short staples for use with thin tissue. In some instances, however, the tissue being stapled does not have a consistent thickness and thus, the staples cannot achieve the desired fired configuration for every section of the stapled tissue (e.g., thick and thin tissue sections). The inconsistent thickness of tissue can lead to undesirable leakage and/or tearing of tissue at the staple site when staples with the same or substantially greater height are used, particularly when the staple site is exposed to intra-pressures at the staple site and/or along the staple line.

Accordingly, various embodiments of non-fibrous adjuncts are provided that can be configured to compensate for varying thickness of tissue that is captured within fired (deployed) staples to avoid the need to take into account staple height when stapling tissue during surgery. That is, the adjuncts described herein can allow a set of staples with the same or similar heights to be used in stapling tissue of varying thickness (e.g., from thin to thick tissue) while also, in combination with the adjunct, providing adequate tissue compression within and between fired staples. Thus, the adjuncts described herein can maintain suitable compression against thin or thick tissue stapled thereto to thereby minimize leakage and/or tearing of tissue at the staple sites.

Alternatively or in addition, the non-fibrous adjuncts can be configured to promote tissue ingrowth. In various instances, it is desirable to promote the ingrowth of tissue into an implantable adjunct, to promote the healing of the treated tissue (e.g., stapled and/or incised tissue), and/or to accelerate the patient's recovery. More specifically, the ingrowth of tissue into an implantable adjunct may reduce the incidence, extent, and/or duration of inflammation at the surgical site. Tissue ingrowth into and/or around the implantable adjunct may, for example, manage the spread of infections at the surgical site. The ingrowth of blood vessels, especially white blood cells, for example, into and/or around the implantable adjunct may fight infections in and/or around the implantable adjunct and the adjacent tissue. Tissue ingrowth may also encourage the acceptance of foreign matter (e.g., the implantable adjunct and the staples) by the patient's body and may reduce the likelihood of the patient's body rejecting the foreign matter. Rejection of foreign matter may cause infection and/or inflammation at the surgical site.

Unlike conventional adjuncts (e.g., adjuncts that are not three-dimensionally printed, such as foam adjuncts and woven/non-woven fibrous adjuncts), these non-fibrous adjuncts are three-dimensionally (3D) printed and therefore can be formed with microstructures (units) that are consistent and reproducible. That is, unlike with other methods of manufacture, 3D printing significantly improves control over microstructural features such as placement and connection of elements. As a result, variability in both the microstructure(s) and attendant properties of the present adjuncts is decreased, as compared to conventional adjuncts. For example, the present adjuncts can be structured such that they compress a predetermined amount in a substantially uniform matter. The fine control over the microstructure can also allow the porosity of the adjuncts to be tailored to enhance tissue ingrowth. The present non-fibrous adjuncts can also be adapted for use with a variety of staples and tissue types.

In general, the adjuncts provided herein are designed and positioned atop a staple cartridge, like staple cartridge 200. When the staples are fired (deployed) from the cartridge, the staples penetrate through the adjunct and into tissue. As the legs of the staple are deformed against the anvil that is positioned opposite the staple cartridge, the deformed legs capture a portion of the adjunct and a portion of the tissue within each staple. That is, when the staples are fired into tissue, at least a portion of the adjunct becomes positioned between the tissue and the fired staple. While the adjuncts described herein can be configured to be attached to a staple cartridge, it is also contemplated herein that the adjuncts can be configured to mate with other instrument components, such as an anvil of a surgical stapler. A person of ordinary skill will appreciate that the adjuncts provided herein can be used with replaceable cartridges or staple reloads that are not cartridge based.

Methods of Stapling Tissue

Figure 6A:
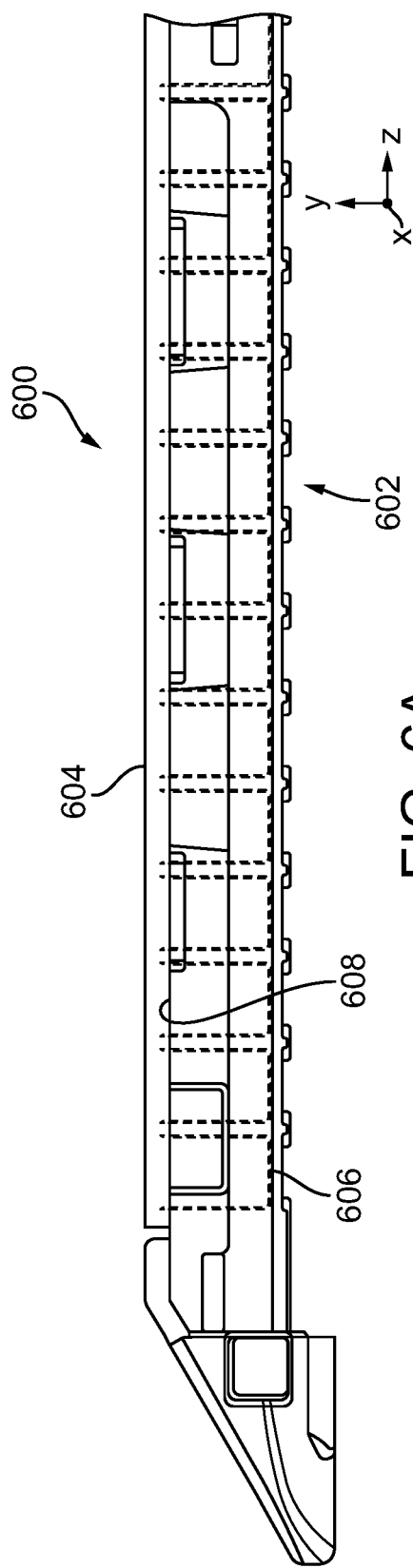
FIG. 6A is a longitudinal cross-sectional view of an exemplary embodiment of a surgical cartridge assembly having a compressible non-fibrous adjunct attached to a top or deck surface of a staple cartridge.
Figure 6B:
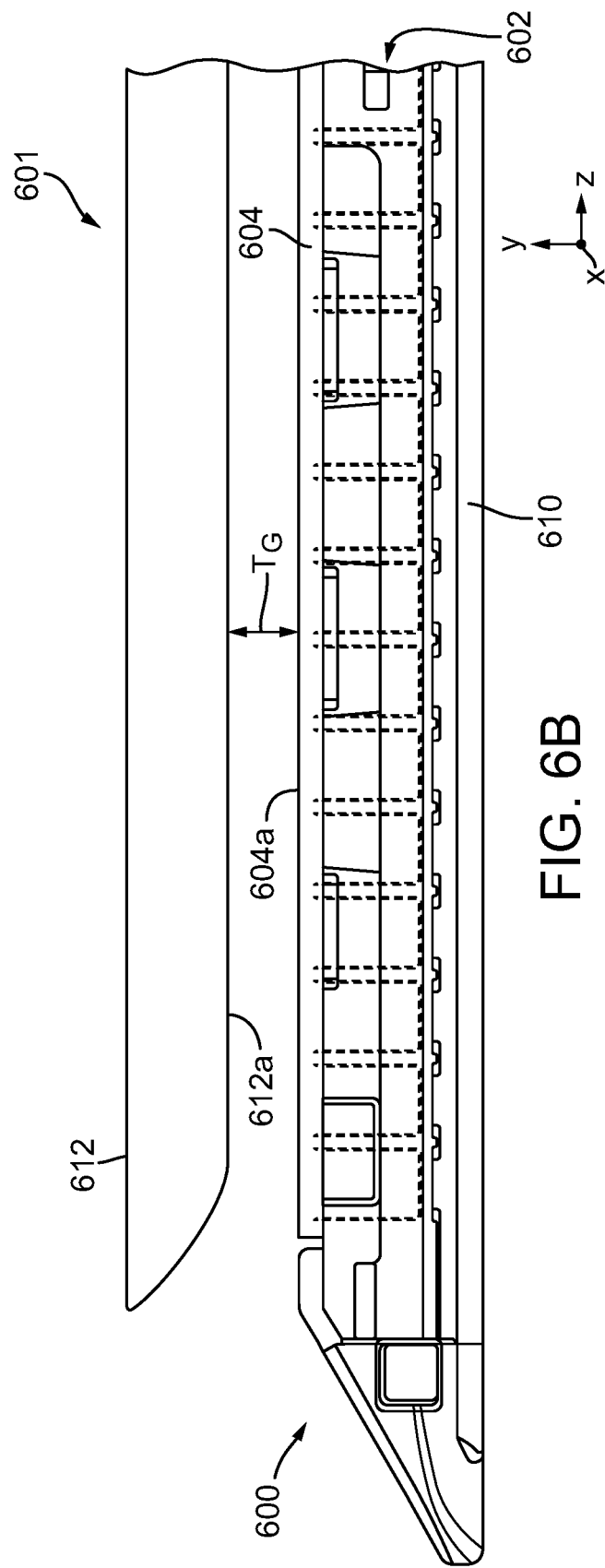
FIG. 6B is a longitudinal cross-sectional view of a surgical end effector having an anvil pivotably coupled to an elongate staple channel and the surgical cartridge assembly of FIG. 6A disposed within and coupled to the elongate staple channel, showing the anvil in a closed positon without any tissue between the anvil and the adjunct.

FIGS. 6A-6B illustrate an exemplary embodiment of a stapling assembly 600 that includes a staple cartridge 602 and an adjunct 604. For sake of simplicity, the adjunct 604 is generally illustrated in FIGS. 6A-6B, and various structural configurations of the adjunct are described in more detail below. Aside from the differences described in detail below, the staple cartridge 602 can be similar to staple cartridge 200 (FIG. 1-3) and therefore common features are not described in detail herein. As shown, the adjunct 604 is positioned against the staple cartridge 602. While partially obstructed in FIG. 6, the staple cartridge 602 includes staples 606, which can be similar to staple 300 in FIG. 3, that are configured to be deployed into tissue. The staples 606 can have any suitable unformed (pre-deployed) height. For example, the staples 606 can have an unformed height between about 2 mm and 4.8 mm. Prior to deployment, the crowns of the staples can be supported by staple drivers (not shown).

Figure 2C:
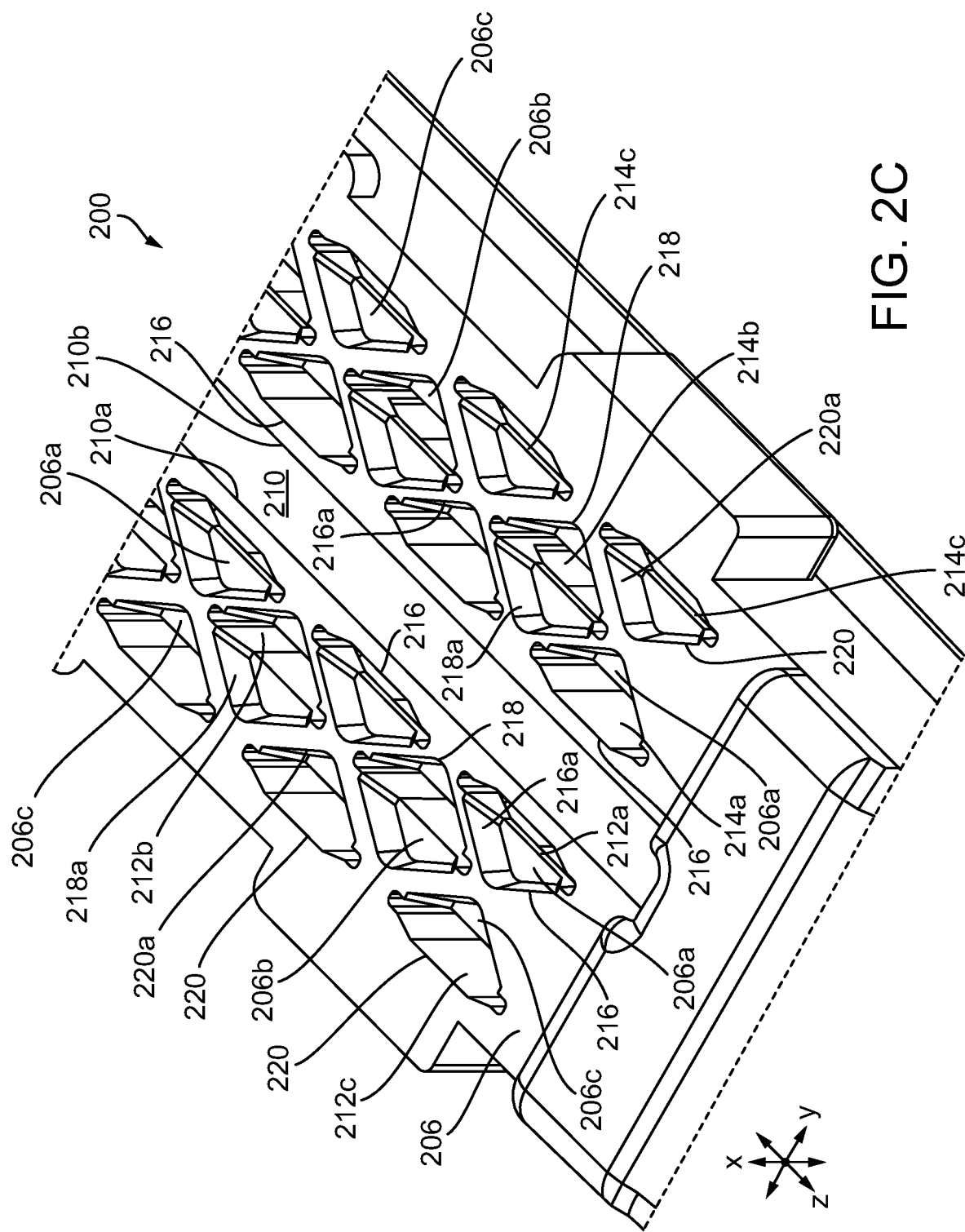
FIG. 2C is a perspective view of a portion of a tissue-contacting surface of the staple cartridge of FIG. 2A.

In the illustrated embodiment, the adjunct 604 can be mated to at least a portion of the top surface or deck surface 608 of the staple cartridge 602. In some embodiments, the top surface 608 of the staple cartridge 602 can include one or more surface features, like recessed channels 216, 218, 220 as shown in FIGS. 2A and 2C. The one or more surface features can be configured to engage the adjunct 604 to avoid undesirable movements of the adjunct 604 relative to the staple cartridge 602 and/or to prevent premature release of the adjunct 604 from the staple cartridge 602. Exemplary surface features are described in U.S. Patent Publication No. 2016/0106427, which is incorporated by reference herein in its entirety.

FIG. 6B shows the stapling assembly 600 placed within and coupled to the elongate staple channel 610 of surgical end effector 601, which is similar to surgical end effector 106 in FIG. 1. The anvil 612 is pivotally coupled to the elongate staple channel 610 and is thus moveable between open and closed positions relative to the elongate staple channel 610, and thus the staple cartridge 602. The anvil 612 is shown in a closed position in FIG. 6B, and illustrates a tissue gap $T_G$ created between the staple cartridge 602 and the anvil 612. More specifically, the tissue gap $T_G$ is defined by the distance between the tissue-compression surface 612a of the anvil 612 (e.g., the tissue-engaging surface between staple forming pockets in the anvil) and the tissue-contacting surface 604a of the adjunct 604. In this illustrated embodiment, both the tissue-compression surface 612a of the anvil 612 and the tissue-contacting surface 604a of the adjunct 604 is planar, or substantially planar (e.g., planar within manufacturing tolerances). As a result, when the anvil 612 is in a closed position, as shown in FIG. 6B, the tissue gap $T_G$ is generally uniform (e.g., nominally identical within manufacturing tolerances) when no tissue is disposed therein. In other words, the tissue gap $T_G$ is generally constant (e.g., constant within manufacturing tolerances) across the end effector 601 (e.g., in the y-direction). In other embodiments, the tissue-compression surface of the anvil can include a stepped surface having longitudinal steps between adjacent longitudinal portions, and thus create a stepped profile (e.g., in the y-direction). In such embodiments, the tissue gap $T_G$ can be varied.

The adjunct 604 is compressible to permit the adjunct to compress to varying heights to thereby compensate for different tissue thickness that are captured within a deployed staple. The adjunct 604 has an uncompressed (undeformed), or pre-deployed, height and is configured to deform to one of a plurality of compressed (deformed), or deployed, heights. For example, the adjunct 604 can have an uncompressed height which is greater than the fired height of the staples 606 disposed within the staple cartridge 602 (e.g., the height (H) of the fired staple 606a in FIG. 7). That is, the adjunct 604 can have an undeformed state in which a maximum height of the adjunct 604 is greater than a maximum height of a fired staple (e.g., a staple that is in a formed configuration). In one embodiment, the uncompressed height of the adjunct 604 can be about 10% taller, about 20% taller, about 30% taller, about 40% taller, about 50% taller, about 60% taller, about 70% taller, about 80% taller, about 90% taller, or about 100% taller than the fired height of the staples 606. In certain embodiments, the uncompressed height of the adjunct 604 can be over 100% taller than the fired height of the staples 606, for example.

In use, once the surgical stapling and severing device, like device 100 in FIG. 1, is directed to the surgical site, tissue is positioned between the anvil 612 and the stapling assembly 600 such that the anvil 612 is positioned adjacent to a first side of the tissue and the stapling assembly 600 is positioned adjacent to a second side of the tissue (e.g., the tissue can be positioned against the tissue-contacting surface 604a of the adjunct 604). Once tissue is positioned between the anvil 612 and the stapling assembly 600, the surgical stapler can be actuated, e.g., as discussed above, to thereby clamp the tissue between the anvil 612 and the stapling assembly 600 (e.g., between the tissue-compression surface 612a of the anvil 612 and the tissue-contacting surface 604a of the adjunct 604) and to deploy staples from the cartridge through the adjunct and into the tissue to staple and attach the adjunct to the tissue.

Figure 7:
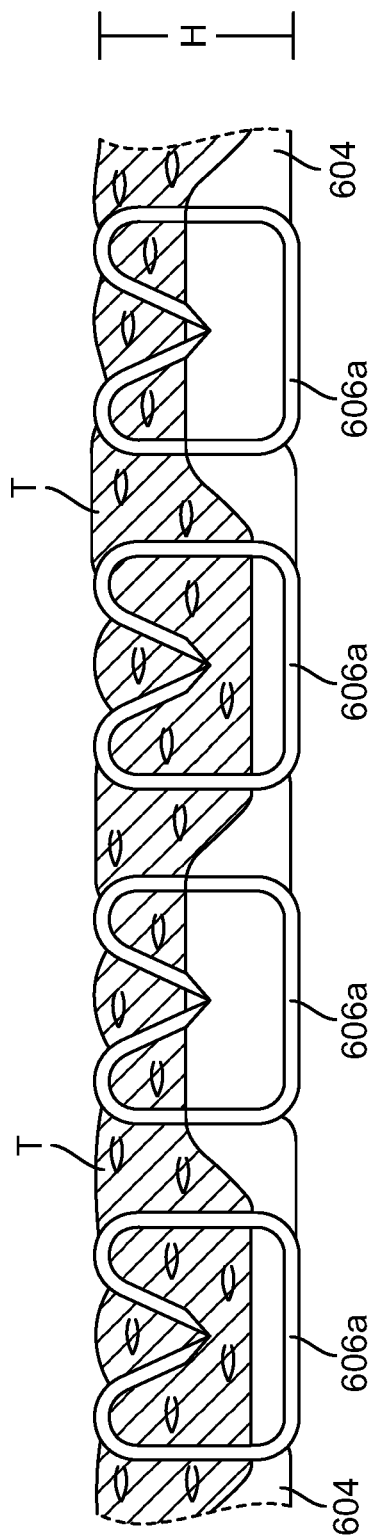
FIG. 7 is a partial-schematic illustrating the adjunct of FIGS. 6A-6B in a tissue deployed condition.

As shown in FIG. 7, when the staples 606 are fired, tissue (T) and a portion of the adjunct 604 are captured by the fired (formed) staples 606a. The fired staples 606a each define the entrapment area therein, as discussed above, for accommodating the captured adjunct 604 and tissue (T). The entrapment area defined by a fired staple 606a is limited, at least in part, by a height (H) of the fired staple 606a. For example, the height of a fired staple 606a can be about 0.160 inches or less. In some embodiments, the height of a first stapled 606a can be about 0.130 inches or less. In one embodiment, the height of a fired staple 606a can be from about 0.020 inches to 0.130 inches. In another embodiment, the height of a fired staple 606a can be from about 0.060 inches to 0.160 inches.

As described above, the adjunct 604 can be compressed within a plurality of fired staples whether the thickness of the tissue captured within the staples is the same or different within each fired staple. In at least one exemplary embodiment, the staples within a staple line, or row can be deformed such that the fired height is about 2.75 mm, for example, where the tissue (T) and the adjunct 604 can be compressed within this height. In certain instances, the tissue (T) can have a compressed height of about 1.0 mm and the adjunct 604 can have a compressed height of about 1.75 mm. In certain instances, the tissue (T) can have a compressed height of about 1.50 mm and the adjunct 604 can have a compressed height of about 1.25 mm. In certain instances, the tissue (T) can have a compressed height of about 1.75 mm and the adjunct 604 can have a compressed height of about 1.00 mm. In certain instances, the tissue (T) can have a compressed height of about 2.00 mm and the adjunct 604 can have a compressed height of about 0.75 mm. In certain instances, the tissue (T) can have a compressed height of about 2.25 mm and the adjunct 604 can have a compressed height of about 0.50 mm. Accordingly, the sum of the compressed heights of the captured tissue (T) and adjunct 604 can be equal, or at least substantially equal, to the height (H) of the fired staple 606a.

Further, most structures typically behave in a way in which strain (deformation) of the material increases as stress exerted on the material increases. For surgical stapling, however, it is desired that strain of the adjunct increase over a relatively narrow stress range, and therefore as discussed in more detail below, the adjuncts described herein can be structured in such a way so that they can exhibit a flat or moderately sloped "stress plateau." In general, a stress plateau is a regime in the stress-strain curve of a cellular material upon compression that corresponds to progressive cell collapse by elastic buckling, and depends on the nature of the solid from which the material is made. That is, when a given structure deforms under compression, the strain can increase without a substantial increase in stress, and therefore leads to a stress plateau, thereby advantageously delaying densification (e.g., solid height) of the structure. As a result, the adjuncts described herein can be designed to undergo compression over extended periods of time throughout a range of stresses that are typically applied to the adjunct while in a tissue deployed state (e.g., when the adjunct is stapled to tissue in vivo).

The structure of the adjunct, therefore, can be designed such that when the adjunct and tissue are captured within the fired staple, the adjunct can undergo a strain in a range of about 0.1 to 0.9 while under an applied stress in a range of about 30 kPa to 90 kPa. When the adjunct is in a tissue deployed state, the applied stress is the stress the stapled tissue is applying against the adjunct. A person skilled in the art will appreciate that the applied stress by the tissue depends on various stapling conditions (e.g., tissue thickness, height of formed staple, intra-tissue pressure). For example, high blood pressure is typically considered 210 mmHg, and therefore it would be desirable for the present adjuncts to withstand an applied stress that is equal to or greater than 210 mmHg for a predetermined time period without reaching densification. In other embodiments, the strain can be in a range of about 0.1 to 0.8, of about 0.1 to 0.7, of about 0.1 to 0.6, of about 0.2 to 0.8, of about 0.2 to 0.7, of about 0.3 to 0.7, of about 0.3 to 0.8, of about 0.3 to 0.9, of about 0.4 to 0.9, of about 0.4 to 0.8, of about 0.4 to 0.7, of about 0.5 to 0.8, or of about 0.5 to 0.9. Thus, the adjuncts described herein can be configured to deform and thus, not reach its solid height, while under a predetermined amount of applied stress.

In order to design an adjunct that is configured to undergo a strain in a range of about 0.1 to 0.9 while under an applied stress of about 30 kPa to 90 kPa, one can use the principles of Hooke's law (F=kD). For example, knowing the forces (stresses) that will be applied to the tissue deployed adjunct, one can design an adjunct to have a predetermined stiffness (k). The stiffness can be set by tuning the geometry of the adjunct (e.g., the shape, the wall thickness, the height, and/or the interconnectivity of the unit cells, e.g., angle and space between unit cells, and/or diameter of struts of a unit cell and/or the interconnectivity of the struts of the unit cell, e.g., angles and space between the struts). Further, one can design the adjunct to have a maximum amount of compression displacement for a minimum thickness of tissue, e.g., 1 mm, and therefore the length of displacement D can be the combination of a minimum thickness of tissue, e.g., 1 mm, plus a thickness of the adjunct when stapled to tissue for a given max staple height, e.g., 2.75 mm. By way of example, in one embodiment, an adjunct can be structured to have a height that is greater than a maximum formed stapled height of 2.75 mm and to compress to a height of 1.75 mm when stapled to tissue having a minimum thickness of 1 mm. Therefore, the adjunct can vary in compressibility to maintain a constant length of displacement D such that the stiffness (k) and total thickness (D) of captured tissue and adjunct can apply a stress of 3 gf/mm$^2$ to the captured tissue. It should be noted a person of skilled in the art will appreciate that the foregoing formula can be modified to take into account variations in temperatures, e.g., when the adjunct is brought from room temperature to body temperature after implantation. Further, this forgoing discussion of Hooke's law represents an approximation. As such, a person skilled in the art will appreciate that principles of large deformation mechanics (also referred to as finite elasticity) can be used to obtain more accurate predictions of the relationship between stress and strain through the use of constitutive equations tailored to the material of interest.

The compressibility profile of the adjunct can therefore be controlled by at least the structural configuration of the unit cells and the interconnectivity between them. As a result, the structural configuration of the unit cells can be tailored to effect an adjunct with desirable mechanical properties for stapling tissue. As there is a finite range of intra-tissue pressures, tissue thicknesses, and formed staple heights, one can determine appropriate geometric structures, and thus unit cells, for the adjunct that can be effective in allowing the adjunct to undergo a desired amount of strain at a substantially constant rate while a desired amount of stress is being applied. Stated differently, the structural configuration of the unit cells can be designed to produce an adjunct that can be effective in applying a substantially continuous desired stress to the tissue (e.g., of at least 3 gf/mm$^2$) to stapled tissue for a given amount of time over a range of stapling conditions. That is, as described in more detail below, the present adjuncts are formed of compressible materials and are geometrically configured so as to allow the adjunct to compress to various heights in predetermined planes when stapled to tissue. Further, this varied response by the adjunct can also allow the adjunct to maintain its application of a continuous desired stress to the tissue when exposed to fluctuations in intra-tissue pressure that can occur when the adjunct is stapled to tissue (e.g., a spike in blood pressure).

Adjuncts

The adjuncts can have a variety of configurations. The adjuncts generally include a tissue-contacting surface and a cartridge-contacting surface with an elongate body (e.g., internal structure) positioned therebetween. The tissue-contacting surface and/or the cartridge-contacting surface can, in certain embodiments, have a structure that differs from the elongate body so as to form tissue-contacting and cartridge-contacting layers, respectively. As described in more detail below, the adjunct can have a strut-based configuration, a non-strut based configuration, or a combination thereof.

Further, each exemplary adjunct is illustrated in partial form (e.g., not in full-length), and therefore a person skilled in the art will appreciate that the adjunct can be longer in length, e.g., along its longitudinal axis ($L_A$) as identified in each embodiment. The length can vary based on a length of the staple cartridge or anvil. The width can also vary as needed. Further, each exemplary adjunct is configured to be positioned atop a cartridge or anvil surface such that the longitudinal axis L of each adjunct is aligned with and extends along the longitudinal axis ($L_A$) of the cartridge or anvil. These adjuncts are structured so as to compress when exposed to compressive forces (e.g., stress or load).

The adjuncts described herein can have a variety of average lengths, widths, and thicknesses. For example, in some embodiments, the adjunct can have an average length in a range of about 20 mm to 100 mm or about 40 mm to 100 mm. In other embodiments, the adjunct can have an average width in a range of about 5 mm to 10 mm. In yet other embodiments, the adjunct can have an average thickness in a range of about 1 mm to 6 mm, from about 1 mm to 8 mm, from about 2 mm to 6 mm, or from about 2 mm to 8 mm. In one embodiment, an exemplary adjunct can have an average length in a range of about 20 mm to 100 mm, an average width from 5 mm to 10 mm, and an average thickness from about 1 mm to 8 mm.

The elongate body can be formed of one or more lattice structures each formed by interconnected unit cells. While the unit cells can have a variety of configurations, in some embodiments, the unit cells can be strut-less based unit cells, whereas in other embodiments, the unit cells can be strut based unit cells. A strut can be a non-hollow rod or bar that is completely, or substantially, formed of solid material. In certain embodiments, the one or more lattice structures can be formed by interconnected repeating unit cells. Further, in certain embodiments, the elongate body can include at least one lattice structure formed of strut-less based unit cells and at least one lattice structure formed of strut based unit cells (see FIG. 54).

Each lattice structure extends from a first surface (e.g., a top surface) to a second surface (e.g., a bottom surface). Depending on the overall structural configuration of the adjunct, at least a portion of the first surface of at least one lattice structure can serve as a tissue-contacting surface of the adjunct, and at least a portion of the second surface of at least one lattice structure can serve as a cartridge-contacting surface of the adjunct. A person skilled in the art will appreciate that each lattice structure can have additional tissue-contacting surfaces (e.g., one or more lateral side surfaces relative to the top surface).

In certain embodiments, an adjunct can include a tissue-contacting layer that is disposed on at least a portion of the first surface of at least one lattice structure of the internal structure. The tissue-contacting layer has a thickness that extends between a first surface (e.g., a top surface) to a second surface (e.g., a bottom surface). As a result, the first surface of the tissue-contacting layer, alone or in combination with at least a portion of the first surface of at least one lattice structure, can function as the tissue-contacting surface of the resulting adjunct. The tissue-contacting layer can have a variety of configurations. For example, in some embodiments, the tissue-contacting layer is in the form of a lattice structure formed of interconnecting repeating cells that can differ from the lattice structure(s) of the elongate body, whereas in other embodiments, the tissue-contacting layer is in the form of a film.

Alternatively, or in addition, the adjunct can include a cartridge-contacting layer that is disposed on at least a portion of the second surface of at least one lattice structure. The cartridge-contacting layer can have a thickness that extends from a first surface (e.g., a top surface) to a second surface (e.g., a bottom surface). As a result, the second surface of the cartridge-contacting layer, alone or in combination with at least a portion of the second surface of at least one lattice structure, can function as the cartridge-contacting surface of the resulting adjunct. The cartridge-contacting layer can have a variety of configurations. For example, in some embodiments, the cartridge-contacting layer is in the form of lattice structure formed of interconnecting repeating cells that can differ from the lattice structure(s) of the elongate body, whereas in other embodiments, the cartridge-contacting layer is in the form of a film. In some embodiments, the film can be a pressure sensitive adhesive, whereas in other embodiments, the film can include one or more attachment features extending Non-Strut Based Adjuncts As noted above, the adjuncts can include a lattice structure formed of strut-less based unit cells (e.g., repeating strut-less based unit cells). Stated differently, in contrast to strut-based unit cells, which are characterized by the presence of sharp corners or angles, non-strut-based unit cells can be characterized by curved surfaces. For example, the unit cells can be based on triply periodic minimal surfaces (TPMS). TPMS is a minimal surface that repeats itself in three dimensions. The term "minimal surface" as used in this description refers to a minimal surface as known in mathematics. As such, in some embodiments, the unit cell can be a Schwarz structure (e.g., Schwarz-P, Schwarz Diamond), a modified Schwarz structure, a gyroid (e.g., Schoen Gyroid) structure, a cosine structure, and a coke-can structure.

As discussed in more detail below, the strut-less based unit cells can have a variety of structural configurations (e.g., height, width, wall thickness, shape). In some embodiments, the strut-less based unit cells of the adjunct can be generally uniform (e.g., nominally identical within manufacturing tolerances), whereas in other embodiments, at least one portion of the strut-less based unit cells of the adjunct can vary in shape and/or dimension relative to the remaining portion(s) of the strut-based unit cells.

For example, in some embodiments, each of the strut-less based unit cells can have a wall thickness from about 0.05 mm to 0.6 mm. In certain embodiments, the wall thickness can be from about 0.1 mm to 0.3 mm. In one embodiment, the wall thickness can be about 0.2 mm. In certain embodiments, the wall thickness of all of the strut-less based unit cells of an adjunct can be generally uniform (e.g., nominally identical within manufacturing tolerances). In other embodiments, e.g., where the adjunct is formed of two or more sets of unit cells, each set of unit cells can have a different wall thickness. For example, in one embodiment, the adjunct can include first repeating unit cells each having a first wall thickness, second repeating unit cells each having a second wall thickness that is greater than the first wall thickness, and third repeating unit cells each having a third wall thickness that is greater than the second wall thickness. Alternatively, or in addition, the first repeating unit cells can have a first height (e.g., the maximum height), a second height (e.g., the maximum height) that is greater than the first height, and a third height (e.g., the maximum height) that is greater than the second height.

In some embodiments, each unit cell can have a surface to volume ratio of about 5 to 30. In certain embodiments, each unit cell can have a surface to volume ratio of about 7 to 20.

Schwarz-P Structures

FIGS. 8A-8F is one exemplary embodiment of an adjunct 800 having a tissue-contacting surface 802 and a cartridge-contacting surface 804. The adjunct 800 includes interconnected repeating strut-less unit cells 810, one of which is shown in more detail in FIGS. 9A-9B. While the adjunct 800 is illustrated as having four longitudinal rows ($L_1$, $L_2$, $L_3$, $L_4$) each with 20 repeating unit cells 810, a person skilled the art will appreciate that the amount of rows and number unit cells of the adjunct can depend at least upon the size and shape of the staple cartridge and/or anvil to which the adjunct will be applied, and therefore, the adjunct is not limited to the number of longitudinal rows and unit cells illustrated in the figures. Further, while only one type of repeating strut-less unit cell is illustrated, in other embodiments, the adjunct can be formed of a combination of a first repeating strut-less unit cell and a second repeating strut-less unit cell that differs from the first, etc.

Figure 9A:
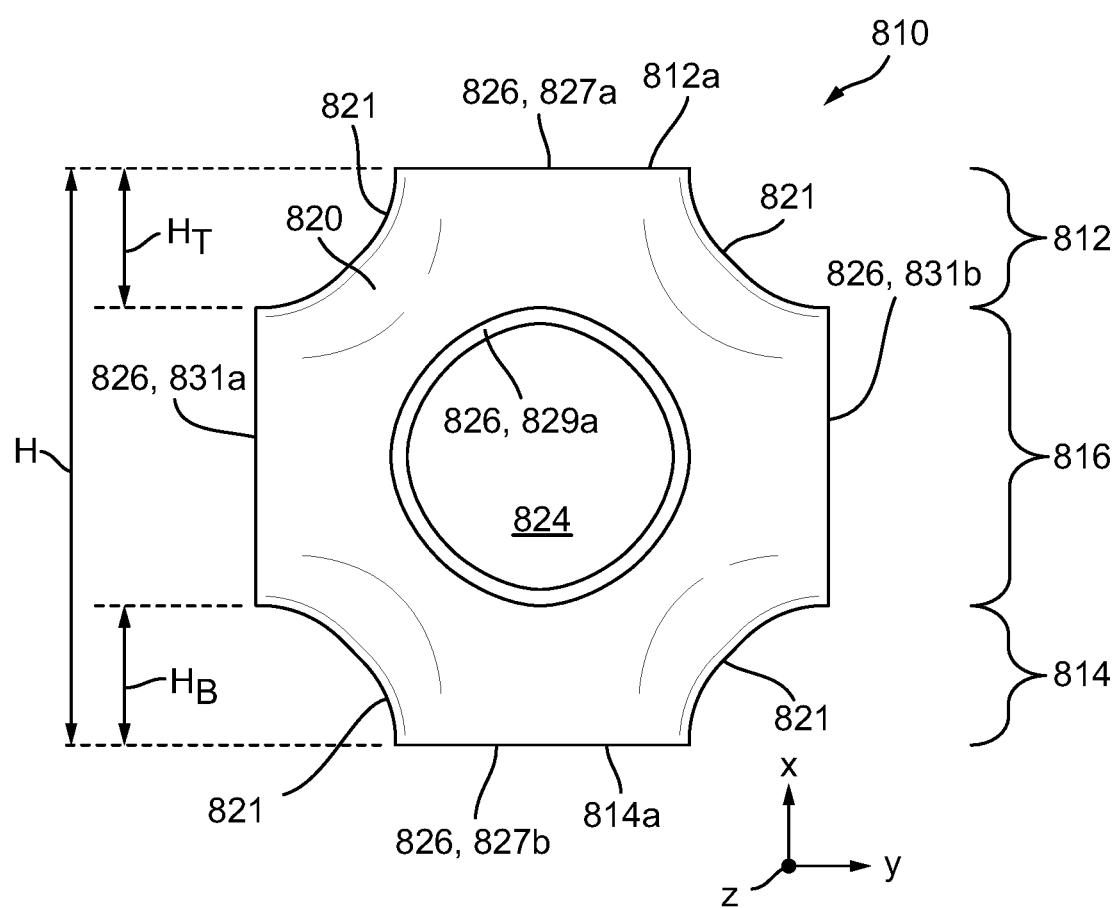
FIG. 9A is a side view of a single unit cell of the adjunct of FIG. 8A.
Figure 9B:
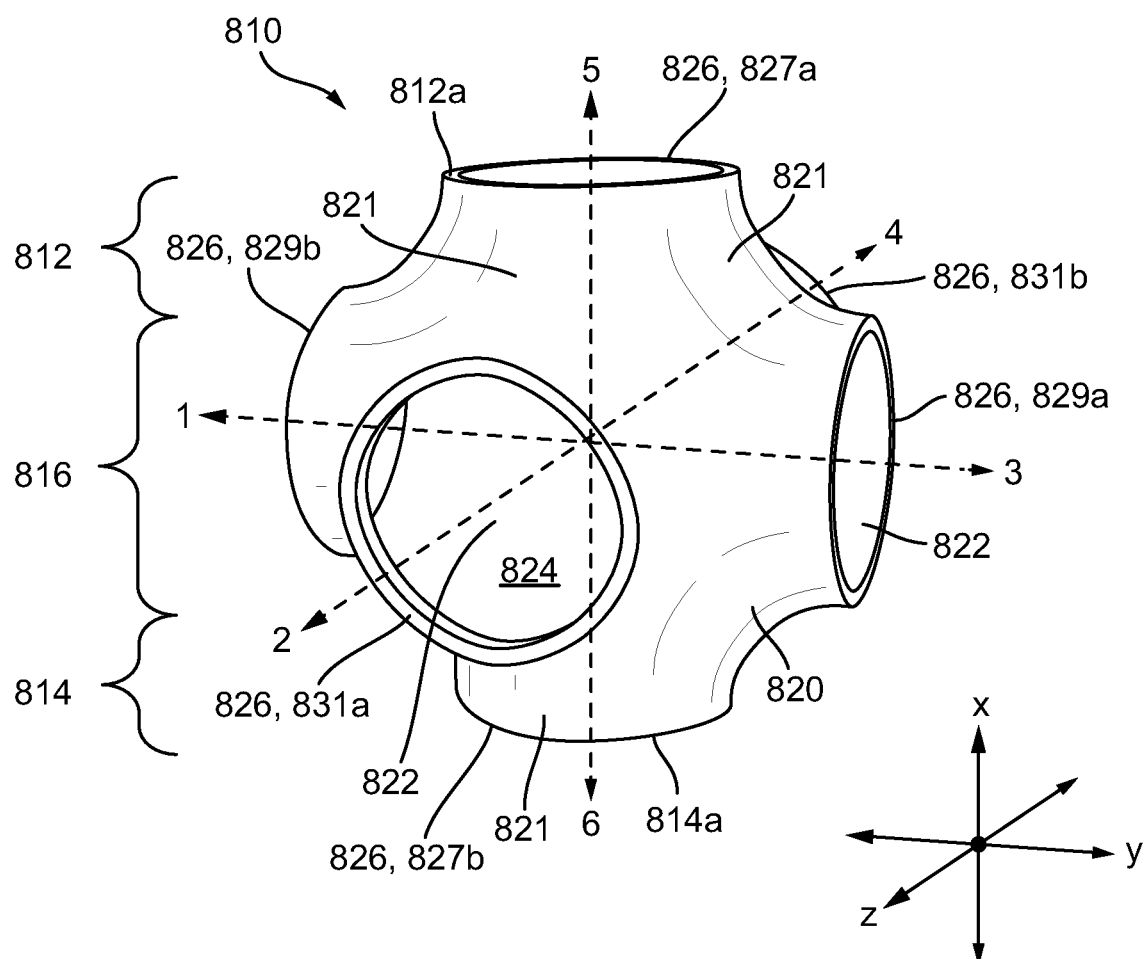
FIG. 9B is a perspective view of the single unit cell of FIG. 9A.

Given that the adjunct 800 is formed of repeating unit cells 810 having substantially the same structural configuration (e.g., nominally identical within manufacturing tolerances), the following discussion is with respect to one repeating unit cell 810. As shown in FIGS. 9A-9B, the repeating unit cell 810 has a top portion 812, a bottom portion 814, and a middle portion 816 extending therebetween.

In this illustrated embodiment, the repeating unit cell 810 is configured as a Schwarz-P structure, and therefore, the surface contour of the unit cell 810 is defined by minimal surfaces. That is, the external and internal surfaces 820, 822 of the unit cell 810 are each defined by minimal surfaces. As such, in this illustrated embodiment, the external and internal surfaces 820, 822 are generally concave in shape, thereby forming arcuate sides 821 of the unit cell 810. Further, the internal surface 822 defines the internal volume 824 of the unit cell 810. As a result, the unit cell 810 can be characterized as being hollow. The Schwarz-P minimal surface may be functionally expressed as: $\cos(x)+\cos(y)+\cos(z)=0$.

The unit cell 810 also includes connecting interfaces 826 that can be used to interconnect the unit cell 810 to other unit cells 810 to thereby form the adjunct 800 shown in FIGS. 8A-8E. In this illustrated embodiment, the unit cell includes six connecting interfaces 826 that form the six outer-most surfaces of the unit cell 810, e.g., top and bottom outer-most surfaces 827a, 827b, left and right outer-most surfaces 829a, 829b, and front and back outer-most surfaces 831a, 831b. The top and bottom outer-most surfaces 827a, 827b are generally planar (e.g., planar within manufacturing tolerances) with respect to each other and offset in the x-direction, the left and right outer-most surfaces 829a, 829b are generally planar (e.g., planar within manufacturing tolerances) with respect to each other and offset in the y-direction, and the front and back outer-most surfaces 831a, 831b are generally planar (e.g., planar within manufacturing tolerances) with respect to each other and offset in the z-direction. As such, the overall outer surface of the unit cell 810 includes planar surfaces, e.g., the outer-most surfaces 827a, 827b, 829a, 829b, 831a, 831b and non-planar surfaces, e.g., the external surfaces 820 that extend between the connecting interfaces 826). Further, since the adjunct 800 is only formed of the repeating unit cells 810, the top portion 812, including the top-most outer surface 812a, forms the tissue-contacting surface 802 of the adjunct 800, and the bottom-most outer surface 814a (e.g., in the x-direction) of the bottom portion 814 of the unit cells forms the cartridge-contacting surface 804 of the adjunct 800. As a result, the tissue-contacting surface 802 is formed of planar and non-planar surfaces.

Further, based on the overall geometry of the repeating unit cells 810 and their interconnectivity to each other at corresponding connecting interfaces 826, the overall outer surface of the resulting adjunct 800 is formed of generally planar surfaces (e.g., planar within manufacturing tolerances) separated by non-planar surfaces. As shown, the top and bottom outer-most surfaces 850a, 850b of the adjunct 800 are furthest from the bisector extending within the YZ plane, the left and right outer-most surfaces 852a, 852b of the adjunct 800 are furthest from the bisector extending within the XZ plane, and the front and back outer-most surfaces 854a, 854b of the adjunct are furthest from the bisector extending within the XY plane. Further, as shown, the top and bottom outer-most surfaces 850a, 850b are generally planar (e.g., planar within manufacturing tolerances) with respect to each other and offset in the x-direction, the left and right outer-most surfaces 852a, 852b are generally planar (e.g., planar within manufacturing tolerances) with respect to each other and offset in the y-direction, and the front and back outer-most surfaces 854a, 854b are generally planar (e.g., planar within manufacturing tolerances) with respect to each other and offset in the z-direction. As such, these outer-most surfaces 850a, 850b, 852a, 852b, 854a, 854b form the planar segments of the outer surface of the adjunct 800. It can be appreciated that the portions of the adjunct 800 that extend between these outer-most surfaces 850a, 850b, 852a, 852b, 854a, 854b, which are defined by the external surfaces 820 of adjacent unit cells 810, thereby forming the non-planar surfaces of the outer surface of the adjunct 800.

As further shown, the six connecting interfaces 826 define respective circular openings that are in fluid communication with the internal volume 824 of the unit cell 810. As a result, the unit cell 810 has openings in all six Cartesian sides (represented as arrows 1, 2, 3, 4, 5, 6 in FIG. 9B). These openings can serve multiple functions, for example: facilitate connections to adjacent cells; create openings that can allow for immediate tissue in-growth when the adjunct is in stapled to tissue; allow drainage of manufacturing materials used in the production of the resulting adjunct, e.g., materials used during a 3D manufacturing process; allow transfer of bodily fluids easily throughout the adjunct; contribute to the mechanical properties of the adjunct, e.g., mechanical properties that create a compression profile that delays densification of the adjunct; and/or minimize the solid height of the fully compressed adjunct.

Figure 8A:
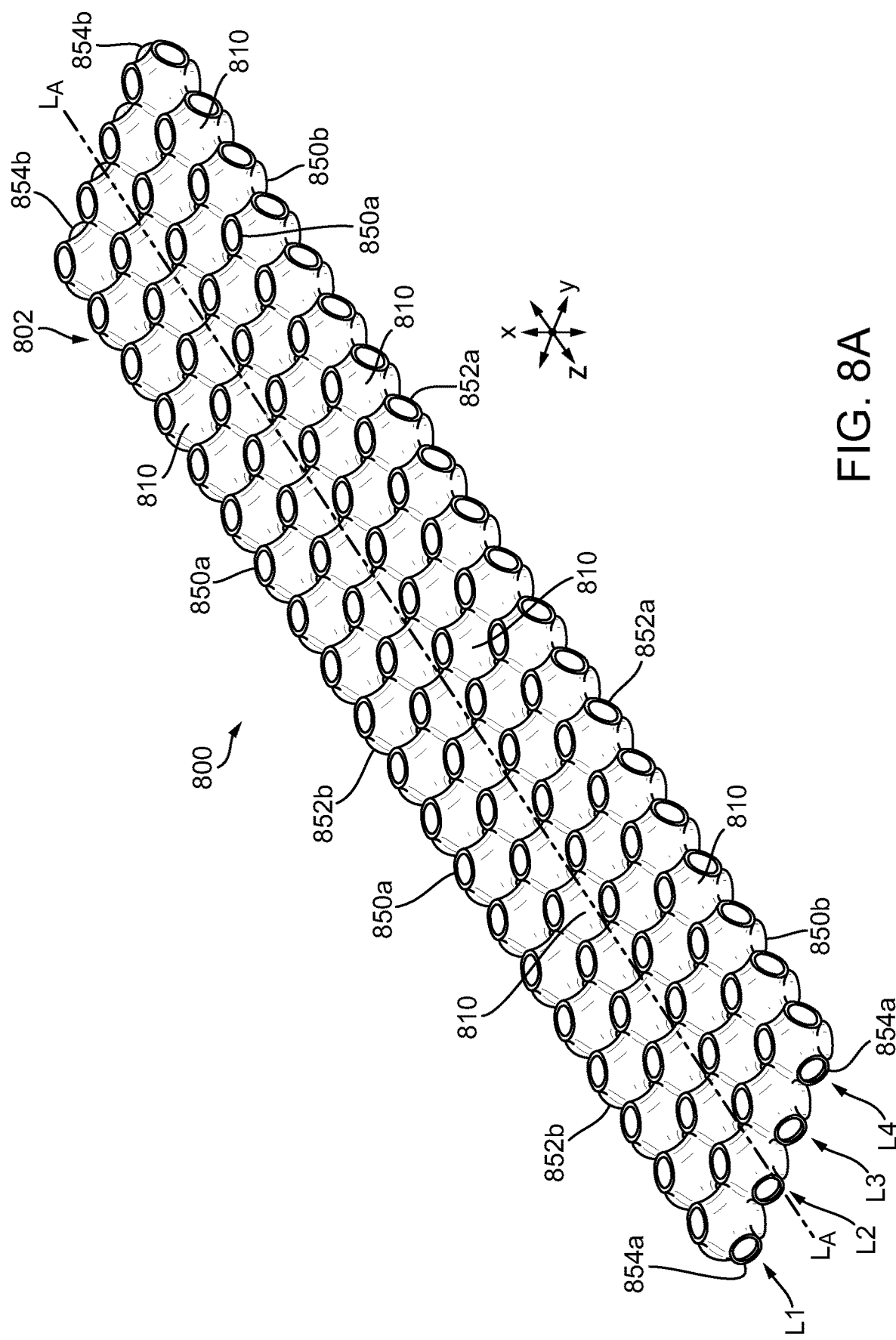
FIG. 8A is a perspective view of another exemplary embodiment of compressible non-fibrous adjunct.
Figure 8F:
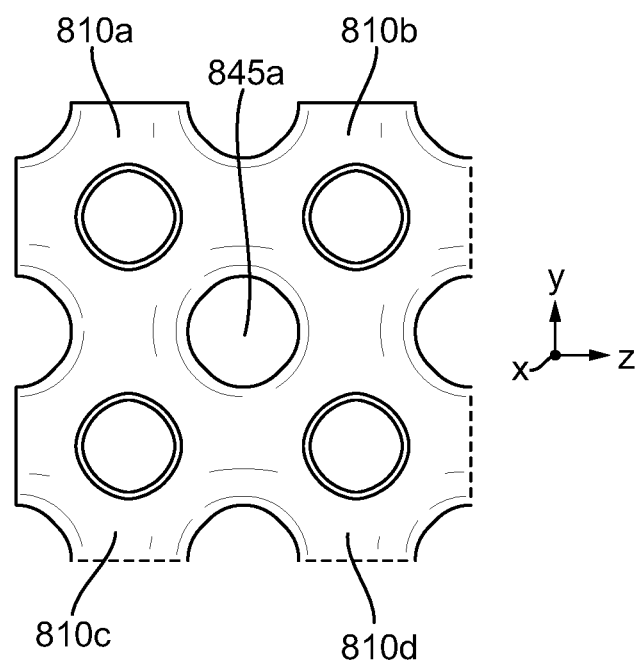
FIG. 8F is a magnified view of a portion of the adjunct of FIG. 8C taken at 8F.
Figure 8G:
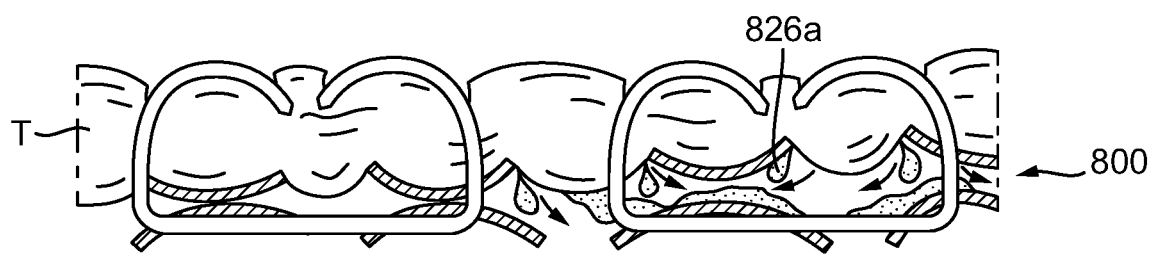
FIG. 8G is a partial-schematic illustrating the adjunct of FIG. 8A in a tissue deployed state.

Moreover, when the unit cells 810 are interconnected to each other at corresponding connecting interfaces, e.g., at least two connecting interfaces, hollow tubular interconnections 828 (e.g., lumens) are formed therebetween, as shown in FIGS. 8D-8E, which allow the internal volumes 824 of the interconnected unit cells 810 to be in fluid communication with each other. As such, a continuous network of channels or pathways are present within the adjunct. As a result, when the adjunct 800 is stapled to tissue (T), and is in a tissue deployed state, as illustrated in FIG. 8G, one or more fluids, including cells that enter into the adjunct 800, e.g., through the opening of a connecting interface 826a of the top portion 812 of at least one unit cell 810, can therefore migrate throughout the adjunct 800, e.g., through interconnected unit cells, when in a tissue deployed state, as illustrated in FIG. 8G, and thus, can ultimately accelerate tissue ingrowth within the adjunct 800. That is, while the adjunct 800 is in a tissue-deployed state, at least a portion of the hollow tubular interconnection 828 can at least partially maintain fluid communication between at least a portion or through all of internal volumes of the unit cells 810, and thus encourage cell mobility throughout the adjunct 800.

While the hollow tubular interconnections 828 define openings that can have variety of sizes (e.g., diameters), in some embodiments the diameter of the openings can be from about 100 micrometers to 3500 micrometers. For example, the diameter of the openings can be from about 100 micrometers to 2500 micrometers or from about 500 micrometers to 2500 micrometers. In certain embodiments, the diameter of the openings can be from about 945 micrometers to 1385 micrometers. In one embodiment, the diameter of the openings can be greater than 2000 micrometers. In certain embodiments, the diameter of all the openings is substantially the same (e.g., nominally identical within manufacturing tolerances). As used herein, "diameter" of an opening is the largest distance between any pair of vertices of the opening.

Since the repeating unit cells 810 are interconnected to each other at corresponding connecting interfaces 826, the adjunct 800 is in the form of a lattice structure having predefined compression areas 830 and predefined non-compression areas 840, as more clearly shown in FIG. 8C. While the predefined compression areas 830 and predefined non-compression areas 840 can have a variety of configurations, in this illustrated embodiment, the predefined compression areas 830 are defined by the unit cells 810, and the predefined non-compression areas 840 are in the form of voids 845 defined between the unit cells 810. In this embodiment, each void 845 is formed between four adjacent interconnect unit cells 810. For example, void 845a is defined between the four adjacent unit cells 810a, 810b, 810c, 810d, as shown in FIG. 8F. Thus, the space that exists between adjacent unit cells define the predefined non-compression areas. Stated differently, the non-compression areas 840 of the adjunct are not defined by the internal volumes of the unit cells.

As described in more detail below, the structural configuration of the repeating unit cell can allow the unit cell to deform or buckle continuously along its height H (see FIG. 9A) at different locations over a period of time (e.g., until opposing sides of the internal surface of the cell come into contact with each other) while under applied stress. As a result, during such time, the unit cell, while under an applied stress (e.g., 30 kPa to 90 kPa), can deform or buckle at a rate that is constant, or substantially constant. Stated differently, in certain embodiments, the structure of the repeating unit cells can lead to a stress plateau while the adjunct is under an applied stress, e.g., as schematically illustrated in FIG. 11.

FIGS. 10A-10D schematically illustrate the compressive behavior of one repeating unit cell, e.g., unit cell 810 in FIGS. 8A-9B, when under a range of applied stress. In particular, the repeating unit cell 1010 is shown in a pre-compressed (undeformed) state in FIG. 10A, a first compressed state FIG. 10B, in which each of the top and bottom portions 1012, 1014 of the unit cell 1010 begin to compress toward the middle portion 1016 of the unit cell 1010 causing the middle portion 1016 to begin deflecting, a second compressed state FIG. 10C, in which the middle portion 1016 continues to deflect outward, and a densified state in FIG. 10D, in which opposing sides 1018a, 1018b of the internal surface 1018 of the middle portion 1016 come into contact with each other causing the unit cell 810 to reach its solid height.

Figure 11:
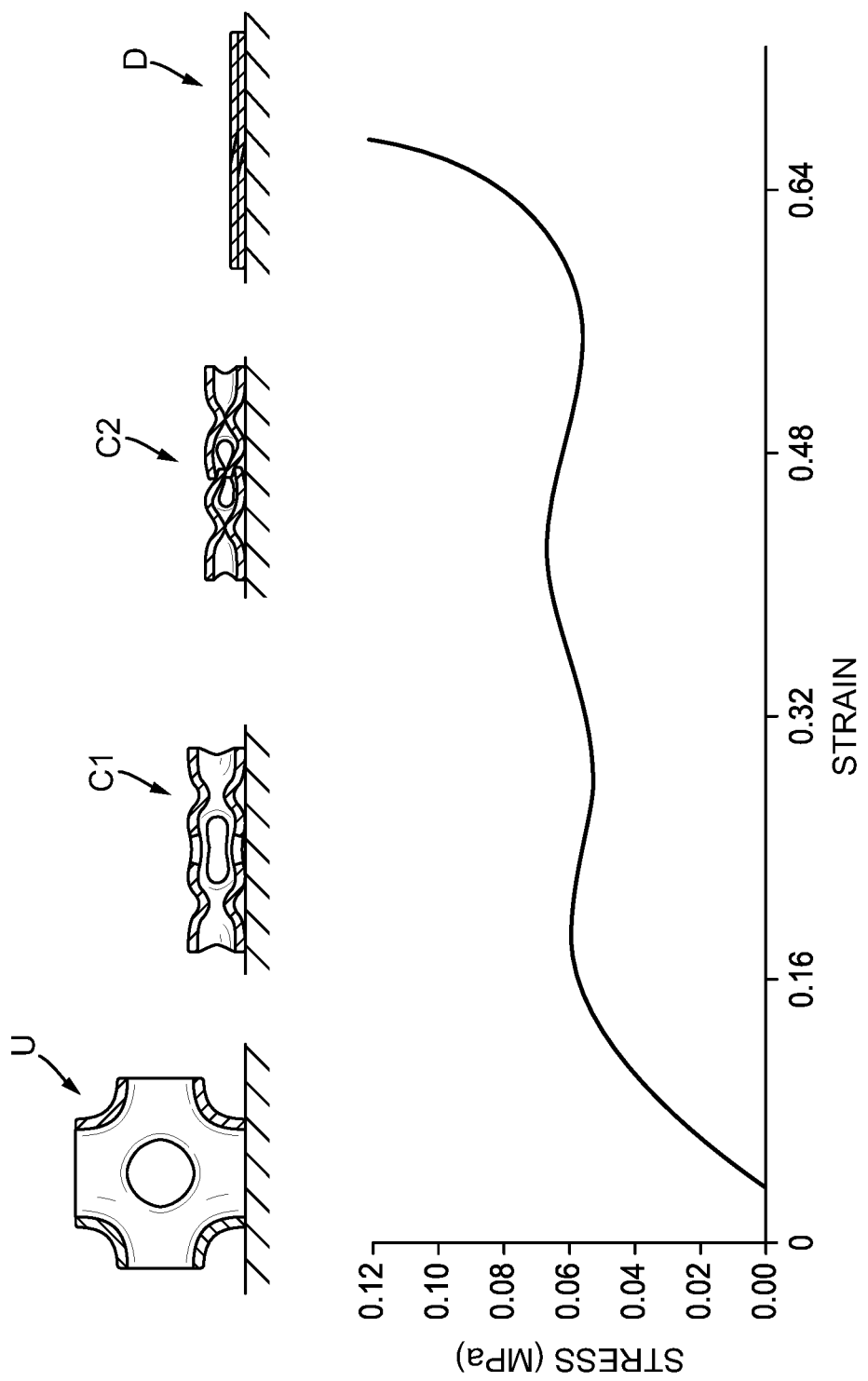
FIG. 11 is a schematic illustration of the relationship between the states of the unit cell of FIG. 10A-10D and the stress-strain curve of the resulting compressible non-fibrous adjunct.

The relationship between the undeformed state U (FIG. 10A), compressed states C1, C2 (FIGS. 10B-10C), and densified state D (FIG. 10D) of the repeating unit cell 1010 and the stress-strain curve of the resulting adjunct is schematically illustrated in FIG. 11.

The stress-strain response of the adjunct starts with an elastic deformation (bending) characterized by the Young's modulus, e.g., as the repeating unit starts to deform from its uncompressed state towards its first compressed state. This elastic deformation continues until the yield stress is reached. Once the yield stress is reached, a stress plateau can occur, which corresponds to the progressive unit cell collapse by elastic buckling, e.g., as the repeating unit cell continues to deform through its first compressed state and second compressed state. A person skilled in the art will appreciate that the stress plateau depends at least upon the nature of the material from which the unit cell is made. The stress plateau continues until densification, which denotes a collapse of the unit cells throughout the adjunct, e.g., as the repeating unit cell reaches its densified state, and thus, the adjunct has reached its solid height.

A person skilled in the art will appreciate that the stress-strain curve for an adjunct depends on various factors, e.g., uncompressed heights, compositional makeup (including material properties), and/or structural configuration. By way of example, Table 1 below illustrates the stress-strain responses for exemplary adjuncts differing only in uncompressed height (UH) and being compressed to a first compressed height (CH1) of 1.75 mm at an applied stress of 30 kPa, compressed to a second compressed height (CH2) of 0.75 mm at an applied stress of 90 kPa, and compressed to a third compressed height (CH3) of 0.45 mm at an applied stress of 90 kPa.

TABLE 1

Stress-Strain Relationship for Various Adjunct Heights

| UH (mm) | CH1 (mm) | CH2 (mm) | CH3 (mm) | Strain | | |
|---|---|---|---|---|---|---|
| | | | | C1 @ 30 kPa | C2 @ 90 kPa | C3 @ 90 kPa |
| 2 | 1.75 | 0.75 | 0.45 | 0.13 | 0.63 | 0.78 |
| 2.25 | 1.75 | 0.75 | 0.45 | 0.22 | 0.67 | 0.80 |
| 2.5 | 1.75 | 0.75 | 0.45 | 0.30 | 0.70 | 0.82 |
| 2.75 | 1.75 | 0.75 | 0.45 | 0.36 | 0.73 | 0.84 |
| 3 | 1.75 | 0.75 | 0.45 | 0.42 | 0.75 | 0.85 |
| 3.25 | 1.75 | 0.75 | 0.45 | 0.46 | 0.77 | 0.86 |
| 3.5 | 1.75 | 0.75 | 0.45 | 0.50 | 0.79 | 0.87 |

Figure 12B:
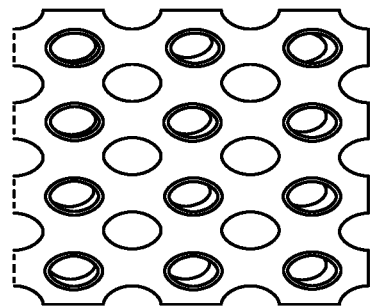
FIG. 12B is top view of an exemplary embodiment of a compressible non-fibrous adjunct formed of repeating unit cells of another embodiment of a modified Schwarz-P structure.
Figure 12D:
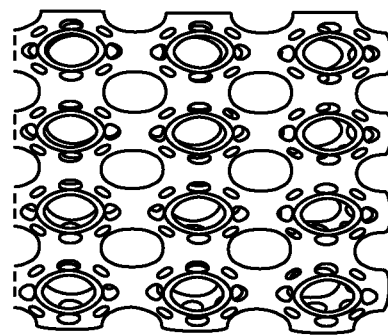
FIG. 12D is top view of an exemplary embodiment of a compressible non-fibrous adjunct formed of repeating unit cells of another embodiment of a modified Schwarz-P structure.
Figure 12A:
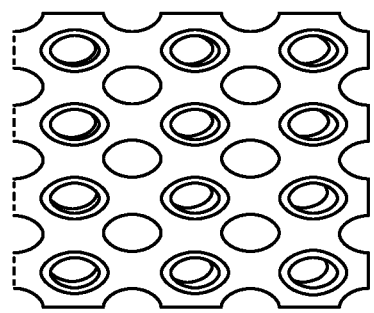
FIG. 12A is top view of an exemplary embodiment of a compressible non-fibrous adjunct formed of repeating unit cells of an embodiment of a modified Schwarz-P structure.
Figure 12C:
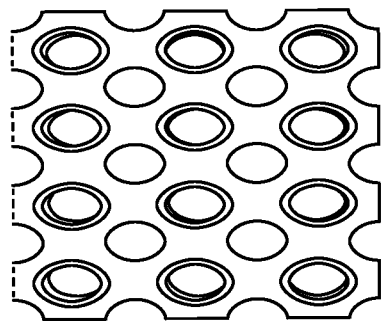
FIG. 12C is top view of an exemplary embodiment of a compressible non-fibrous adjunct formed of repeating unit cells of another embodiment of a modified Schwarz-P structure.

In another embodiment, the repeating strut-less based unit cells can be a modified Schwarz-P structure. For example, the Schwarz-P structure can be stretched in one or more directions to form a stretched Schwarz-P structure, e.g., as illustrated in FIG. 12A. Alternatively or in addition, in certain embodiments, the wall thickness of the Schwarz-P structure can be thinned. For example, as illustrated in FIG. 12B, the Schwarz-P structure is stretched and thinned. In yet another embodiment, as illustrated in FIG. 12C, the Schwarz-P structure can be cropped, e.g., in which the height of the top portion $H_T$ (see FIG. 9A) and/or bottom portion $H_B$ (see FIG. 9A) of the Schwarz-P structure is decreased. Alternatively, or in addition to the forgoing exemplary modifications, additional openings can be added through the walls of the Schwarz-P structure, e.g., as illustrated in FIG. 12D, which can help with densification of the resulting adjunct.

The repeating strut-less based unit cells can take the form of other TPMS structures. For example, as illustrated in 13A, a strut-less based unit cell 1300 can be formed from a sheet diamond structure having a diamond minimal surface with a Schwarz D surface lattice structure. This particular minimal surface is called a "diamond" because it has two intertwined congruent labyrinths where each has the shape of a tubular version of a diamond bond structure. The Schwarz D may be functionally expressed as:

$$\sin(x)\sin(y)\sin(z)+\sin(x)\cos(y)\cos(z)+\cos(x)\sin(y)\cos(z)+\cos(x)\cos(y)\sin(z)=0.$$

Figure 13A:
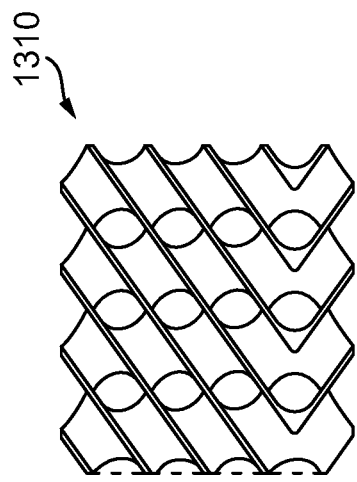
FIG. 13A is a perspective view of another exemplary embodiment of a single unit cell.
Figure 13B:
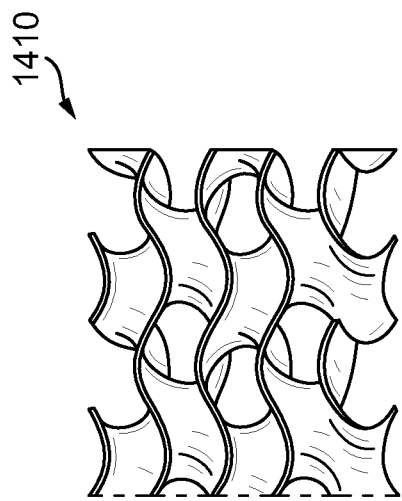
FIG. 13B is a top down view of an exemplary embodiment of a compressible non-fibrous adjunct formed of repeating unit cells of FIG. 13A.

An exemplary adjunct 1310 formed of repeating unit cells 1300, and thus sheet diamond structures, is illustrated in FIG. 13B.

Figure 14A:
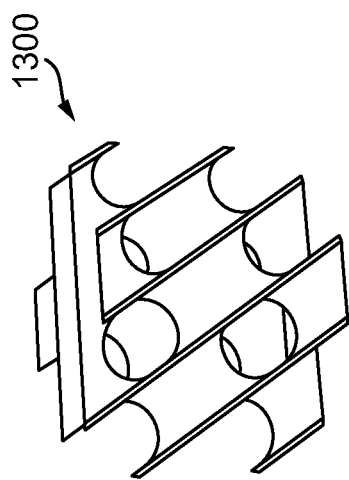
FIG. 14A is a perspective view of another exemplary embodiment of a single unit cell.

In another embodiment, as illustrated in FIG. 14A, a strut-less based unit cell 1400 can be a gyroid structure. The gyroid minimal surface may be functionally expressed as:

$$\sin(x)\cos(y)+\sin(y)\cos(z)+\sin(z)\cos(x)=0.$$

Figure 14B:
FIG. 14B is a top down view of an exemplary embodiment of a compressible non-fibrous adjunct formed of repeating unit cells of FIG. 14A.
Figure 16B:
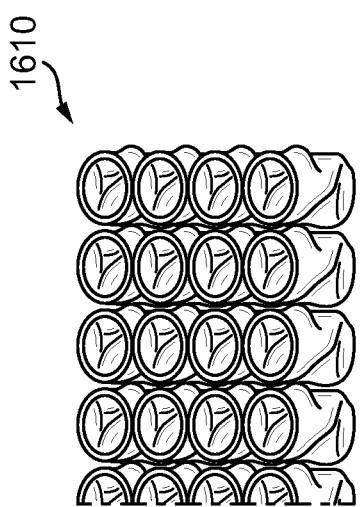
FIG. 16B is a top down view of an exemplary embodiment of a compressible non-fibrous adjunct formed of repeating unit cells of FIG. 16A.
Figure 15B:
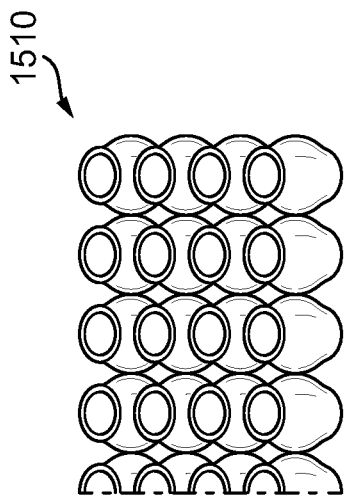
FIG. 15B is a top down view of an exemplary embodiment of a compressible non-fibrous adjunct formed of repeating unit cells of FIG. 15A.
Figure 16A:
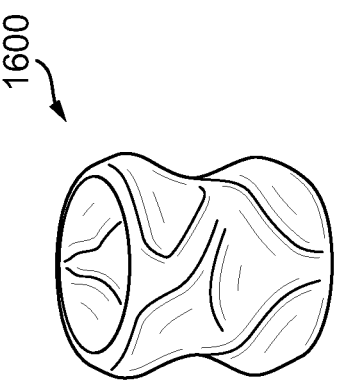
FIG. 16A is a perspective view of another exemplary embodiment of a single unit cell.
Figure 15A:
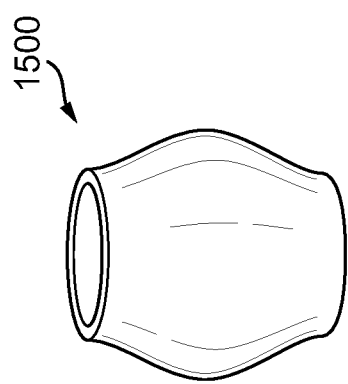
FIG. 15A is a perspective view of another exemplary embodiment of a single unit cell.

An exemplary adjunct 1410 formed of repeating unit cells 1500, and thus gyroid structures, is illustrated in FIG. 14B. In other embodiments, a strut-less based unit cell can be in the form of a cosine structure 1500 (FIG. 15A) or in the form of a coke can structure 1600 (FIG. 16A), each of which is defined by curved minimal surfaces. Exemplary adjuncts 1510, 1610 formed of respective repeating unit cells 1500 (cosine structures), 1600 (coke can structures) are illustrated in FIGS. 15B and 16B.

Edge Conditions

In some embodiments, certain strut-less based unit cells, when interconnected to form an adjunct, can form undesirable edge conditions for tissue stapling. For example, as tissue slides across the adjunct during use, the edge conditions can interact with tissue in such a way that causes at least a portion of the adjunct to prematurely detach from the staple cartridge. These edge conditions can be a result of the geometry (e.g., having generally planar (e.g., planar within manufacturing tolerances) and non-planar outer surfaces) and interconnectivity of the strut-less based unit cells that make up the adjunct. As such, to improve these edge conditions, and thus inhibit premature detachment of the adjunct, an outer layer having a different geometry can be placed atop one or more tissue-contacting surfaces of the adjunct.

Referring back to FIGS. 9A-9B, as noted above, a Schwarz-P structure 810 has non-planar external surfaces that form the arcuate sides 821 that extend between the connecting interfaces 826 of the unit cell 810. As a result, when the Schwarz-P structures 810 are interconnected to form an adjunct, such as adjunct 800 in FIGS. 8A-8F, tissue-contacting surface(s) can form having planar and non-planar surfaces, like tissue-contacting surface 802 in FIGS. 8A-8B. This is a result of at least the structural configuration of the top portion 812 of each unit cell 810 (e.g., exposed top-most outer surface 827a and arcuate sides 821 of the top portion 812) and the spaced apart relationship between them. Thus, the edge conditions of the adjunct can be minimized with the application of an outer layer having a generally planar (e.g., planar within manufacturing tolerances) geometry positioned atop at least one otherwise tissue-contacting surface of the adjunct, like tissue-contacting surface 802 of adjunct 800 in FIGS. 8A-8F. As a result, this can lower the tissue loads (applied stress) on the adjunct during placement of the stapling device. Further, this can ease the attachment requirements between the adjunct and cartridge.

While the outer layer can have a variety of configurations, in some embodiments, the outer layer can be formed of one or more planar arrays of struts (FIGS. 17A-17C), whereas in other embodiments, the outer layer can be in the form of a film (FIG. 18).

Figure 17A:
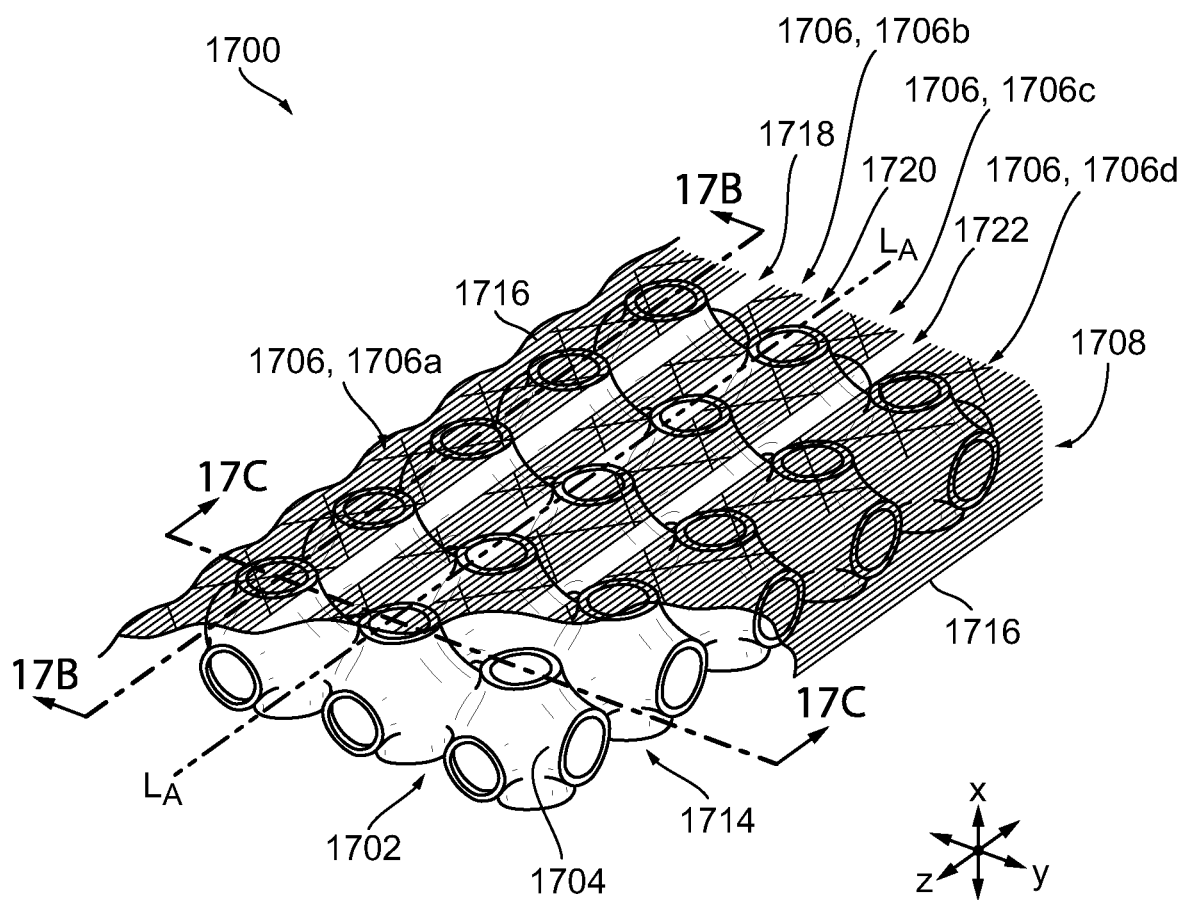
FIG. 17A is a perspective view of another exemplary embodiment of a compressible non-fibrous adjunct.

FIGS. 17A-17C illustrate an exemplary adjunct 1700 having a first lattice structure 1702 formed of interconnecting repeating unit cells 1704 and at least one planar array 1706, 1708. Each unit cell 1704 is similar to unit cell 810 in FIG. 9A-9B and therefore common features are not described in detail herein. In this illustrated embodiment, there are two planar arrays 1706, 1708, in which the first planar array 1706 (e.g., in the YZ plane) extends across the top tissue-facing surface 1712 of the first lattice structure 1702 and the second planar array 1706 (e.g., in the XZ plane) extends across at least one side tissue-facing surface 1714 of the first lattice structure 1702. In other embodiments, the first or second planar arrays 1706, 1708 can be omitted. In further embodiments, the adjunct 1700 can include additional planar arrays.

While the planar arrays 1706, 1708 can have a variety of configurations, in this illustrated embodiment, the first and second planar arrays 1706, 1708 each include longitudinal struts 1716 extending parallel and along the longitudinal axis ($L_A$) of the adjunct 1700. While not shown, it is also contemplated that additional struts can be added to the first and second planar arrays 1706, 1708. For example, in one embodiment, the first planar array 1706 and/or second planar array 1708 can include cross struts that extend at an angle relative to the longitudinal axis and intersect the first and/or second longitudinal struts, e.g., thereby creating a repeating X-pattern.

In use, when the adjunct 1700 is releasably retained on a cartridge, such as cartridge 200 in FIGS. 1-2C, the adjunct 1700 overlaps with the rows of staples disposed within the cartridge. As a result, the first planar array 1706 can add to the ultimate solid height of the adjunct 1700, and therefore accelerate densification thereof. However, in an effort to minimize the impact the first planar array 1706 can have on the densification, the first planar array 1706 can be designed in such a way that it does not overlap with the staple rows. For example, as shown in FIGS. 17A-17C, the first planar array 1706 is divided into four spaced apart portions 1706a, 1706b, 1706c, 1706d such that three gaps 1718, 1720, 1722 are formed therebetween and along the longitudinal axis ($L_A$) for the adjunct 1700. As shown in FIG. 17C, these three gaps 1718, 1720, 1722 can coincide with three staple rows 1724, 1726, 1728 of the cartridge (not shown), and therefore, the first planar array 1706 will not be captured, or will be minimally captured, by the staples during deployment.

As noted above, in some embodiments, an absorbable film can be positioned on at least a portion of at least one of the non-planar tissue-facing surfaces of a lattice structure to thereby substantially prevent tissue from causing the adjunct to prematurely detach from the cartridge while the tissue slides across the adjunct. That is, the absorbable film can minimize edge conditions, and thus decrease the friction that would otherwise be present on the tissue-contacting surface(s) of the adjunct.

FIG. 18 illustrates an exemplary embodiment of an adjunct 1800 disposed on a cartridge 1801. The adjunct 1800 includes a lattice structure 1802 with an absorbable film 1804 disposed on at least a portion thereof. The lattice structure 1802, which is similar to the lattice structure of adjunct 800 in FIG. 8A, is formed of interconnecting repeating unit cells 1806, each of which is similar to unit cell 810 in FIGS. 9A-9B, and therefore common features are not described in detail herein. As shown, the absorbable film 1804 is disposed on all tissue-facing surfaces of the lattice structure 1802, which, in this illustrated embodiment, includes a top-tissue facing surface 1808 (e.g., extending in the x-direction), a first longitudinal side surface 1810a (e.g., extending in the z-direction), a second opposing longitudinal side surface 1810b, a first lateral side surface 1812a (e.g., extending in the y-direction), and a second opposing lateral side surface (obstructed). In other embodiments, the absorbable film is not disposed on all tissue-facing surfaces of a lattice structure, e.g., the first lateral side surface and/or the second lateral side surface.

The absorbable film can have a variety of configurations. For example, in some embodiments, the absorbable film is designed to have a thickness that nominally impacts densification of an adjunct when the adjunct is under applied stress and/or formed of one or more materials that help reduce friction of the tissue-contacting layers for tissue manipulation. In some embodiments, the absorbable film can have a thickness that is less than or equal to about 15 microns, e.g., from about 5 microns to 15 microns, or from about 8 microns to 11 microns. In one embodiment, the absorbable film can be formed of polydioxanone.

Attachment Features

Figure 24:
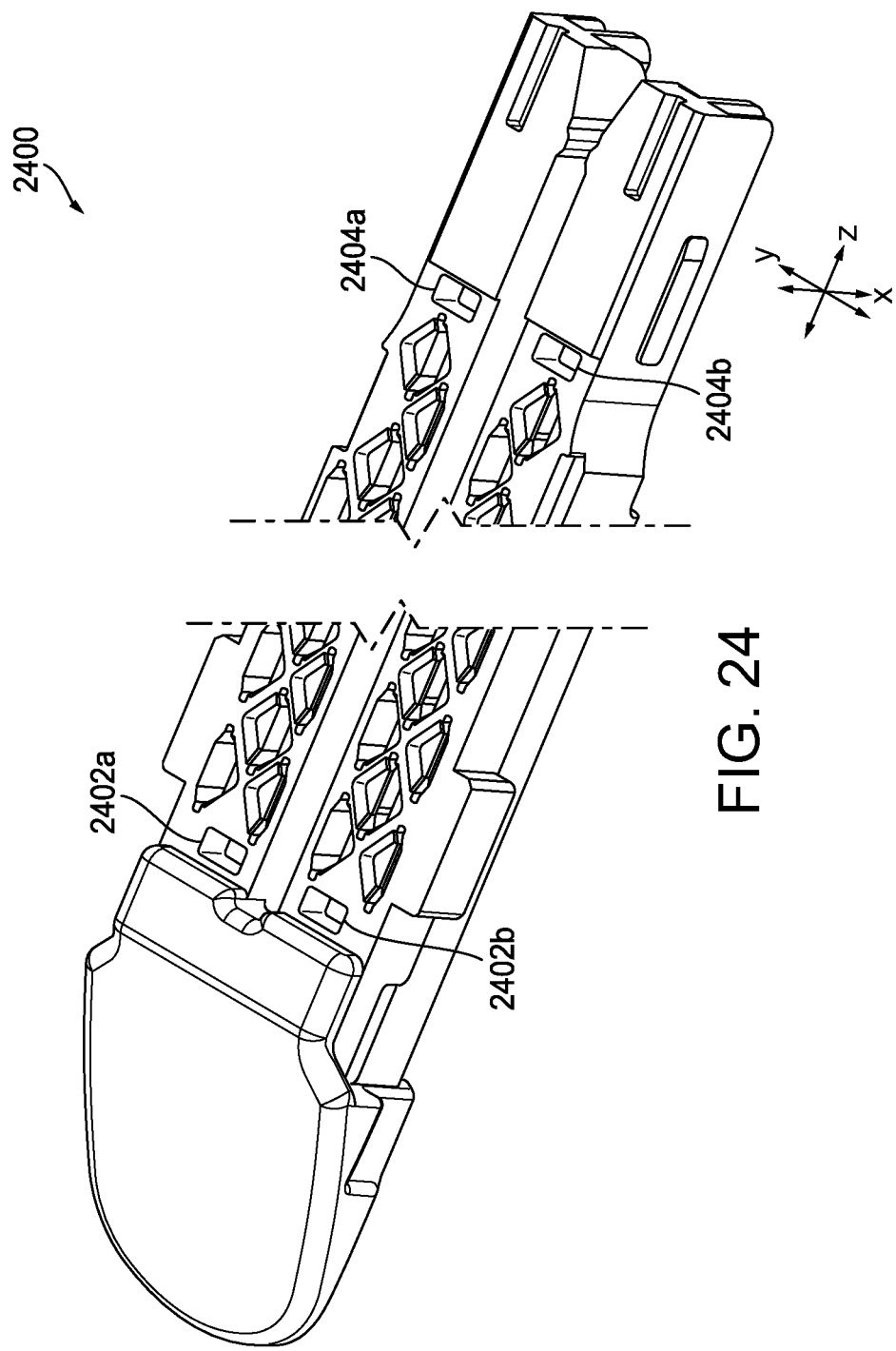
FIG. 24 is a perspective view of another exemplary embodiment of a staple cartridge having end attachment features.
Figure 25:
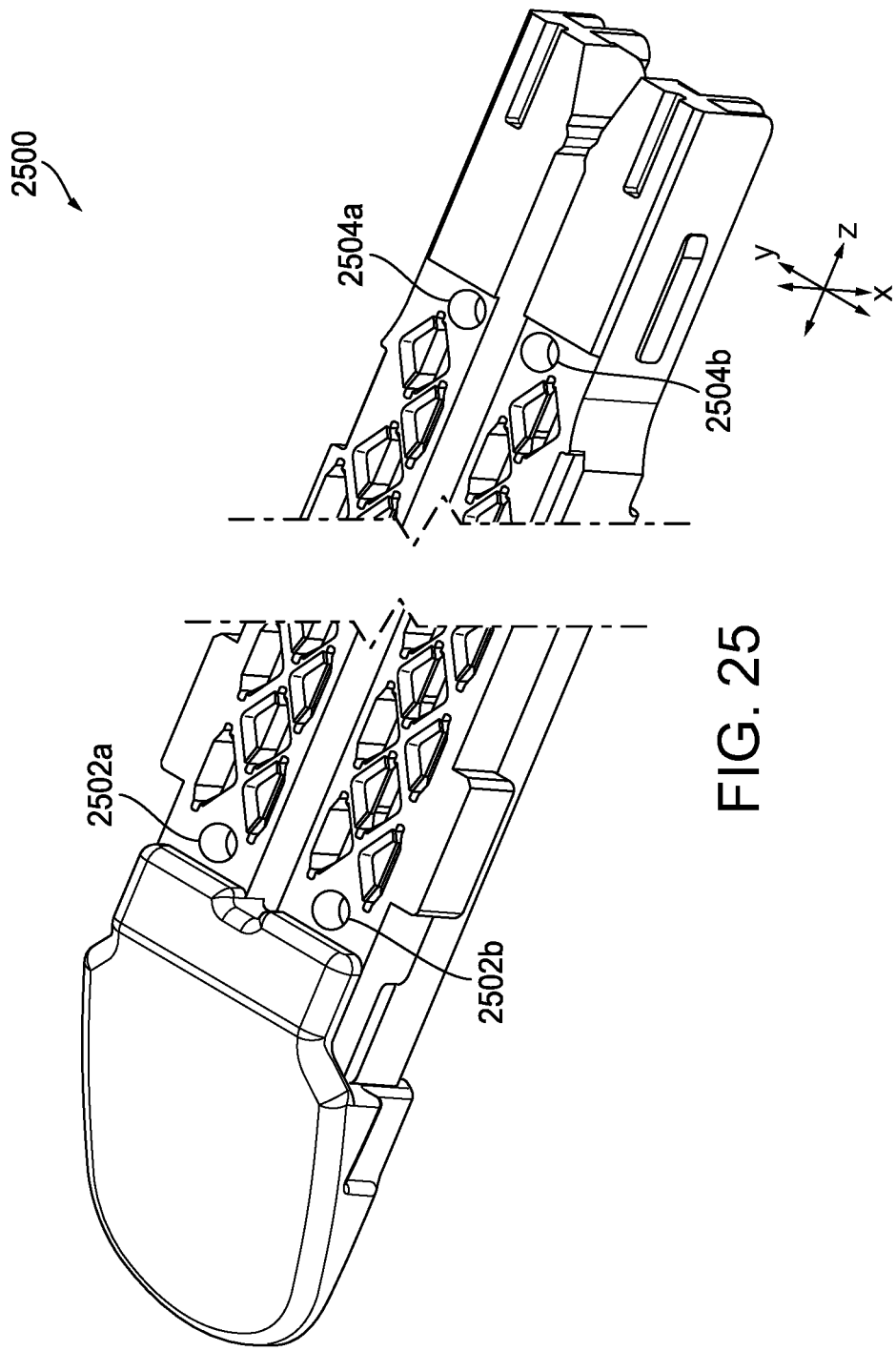
FIG. 25 is a perspective view of another exemplary embodiment of a staple cartridge having end attachment features.

In some embodiments, non-strut-based adjuncts include one or more attachment features that extend at least partially along the length of adjunct and that are configured to engage the staple cartridge to thereby retain the adjunct on the cartridge prior to staple deployment. The one or more attachment features can have a variety of configurations. For example, the one or more attachment features can be channel attachments (FIGS. 19A-21), (FIGS. 22A-22B) that are configured to engage (e.g., press-fit or snap into) the elongate cutting slot formed between opposing longitudinal edges thereof in the staple cartridge, and/or end attachments (FIGS. 24-25) that are configured to engage with recessed end channels defined within the staple cartridge. Aside from the differences discussed in detail below, adjuncts 1900, 2000, 2100, 2200 are substantially similar to adjunct 800 in FIGS. 8A-8F, and therefore common features are not discussed in detail herein.

In some embodiments, the channel attachment can include one or more compressible members that are structurally configured to be inserted into a longitudinal slot of a staple cartridge to engage the opposing walls of the longitudinal slot. In certain embodiments, one or more compressible members can include a compressible opening that extends therethrough, e.g., in a longitudinal direction along a length of the cartridge-contacting surface of the adjunct.

Figure 19A:
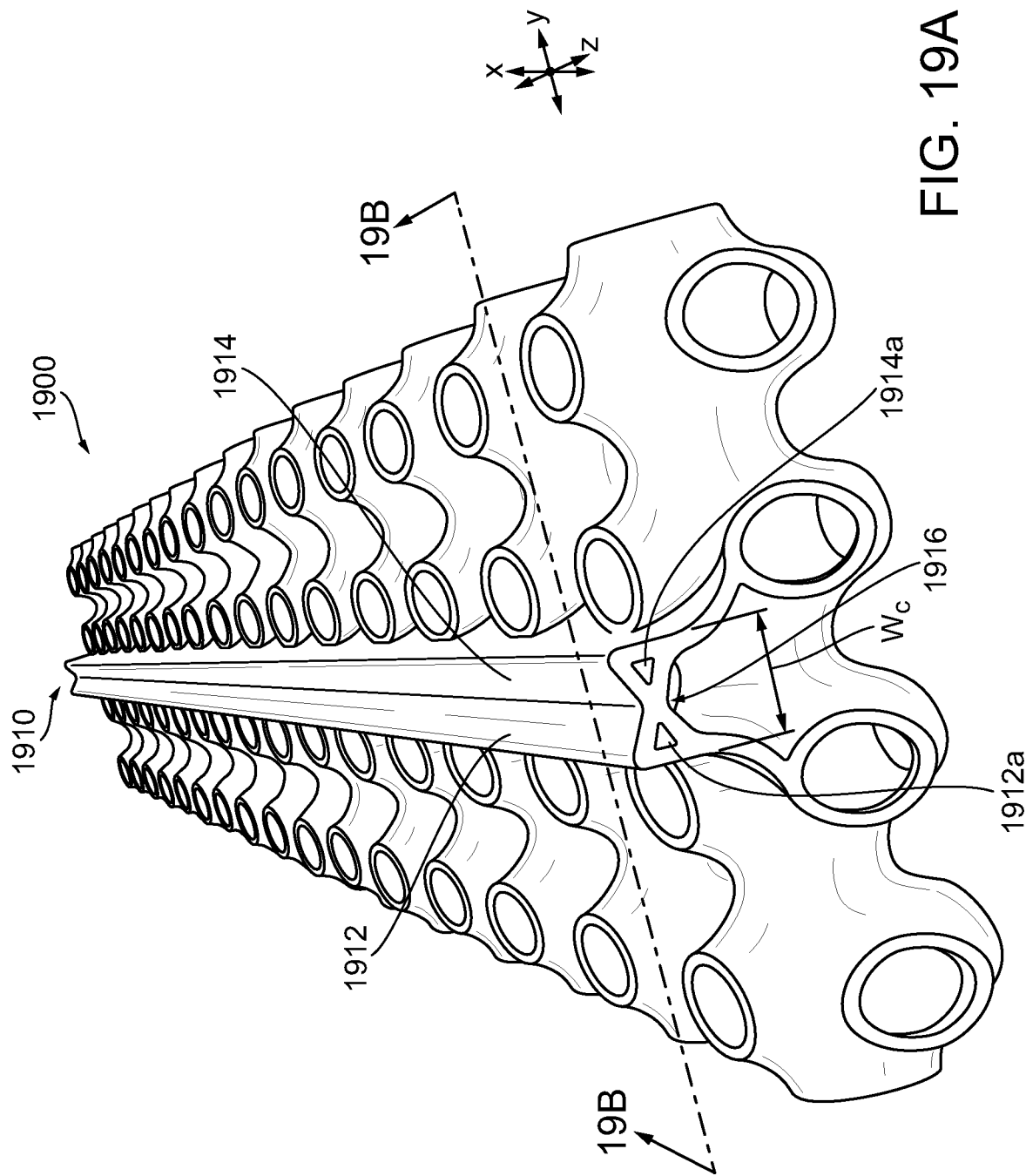
FIG. 19A is a perspective view of another exemplary embodiment of a compressible non-fibrous adjunct having a channel attachment.
Figure 19B:
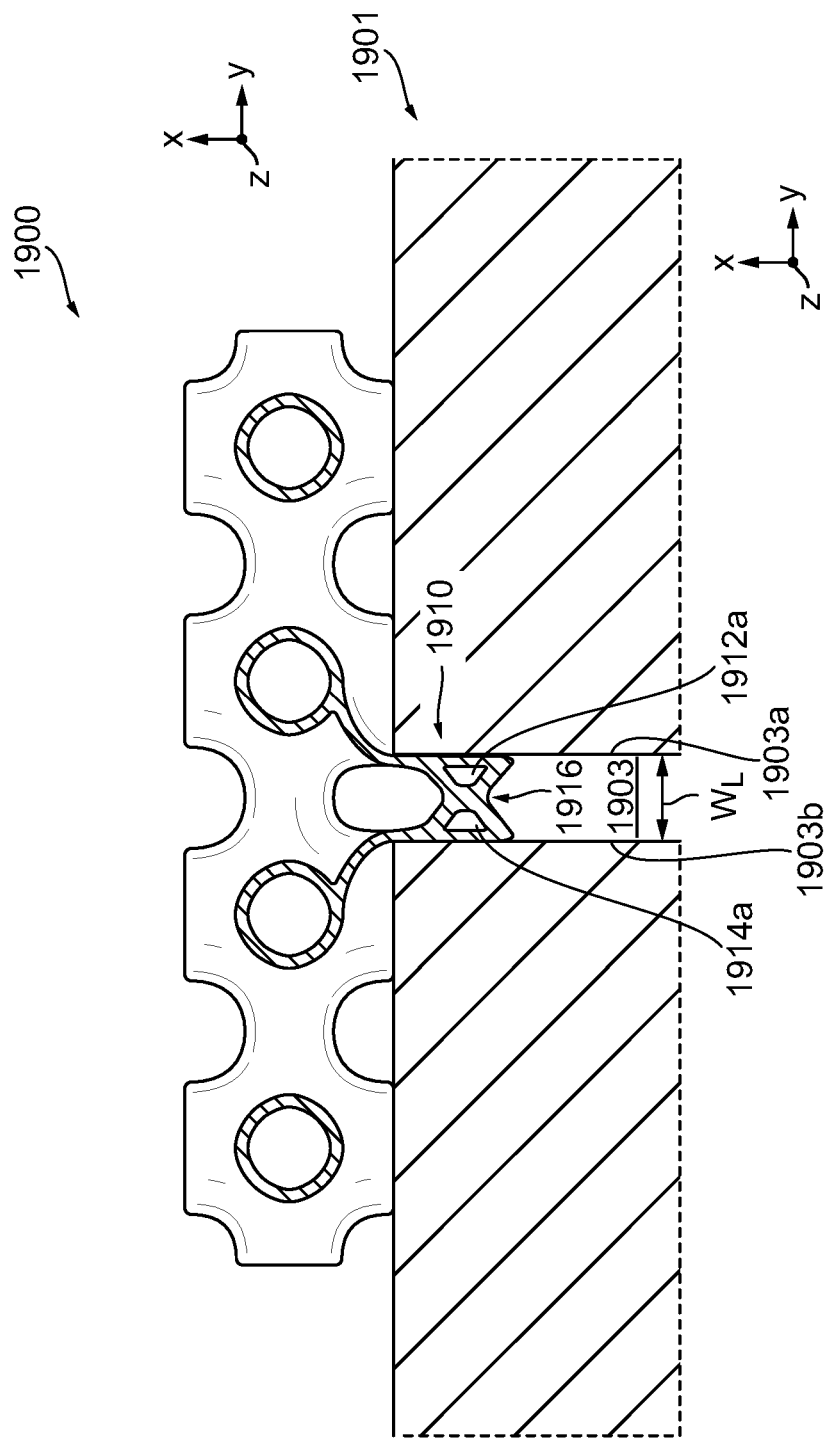
FIG. 19B is a cross-sectional view of the adjunct of FIG. 19A taken at line 19B-19B.

FIGS. 19A-19B illustrate an exemplary embodiment of an adjunct 1900 that includes a channel attachment 1910 having two compressible members 1912, 1914 that are interconnected by at least one common elongated joint 1916. While the two compressible members 1912, 1914 can have a variety of configurations, in this illustrated embodiment, each compressible member 1912, 1914 is in the form of an elongated rod having a triangular cross-sectional shape taken across the width thereof (e.g., in the y-direction) with a hollow triangular channel 1912a, 1914a extending therethrough along the length thereof (e.g., in the z-direction). As shown, the two elongated rods 1912, 1914 are interconnected at corresponding apexes, thereby forming the elongated joint 1916 that defines a central connection region with a narrow thickness (e.g., in the x-direction). As shown in FIG. 19B, when the adjunct 1900 is disposed on a cartridge 1901, which is similar to cartridge 200 in FIGS. 1-2C, the at least one elongated joint 1916, and thus the central connection region, is positioned equidistance from the opposing walls 1903a, 1903b of the longitudinal slot 1903, as shown in FIG. 19. As a result, the central connection region aligns with the advancement line of the cutting member, and therefore, due to the narrow width of the central connection region, the risk of jamming of the cutting member as it advances through the adjunct 1900 can be minimized or prevented. That is, the central connection region minimizes the additional adjunct material the cutting member would need to otherwise cut through as it advances through the longitudinal slot 1903. Further, the hollow triangular channels 1912a, 1914a decrease the amount of material on each side of the advancement line, which can also minimize the cut edges of the adjunct from binding to the cutting member as it further advances through the longitudinal slot 1903.

While the overall width $W_C$ of the channel attachment 1910 can vary, in this illustrated embodiment, the overall width $W_C$ is greater than the width WL of the longitudinal slot 1903 (e.g., the distance between the two opposing slot walls 1903a, 1903b). As a result, when the channel attachment 1910 is inserted into the longitudinal slot 1903, the compressible members deform and engage (e.g., compress against) respective slot walls 1903a, 1903b due to the outward lateral force created by the hollow triangle channels 1912a, 1914a. As such, a press fit or friction fit is created between the compressible members 1912, 1914 and respective slot walls 1903a, 1903b of the cartridge 1901.

Figure 20:
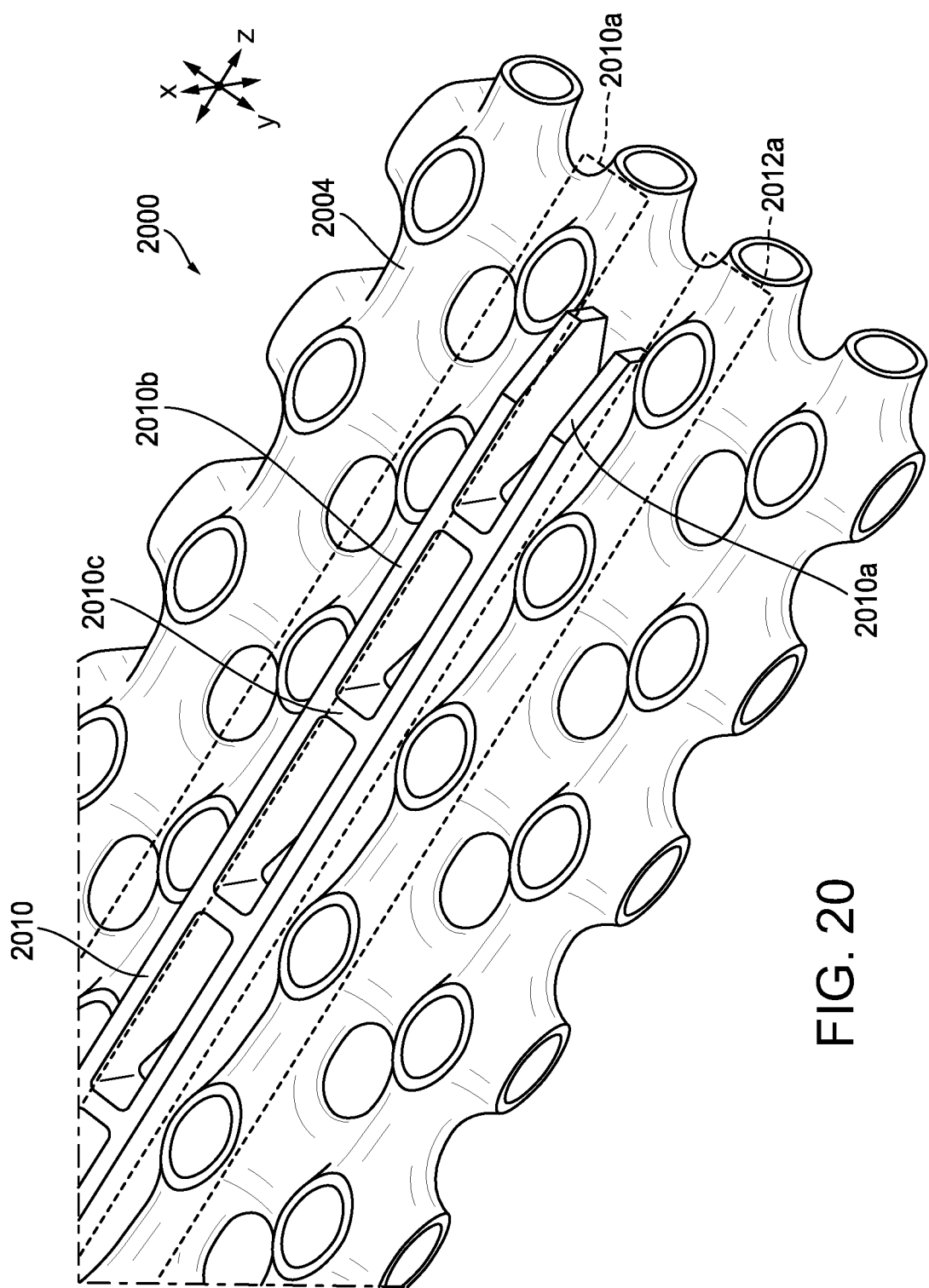
FIG. 20 is a partial perspective of another exemplary embodiment of a compressible non-fibrous adjunct having a channel attachment.

The channel attachment can have other configurations (e.g., shapes and/or dimensions). For example, as shown in FIG. 20, adjunct 2000 is similar to adjunct 800 shown in FIGS. 8A-8X except that adjunct 2000 also includes a channel attachment 2010 in the form of an elongated projection that extends outward from the cartridge-contacting surface 2004 of the adjunct 2000 and is positioned between the two inner rows of repeating unit cells 2010a, 2012a. The elongated projection 2010 is configured to be inserted into a longitudinal slot of a cartridge, like longitudinal slot 210 of cartridge 200 in FIGS. 2A and 2C.

While the elongated projection 2010 can have a variety of configurations, in this illustrated embodiment, the elongated projection 2010 is formed of two compressible longitudinal rods 2010a, 2010b with cross rods 2010c extending therebetween. In some embodiments, the width of the elongated projection 2010 (e.g., in the y-direction) is greater than a width of a longitudinal slot (e.g., the distance between the two opposing slot walls) of a staple cartridge. As a result, when the elongated projection 2010 is inserted into the longitudinal slot, like longitudinal slot 210 of cartridge 200 in FIGS. 2A-2C, the two longitudinal rods are configured to engage (e.g., compress against) the opposing slot walls due to the outward lateral force being created by the cross rods 2010c. As such, a press fit or friction fit is formed between the elongated projection 2010 and the slot walls of the cartridge.

Figure 21:
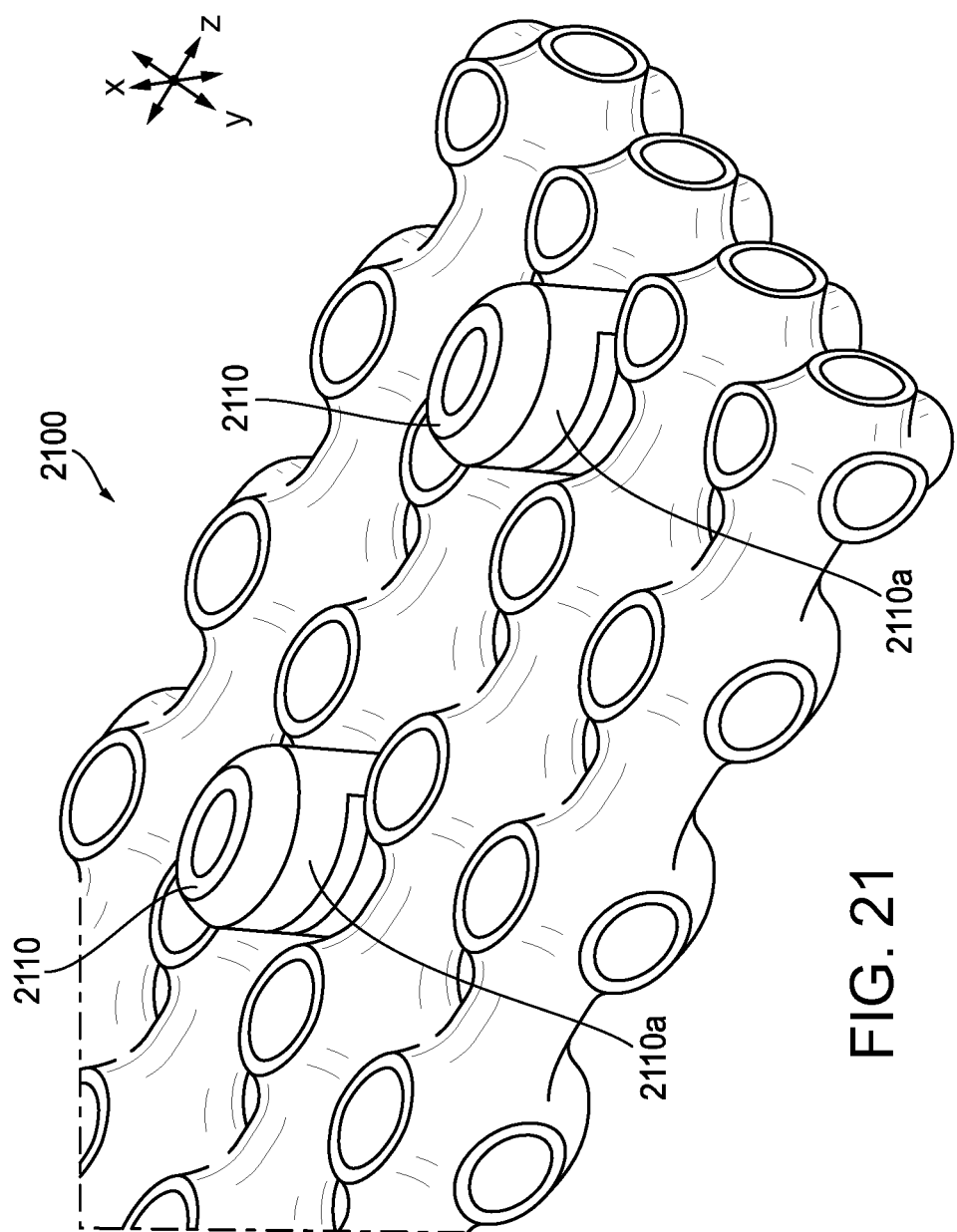
FIG. 21 is a partial perspective view of another exemplary embodiment of a compressible non-fibrous adjunct having a channel attachment.

FIG. 21 illustrates another embodiment of an adjunct 2100 having a channel attachment. Adjunct 2100 is similar to adjunct 2000 shown in FIG. 20 except that the channel attachment is in the form of discrete projections 2110 (only two are illustrated in FIG. 21) that are spaced apart relative to each other along the longitudinal axis $L_A$ of the adjunct 2100. While the projections 2110 can have a variety of configurations, in this illustrated embodiment, each projection 2110 is in the form of an annular boss having an oblong shape. In other embodiments, the projections 2110 can be any other suitable shape and/or vary in size/shape relative to each other. Each annular boss 2110 can be configured to be compressible, and in some embodiments, dimensioned such that the width of each boss (e.g., in the y-direction) can be greater than the width of a longitudinal slot (e.g., the distance between the two opposing slot walls) of a staple cartridge, like longitudinal slot 210 in cartridge 200 in FIGS. 2A-2C. As a result, when the discrete annular bosses 2110 are inserted into a longitudinal slot of a cartridge, their outer surface 2110a is configured to engage (e.g., compress against) the opposing slot walls due to the outward radial force of the annular boss. As such, a press fit or friction fit is formed between the annular bosses 2110a and the slot walls of the longitudinal slot.

Figure 22A:
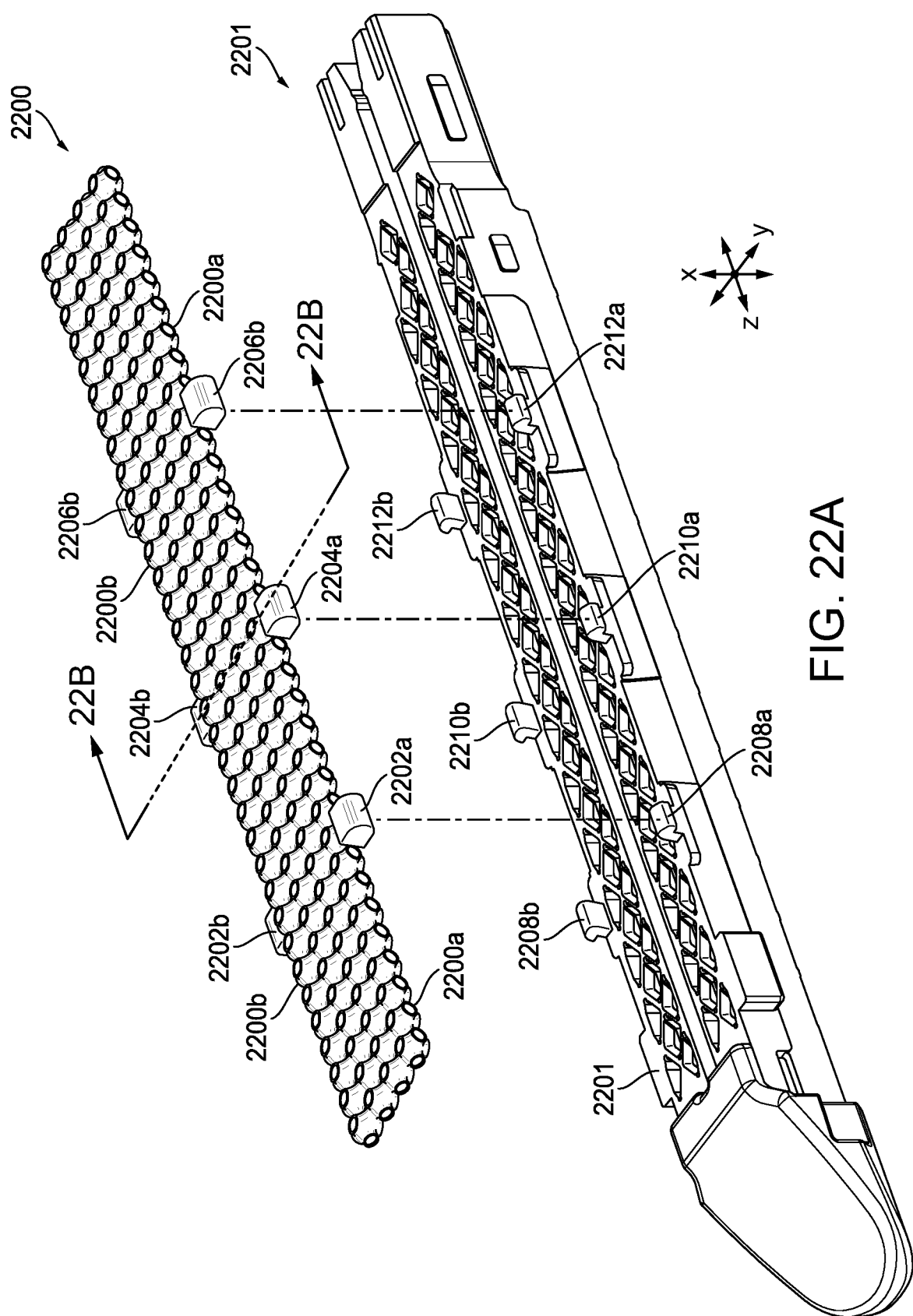
FIG. 22A is a partial exploded perspective view of an exemplary embodiment of a stapling assembly having a compressible non-fibrous adjunct releasably retained on a staple cartridge, each with corresponding edge attachment features.
Figure 22C:
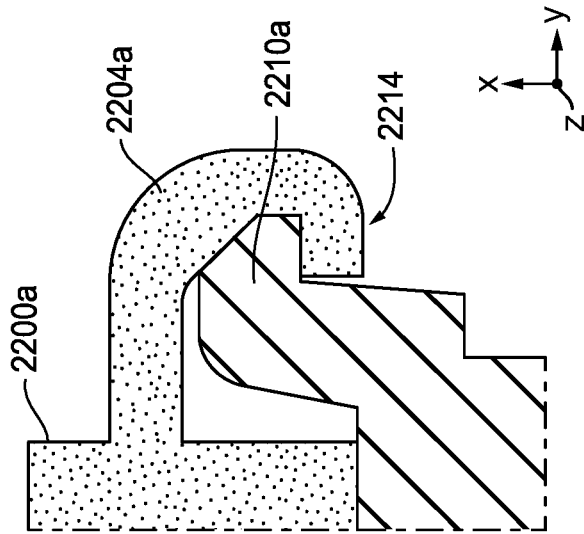
FIG. 22C is cross-sectional view of the portion of the stapling assembly of FIG. 22B, showing the two edge attachment features engaged.
Figure 22B:
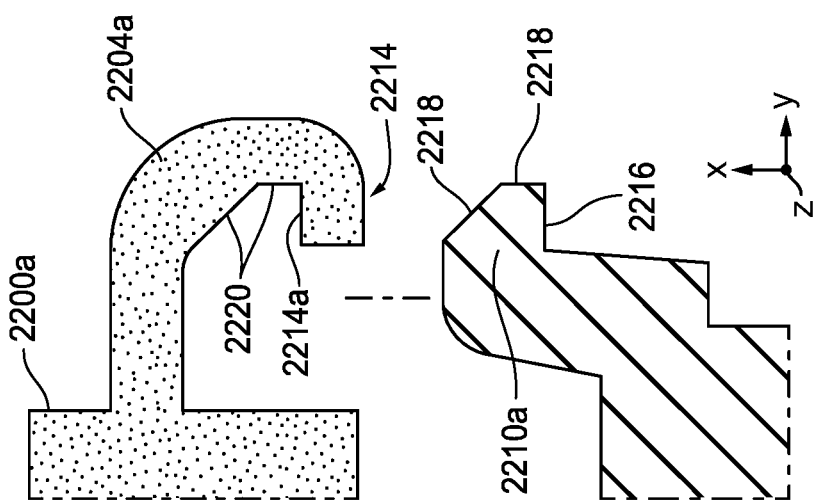
FIG. 22B is a magnified cross-sectional view of a portion of the stapling assembly taken at line 22B-22B, showing two edge attachment features prior to engagement.

Alternatively, or in addition, in some embodiments, an adjunct can include edge attachment features which are configured to engage corresponding edge attachment features of an adjunct. For example, as illustrated in FIGS. 22A-22C, an adjunct 2200 can include three sets of opposing clips 2202a, 2202b, 2204a, 2204b, 2206a, 2206b that each extend laterally outward and away from opposing outer sides surfaces 2200a, 2200b of the adjunct 2200. While the three sets of clips 2202a, 2202b, 2204a, 2204b, 2206a, 2206b can have a variety of configurations, in this illustrated embodiment, the three sets of clips 2202a, 2202b, 2204a, 2204b, 2206a, 2206b each have a hooked shaped configuration that engages with respective edge attachment features 2208a, 2208b, 2210a, 2210b, 2212a, 2212b of the cartridge 2201. In this illustrated embodiment, each edge attachment feature 2208a, 2208b, 2210a, 2210b, 2212a, 2212b has an inverted L-shaped configuration thereby creating a flange extending laterally outward from the staple cartridge 2201 (only one flange is shown in detail in FIGS. 22B-22C).

The engagement of one clip 2204a of the adjunct 2200 and one flange 2210a of the cartridge 2201 is illustrated in FIG. 22C. For sake of simplicity, the repeating unit cells of adjunct 2200 are omitted. As shown, the inner surface 2214a of the end portion 2214 of the clip 2204a engages the outer bottom surface 2216 of the flange 2210a, thereby causing a portion of the outer surface 2218 of the flange 2210a to nest against a corresponding portion of the inner surface 2220 of the clip 2204a (e.g., male/female engagement). Further, as shown in FIG. 22C, the flange 2210a is biased outward, and as a result, the portion of outer surface 2218 of the flange 2210a is forced against the corresponding portion of the inner surface 2220a of the clip 2204a when they are engaged.

Figure 23A:
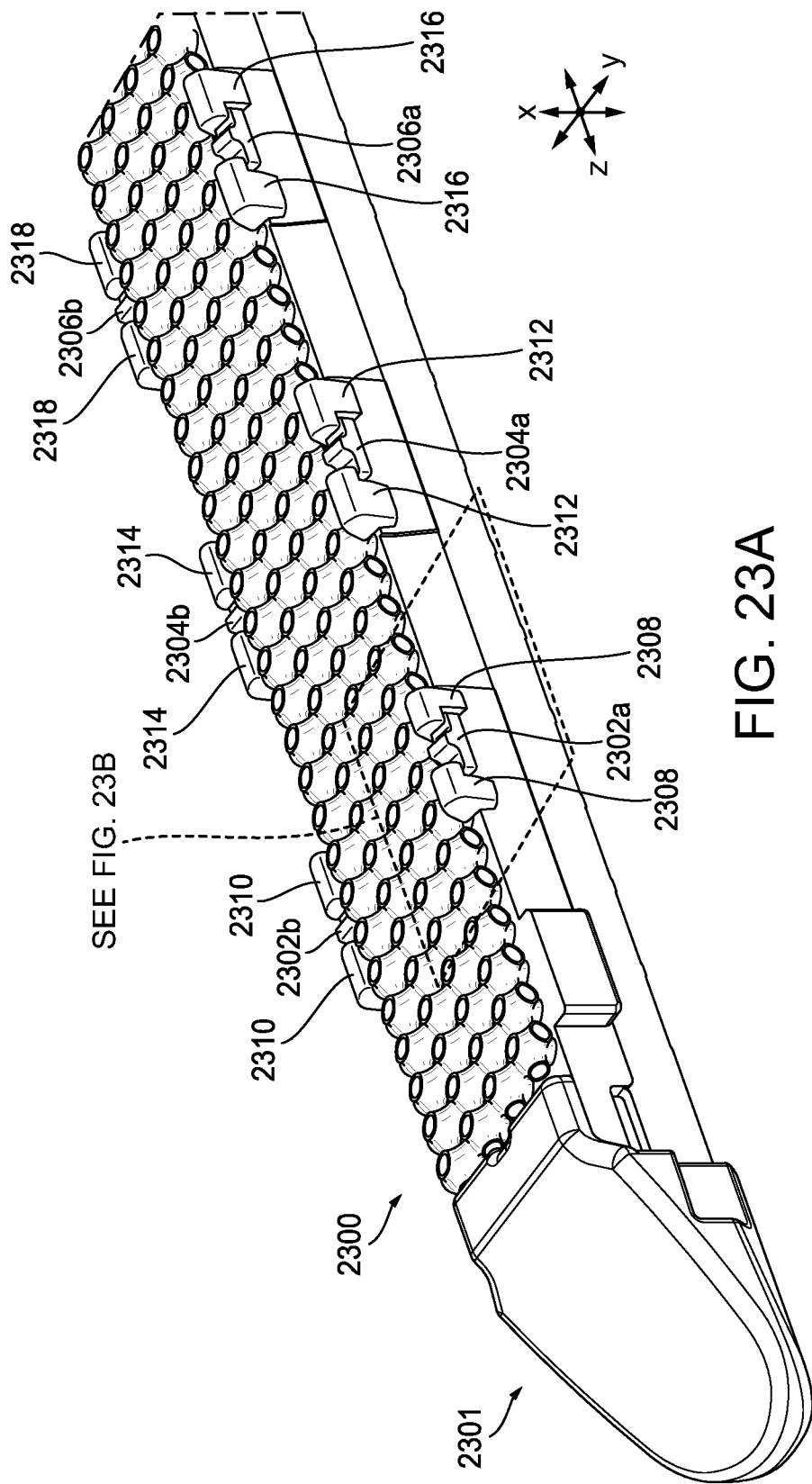
FIG. 23A is perspective view of another exemplary embodiment of stapling assembly having a compressible non-fibrous adjunct releasably retained on a staple cartridge, each with corresponding edge attachment features, showing the edge attachment features engaged.
Figure 23B:
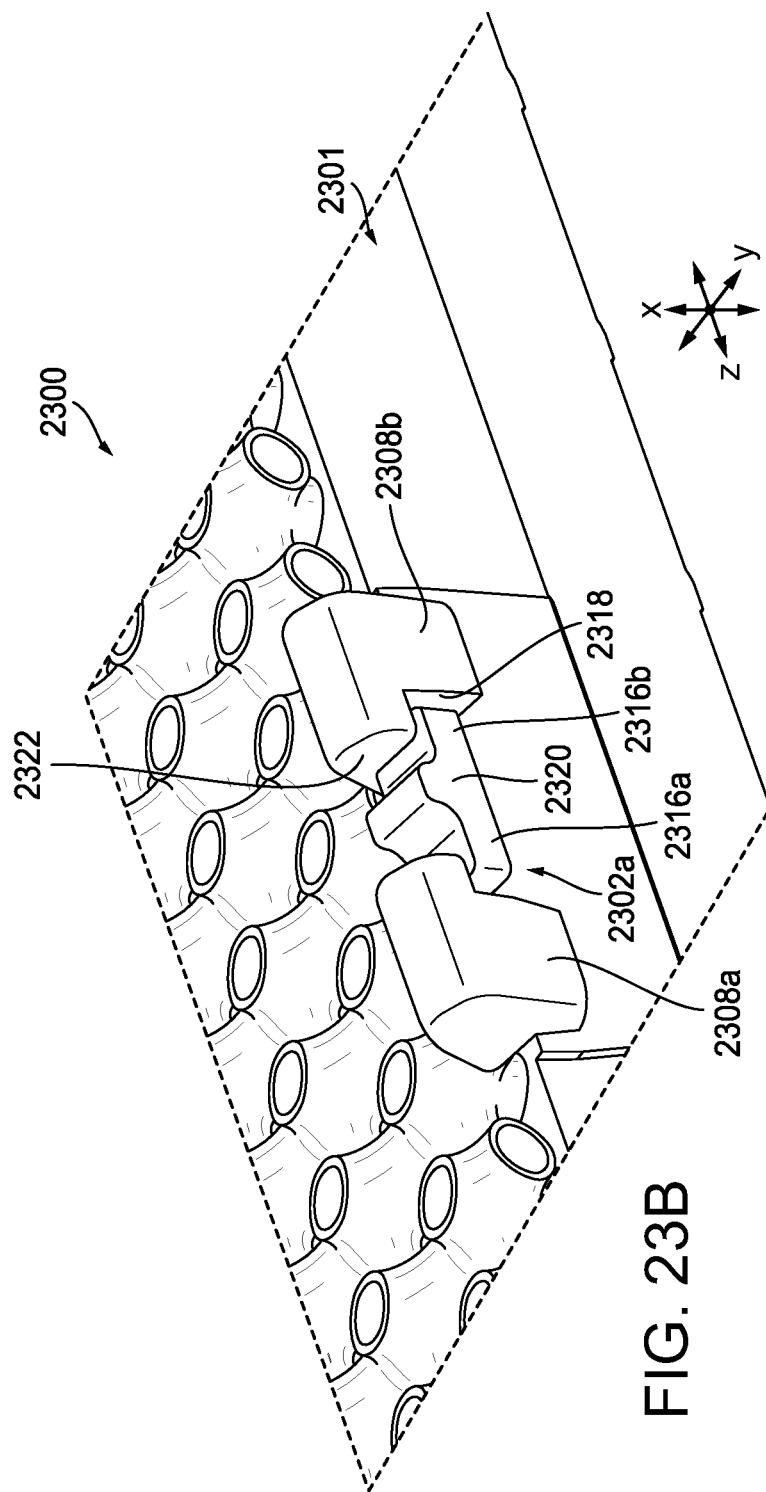
FIG. 23B is a magnified view of a portion of the stapling assembly of FIG. 23B.

FIGS. 23A-23B illustrate another embodiment of an adjunct having three sets of opposing clips 2302a, 2302b (partially obstructed), 2304a, 2304b (partially obstructed), 2306a, 2306b (partially obstructed) that are configured to engage a corresponding set of opposing receiving members 2308, 2310 (partially obstructed), 2312, 2314 (partially obstructed), 2316, 2318 (partially obstructed) of the staple cartridge 2301.

In this illustrated embodiment, each clip is structurally the same and has an inverted T-shaped configuration. Further, as shown, each set of receiving members is the structurally the same and includes two inverted L-shaped members that are spaced apart and face each other to form a t-shaped void therebetween. By way of example, the engagement of one clip 2302a with its corresponding set of receiving members 2308a, 2308b is shown in more detail in FIG. 23B. As shown, the lateral segments 2316a, 2316b (e.g., extending in the z-direction) of the clip 2302a are configured to be engage with the respective inner surfaces (only one inner surface 3118 is illustrated) of each L-shaped member 2308a, 2308b, and the vertical segment 2320 (e.g., extending in the x-direction) of the clip 2302a is configured to be positioned between the two facing surfaces (only one facing surface 2322 is illustrated) of the L-shaped members 2308a, 2308b. As such, the vertical segment 2320 can help with maintaining the longitudinal alignment of the adjunct 2300 relative to the staple cartridge 2301, and thus the staples disposed therein (not shown). During use, the vertical segment 2320 can also help prevent premature disengagement of the clip 2302a from the corresponding set of receiving members 2308a, 2308b, and thus the adjunct 2300 from the cartridge 2301.

Alternatively, or in addition, in some embodiments, an adjunct can include end attachment features, such as opposing proximal and distal sets of bosses that are configured engage (e.g., press fit) into corresponding proximal and distal sets of recesses defined in the staple cartridge. For example, in one embodiment, an adjunct can have rectangular bosses that are configured to engage proximal and distal sets of rectangular recesses 2402a, 2402b, 2404a, 2404b of staple cartridge 2400 in FIG. 24. In another embodiment, an adjunct can have circular bosses that are configured to engage proximal and distal sets of circular recesses 2502a, 2502b, 2504a, 2504b of staple cartridge 2500 in FIG. 25.

As noted above, in certain embodiments, the staple cartridge can include surface features that are in the form of recessed channels, like recessed channels 216, 218, 220 as shown in FIGS. 2A and 2C. In such embodiments, the adjunct can be designed to engage with the recessed channels to effect a releasable attachment mechanism between the adjunct and the staple cartridge, even when the frequency of staples within a longitudinal staple row (e.g., the number of staples per length of staple row) are different (e.g., greater) than the frequency of the repeating unit cells within a corresponding longitudinal unit cell row (e.g., the number of unit cells per length of the cell row).

Figure 26A:
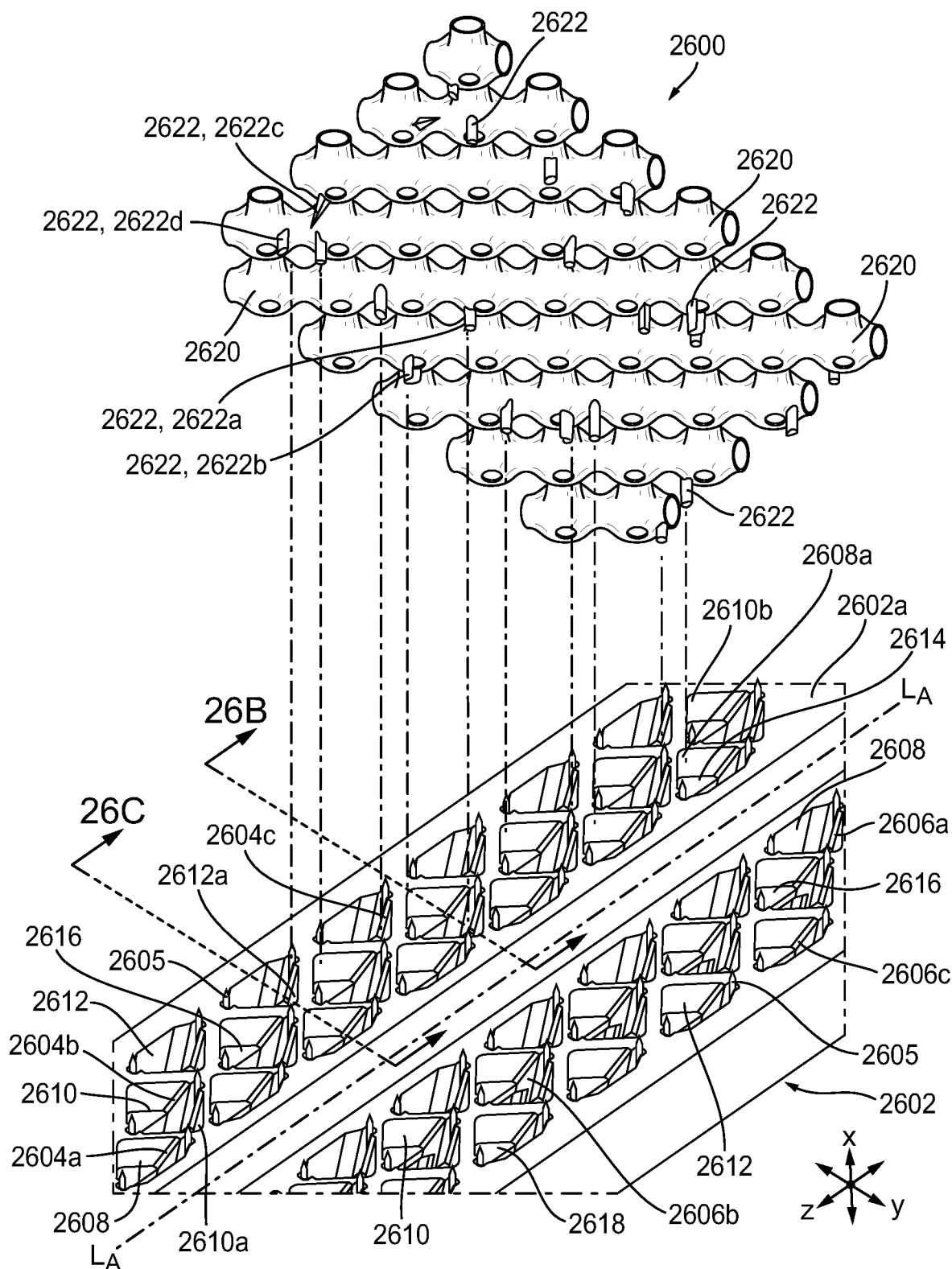
FIG. 26A is a exploded view of another exemplary embodiment of a stapling assembly having a staple cartridge and a compressible non-fibrous adjunct with attachment features releasably retained thereon.
Figure 26B:
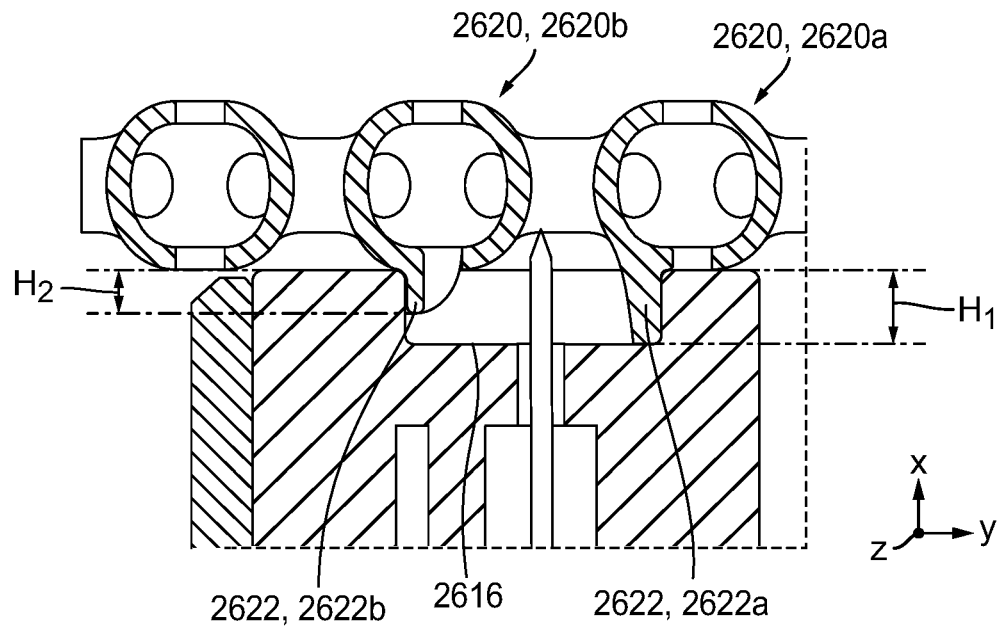
FIG. 26B is a cross-sectional view of the stapling assembly of FIG. 26A taken at line 26B-26B.
Figure 26C:
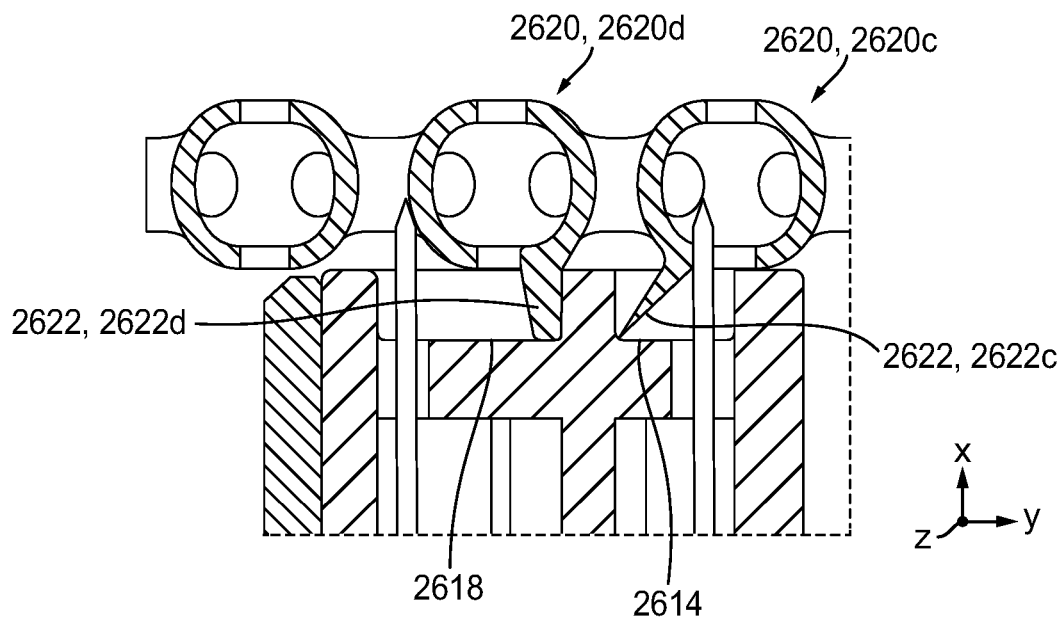
FIG. 26C is a cross-sectional view of the stapling assembly of FIG. 26A taken at line 26C-26C.

FIGS. 26A-26C illustrate an adjunct 2600 disposed on a staple cartridge 2602 which is similar to staple cartridge 200 in FIGS. 2A-2C and therefore common features are not described in detail herein. The staple cartridge 2602 includes staple cavities that are arranged in longitudinal rows 2604a, 2604b, 2604c, 2606a, 2606b, 2606c and recessed channels that surround each staple cavity 2604a, 2604b, 2604c, 2606a, 2606b, 2606c. As shown, a first recessed channel 2608 surrounds each first staple cavity 2604a, 2606a, a second recessed channel 2610 surrounds each second staple cavity 2604b, 2606b, and a third recessed channel 2612 surrounds each third staple cavity 2604c, 2606c. The first, second, and third recessed channels each include a respective floor 2614, 2616, 2618 which is at a respective height (e.g., extending in the x-direction) from the top surface 2602a of the staple cartridge 2602. In this illustrated embodiment, the respective heights are the same, whereas in other embodiments, the respective heights can be different.

While the adjunct 2600 can have a variety of configurations, in this illustrated embodiment, the adjunct 2600 is formed of repeating unit cells 2620 and attachment features 2622 that extend from at least a portion of the plurality of unit cells 2620. The attachment features 2622 are each configured to be inserted into and engage with at least a portion of the recessed channels 2608, 2610, 2612 of the staple cartridge 2602 to thereby retain the adjunct 2600 to the cartridge 2602 prior to staple deployment.

While the attachment features 2622 can have a variety of configurations, each attachment feature has a different geometry so that the each attachment feature can engage a respective recessed channel. This difference in geometry is due to difference in the frequency of unit cells compared to the frequency of the staples 2605 of the staple cavities 2604a, 2604b, 2604c, 2606a, 2606b, 2606c of the staple cartridge 2602. Thus, the attachment features 2622 are positioned on respective unit cells 2620 at predefined positions that correspond to the recessed channels 2608, 2610, 2612. As shown in FIG. 26A, and in more detail in FIGS. 26B-26C, which only illustrates one half (e.g., the left half) of the adjunct 2600, the respective geometries of the attachment features 2622 are configured to engage respective vertices 2608a, 2610a, 2610b, 2612a of the recessed channels 2608, 2610, 2612 that point laterally outward relative to the longitudinal axis $L_A$ of the staple cartridge 2602. In other embodiments, the geometries of the attachment features can be configured to engage other portions of the recessed channels.

The geometry of the attachment features 2622 can vary laterally and/or longitudinally relative to the longitudinal axis of the cartridge. The geometric variations depend at least upon the frequency of the unit cells 2620 relative to the frequency of the staples 2605 and the shape(s) of the staple cavities 2604a, 2604b, 2604c, 2606a, 2606b, 2606c. For example, the attachment features 2622 can vary in at least one of height (e.g., in the x-direction), width (e.g., in the y-direction), length (e.g., in the z-direction), and shape relative to each other. For example, as shown in FIG. 26B, the height $H_1$ of a first attachment feature 2622a extending from first repeating unit cell 2620a is greater than the height $H_2$ of a second attachment 2622b extending from second repeating unit cell 2620b, and thus the height of the first and second attachment features 2622a, 2622b differ laterally relative to the longitudinal axis $L_A$ of the cartridge 2602. In this illustrated embodiment, as further shown in FIGS. 26A and 26B, the shape of each of the first and second attachment features 2622a, 2622b also varies laterally relative to the longitudinal axis $L_A$ of the cartridge 2602. The first attachment feature 2622a has a cylindrical shaped configuration and the second attachment feature 2622b has an arcuate configuration. Alternatively, or in addition, the length of two or more of the attachment features can vary along the longitudinal axis $L_A$ of the cartridge 2602. For example, as shown in FIG. 26A, third and fourth repeating unit cells 2620c, 2620d include third and fourth attachment features 2622c, 2622d, respectively, that vary in length (e.g., extending in the z-direction) and shape along the longitudinal axis $L_A$ of the cartridge 2602. In this illustrated embodiment, the third attachment feature 2622c has an cylindrical configuration, whereas the fourth attachment feature 2622d has a triangular configuration.

In certain embodiments, lateral variations in the shape and/or height of the attachment features can correspond to lateral variations of the recessed channels. For example, while not illustrated, in some embodiments the walls of at least a portion of the recessed channels can extend at an angle relative to the longitudinal axis of the cartridge, and a result one or more of the attachment features can vary in shape and/or height to correspond thereto. In other embodiments, the length of the recessed channels can vary laterally, and one or more of the attachment features can vary in shape and/or height to correspond thereto.

Unit Cell Frequency

Non-strut-based adjuncts can vary in thickness longitudinally (e.g., along its length, e.g., in the z-direction) and/or laterally (e.g., along its width, e.g., in the y-direction). As a result, where the frequency of staples within a longitudinal staple row (e.g., the number of staples per length of staple row) is different (e.g., greater) than the frequency of the repeating unit cells within a corresponding longitudinal unit cell row (e.g., the number of unit cells per length of the cell row), the staple legs of each staple can advance through different portions of the adjunct with each portion having a relative thickness difference, as illustrated in FIG. 27.

Figure 27:
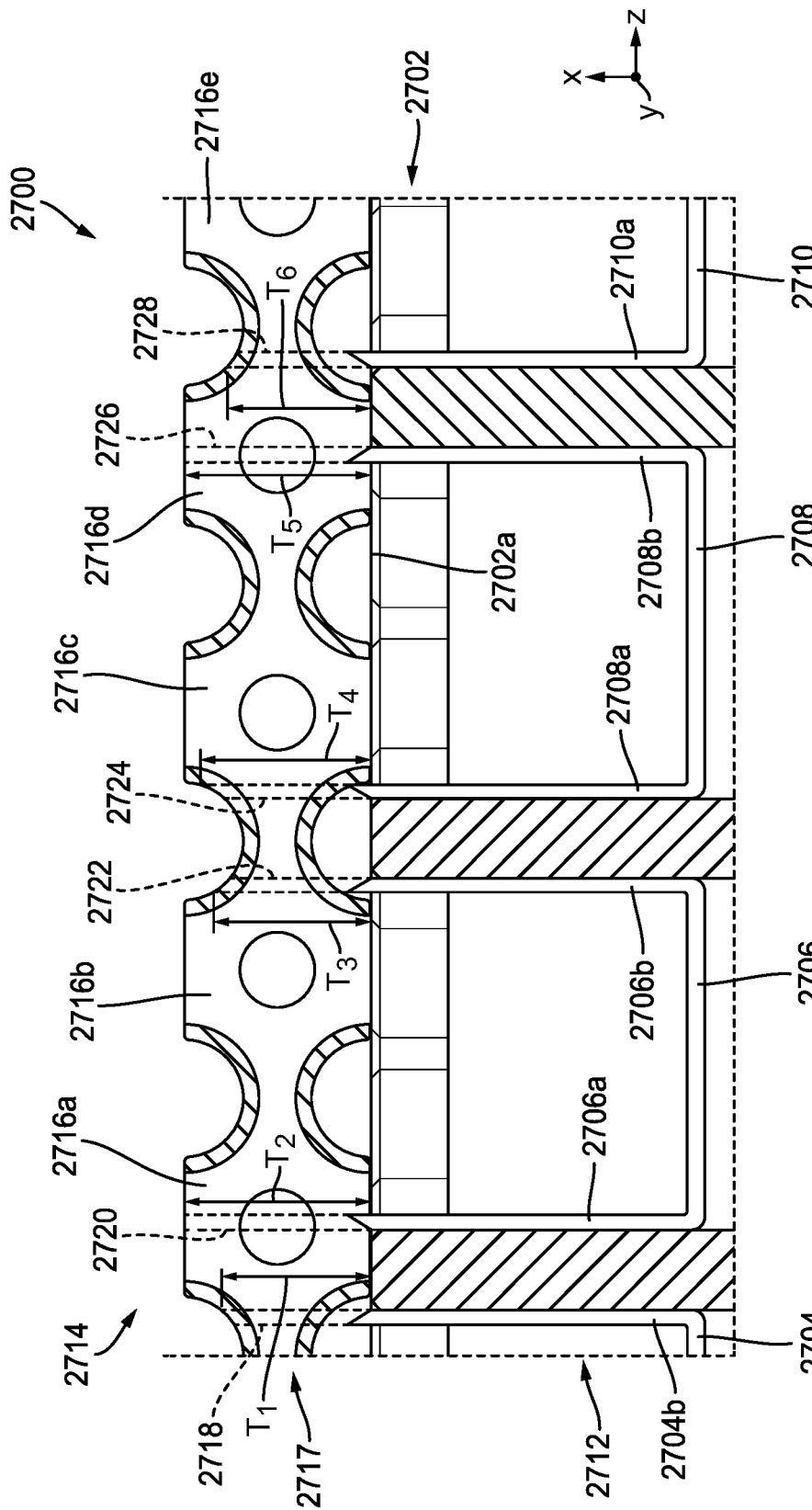
FIG. 27 is a partial cross-sectional view of another exemplary embodiment of a stapling assembly having a compressible non-fibrous adjunct releasably retained on a staple cartridge.

FIG. 27 illustrates an exemplary embodiment a stapling assembly 2700 having a staple cartridge 2702, like staple cartridge 200 in FIGS. 1-2C, and having staples arranged in longitudinal rows (only illustrating four staples 2704, 2706, 2708, 2710 of a portion of a first longitudinal staple row 2712 is being illustrated). An adjunct 2714 is disposed on a top surface 2702a of the staple cartridge 2702. The adjunct 2714 includes interconnected repeating strut-less unit cells, like repeating unit cells 810 in FIGS. 8A-9C, (only five repeating unit cells 2716a, 2716b, 2716c, 2716d, 2716e being illustrated) that are arranged in longitudinal rows (only a portion of a first longitudinal unit cell row 2717 being illustrated). As shown, the first longitudinal unit row 2717 overlaps with the first longitudinal staple row 2712, and the frequency of staples 2704, 2706, 2708, 2710 is different than the frequency of unit cells 2716a, 2716b, 2716c, 2716d, 2716e (e.g., non-multiple). As a result, each staple leg 2704b, 2706a, 2706b, 2708a, 2708b, 2710a of respective staples 2704, 2706, 2708, 2710 is aligned with, and thus will penetrate through, different respective portions 2718, 2720, 2722, 2724, 2726 of the first longitudinal unit cell row 2712, and thus the adjunct 2714, e.g., when the adjunct 2714 is stapled to tissue. Further, as illustrated in FIG. 27, due to the structural configuration of the repeating unit cells 2716a, 2716b, 2716c, 2716d, 2716e (e.g., generally not square), at least two or more of these different portions 2718, 2720, 2722, 2724, 2726, 2728 can have a different relative thicknesses $T_1$, $T_2$, $T_3$, $T_4$, $T_5$ (e.g., thick vs thin), and thus the thickness of the adjunct 2714 captured within a fired staple will vary among adjacent staples stapled to consistent tissue.

In some embodiments, the difference in relative thickness of the adjunct can be paired with a corresponding difference in staple leg length. For example, when the staple and unit cell frequencies are the same, the legs of any staples configured to advance through a thicker portion of the adjunct can be longer in length than the legs of any staples configured to advance through a thinner portion of the adjunct. Alternatively, or in addition, the difference in relative thickness can be paired with corresponding differences in anvil pocket depth, or, if the staple driver is at the same height, with tissue gap differences between the first staple leg to the second staple if the staple driver is at the same height.

Figure 28A:
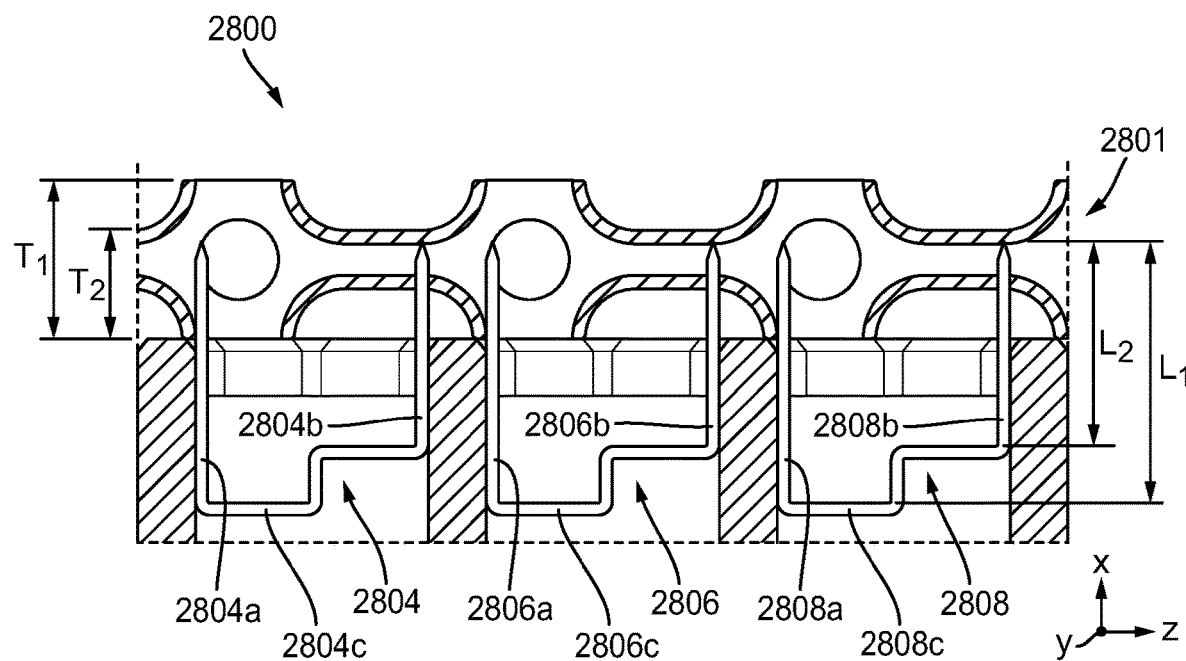
FIG. 28A is a partial cross-sectional view of another exemplary embodiment of a stapling assembly having a compressible non-fibrous adjunct releasably retained on a staple cartridge.
Figure 28B:
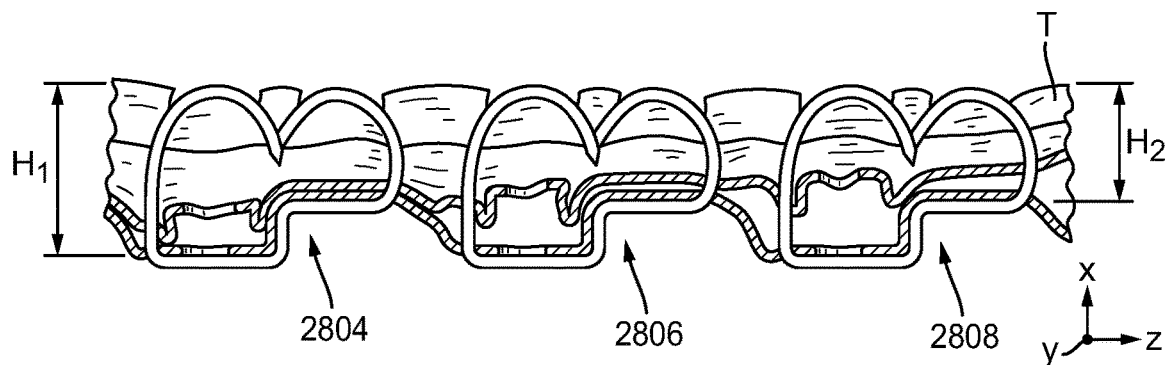
FIG. 28B is a partial-schematic illustrating the adjunct of FIG. 28A in a tissue deployed condition.
Figure 29:
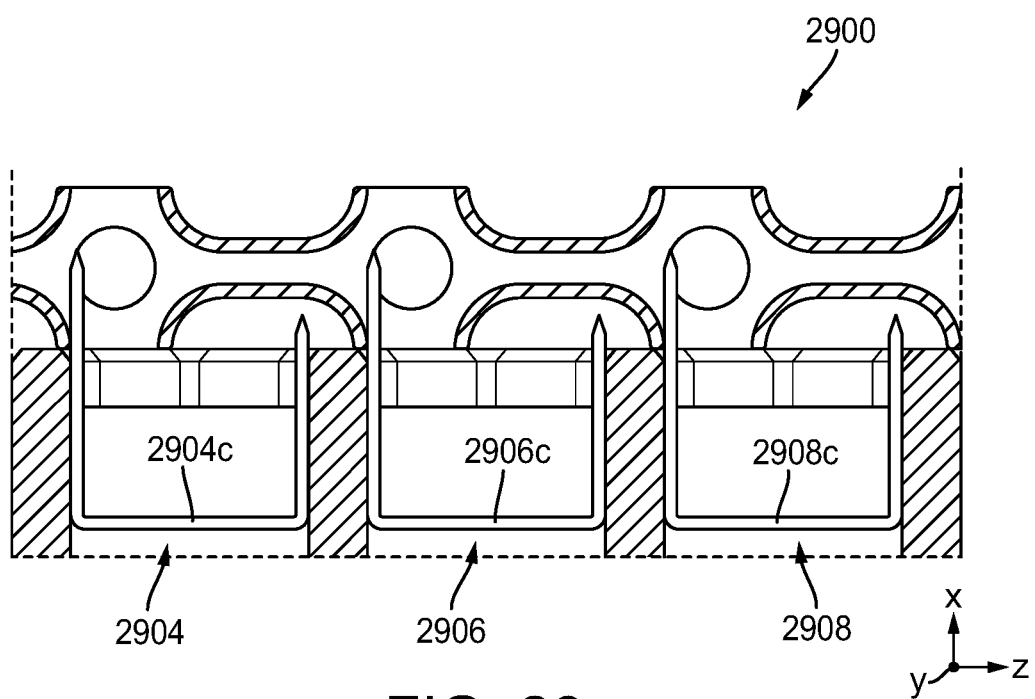
FIG. 29 is a partial cross-sectional view of another exemplary embodiment of a stapling assembly having a compressible non-fibrous adjunct releasably retained on a staple cartridge.

FIG. 28A illustrates an exemplary embodiment of a stapling assembly 2800 that is similar to stapling assembly 2700 in FIG. 27 except that the structural configuration of the adjunct 2801 has been modified such that the staple and unit cell frequencies are the same. As a result, the first staple leg 2804a, 2806a, 2808a of each staple 2804, 2806, 2808 is configured to go through respective portions of the adjunct having the same first thickness $T_1$ and the second staple leg 2804b, 2806b, 2808b of each staple 2804, 2806, 2808 is configured to go through respective portions of the adjunct 2801 have the same second thickness $T_2$. As shown, the first thickness $T_1$ is greater than the second thickness $T_2$, and therefore, to offset the difference in thickness, the first leg length $L_1$ can be greater than the second leg length $L_2$ for each staple 2804, 2806, 2808. In this illustrated embodiment, the crown 2804c, 2806c, 2808c of each staple 2804, 2806, 2808 has a non-planar configuration (e.g., a step-up configuration) to effect the difference in staple leg length. Further, when the staples 2804, 2806, 2808 are deployed and the adjunct 2801 is stapled to tissue T, each staple will have two different formed staple heights $H_1$, $H_2$, as illustrated in FIG. 28B. FIG. 29 illustrates another exemplary embodiment of a stapling assembly 2900 that is similar to stapling assembly 2800 except that the crown 2904c, 2906c, 2908c of each staple 2904, 2906, 2908 is generally planar (e.g., generally straight or linear within manufacturing tolerances), and as a result, the formed staple height of the first staple will be generally uniform (e.g., nominally identical within manufacturing tolerances).

Strut-Based Adjuncts

As noted above, the adjuncts can include a lattice structure formed of strut-based unit cells (e.g., defined by planar interconnected struts). In general, such adjuncts can include a tissue-contacting layer, a cartridge-contacting layer, and an internal structure (e.g., buckling structure). The internal structure generally includes struts (e.g., spacer struts) connecting the tissue-contacting layer and the cartridge-contacting layer together in a spaced-apart relation. These struts can be configured to collapse without contacting one another while the adjunct compresses under stress. As a result, densification of the adjunct can be delayed, and thus can occur at a higher strain.

The tissue-contacting layer and cartridge-contacting layer can have a variety of configurations. In some embodiments, at least one of the tissue-contacting layer and the cartridge-contacting layer can include a plurality of struts that define openings. In some embodiments, the tissue-contacting layer and the cartridge-contacting layer are both generally planar (e.g., planar within a manufacturing tolerance). The tissue-contacting layer and the cartridge-contacting layer can be oriented parallel to one another along a longitudinal axis extending from a first end to a second end of the adjunct, and can further define a vertical axis extending therebetween.

The strut can have various configurations. For example, in some embodiments, a strut can have a generally uniform cross-section (e.g., uniform within manufacturing tolerances), whereas in other embodiments the strut can have a varying cross-section. In some embodiments, the adjunct can have an average strut thickness in a range of about 0.1 mm to 0.5 mm, from about 0.1 mm to 0.4 mm, or from about 0.1 mm to 0.3 mm.

Figure 30A:
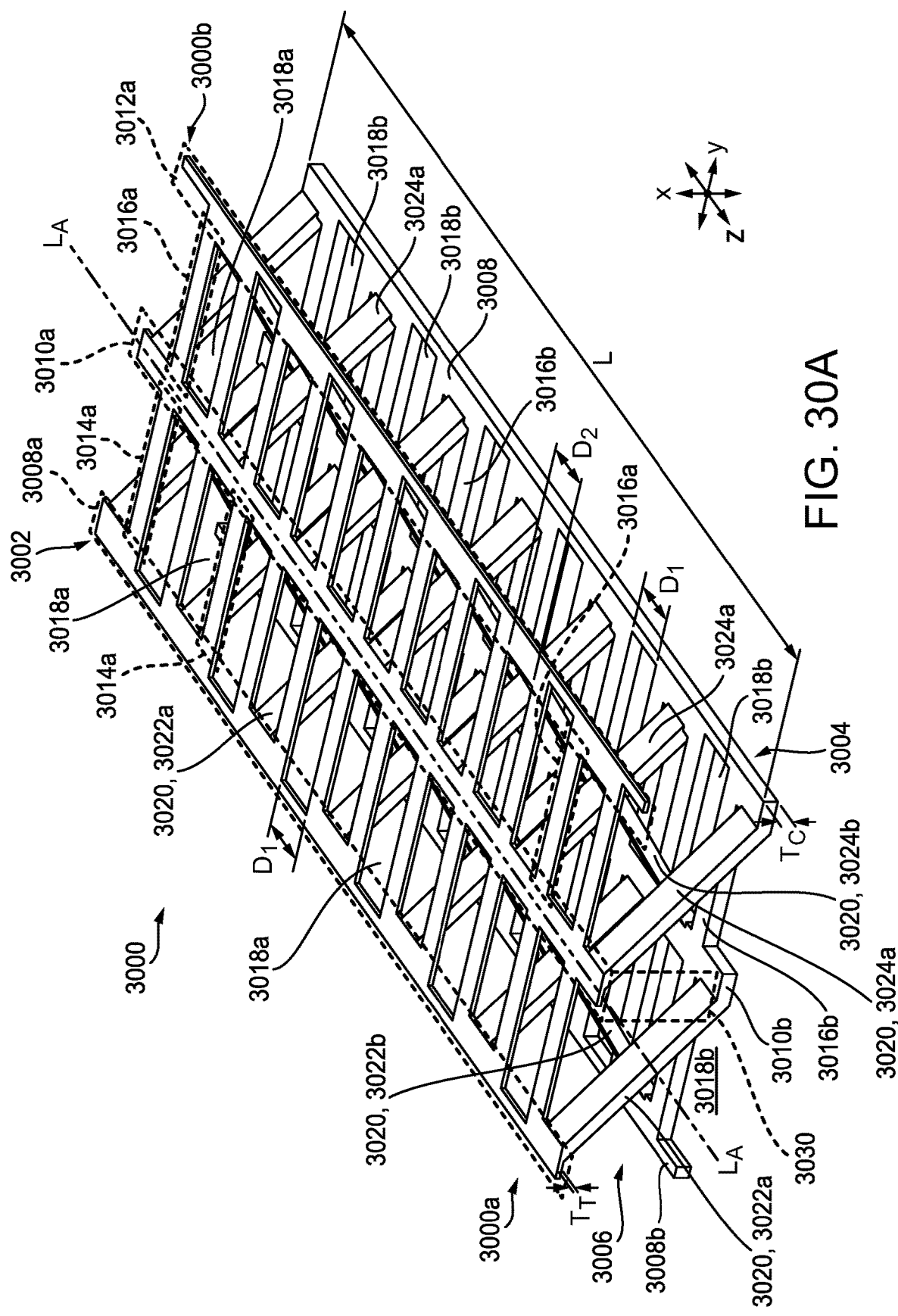
FIG. 30A is a perspective view of another exemplary embodiment of a compressible non-fibrous adjunct.
Figure 30B:
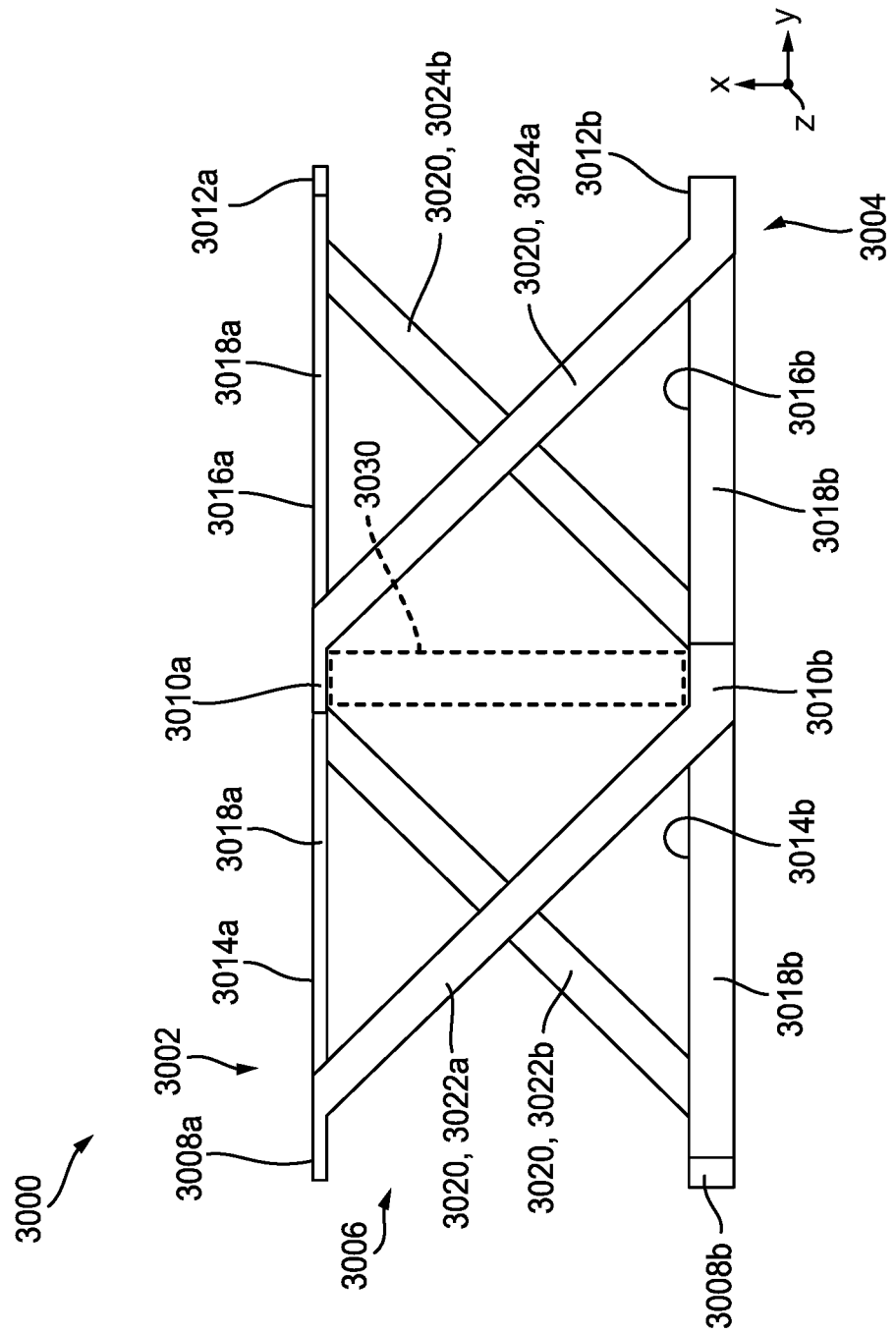
FIG. 30B is a front plan view of the adjunct of FIG. 30A.

FIGS. 30A-30B illustrate an exemplary strut-based adjunct 3000. The adjunct 3000 includes a tissue-contacting layer 3002, a cartridge-contacting layer 3004, and an internal structure 3006 extending therebetween. The internal structure 3006 is configured to collapse (compress) while the adjunct 3000 is under an applied stress, and therefore cause the adjunct 3000 to compress when stapled to tissue.

While the tissue-contacting layer 3002 and the cartridge-contacting layer 3004 can have a variety of configurations, in this illustrated embodiment they are both generally planar (e.g., planar within manufacturing tolerances). Further, the tissue-contacting layer 3002 and the cartridge-contacting layer 3004 are parallel to one another along a longitudinal axis ($L_A$) extending from a first end 3000a to a second end 3000b of the adjunct 3000. As shown, the tissue-contacting layer 3002 and the cartridge-contacting layer 3004 are inverted images of each other, with the thickness ($T_C$) of the cartridge-contacting layer 3004 being greater than the thickness ($T_T$) of the tissue-contacting layer 3002. As such, for sake of simplicity, the following description is with respect to the tissue-contacting layer 3002. A person skilled in the art will appreciate, however, that the following discussion is also applicable to the cartridge-contacting layer 3004.

The tissue-contacting layer 3002 has first, second, and third longitudinal struts 3008a, 3010a, 3012a extending along and parallel to the longitudinal axis (L) of the adjunct 3000, in which the second longitudinal strut 3010a is positioned between, but spaced apart from, the first and third longitudinal struts 3008a, 3012a. The tissue-contacting layer 3002 also includes first cross struts 3014a and second cross struts 3016a. Each of the first cross struts 3014a is connected to the first and second longitudinal struts 3008a, 3010a. While the first cross struts 3014a can be oriented in a variety of different positions, in this illustrated embodiment, the first cross struts 3014a are oriented orthogonally relative to the first and second longitudinal struts 3008a, 3010a. Similarly, each of the second cross struts 3016a is connected to the second and third longitudinal struts 3010a, 3012a. While the second cross struts 3016a can be oriented in a variety of different positions, in this illustrated embodiment, the second cross struts 3016a are oriented orthogonally relative to the second and third longitudinal struts 3010a, 3012a. Further, as shown, the first cross struts 3014a are in alignment with the second cross struts 3016a in the y-direction.

Further, the first cross struts 3014a are longitudinally spaced apart from one another at a first distance $D_1$, and the second cross-struts are longitudinally spaced apart from one another at a second distance $D_2$. As a result, openings 3018a are created within the tissue-contacting layer 3002. While the openings 3018a can have a variety of sizes and shapes, in this illustrated embodiment, $D_1$ and $D_2$ are equal, or substantially equal, and therefore, combined with the orientation of the first and second cross struts 3014a, 3016a, the resulting openings 3018a are in the form of rectangles that have generally uniform dimensions (e.g., nominally identical within manufacturing tolerances).

While the internal structure 3006 can have a variety of configurations, in this illustrated embodiment, the internal structure 3006 includes spacer struts 3020 that extend between the tissue-contacting layer 3002 and the cartridge-contacting layer 3004. The spacer struts 3020 include a first set of angled struts 3022a, 3022b and a second set of angled struts 3024a, 3024b, each of which extend at an angle (e.g., 45 degrees) relative to the tissue-contacting and cartridge-contacting layers 3002, 3004. The first set of angled struts includes first angled struts 3022a extending from the first longitudinal strut 3008a of the tissue-contacting surface 3002 to the second longitudinal strut 3010b of the cartridge-contacting layer 3004, and second angled struts 3022b extending from the first longitudinal strut 3008b to the cartridge-contacting layer 3004 to the second longitudinal strut 3010a of the tissue-contacting layer 3002. As a result, the first and second angled struts 3022a, 3022b alternate along the length (L) of the adjunct. The second set of alternating angled struts includes third angled struts 3024a and fourth angled struts 3024b. The third angled struts 3024a are similar to the first angled struts 3022a except that the third angled struts 3024a extend from the second longitudinal strut 3010a of the tissue-contacting layer 3002 to the third longitudinal strut of 3012b of the cartridge-contacting layer 3004. The fourth angled struts 3024b are similar to the second angled struts 3022b except that the fourth angled struts 3024b extend from the second longitudinal strut 3010*b* of the cartridge-contacting layer 3004 to the third longitudinal strut of 3012*a* of the tissue-contacting layer 3002. As a result, in this illustrated embodiment, the first and third angled struts 3022*a*, 3024*a* extend in the same direction relative to each other and the second and fourth angled struts 3022*b*, 3024*b* extend in the same direction relative to each other.

As further shown in FIG. 30A, openings 3018*b* are created within the cartridge-contacting layer 3004 between the first cross struts 3014*b* and between the second cross-struts 3016*b*. Further, the angled struts 3022*a*, 3022*b*, 3024*a*, 3024*b* substantially overlap with a corresponding opening 3018*b* in at least the cartridge-contacting layer 3004, and as noted above, the cartridge-contacting layer 3004 has a thickness $T_C$ that is greater than the thickness $T_T$ of the tissue-contacting layer 3002. The openings 3018*b* defined in the cartridge-contacting layer 3004 can therefore be configured to receive at least a portion of the corresponding angled strut as it bends while the adjunct 3000 is being compressed under applied stress. This creates additional space within the internal structure 3006 for buckling, and thus reduces the solid height of the adjunct 3000. As a result, in use, densification of the adjunct 3000 can be delayed such that the adjunct 3000 can undergo a more broad range of deformation without reaching its solid height.

Further, by alternating the angled struts 3022*a*, 3022*b*, 3024*a*, 3024*b*, a centralized zone 3030 within the internal structure 3006 is created. As shown, this centralized zone 3030 extends along the adjunct in a longitudinal direction between the first and second sets of angled struts 3022*a*, 3022*b*, 3024*a*, 3024*b*. As a result, none of the struts 3020 within the internal structure 3006 overlap with this centralized zone 3030, as shown in more detail in FIG. 30B. Stated differently, this centralized zone 3030 is designed to be a strut-free space in which none of the struts cross into prior to or during compression of the adjunct. The presence of this centralized zone 3030 can therefore increase the densification point of the adjunct 3000 while the adjunct is stapled to tissue (e.g., decrease the solid height of the adjunct.). Additionally, the centralized zone can overlap with the cut-line of the adjunct, and therefore the amount of material along this cut-line can be decreased. This can help facilitate the advancement of a cutting element of a stapling device, and therefore make cutting of the adjunct easier.

FIGS. 31A, 32A, 33A, and 34A illustrate various other exemplary strut-based adjuncts 3100, 3200, 3300, and 3400. Each exemplary adjunct has a lattice structure formed from repeated interconnected strut-based unit cells, which are shown in more detail in FIGS. 31B-31D, 32B-32D, 33B-33E, and 34B-34E. These adjuncts are structured so as to compress when exposed to compressive forces (e.g., applied stress when stapled to tissue).

Figure 31A:
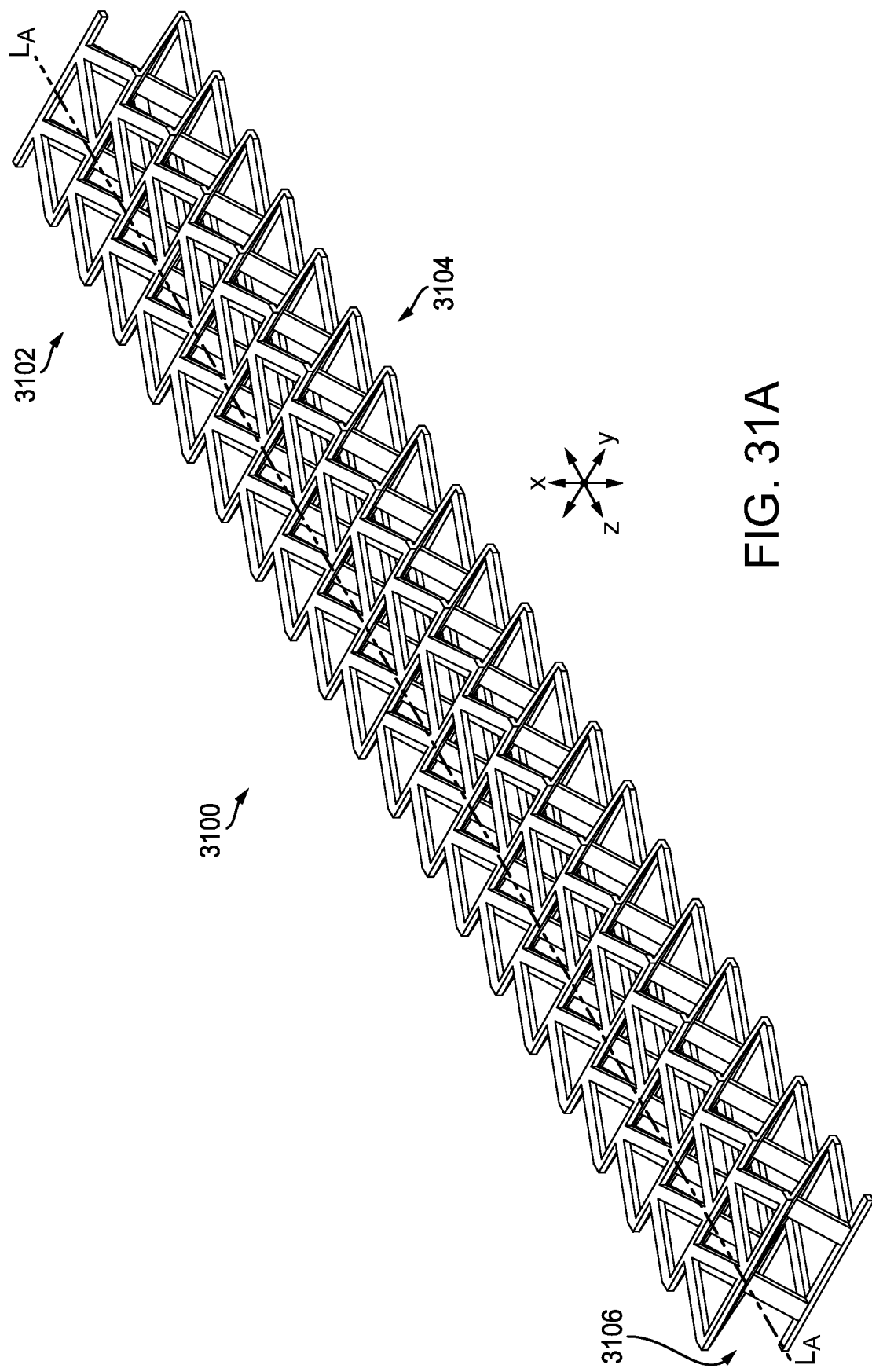
FIG. 31A is a perspective view of one embodiment of a compressible non-fibrous adjunct.

FIG. 31A illustrates another exemplary adjunct 3100 that is in the form of a lattice structure that includes a top portion 3102, a bottom portion 3104, and an internal structure 3106 extending therebetween. The top portion 3102 is configured to contact tissue, and therefore forms the tissue-contacting layer of the adjunct 3100, whereas the bottom portion 3104 is configured to attach to a cartridge, and therefore forms the cartridge-contacting layer of the adjunct 3100. The internal structure 3106 can be configured to compress into a deformed state under load, e.g., when stapled to tissue. The lattice is formed of an array of repeating unit cells 3110, one of which is shown in more detail in FIGS. 31B-31D. As such, for sake of simplicity, the following description is with respect to the top portion 3102, the bottom portion 3104, and the internal structure 3106 of one unit cell.

While the top portion 3102 and the bottom portion 3104 can have a variety of configurations, in this illustrated embodiment, the top portion 3102 and bottom portion 3104 are inverted images of each other, and therefore for sake of simplicity, the following description is with respect to the top portion 3102 of one unit cell 3110. A person skilled in the art will understand, however, that the following discussion is also applicable to the bottom portion 3104.

As shown in FIGS. 31A-31D, the top portion 3102 includes first and second cross struts 3112, 3114, and first and second angled struts 3116, 3118 extending therebetween. In this illustrated embodiment, the first angled strut 3116 extends from a first end of the first cross strut 3112 at a first angle and terminates at a mid-portion of the second cross strut 3114, and the second angled strut 3118 extends from a second opposite end of the first cross strut 3112 at a second angle and terminates at the mid-portion of the second cross strut 3114. As a result, the first and second angled struts 3116, 3118 converge and connect at a central segment 3114*a* of the second cross strut 3114. In other embodiments, the first and second angled struts 3116, 3118 can extend at any other suitable angle.

While the internal structure 3106 can have a variety of configurations, in this illustrated embodiment, the internal structure 3106 includes three spacer struts 3120*a*, 3120*b*, 3120*c*. As shown in FIGS. 31B-31D, the first and third spacer struts 3120*a*, 3120*c* each interconnect the first cross strut 3112 of the top portion 3102 to the first cross strut 3112 of the bottom portion 3104, and the second spacer strut 3120*b* interconnects the central segment 3114*a* of the second cross strut 3114 of the top portion 3102 to the central segment 3114*a* of the second cross strut 3114 of the bottom portion 3104.

Figure 32A:
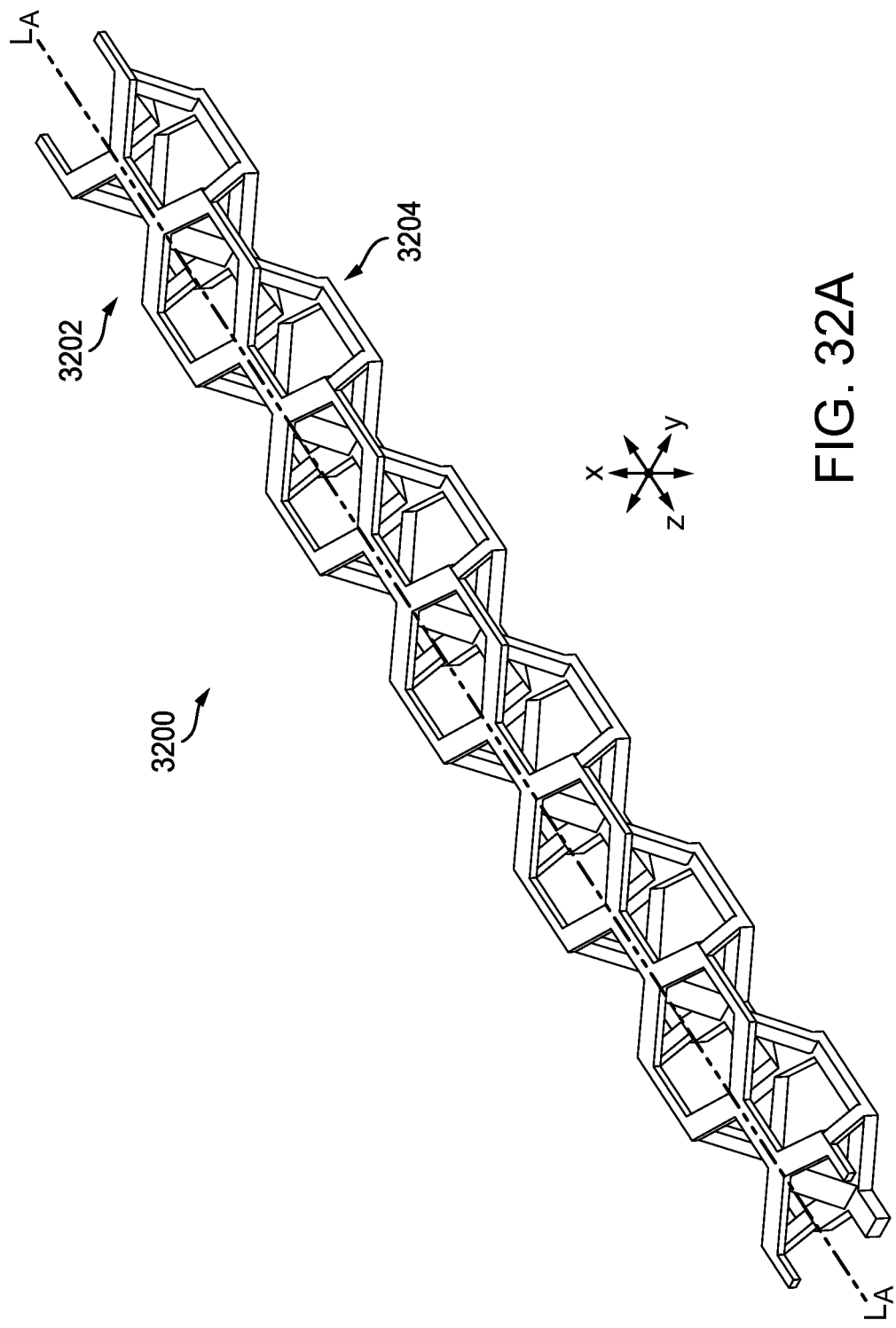
FIG. 32A is a perspective view of another exemplary embodiment of a compressible non-fibrous adjunct.

FIG. 32A illustrates another exemplary adjunct 3200 that is in the form of a lattice structure that includes a top portion 3202, a bottom portion 3204, and an internal structure 3206 extending therebetween. The top portion 3202 is configured to contact tissue, and therefore forms the tissue-contacting layer of the adjunct 3200, whereas the bottom portion 3204 is configured to attach to a cartridge, and therefore forms the cartridge-contacting layer of the adjunct 3200. Adjunct 3200 is similar to adjunct 3100 shown in FIGS. 31A-31D except for the differences described below. The lattice is formed of an array of repeating unit cells 3201, one of which is shown in more detail in FIGS. 32B-32D. As such, for sake of simplicity, the following description is with respect to the top portion 3202, the bottom portion 3204, and the internal structure 3206 of one unit cell.

Figure 32C:
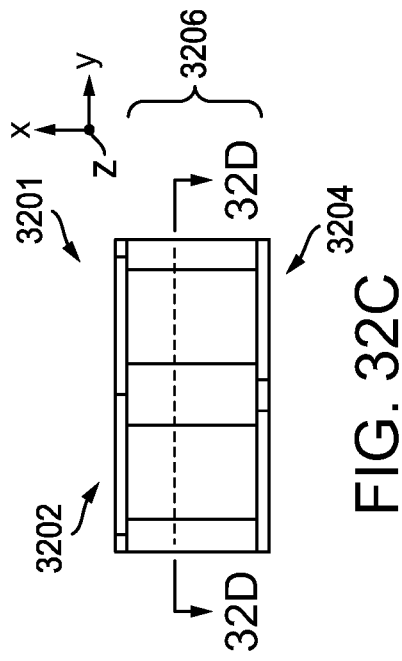
FIG. 32C is a side view of the unit cell of FIG. 32B.
Figure 32D:
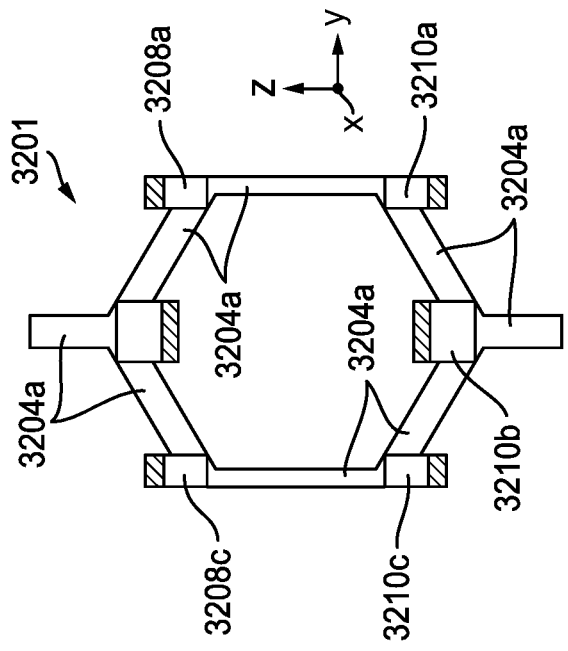
FIG. 32D is a sectional top view of the unit cell of FIGS. 32B-32C, taken along line 32D-32D of FIG. 32C.
Figure 32B:
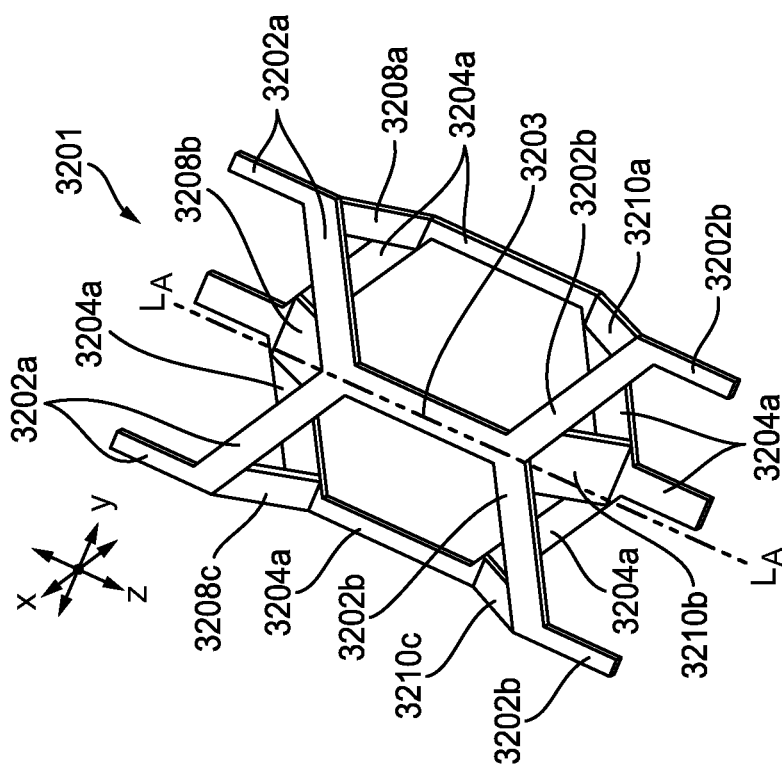
FIG. 32B is a perspective view of a single unit cell of the adjunct of FIG. 32A.

As shown in FIGS. 32B-32D, the top portion 3202 is offset from the bottom portion 3204 in first and second dimensions (X, Z). The top portion 3202 includes two separate sets of interconnected struts 3202*a*, 3202*b*, which are connected to each other via a connecting strut 3203. The bottom portion 3204 includes eight interconnected struts 3204*a*, six of which form a first hexagonal face of the unit cell 3201. The internal structure 3206 includes two sets of spacer struts 3208*a*, 3208*b*, 3208*c*, 3210*a*, 3210*b*, 3210*c* that extend from the top portion 3202 to the bottom portion, thereby forming two additional hexagonal faces of the unit cell 3201, as shown in FIG. 32B.

Figure 33A:
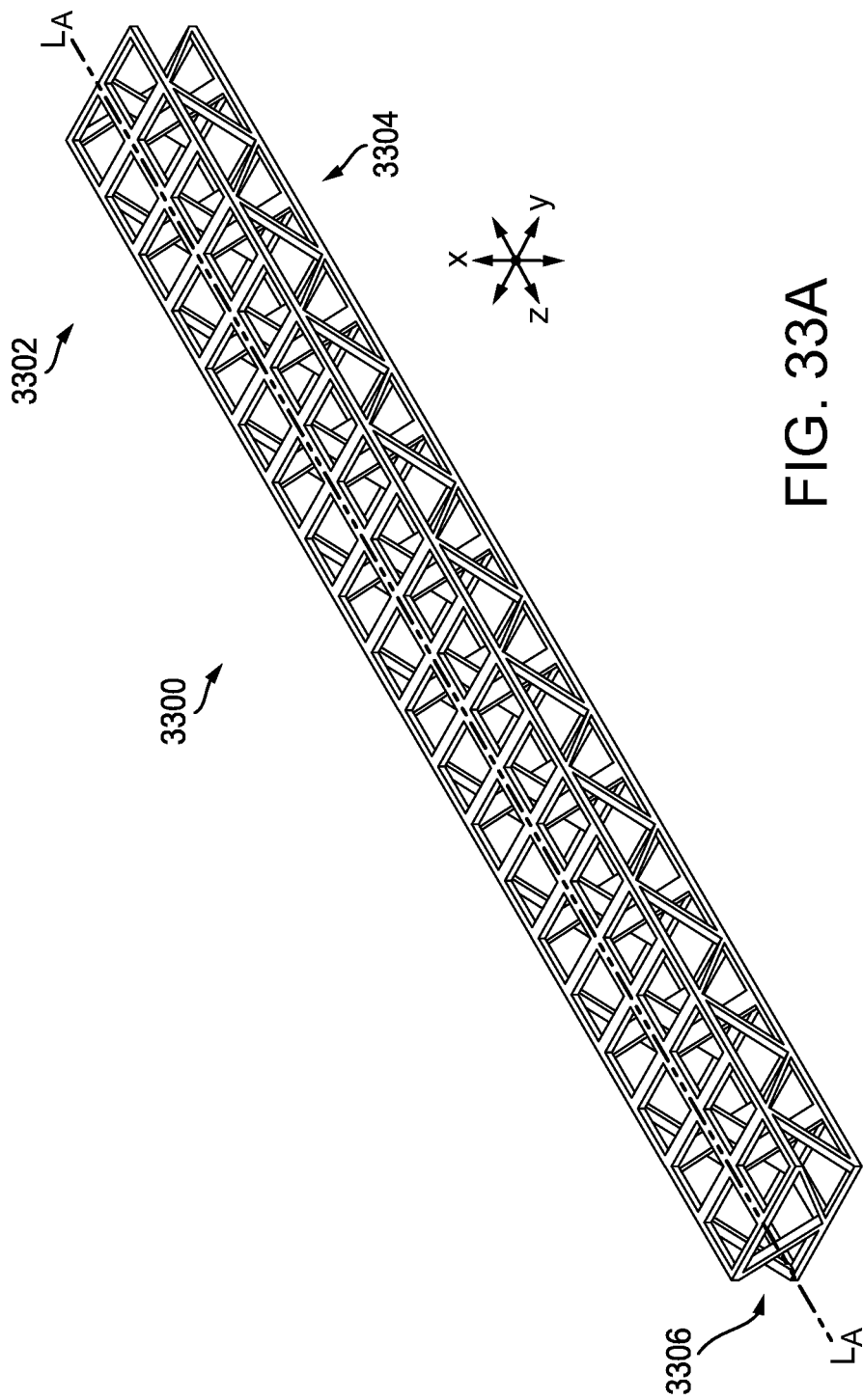
FIG. 33A is a perspective view of another exemplary embodiment of a compressible non-fibrous adjunct.

FIG. 33A illustrates another exemplary adjunct 3300 that is in the form of a lattice structure that includes a top portion 3302, a bottom portion 3304, and an internal structure 3306 extending therebetween. The top portion 3302 is configured to contact tissue, and therefore forms the tissue-contacting layer of the adjunct 3300, whereas the bottom portion 3304 is configured to attach to a cartridge of a surgical stapler, and therefore forms the cartridge-contacting layer of the adjunct 3300. Adjunct 3300 is similar to adjunct 3100 shown in FIGS. 31A-31D except for the differences described below. The lattice is formed of an array of repeating unit cells 3310, one of which is shown in more detail in FIGS. 33B-33E. As such, for sake of simplicity, the following description is with respect to the top portion 3302, the bottom portion 3304, and the internal structure 3306 of one unit cell 3310.

While the top portion 3302 and bottom portion 3304 can have a variety of configurations, in this illustrated embodiment, the top portion 3302 and bottom portion 3304 are substantially identical to each other, and therefore for sake of simplicity, the following description is with respect to the top portion 3302 of one unit cell 3310. A person skilled in the art will understand, however, that the following discussion is also applicable to the bottom portion 3304.

As shown in FIGS. 33A-33E, the top portion 3302 includes a first pair of opposing outside struts 3312a, 3312b and a second pair of opposing outside struts 3312c, 3312d. The first and second pairs of outside struts 3312a, 3312b, 3312c, 3312d are connected in such a way in which the top portion 3302 is in the form of a parallelogram having four corners 3316a, 3316b, 3316c, 3316d. In this illustrated embodiment, the parallelogram is a square. The top portion 3302 also includes a first cross strut 3318 that connects the first pair of opposing outside struts 3312a, 3312b and a second cross strut 3320 that connects the second pair of opposing outside struts 3312c, 3312d. As shown, the first and second cross struts 3318, 3320 intersect at 90 degrees relative to each other in the middle of the top portion 3302.

Figure 33D:
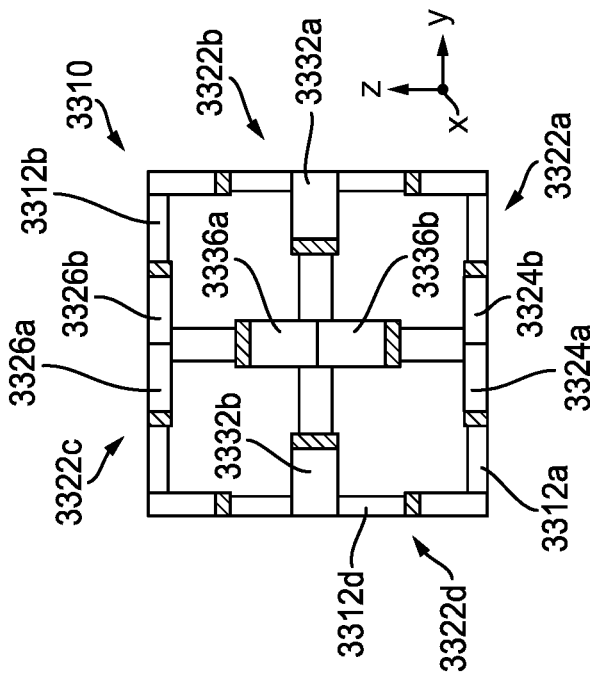
FIG. 33D is a sectional top view of the unit cell of FIGS. 33B-33C, taken along line 33D-33D of FIG. 33C.
Figure 33E:
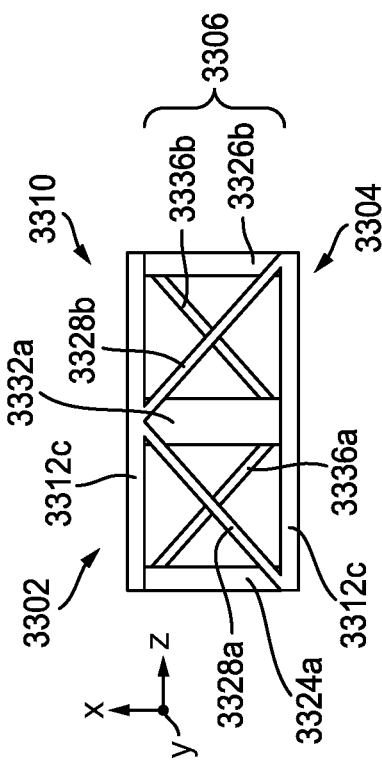
FIG. 33E is an alternate side view of the unit cell of FIGS. 33B-33C.
Figure 33B:
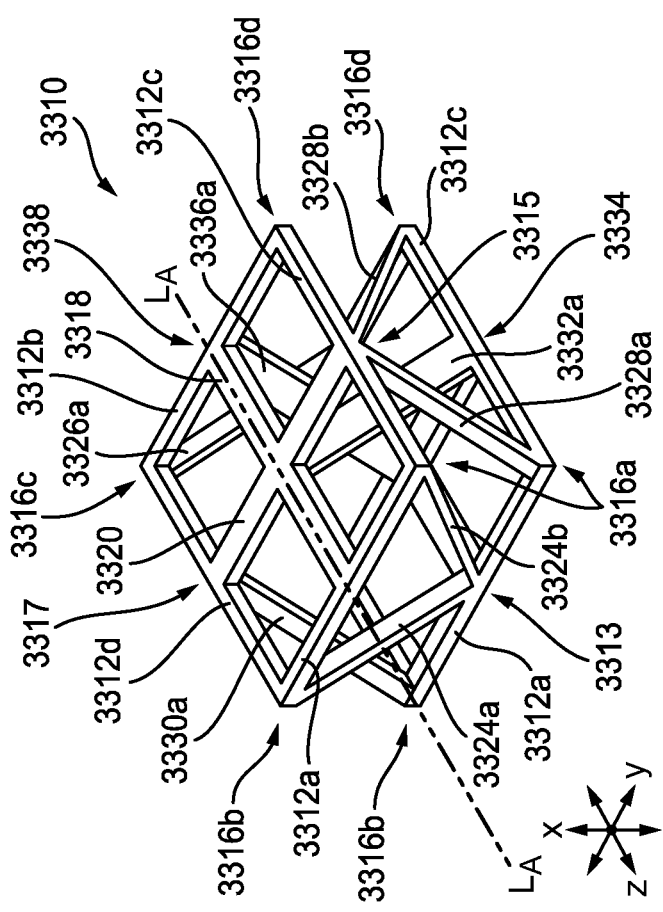
FIG. 33B is a perspective view of a single unit cell of the adjunct of FIG. 33A.
Figure 33C:
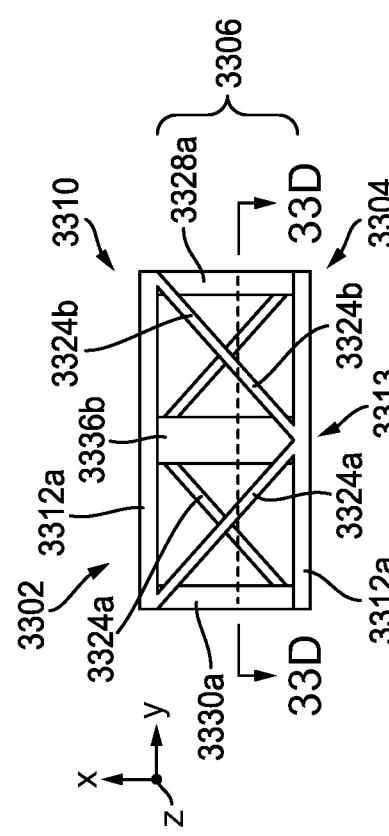
FIG. 33C is a side view of the unit cell of FIG. 33B.

While the internal structure 3306 can have a variety of configurations, in this illustrated embodiment, the internal structure 3306 includes a first side 3322a, a second adjacent side 3322b, a third side 3322c that is opposite the first side 3322a, and a fourth side 3322d that is opposite the second side 3322b (see FIG. 33D). While each side can have a variety of configurations, in this illustrated embodiment, the first and third sides 3322a, 3322c are substantially identical to each other and the second and fourth sides 3322b, 3322d are substantially identical to each other.

As shown in FIGS. 33B-33E, the first side 3322a of the internal structure 3306 includes first and second angled spacer struts 3324a, 3324b that extend in opposite directions from a central segment 3313 of the outside strut 3312a of the bottom portion 3304 to first and second corners 3316a, 3316b, respectively, of the top portion 3302. Similarly, the third side 3322c of the internal structure includes a third angled spacer strut 3326a and a fourth angled spacer strut 3326b that extend in opposite directions from a central segment (obstructed) of the outside strut 3312b (obstructed) of the bottom portion 3304 to third and fourth corners 3316c, 3316d, respectively, of the top portion 3302.

Further, the second side 3322b of the internal structure 3306 includes fifth and sixth angled spacer struts 3328a, 3328b that extend in opposite directions from a central segment 3315 of the outside strut 3312c of the top portion 3302 to first and fourth corners 3316a, 3316d, respectively, of the bottom portion 3304. Similarly, the fourth side 3322d of the internal structure 3306 includes a seventh spacer strut 3330a and eighth angled spacer strut (obstructed) that extend in opposite directions from a central segment 3317 of the outside strut 3312d of the top portion 3302 to second and third corners 3316b (the third corner of the bottom portion 3304 is obstructed), respectively, of the bottom portion 3304.

The internal structure 3306 also includes a first pair of angled spacer struts 3332a, 3332b. The first angled spacer strut 3332a extends from the middle of the top portion 3302 to the central segment 3334 of outside strut 3312c of the bottom portion 3304. Similarly, the second spacer strut 3332b extends from the middle of the top portion 3302 to the central segment (obstructed) of outside strut 3312d of the bottom portion 3304. As such, the first pair of angled spacer struts 3332a, 3332b extend in opposite directions from the middle of the top portion 3302.

Further, the internal structure 3306 includes a second pair of angled spacer struts 3336a, 3336b. The first angled spacer strut 3336a extends from the middle of the bottom portion 3304 to the central segment 3338 of outside strut 3312b of the top portion 3302. Similarly, the second spacer strut 3336b extends from the middle of the bottom portion 3304 to the central segment (obstructed) of outside strut 3312a of the top portion 3302. As such, the second pair of angled spacer struts 3336a, 3336b extend in opposite directions from the middle of the bottom portion 3304.

Figure 34A:
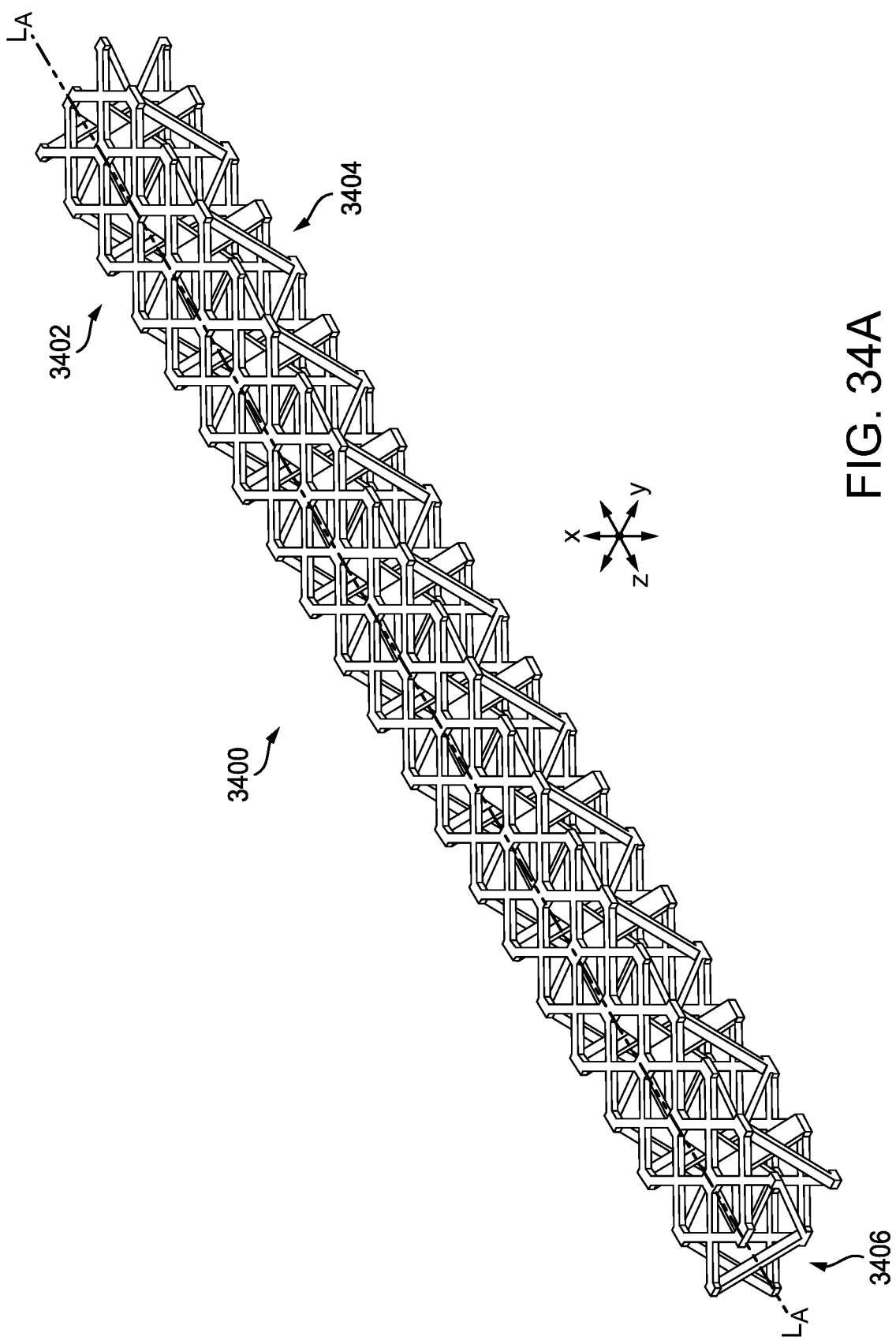
FIG. 34A is a perspective view of another exemplary embodiment of a compressible non-fibrous adjunct.

FIG. 34A illustrates another exemplary adjunct 3400 that is in the form of a lattice structure that includes a top portion 3402, a bottom portion 3404, and an internal structure 3406 extending therebetween. The top portion 3402 is configured to contact tissue, and therefore forms the tissue-contacting layer of the adjunct 3400, whereas the bottom portion 3404 is configured to attach to a cartridge a surgical stapler, and therefore forms the cartridge-contacting layer of the adjunct 3400. Adjunct 3400 is similar to adjunct 3100 shown in FIGS. 31A-31D except for the differences described below. The lattice is formed of an array of repeating unit cells 3410, one of which is shown in more detail in FIGS. 34B-34E. As such, for sake of simplicity, the following description is with respect to the top portion 3402, the bottom portion 3404, and the internal structure 3406 of one unit cell.

While the top portion 3402 and bottom portion 3404 can have a variety of configurations, in this illustrated embodiment, the top portion 3402 and bottom portion 3404 are substantially identical to each other, and therefore for sake of simplicity, the following description is with respect to the top portion 3402 of one unit cell 3410. A person skilled in the art will understand, however, that the following discussion is also applicable to the bottom portion 3404.

As shown in FIGS. 34B-34E, the top portion 3402 includes four cross struts 3408a, 3408b, 3408c, 3408d that connect together at the middle of the top portion 3402. While the four cross struts 3408a, 3408b, 3408c, 3408d can connect together at different angles relative to each other, in this illustrated embodiment, the four cross struts 3408a, 3408b, 3408c, 3408d connect at 90 degrees relative to each other, and thus form a cross having four outer ends 3411a, 3411b, 3411c, 3411d. The top portion 3402 also includes four struts 3412a, 3412b, 3412c, 3412d that are connected in such a way as to form a square having four corners 3414a, 3414b, 3414c, 3414d. Each strut 3412a, 3412b, 3412c, 3412d of the square intersects a central segment 3416a, 3416b, 3416c, 3416d (see FIG. 34D) of one of the four struts 3408a, 3408b, 3408c, 3408d of the cross.

While the internal structure 3406 can have a variety of configurations, in this illustrated embodiment, the internal structure 3406 includes four sets of angled outer struts, in which each set of angled outer struts includes two angled struts 3418a, 3418b, 3420a, 3420b, 3422a, 3422b, 3424a, 3424b. The four sets of angled outer struts can have a variety of configurations. As shown, in this illustrated embodiment, the first and second sets of outer struts are mirror images of each other and the third and fourth sets are mirror images of each other.

Figure 34B:
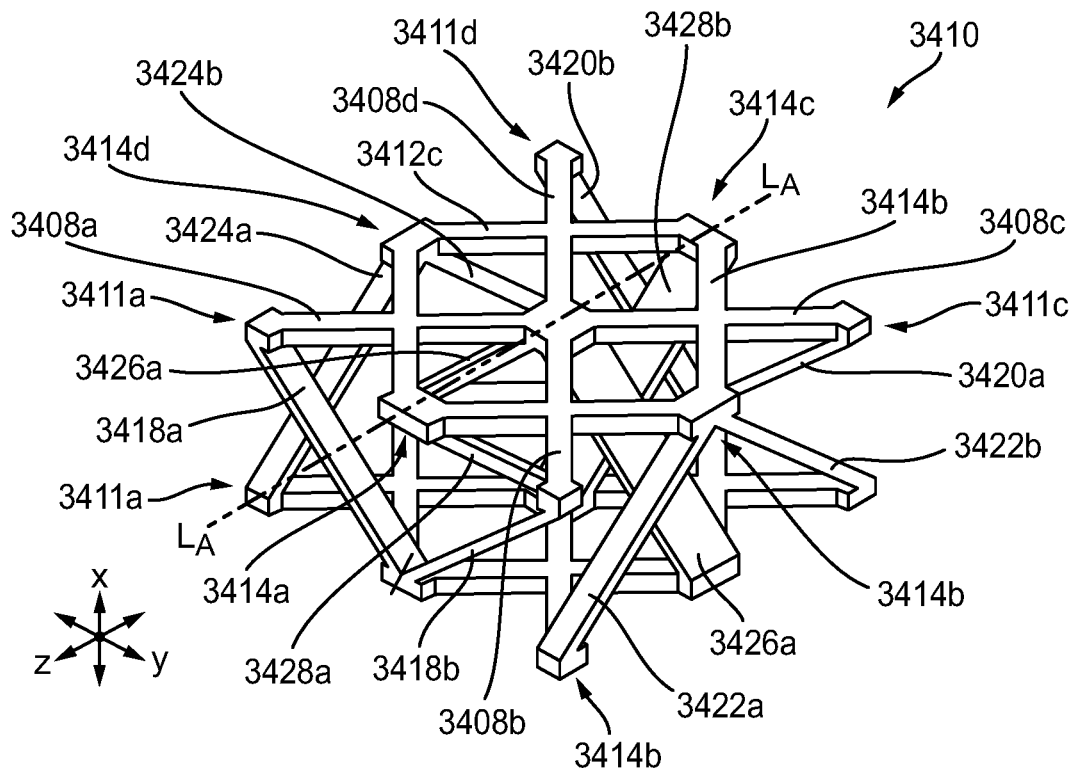
FIG. 34B is a perspective view of a single unit cell of the adjunct of FIG. 34A.
Figure 34C:
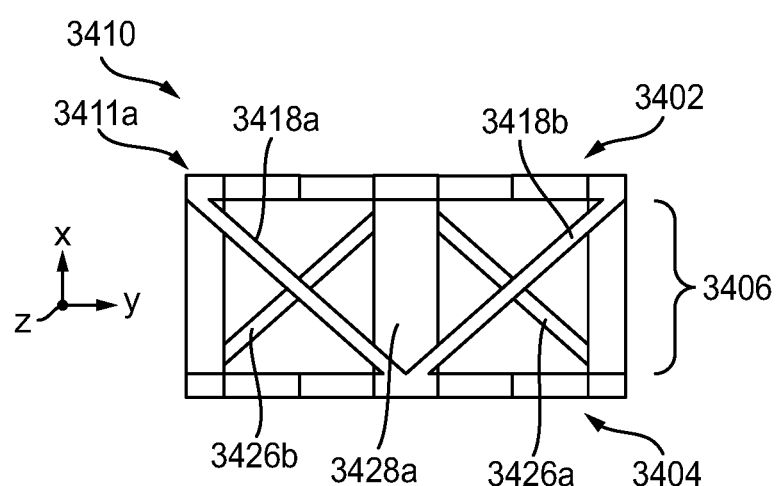
FIG. 34C is a side view of the unit cell of FIG. 34B.
Figure 34D:
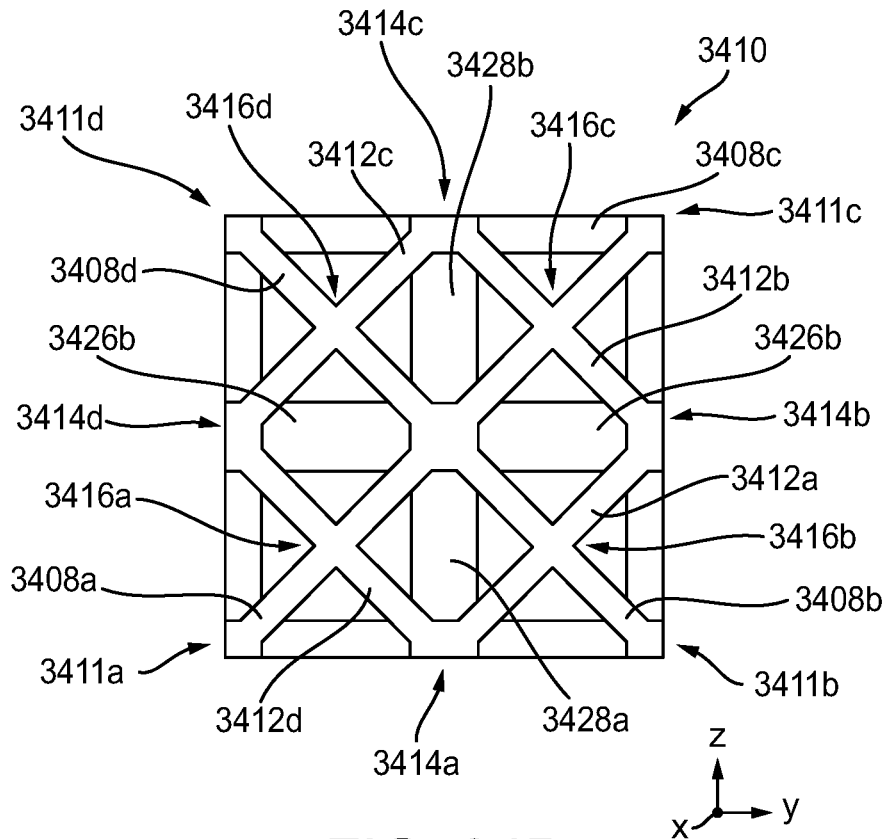
FIG. 34D is a top view of the unit cell of FIGS. 34B-34C.
Figure 34E:
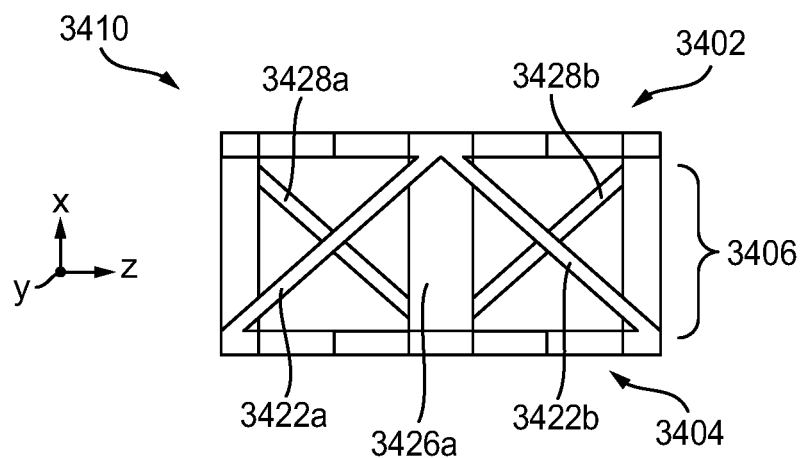
FIG. 34E is an alternate side view of the unit cell of FIGS. 34B-34C.

As shown in FIG. 34B, the first and second angled struts 3418a, 3418b of the first set of angled outer struts each extend in opposite directions from the first corner 3414a of the square of the bottom portion 3404 to one of the first and second corners 3411a, 3411b, respectively, of the cross of the top portion 3402. Similarly, the first and second angled struts 3420a, 3420b of the second set of angled outer struts each extend in opposite directions from the third corner 3414c (obstructed) of the square of the bottom portion 3404 to one of remaining corners (e.g., the third and fourth corners 3411c, 3411d, respectively) of the cross of the top portion 3402.

As further shown in FIG. 34B, the first and second angled struts 3422a, 3422b of the third set of angled outer struts each extend in opposite directions from the second corner 3414b of the square of the top portion 3404 to one of the second and third corners 3411b, 3411c, respectively, of the cross of the bottom portion 3404. Similarly, the first and second angled struts 3424a, 3424b of the fourth set of angled outer struts each extend in opposite directions from the fourth corner 3414d of the square of the top portion 3404 to one of the first corner 3411a and fourth corner 3411d (obstructed), respectively, of the cross of the bottom portion 3404.

The internal structure 3406 also includes two sets of inner angled struts, in which each set includes two angled struts 3426a, 3426b, 3428a, 3428b. The two sets of angled inner struts can have a variety of configurations. As shown in FIG. 34B, the first and second angled struts 3426a, 3426b of the first set of angled inner struts each extend in opposite directions from the middle of the cross of the top portion 3402 to one of the second corner 3414b and fourth corner 3414d (obstructed) of the square of the bottom portion 3404. In this illustrated embodiment, the first and second angled struts 3428a, 3428b of the second set of angled inner struts are inverse to the first and second angled struts 3426a, 3426b. That is, as shown in FIG. 34B, the first and second angled struts 3428a, 3428b of the second set of angled inner struts each extend in opposite directions from the middle of the cross of the bottom portion 3404 to one of the first corner 3414a and the third corner 3414c (obstructed) of the square of the top portion 3402.

As shown in FIGS. 30A-34E, the strut-based configuration of the adjuncts produce a plurality of openings throughout the adjuncts, thereby creating less of a barrier for cell infiltration as compared to non-strut-based adjunct configurations. That is, these plurality of openings can allow for a more rapid influx of cells into the adjunct when the adjunct is stapled to tissue. This increased rate can thereby enhance the rate of tissue ingrowth as compared to other adjuncts.

While the openings in the top portions and bottom portions of the adjuncts shown in FIGS. 31A-34E are regular and symmetrically defined by struts, in other embodiments, the top portions and bottom portions could alternatively be planar sheets with regular or irregular openings formed therein (e.g., "Swiss cheese" style), or non-planar (for example, rippled or wavy) sheets with regular openings or irregular openings formed therein. These openings of planar and non-planar adjunct configurations can also promote cell ingrowth within the adjuncts when the adjuncts are stapled to tissue.

Figure 35:
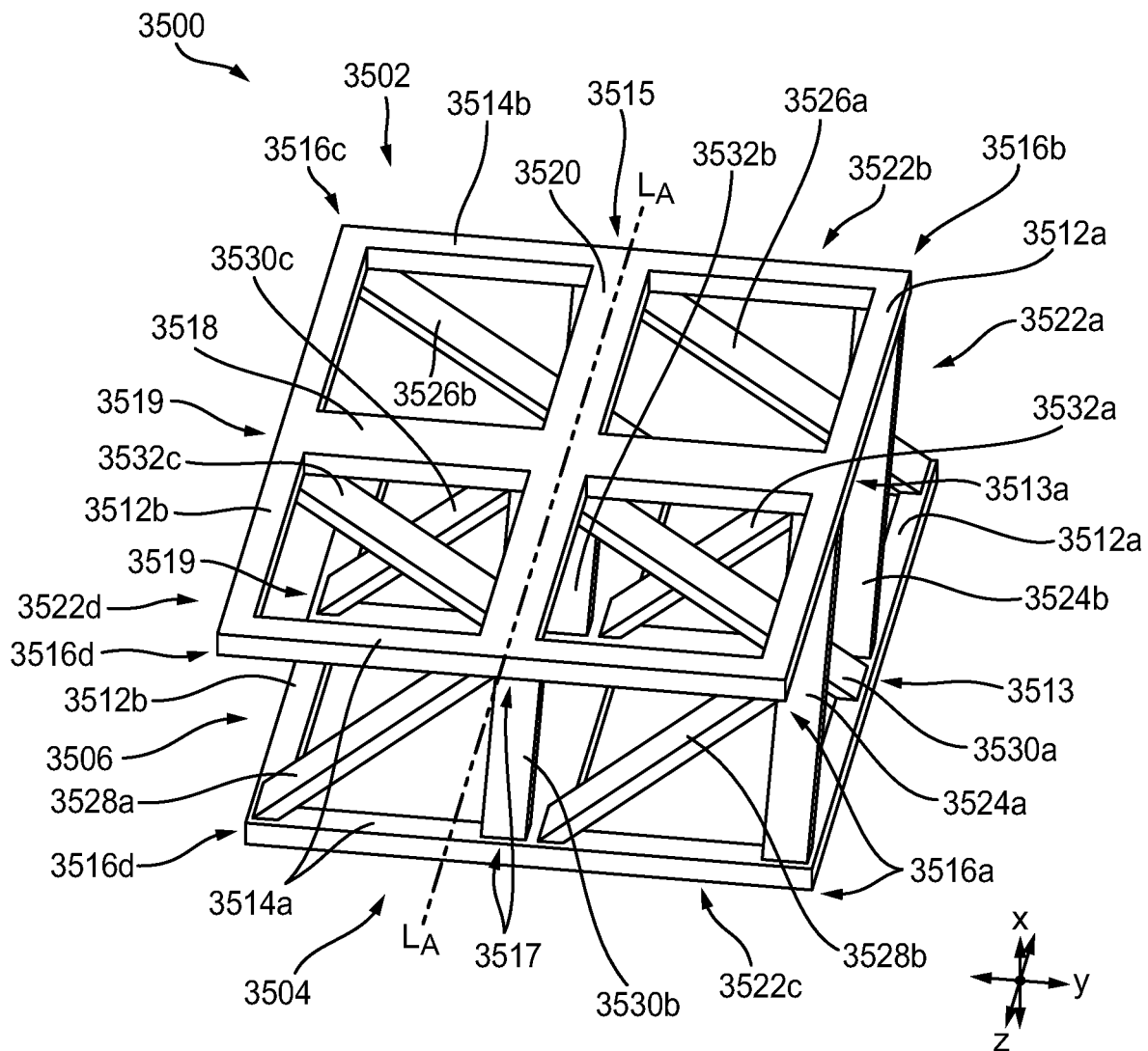
FIG. 35 is a perspective of view of another exemplary embodiment of a unit cell.

In other embodiments, the repeating units of the strut-based adjuncts can have other structural configurations. For example, FIG. 35 illustrates an exemplary strut-based unit cell 3500 that can be used to form the adjuncts described herein. The unit cell 3500 includes a top portion 3502, a bottom portion 3504, and an internal structure 3506 extending therebetween.

While the top and bottom portions 3502, 3504 can have a variety of configurations, in this illustrated embodiment, the top and bottom portions 3502, 3504 are substantially identical to each other, and therefore for sake of simplicity, the following description is with respect to the top portion 3502. A person skilled in the art will understand, however, that the following discussion is also applicable to the bottom portion 3504.

As shown in FIG. 35, the top portion 3502 includes a first pair of opposing outside struts 3512a, 3512b and a second pair of opposing outside struts 3514a, 3514b. The first and second pairs of outside struts 3512a, 3512b, 3514a, 3514b are connected in such a way in which the top portion 3502 is in the form of a parallelogram having four corners 3516a, 3516b, 3516c, 3516d. In this illustrated embodiment, the parallelogram is a square. The top portion 3502 also includes a first cross strut 3518 that connects the first pair of opposing outside struts 3512a, 3512b and a second cross strut 3520 that connects the second pair of opposing outside struts 3514a, 3514b. As shown, the first and second cross struts 3518, 3520 intersect at 90 degrees relative to each other in the middle of the top portion 3502.

While the internal structure 3506 can have a variety of configurations, in this illustrated embodiment, the internal structure 3506 includes a first side 3522a, a second adjacent side 3522b, and a third side 3522c that is opposite the second side 3522b, and a fourth side 3522d that is opposite the first side 3522a. While each side can have a variety of configurations, in this illustrated embodiment, the first, second, third, fourth sides 3522a, 3522b, 3522c, 3522d are different. In this illustrated embodiment, the fourth side 3522d does not include any spacer struts.

As shown in FIG. 35, the first side 3522a of the internal structure 3506 includes first and second angled spacer struts 3524a, 3524b that extend parallel to each other. The first angled spacer 3524a strut extends from the first corner 3516a of the bottom portion 3504 to a center segment 3513a of the first outer strut 3512a of the top portion 3502, and the second angled spacer strut extends from a central segment 3513b of the of the first outside strut 3512a of the bottom portion 3504 to the second corner 3516b of the top portion 3502.

The second side 3522b of the internal structure 3506 includes third and fourth angled spacer struts 3526a, 3526b that extend parallel to each other. The third angled spacer strut 3526c extends from the second corner 3516b of the bottom portion 3504 to a central segment 3515 of the second outside strut 3514b of the top portion 3502, and the fourth angled spacer strut 3526b extends from a central segment (obstructed) of the second outside strut (obstructed) of the bottom portion 3504 to the third corner 3516c of the top portion 3502.

Further, the third side 3522c of the internal structure 3506 includes fifth and sixth angled spacer struts 3528a, 3528b that extend parallel to each other. The fifth angled spacer strut 3528a extends from the fourth corner 3516d of the bottom portion 3504 to a central segment 3517 of the second outside strut 3514a of the top portion 3502, and the sixth angled spacer strut 3528b extends from a central segment 3517 of the first outside strut 3514a of the bottom portion 3504 to the first corner 3516a of the top portion 3502.

The internal structure 3506 also includes two sets of internal angled struts. The first set includes three internal angled struts 3530a, 3530b, 3530c that each extend from the middle of the top portion 3502 to central segments 3513, 3517, 3519 of outside struts 3512a, 3514a, 3512b, respectively, of the bottom portion 3504. As such, in the first set, the first internal angled strut 3530a and the third internal angled strut 3530c extend in opposite directions, and the second internal angled strut 3530b extends in a different direction relative to the first and third internal angled struts 3530a, 3530c. The second set includes three internal angled struts 3532a, 3532b, 3532c that each extend from the middle of the bottom portion 3504 to central segments 3513, 3515, 3519 of outside struts 3512a, 3514b, 3512b, respectively, of the top portion 3502. As such, in the second set, the first internal angled strut 3532a and the third internal angled strut 3532c extend in opposite directions, and the second internal angled strut 3532b extends in a different direction relative to the first and third internal angled struts 3532a, 3532b.

Figure 36:
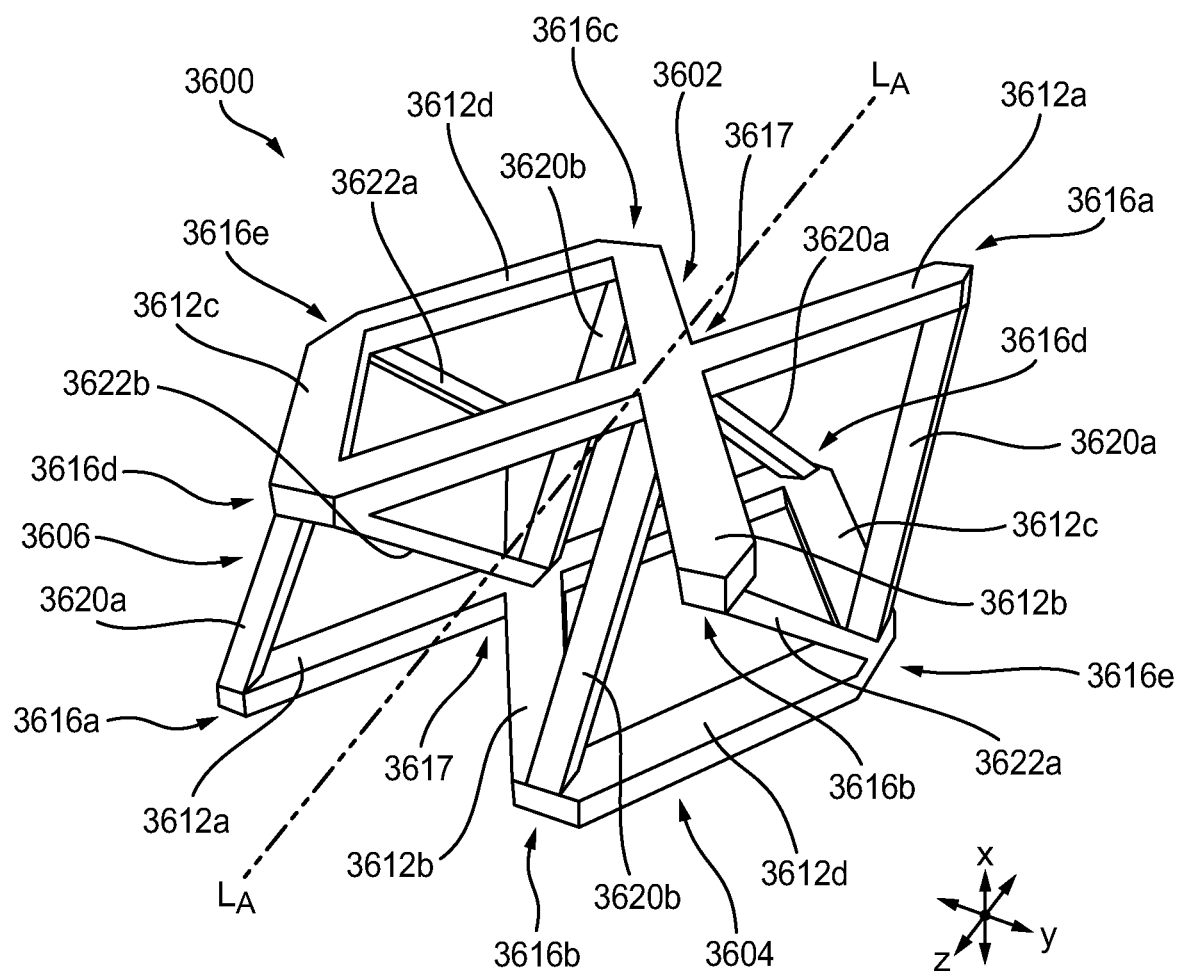
FIG. 36 is a perspective of view of another exemplary embodiment of a unit cell.

In other embodiments, the repeating units of the strut-based adjuncts can have other structural configurations. For example, FIG. 36 illustrates an exemplary strut-based unit cell 3600 that can be used to form the adjuncts described herein. The unit cell 3600 includes a top portion 3602, a bottom portion 3604, and an internal structure 3606 extending therebetween.

While the top and bottom portions 3602, 3604 can have a variety of configurations, in this illustrated embodiment, the top and bottom portions 3602, 3604 are substantially identical to each other, and therefore for sake of simplicity, the following description is with respect to the top portion 3602. In an embodiment, the bottom portion 3604 is an inverted image of the top portion 3602. A person skilled in the art will understand, however, that the following discussion is also applicable to the bottom portion 3604.

As shown in FIG. 36, the top portion 3602 includes a first pair of cross struts 3612a, 3612b and a second pair of cross struts 3612c, 3612d. The first and second pairs of cross struts 3612a, 3612b, 3612c, 3612d are connected in such a way in which the top portion 3602 is in the form of a sparse tetrahedral having five corners 3616a, 3616b, 3616c, 3616d, 3616e. The first pair of cross struts 3612a, 3612b intersect at intersection 3617 on the top portion. Cross strut 3612a connects to cross strut 3612c at the corner 3616d, and cross strut 3612b connects to cross strut 3612d at the corner 3616c. As shown, cross struts 3612a, 3612b intersect at 90 degrees relative to each other in the middle of the top portion 3602 at intersect 3617.

As shown in FIG. 36, the internal structure 3606 includes first and second angled spacer struts 3620a, 3620b that extend parallel to each other. The first angled spacer strut 3620a extends from the first corner 3616a of the top portion 3602 to the corner 3616e of the bottom portion 3604, and the second angled spacer strut 3620b extends from the third corner 3616c of the top portion 3602 to the intersection 3617 of the bottom portion 3604. Additionally, the internal structure 3606 includes third and fourth angled spacer struts 3622a, 3622b that extend parallel to each other. The third angled spacer strut 3622a extends from the second corner 3616b of the top portion 3602 to the corner 3616e of the bottom portion 3604, and the fourth angled spacer strut 3622b extends from the fourth corner 3616d of the top portion 3602 to the intersection 3617 of the bottom portion 3604. As such, the first angled spacer strut 3620a and the third angled spacer strut 3622a extend in opposite directions, and the second angled spacer strut 3620b and the fourth angled spacer strut 3622b extend in in opposite directions.

Outer Layer(s)

In some embodiments, the adjunct can include a lattice structure (e.g., a first lattice structure or an internal lattice structure) extending from a top surface to a bottom surface, and at least one outer layer, each having different compression ratios (e.g., precompressed height to compressed height). As a result, the compressive properties of the lattice structure and the at least one outer layer are different, and therefore can be tailored to carry out different functions (e.g., tissue ingrowth, cartridge connection, etc.) while also in combination effecting an overall compression profile for the adjunct that is desirable for varying staple conditions and/or staple heights. For example, based on the overall compression profile of the resulting adjunct, the adjunct can be configured, while under an applied stress in a range of about 30 kPa to 90 kPa, to undergo a strain in a range of about 0.1 kPa to 0.9 kPa. In other embodiments, the strain can be in the range of about 0.1 to 0.8, of about 0.1 to 0.7, of about 0.1 to 0.6, of about 0.2 to 0.8, of about 0.2 to 0.7, of about 0.3 to 0.7, of about 0.3 to 0.8, of about 0.3 to 0.9, of about 0.4 to 0.9, of about 0.4 to 0.8, of about 0.4 to 0.7, of about 0.5 to 0.8, or of about 0.5 to 0.9

While the lattice structure and at least one outer layer can have a variety of configurations, in some embodiments, the first lattice structure has a compression ratio that is greater than the compression ratio of the at least one outer layer. For example, in one embodiment, the first lattice structure can be configured, while under an applied stress, to compress in a range of about 3 mm to 1 mm, and thus, can have a compression ratio of 3, whereas the at least outer layer can be configured, while under the same applied stress, to compress in a range of about 2 mm to 1 mm, and thus can have a compression ratio of 2.

In certain embodiments, the adjunct can include an outer layer that is in the form of a second lattice structure or absorbable film positioned on at least a portion of the top surface of the first lattice structure and configured to be positioned against tissue. This outer layer can be configured to promote tissue ingrowth within the adjunct and/or create a smooth, or substantially smooth, tissue-contacting surface that can slide easily against tissue, and thus, lower the tissue loads (applied stress) on the adjunct during placement of the stapling device and/or ease the attachment requirements between the adjunct and cartridge. Alternatively, or in addition, the adjunct can include an outer layer that is in the form of a film or a third lattice structure positioned on at least a portion of the bottom surface of the first lattice structure and configured to be positioned against a cartridge. As such, this outer layer can be configured to attach the adjunct to a cartridge. For example, this outer layer can be in the form of an adhesive film and/or include one or more attachment features designed to releasably mate with the staple cartridge. In certain embodiments, the compression ratio of the lattice structure is greater than the compression ration of the at least one outer layer.

Figure 37A:
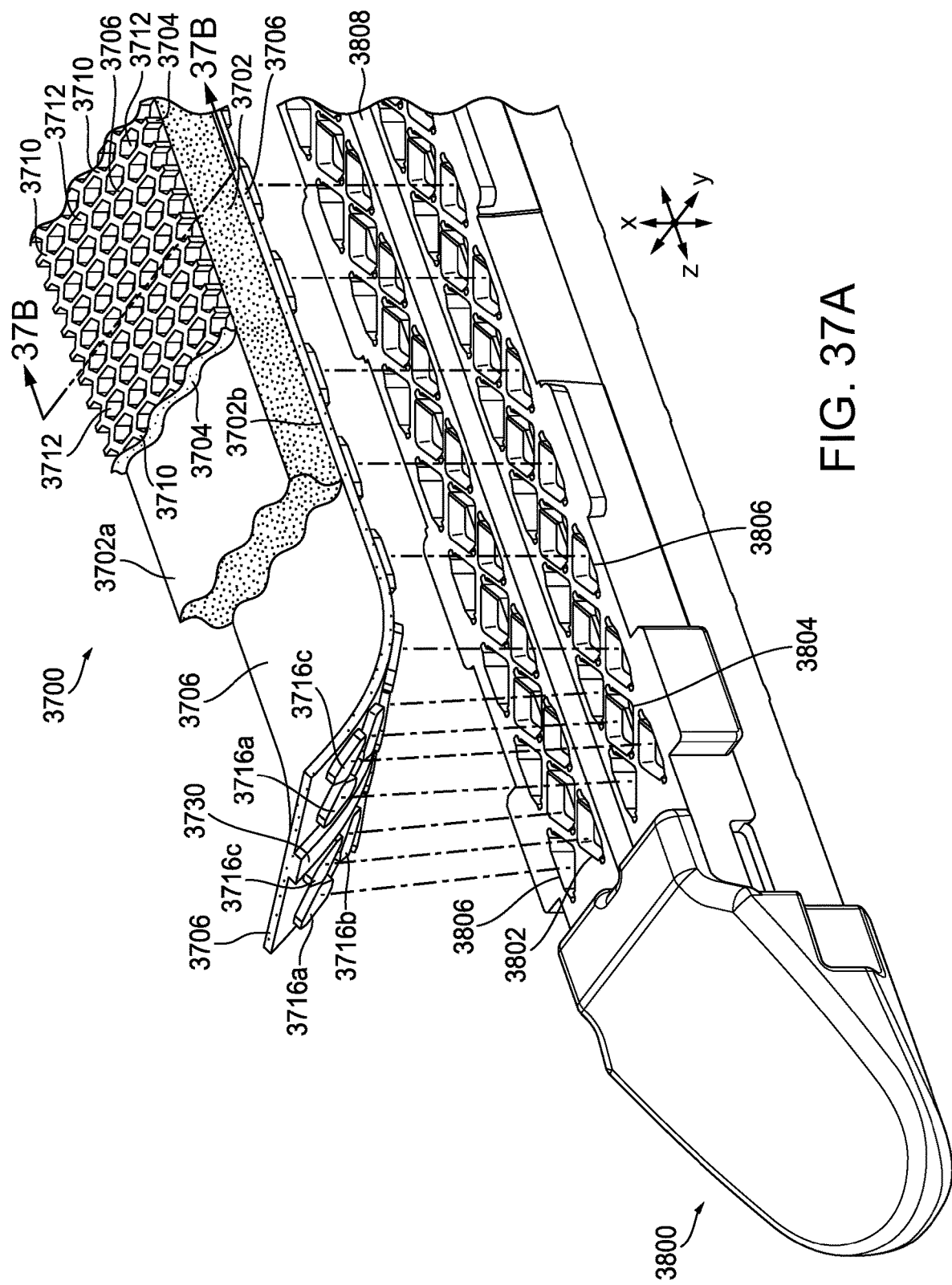
FIG. 37A is a partially exploded perspective view of another exemplary embodiment of a stapling assembly having a staple cartridge and a compressible non-fibrous adjunct.
Figure 37B:
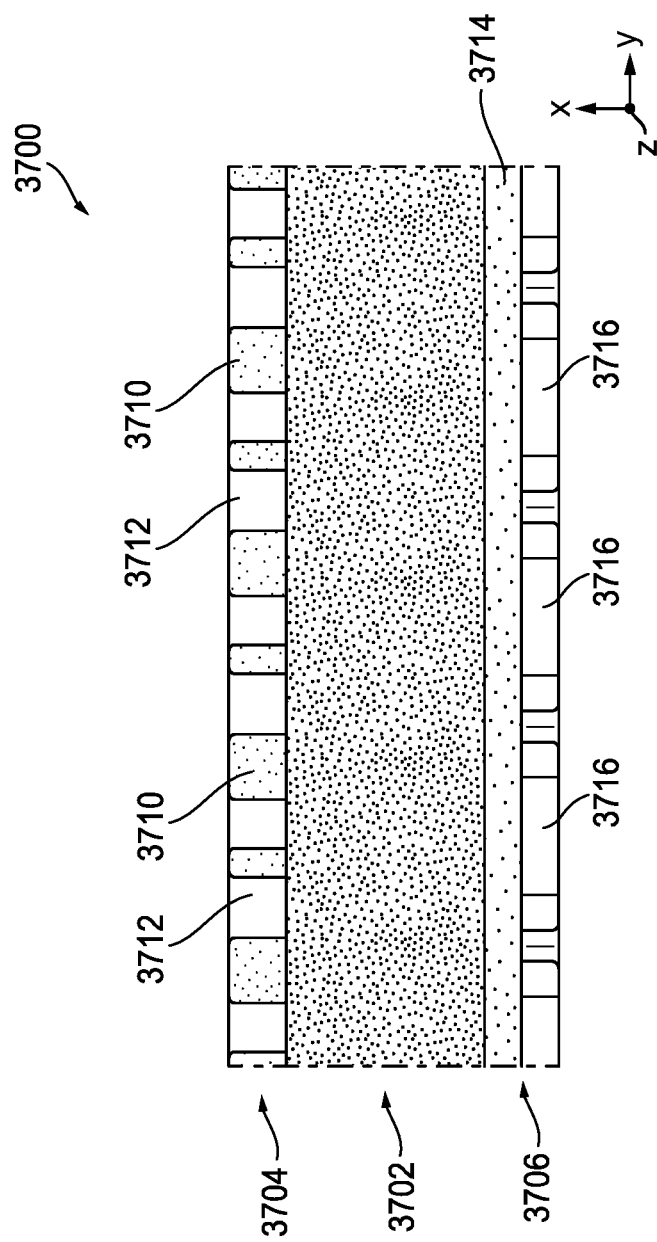
FIG. 37B is a cross-sectional view of a portion of the stapling assembly taken at line 37B-37B of FIG. 37A.

FIG. 37A-37B illustrate an exemplary embodiment of an adjunct 3700 disposed on a cartridge 3800. The cartridge 3800 is similar to cartridge 200 in FIGS. 1-2C, and therefore common features are not described in detail herein. The adjunct 3700 includes an internal lattice structure 3702 and two outer layers 3704, 3710, each having a different compression ratio relative to each other. The internal lattice structure 3702 is generally formed of interconnected repeating unit cells, and while the repeating unit cells are omitted from this illustration, any of the repeating unit cells disclosed herein can be used, e.g., strut-less based repeating unit cells or strut-based repeating unit cells. Further, the first outer layer 3704 is disposed on the top surface 3702a of the internal lattice structure 3702 and is configured to contact tissue, and the second outer layer 3706 is disposed on the bottom surface 3702b of the internal lattice structure 3702 and is configured to contact the cartridge 3800.

While the first outer layer 3704 can have a variety of configurations, in this illustrated embodiment, the first outer layer 3704 is a lattice structure formed of struts 3710 that are interconnected in such a way that create hexagonal-shaped openings 3712 that extend through the first outer layer 3704. These openings 3712 can be configured to promote tissue-ingrowth. A person skilled in the art will appreciate that the struts can be interconnected in a variety of other ways that would effect openings of different sizes and shapes, and thus, the lattice structure of the first outer layer is not limited to what is illustrated in the figures. Further, the first outer layer 3704 can have a lower compression ratio, and therefore can be less compressible, compared to at least the internal lattice structure 3702. As a result, this can allow tissue to further penetrate into the openings 3712, and thus the adjunct 3700, when the adjunct 3700 is stapled to tissue, thereby further promoting tissue ingrowth (see FIGS. 38A and 38B).

While the second outer layer 3706 can have a variety of configurations, in this illustrated embodiment, the second outer layer 3706 is in the form of a film 3714 having projections 3716 extending outward therefrom. The projections 3716a, 3716b, 3716c are configured to mate with the surface features 3802, 3804, 3806, of the cartridge 3800, like surface features 216, 218, 220 of cartridge 200 in FIGS. 1-2C. This mating interaction, as illustrated in FIGS. 37B and 38A, substantially prevents slideable movement of the adjunct 3700 relative to the cartridge 3800. The shape and size of the projections 3716a, 3716b, 3716c, which can be triangular or diamond-shaped, are complementary to the shape and size of the corresponding surfaces features 3802, 3804, 3806, which can be triangular or diamond-shaped recess channels. In other embodiments, the shape and size of the projections and the surface features can differ.

Alternatively, or in addition, the second outer layer 3706 can include an elongated projection 3730 that is configured to be inserted into the longitudinal slot 3808 of the cartridge 3800. While the elongated projection can have a variety of configurations, in this illustrated embodiment, the elongated projection 3730 has a rectangular shape, In some embodiments, the elongated projection 3730 can extend along the entire length of the adjunct (e.g., in the z-direction), whereas in other embodiments, the elongated projection 3730 can extend along a portion of the length. In certain embodiments, the elongated projection 3730 can be broken up into smaller elongated discrete portions.

Figure 39A:
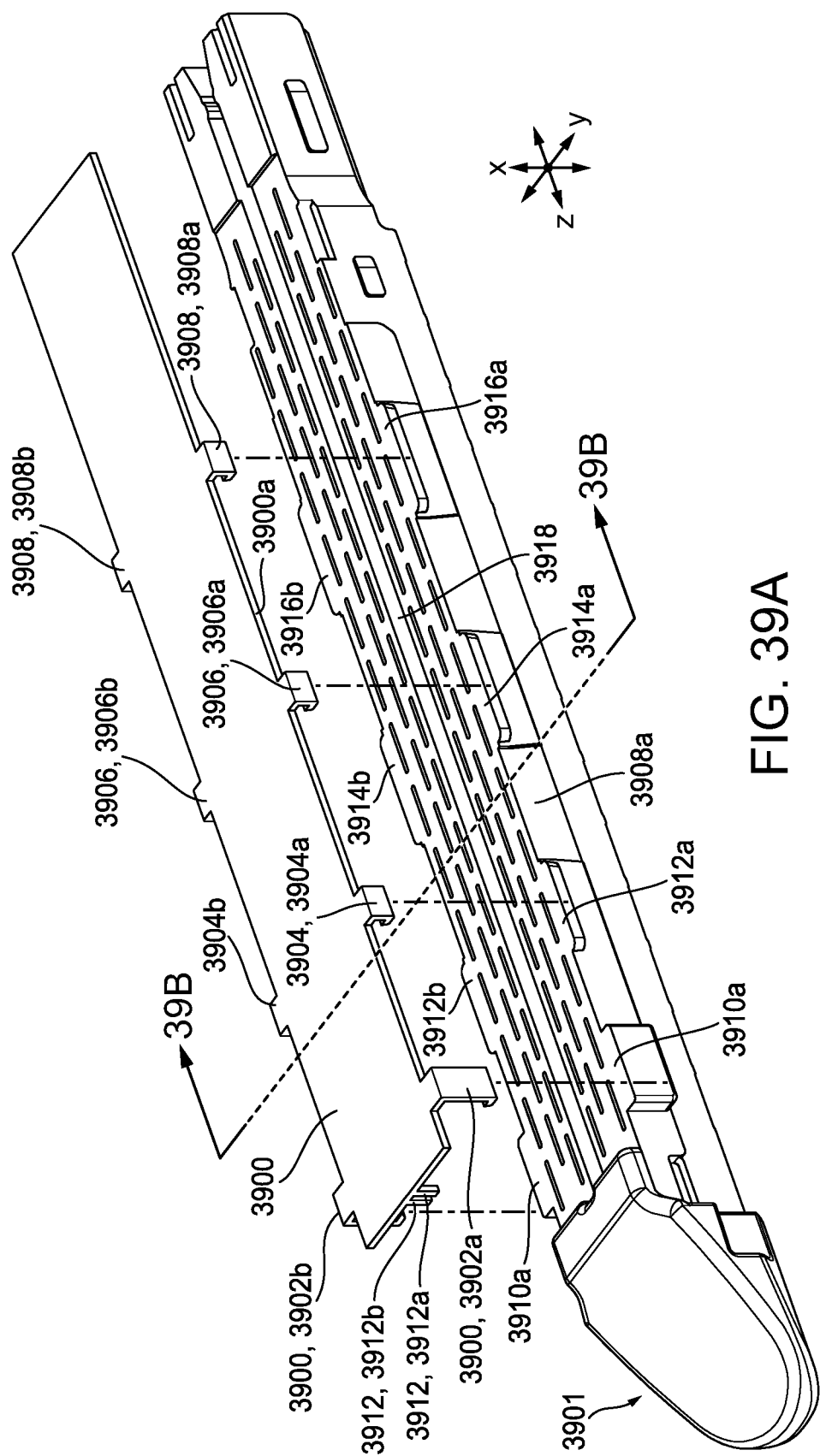
FIG. 39A is an exploded view of an exemplary embodiment stapling assembly having a staple cartridge and an adjunct, in which only a second outer layer of the adjunct is illustrated.
Figure 39B:
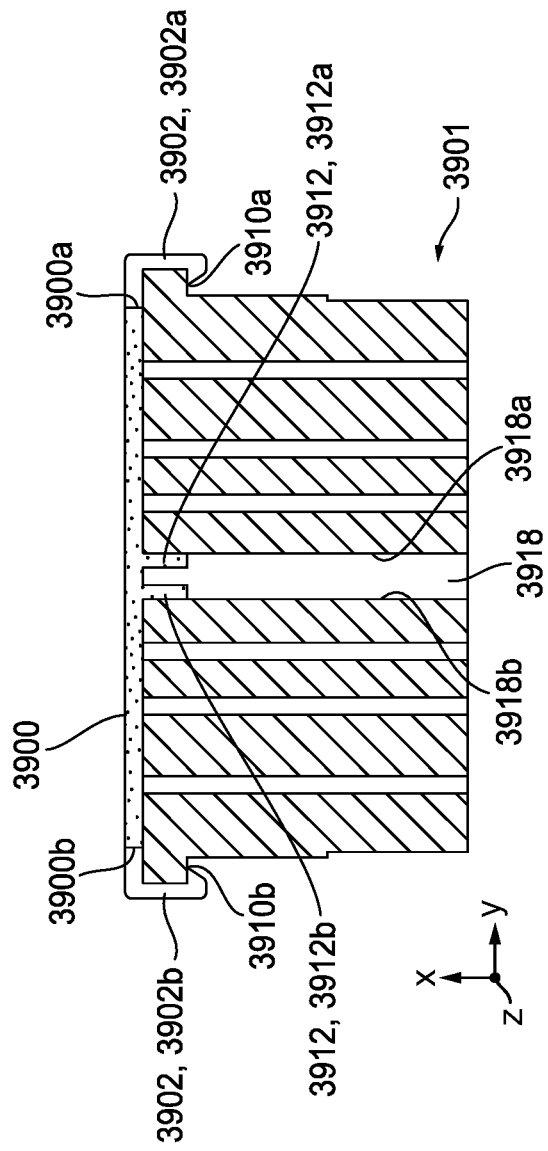
FIG. 39B is a front view of the stapling assembly of FIG. 39A.

In other embodiments, as shown in FIG. 39A, a second outer layer 3900 can include four sets of tabs 3902a, 3902b, 3904a, 3904b, 3906a, 3906b, 3908a, 3908b (3902b, 3904b, 3906b, and 3908b, being partially obstructed in FIG. 39A) that each extend outward and away from opposing outer sides surfaces 3900a, 3900b (FIG. 39B) of the second outer layer 3900. While the four sets of tabs 3902, 3904, 3906, 3908 can have a variety of configurations, in this illustrated embodiment, the four sets of tabs 3902, 3904, 3906, 3908 each have a hooked shaped configuration that engage with respective portions of opposing, outer flanges 3910a, 3910b, 3910a, 3910b, 3914a, 3914b, 3914a, 3914b of the cartridge 3901. In addition, when the cartridge 3901 includes a longitudinal slot 3918, e.g., a knife slot, the second outer layer 3900 can include pin features 3912 that are configured to engage the longitudinal slot 3918. For example, the pin features 3912 can include sets of two opposing pins (only one set of two opposing tabs 3912a, 3912b are illustrated in FIGS. 39A-39B) that are spaced intermittently along the longitudinal slot 3918 relative to each other. As shown in more detail in FIG. 39B, the first pin 3912a engages a first wall 3918a of the longitudinal slot 3918 and the second pin 3912b engages a second, opposing wall 3918b of the longitudinal slot 3918.

Figure 40:
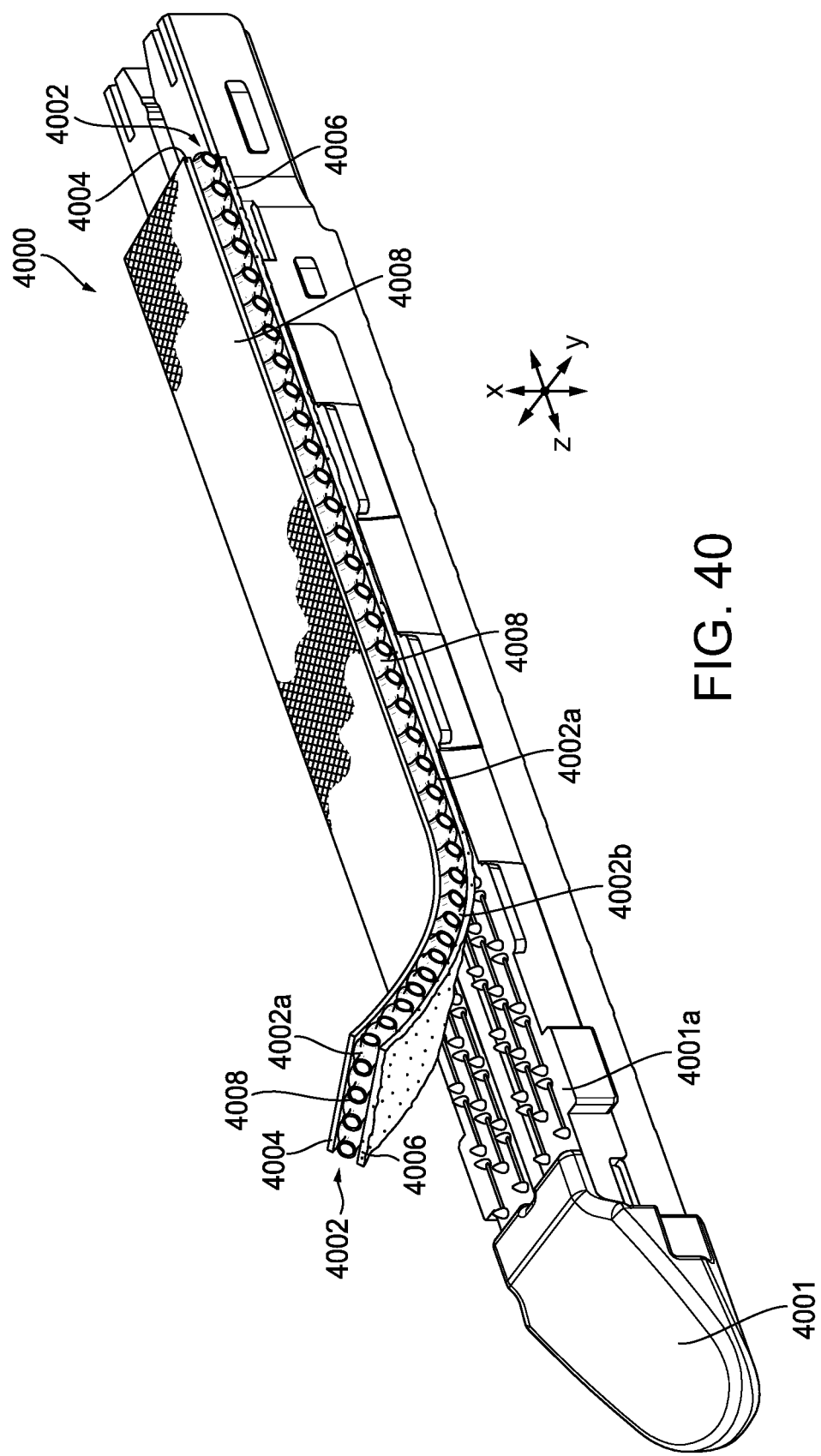
FIG. 40 is a perspective view of another exemplary embodiment of a stapling assembly having a compressible non-fibrous adjunct releasably retained on a staple cartridge.

As noted above, in some embodiments, the second outer layer can be an adhesive film. In one exemplary embodiment, as shown in FIG. 40, an adjunct 4000 is disposed on a top surface 4001a of a cartridge 4001, like cartridge 200 in FIGS. 1-2C. The adjunct 4000 includes an internal structure 4002, a first outer layer 4004 disposed on the top surface 4002a of the internal structure 4002, and a second outer layer 4006 disposed on the opposing bottom surface 4000b, which opposes the top surface 4002a, of the internal structure 4002. Aside from the differences discussed below, the adjunct 4000 can be similar to adjunct 3700 in FIGS. 37A-38B and therefore common features are not described in detail herein. As shown, the internal structure 4002 is formed of interconnected repeating unit cells 4008, like unit cell 810 in FIGS. 8A-9B. Further, the second outer layer 4006 is the form of an adhesive film that is attached to the top surface 4001a of the cartridge 4001. In this illustrated embodiment, the second layer 4006 is an adhesive film formed of a pressure sensitive adhesive. Additional details on the adhesive film and other attachment methods can be found in U.S. Pat. No. 10,349,939, which is incorporated by reference herein in its entirety.

Staple Pocket Lattices

Figure 41A:
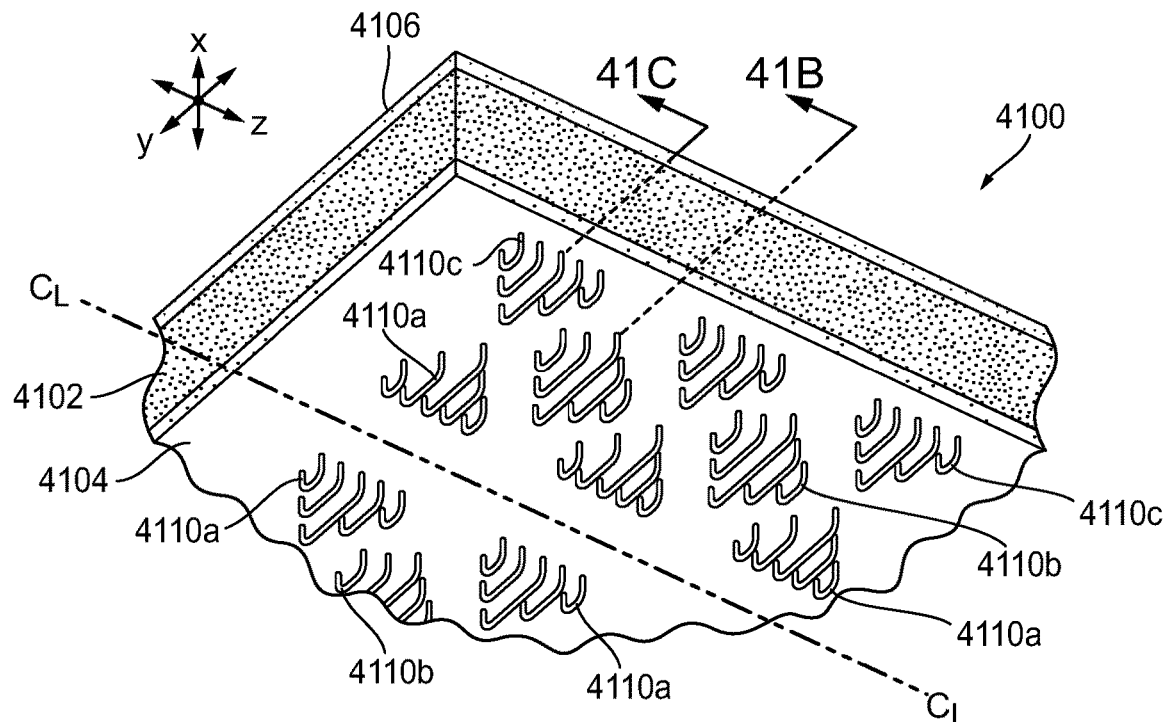
FIG. 41A is a perspective view of another exemplary embodiment of a compressible non-fibrous adjunct.
Figure 41B:
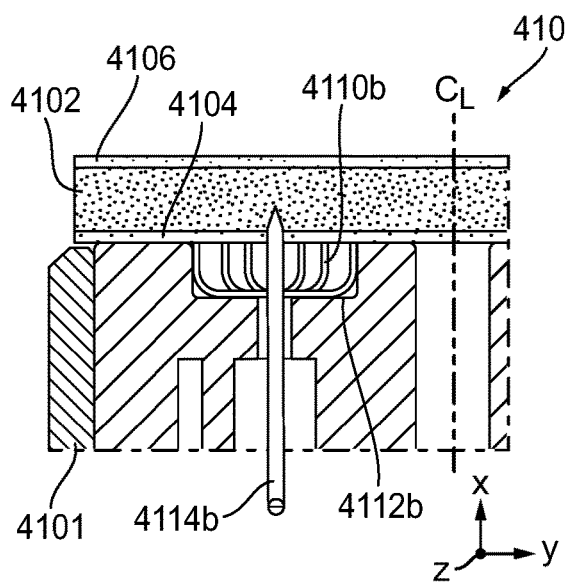
FIG. 41B is a cross-sectional view of a portion of the adjunct of FIG. 41A taken at line 41B-41B and releasably retained on a staple cartridge.
Figure 41C:
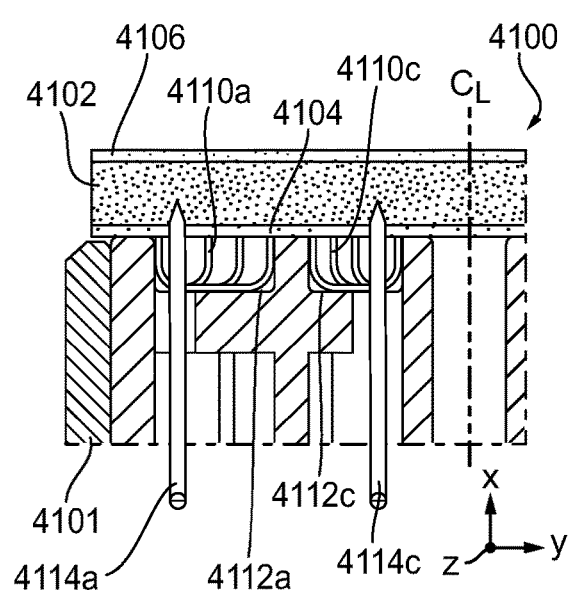
FIG. 41C is a cross-sectional view of a portion of the adjunct of FIG. 41A taken at line 41C-41C and releasably retained on a staple cartridge.

In some embodiments, the adjunct can also include lattice structures extending from the second outer layer and configured to be inserted into staple pockets or recess channels of a staple cartridge. For example, as shown in FIG. 41A, an adjunct 4100 includes an internal lattice structure 4102 extending between two outer layers 4104, 4106. The internal lattice structure 4102 is generally formed of interconnected repeating unit cells, and while the repeating unit cells are omitted from this illustration, any of the repeating unit cells disclosed herein can be used. Further, each of the two outer layers 4104, 4106 can be formed of either lattice structures or as a film, and therefore, the two outer layers are each generally illustrated in FIGS. 41A-41C. The first outer layer 4106 is configured to contact tissue, and, as shown in FIGS. 41B-41C, the second outer layer 4104 is configured to contact a cartridge 4101. The cartridge 4101 is similar to cartridge 200 in FIGS. 1-2C, and therefore common features are not described in detail herein.

As further shown in FIGS. 41A-41C, the adjunct 4100 includes staple pocket lattices 4110a, 4110b, 4110c that extend outward from the second outer layer 4104. The staple pocket lattices can function as a separate compression zone of the adjunct 4100, e.g., the staple pocket lattices 4110a, 4110b, 4110c can have a different compression rate than that the bulk of the adjunct so as to not substantially add to the solid height of the overall adjunct. While the staple pocket lattices can have a variety of configurations, in this illustrated embodiment, there are two sets of three longitudinal rows of staple pocket lattices 4110a, 4110b, 4110c on opposite sides of the intended cut-line of the adjunct. While the staple pocket lattices can have a variety of configurations, each staple pocket lattice is formed of five U-shaped struts. The shape and size of the perimeter surrounding the each staple pocket lattice 4110a, 4110b, 4110c can be triangular or diamond-shaped, and can be complementary to the shape and size of the corresponding staple pockets 4112a, 4112b, 4112c, which can also be triangular or diamond-shaped. In other embodiments, the shape and size of the lattice structures and the staple pockets can differ. As shown in FIGS. 41B-41C, once the adjunct 4100 is disposed on the cartridge 4101, at least a portion of the staples 4114a, 4114b, 4114c within the cartridge 4101 extend through the respective staple pocket lattices 4110a, 4110b, 4110c, and therefore captured by the staple crowns when the adjunct is stapled to tissue. Thus, the staple pocket lattices can also help with attachment of the adjunct to the staple cartridge and/or the alignment of the adjunct relative to the staples.

The structural configurations of the unit cells disclosed herein can also be tailored to effect variable mechanical responses within the same adjunct, e.g., in the lateral and/or longitudinal directions (e.g., y- and/or z-directions, respectively). For example, in certain embodiments, an adjunct can be formed of at least two or more different lattice structures placed side by side so as to create at least two substantially different compressive properties within the same adjunct.

Figure 42A:
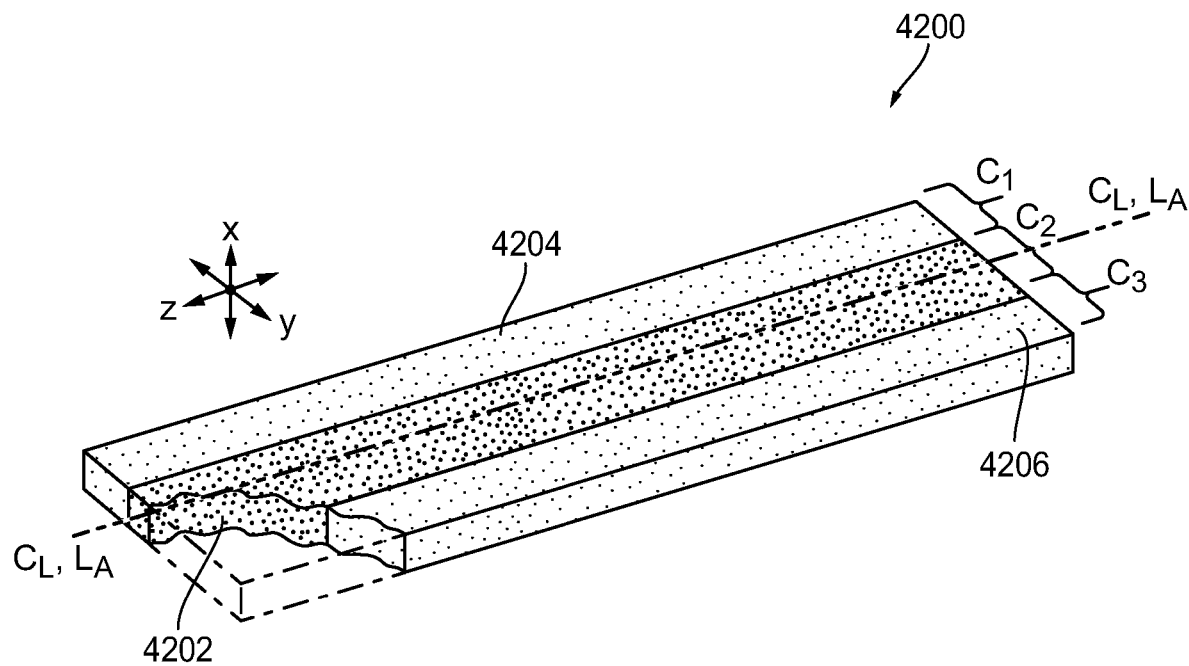
FIG. 42A is a perspective view of another exemplary embodiment of a compressible non-fibrous adjunct.

As generally illustrated in FIG. 42A, an adjunct 4200 can have one internal lattice structure 4202 and two outside lattice structures 4204, 4206, in which each lattice structure 4202, 4204, 4206 defines respective compression zones $C_1$, $C_2$, $C_3$ of the adjunct 4200. In this embodiment, the first and second outside lattice structures are structurally identical, and therefore $C_2$ and $C_3$ are the same. As shown, the lattice structures 4202, 4204, 4206 are laterally offset from each other relative to the longitudinal axis of the adjunct 4200. That is, the first outside lattice structure 4204 is positioned directly adjacent to a first longitudinal side (obstructed) of the internal lattice structure 4202, and the second outside lattice structure 4206 is positioned directly adjacent to a second, opposing longitudinal side (obstructed) of the internal lattice structure 4202. Since each lattice structure can be formed by any of the repeating unit cells disclosed herein, the three lattice structures 4202, 4204, 4206 are illustrated without any unit cells. A person skilled in the art will appreciate that each lattice structure can be formed of strut-based repeating unit cells or strut-less based repeating unit cells.

Figure 42B:
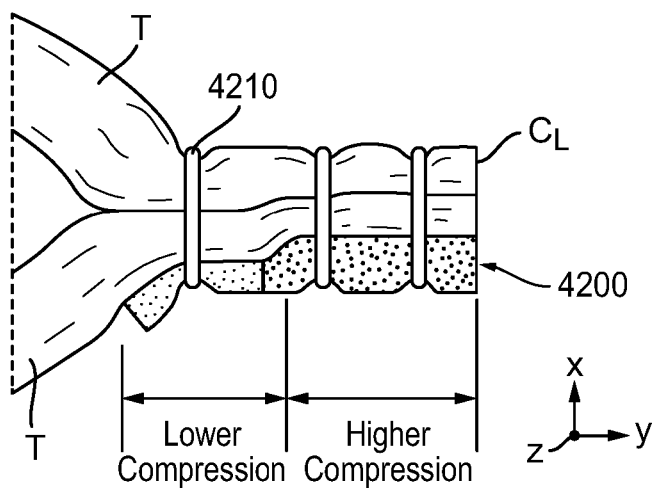
FIG. 42B is a partial-schematic illustrating the adjunct of FIG. 42A in a tissue deployed condition.

As further shown, the intended cut-line $C_L$ of the adjunct 4200 is defined across the internal lattice structure 4202 and along the longitudinal axis $L_A$ of the adjunct 4200. As such, in this illustrated embodiment, the internal lattice structure 4202 can be configured to be stiffer, and thus exhibit a higher resistance to compression, compared to the outside lattice structures 4204, 4206. Thus, the resulting adjunct 4200 can have a variable compression strength in the lateral direction (e.g., the y-direction) relative to the cut-line $C_L$ of the adjunct 24200. This variable compression strength can therefore ease transition of tissue compression at the outer-most staple row 4210 when the adjunct is stapled to tissue, as shown in FIG. 42B.

Figure 43A:
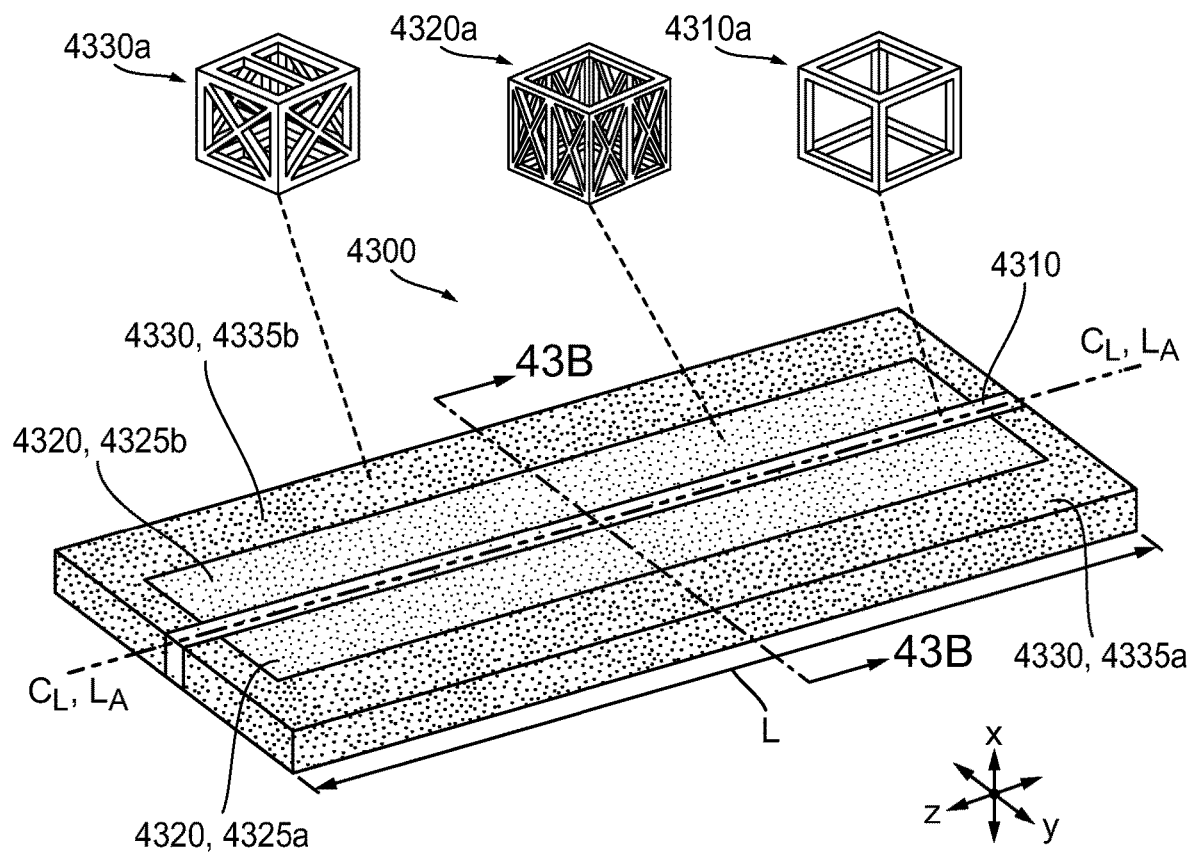
FIG. 43A is a perspective view of another exemplary embodiment of a compressible non-fibrous adjunct.
Figure 43B:
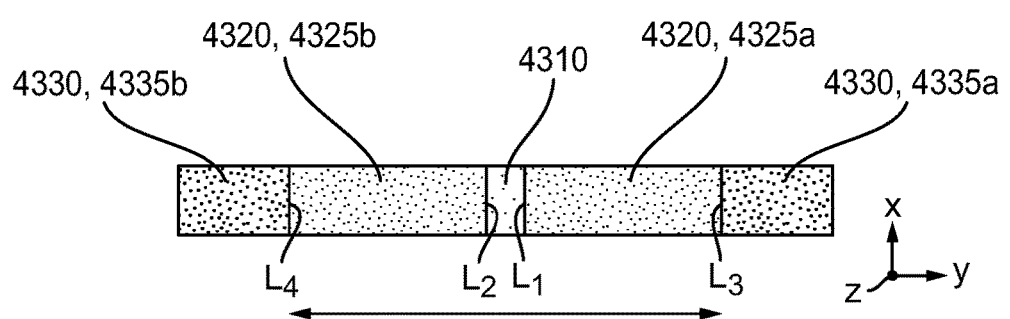
FIG. 43B is a cross-sectional view of the adjunct of FIG. 43A taken at line 43B-43B.

FIGS. 43A-43B illustrate another embodiment of an adjunct 4300 having variable compression strength along a lateral direction (e.g., the y-direction) relative to its longitudinal axis $L_A$. In this illustrated embodiment, the adjunct 4300 is formed of three different lattice structures 4310, 4320, 4330, each being formed of different repeating units. More specifically, the first lattice structure 4310 is formed of interconnected first repeating unit cells 4310a, one of which is illustrated in FIG. 43A, the second lattice structure 4320 is formed of interconnected second repeating unit cells 4320a, one of which is illustrated FIG. 43A, and the third lattice structure 4330 is formed of interconnected third repeating unit cells 4330a, one of which is illustrated in FIG. 43A. As described in more detail below, by designing each lattice structure differently, the resulting adjunct can have a variety of lateral compression responses.

While the repeating unit cells 4310a, 4320a, 4330a can have a variety of configurations, in this illustrated embodiment, the repeating unit cells 4310a, 4320a, 4330a are all strut-based unit cells. Further, depending on the position of the corresponding lattice structure, the repeating unit cells can be structurally configured such that they are more or less stiff compared to the repeating unit cells of the other lattice structures, as described in more detail below.

While the three lattice structures 4310, 4320, 4330 can be positioned relative to each other in a variety of different configurations, the first lattice structure 4310 is the center-most lattice structure of the adjunct in which the intended cut-line $C_L$ of the adjunct 4300 extends therethrough and along the longitudinal axis $L_A$. As such, the first repeating unit cell 4310a can have a structural configuration that is less dense, and thus more pliable, compared to the second and third repeating unit cells, e.g., as shown in FIG. 43A. Further, the first lattice structure 4310 extends along the entire length L of the adjunct 4300. The second lattice structure 4320 is divided into two longitudinal portions 4325a, 4325b. The first longitudinal portion 4325a of the second lattice structure 4320 is positioned against a first longitudinal side wall $L_1$ of the first lattice structure 4310 and the second longitudinal portion 4325b of the second lattice structure 4320 is positioned against a second, opposing longitudinal side wall $L_2$ of the first lattice structure 4310 (see FIG. 43B). Based on their position relative to the cut-line $C_L$, the second repeating unit cells 4320a can be configured to be the most dense, and thus most stiff, compared to the first and third repeating unit cells 4310a, 4330a, e.g., as shown in FIG. 43A.

As further shown in FIG. 43A, the third lattice structure is divided into two U-shaped portions 4335a, 4335b each of which are positioned against the outer walls of the respective first and second longitudinal portions 4325a, 4325b of the second lattice structure 4320 (only the outer longitudinal walls $L_3$ and $L_4$ of each portion 4325a, 4325b are illustrated in FIG. 43B). As a result, the third lattice structure 4320 defines at least a portion of the outer perimeter of the adjunct 4300. Based on the position of the third lattice structure 4330, the third repeating unit cells can be configured to impart an intermediate density, and thus intermediate stiffness, compared to the first and second repeating cells 4310a, 4320a, as shown in FIG. 43A, which can help ease the transition of tissue compression. Further, the structural configuration of the third repeating unit 4330a can be configured so as to promote tissue in-growth. In certain embodiments, the third lattice structure can also be disposed onto at least a portion of the top surface of the second lattice structure, which can further enhance tissue in-growth into the adjunct.

Figure 44A:
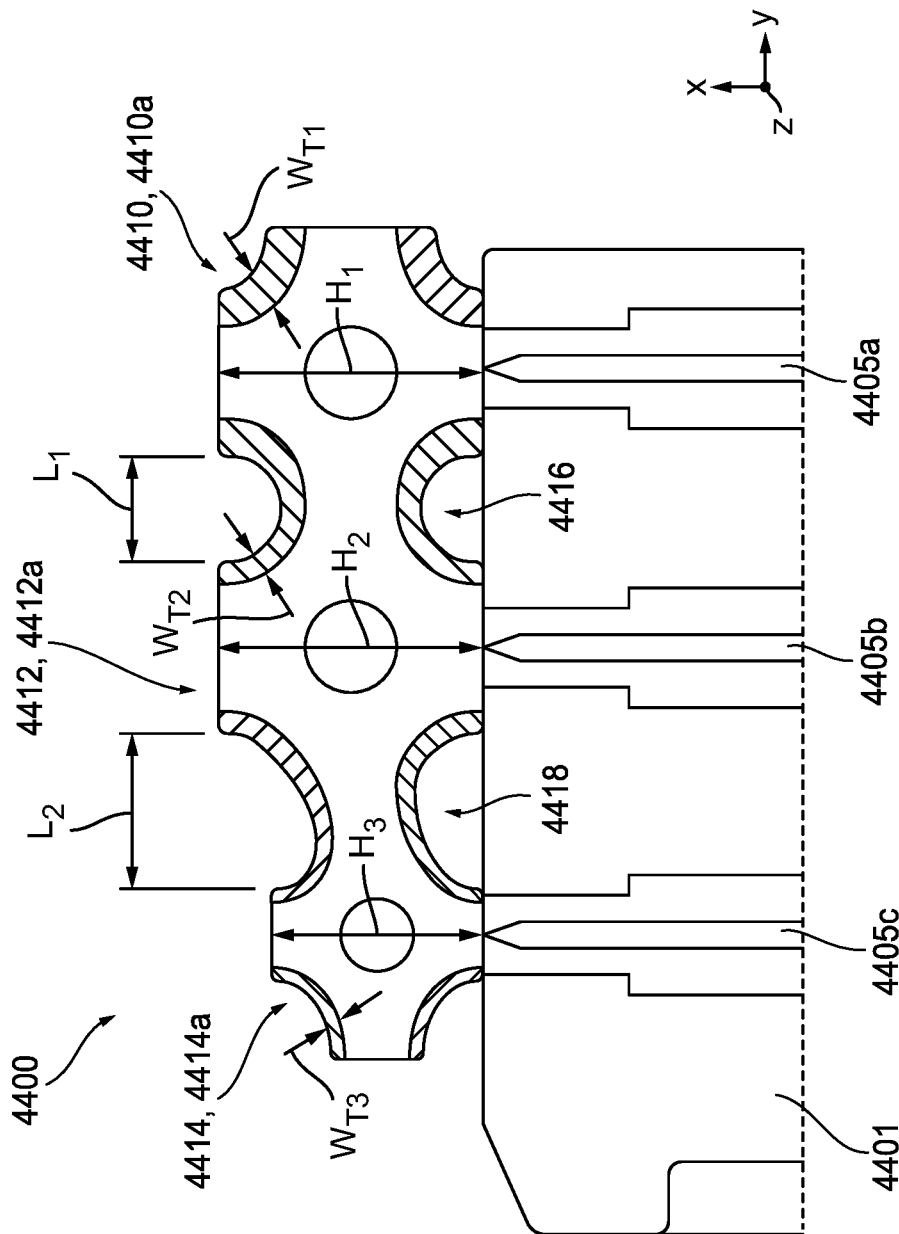
FIG. 44A is cross-sectional view of another exemplary embodiment of a compressible non-fibrous adjunct, showing only a portion of the adjunct releasably retained on a staple cartridge.
Figure 44B:
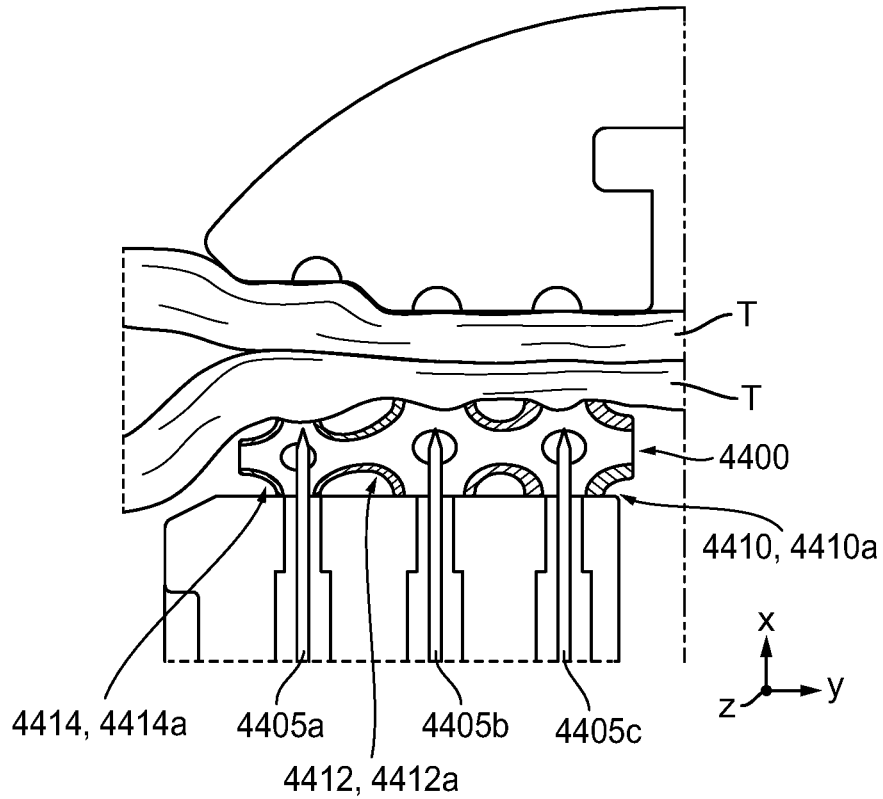
FIG. 44B is a partial-schematic illustrating tissue being clamped between an anvil and the portion of the adjunct of FIG. 44A with staples partially deployed through the adjunct from the staple cartridge.
Figure 44C:
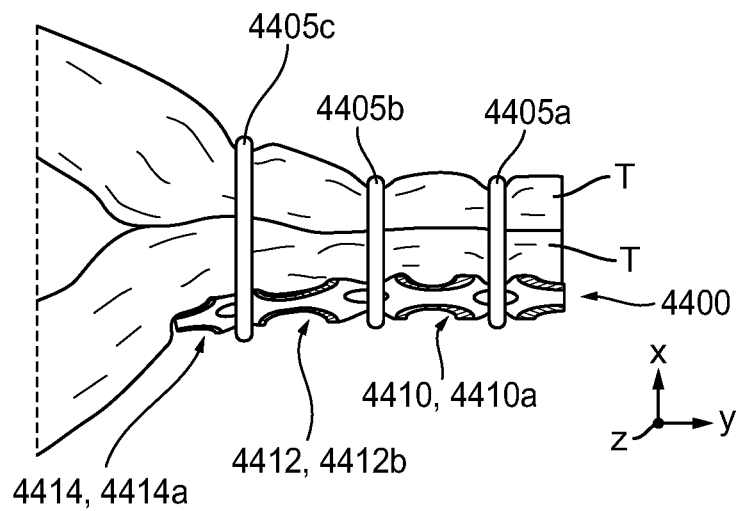
FIG. 44C is a partial-schematic illustrating the adjunct of FIG. 44A in a tissue deployed condition.

In some embodiments, the dimensions (e.g., wall thickness and/or height) of the repeating unit cell can vary among other repeating unit cells. For example, FIGS. 44A-44C illustrate another embodiment of an adjunct 4400 having variable compression strength along a lateral direction (e.g., the y-direction) relative to its longitudinal axis (e.g., the z-direction) as a result of varying dimensions of strut-less based repeating unit cells. As shown in FIGS. 44A-44B, only one half (e.g., the left half) of the adjunct 4400 is illustrated on a staple cartridge 4401 with three rows of staples 4405a, 4405b, 4405c. While the three rows of staples 4405a, 4405b, 4405c can be generally uniform (e.g., nominally identical within manufacturing tolerances), in this illustrated embodiment, the staple height of third row of staples 4405c (e.g., the outer-most staple row) is greater than the staple height of the first and second rows of staples 4405a, 4405b. This difference in staple height can be a contributor to the overall compression behavior of the adjunct. In this illustrated embodiment, the third row of staples 4405c will apply a compressive force to the captured tissue and adjunct, e.g., within the staple's entrapment area, that is less than the compressive force applied by the first and second rows of stapes 4405a, 4405b to respective captured tissue and adjunct, e.g., within respective staple entrapment areas. The adjunct 4400 includes two sets of three longitudinal arrays of repeating unit cells. Since both sets are the same, only one set of three arrays 4410, 4412, 4414 and only one repeating unit cell 4410a, 4412a, 4414a of each of the three arrays are illustrated in FIGS. 44A-44C.

The repeating unit cells 4410a, 4412a, 4414a can have a variety of configurations. In this illustrated embodiment, the repeating unit cells 4410a, 4412a, 4414a are similar in overall shape to that of repeating unit cell 810 in FIG. 9A-9B. However, the wall thickness and height between at least two repeating cells can vary. As shown, the wall thickness $W_T$ from the inner-most repeating unit cells 4410a (e.g., the first repeating unit cells) to the outer-most repeating unit cell 4414a (e.g., third repeating unit cells) decreases. That is, the wall thickness $W_{T1}$ of inner-most repeating unit cell 4410a is greater than the wall thickness $W_{T2}$ of the intermediate repeating cell 4412a, and the wall thickness $W_{T2}$ of the intermediate repeating cell 4412a is greater than the wall thickness $W_{T3}$ of the outer-most repeating unit cell 4414. Further, while the height $H_1$, $H_2$ of each of the inner-most repeating unit cells 4410a and intermediate repeating unit cells 4412a are the same, the height $H_1$, $H_2$ is greater than the height $H_3$ of the outer-most repeating unit cells 4414a. In other embodiments, only the wall thickness or the height vary among the arrays, or the wall thickness varies between only two of the three arrays, or the height varies among all three arrays.

Alternatively or in addition, in instances where the repeating unit cells are similar in shape to Schwarz-P structures, such as Schwarz-P structure 810 in FIGS. 8A-9B, the length of the hollow tubular interconnections between repeating unit cells of different arrays can vary. For example, as further shown in FIG. 44A, the hollow tubular interconnection 4416 between the inner-most repeating unit cell 4410a and the intermediate repeating unit cell 4412a extend at a first length $L_1$, and the hollow tubular interconnection 4418 between the intermediate repeating unit cell 4412a and the outer-most repeating unit cell 4414a extend at a second length $L_2$ that is greater than the first length $L_1$.

The compression behavior of the repeating unit cells 4410, 4410a of the adjunct 4400 is schematically illustrated in FIGS. 44B-44C as the adjunct 4400 is stapled to tissue. As such, the varying dimensions of the repeating unit cells in the lateral direction cause three different compression zones with different compressive strengths, the first zone being defined by the first longitudinal array 4410 of the first repeating units 4410a having a first compressive strength (e.g., the capacity of a structure to withstand a compressive force in the x-direction), the second zone being defined by the second longitudinal array 4412 of the second repeating unit cells 4412a having a second compressive strength, and the third zone being defined by the third longitudinal array 4414 of the third repeating units 4414a having a third compressive strength. While the compressive strengths among each array can vary, in this illustrated embodiment, the first compressive strength is greater than the second compressive strength, and the second compressive strength is greater than the third compressive strength. Thus, the first repeating units 4410a are stiffer than the second repeating unit cells 4412a, and the second repeating unit cells 4412a are stiffer than the third repeating unit cells 4414a.

Cartridge Surface Features

In some embodiments, the staple cartridge can include surface features (e.g., staple pocket projections) that can be configured to interact with the adjunct to help retain the adjunct to the staple cartridge prior to staple deployment. For example, in certain embodiments, the surface features can include projections extending outward from the top surface of the staple cartridge. Alternatively, or in addition, the surface features can include recessed channels defined within the top surface of the staple cartridge. As such, the adjuncts described herein can be designed in a variety of different configurations that are suitable for interacting with the surface features of a staple cartridge, if present, and thus, effect a releasable attachment mechanism between the adjunct and the staple cartridge. Alternatively, or in addition, the adjuncts described herein can be designed in a variety of configurations that are suitable for interacting with staple legs that partially extend outward from their respective cavities within the staple cartridge.

Figure 45A:
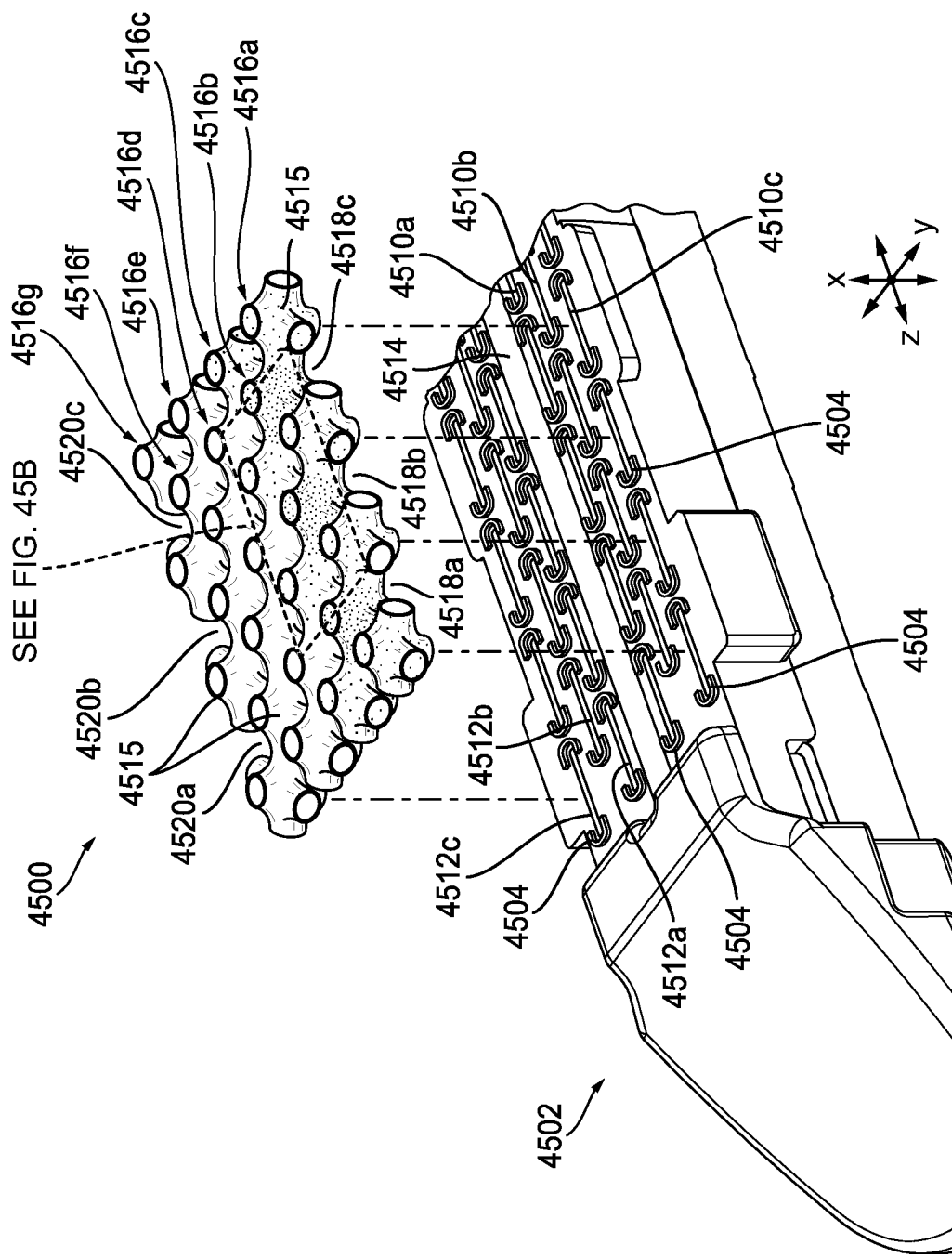
FIG. 45A is a partially exploded perspective view of another exemplary embodiment of a stapling assembly having a compressible non-fibrous adjunct releasably retained on a staple cartridge.
Figure 45B:
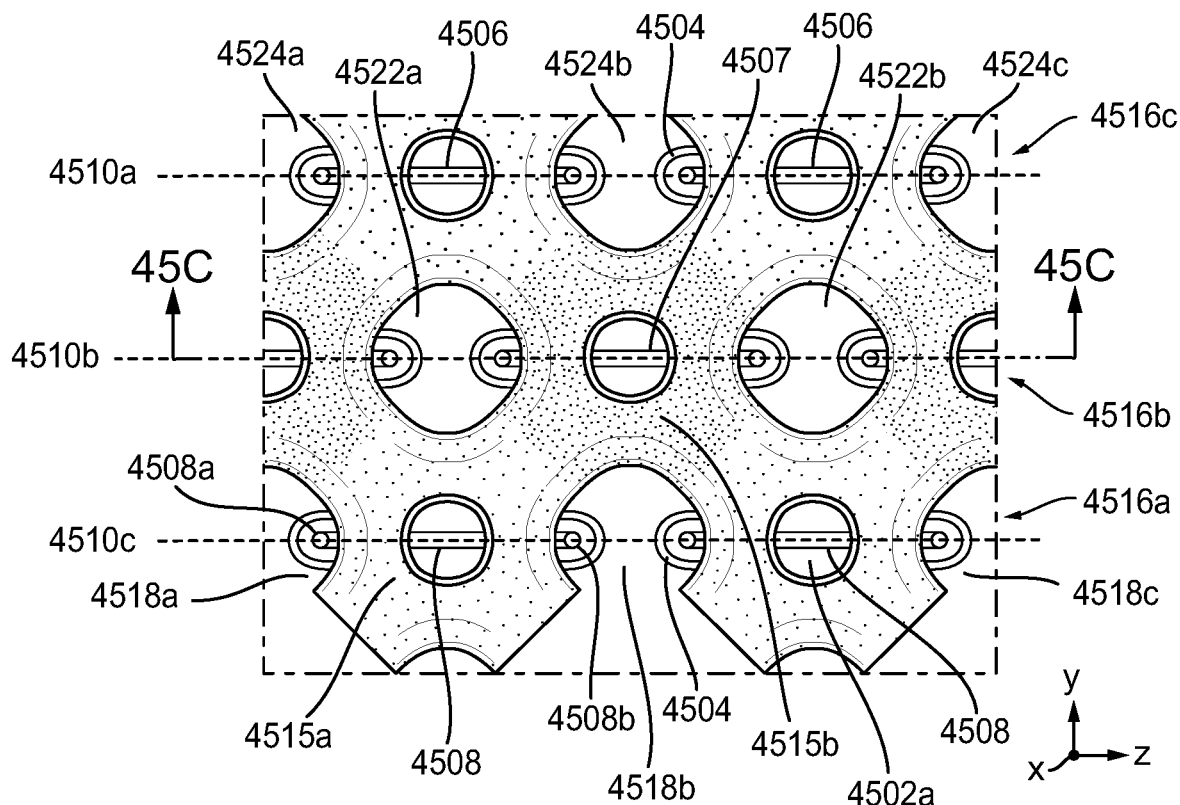
FIG. 45B is a top down view of a portion of the stapling assembly of FIG. 45A.
Figure 45C:
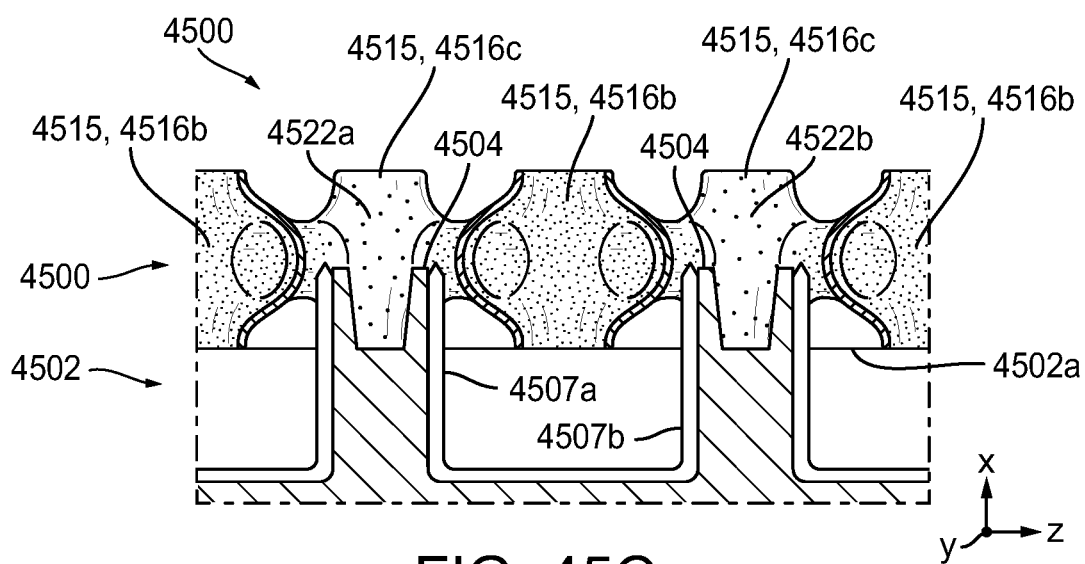
FIG. 45C is a cross-sectional view of the stapling assembly of FIG. 45B taken at line 45C-45C.

FIGS. 45A-45C illustrate an exemplary embodiment of a strut-less based adjunct 4500 that can be configured to interact with surface features 4504 of a staple cartridge 4502. Alternatively, or in addition, the adjunct 4500 can be configured to interact with the legs of the staples 4506. 4507, 4508 that are at least partially disposed within the staple cartridge 4502 (see FIGS. 45B-45C). While the staple cartridge 4502 can have a variety of configurations, in this illustrated embodiment the staple cartridge 4502 is similar to staple cartridge 200 in FIGS. 1-2C except that the surface features 4504 are U-shaped projections that extend outward from the top surface 4502a of the staple cartridge and positioned about a respective end portion of a staple cavity defined within the cartridge 4502. As shown, the staple cavities are arranged in first and second sets of three longitudinal rows 4510a, 4510b, 4510c, 4512a, 4512b, 4512c and positioned on first and second sides of the longitudinal slot 4514, respectively. Further, for each set, the first and third longitudinal rows 4510a, 4510c, 4512a, 4512c are parallel to one another, while the second longitudinal row 4510b, 4512b is staggered with respect thereto.

As further shown in FIGS. 45A-45C, the adjunct 4500 is formed of interconnected repeating unit cells 4516 with each unit cell being structurally similar to the repeating unit cell 810 in FIGS. 9A-9B. Adjunct 4500 is therefore similar to adjunct 800 in FIGS. 8A-8F except that the repeating unit cells 4515 are rotated 45 degrees about the X-axis with respect to FIG. 8A. In other words, the adjunct 800 is illustrated in a 0-90 configuration, whereas the adjunct 4500 is illustrated in ±45 degrees orientation. As a result, the repeating unit cells 4516 are oriented in a way (e.g., a repeating pattern) that can coincide with positions of the surface features 4504 and/or staple cavities 4510a, 4510b, 4510c, 4512a, 4512b, 4512c.

As shown in FIG. 45A, the repeating unit cells 4516 are interconnected to each other and arranged in seven longitudinal rows 4516a, 4516b, 4516c, 4516d, 4516e, 4516f, 4516g each with voids being defined between adjacent unit cells (only voids 4518a, 4518b, 4518c, 4520a, 4520b, 4520c being illustrated in FIG. 45 and voids 4518a, 4518b, 4518c, 4522a, 4522b, 4524a, 4524b, 4524c being illustrated in FIGS. 45B-45C). The first three longitudinal rows 4516a, 4516b, 4516c are configured to overlap respective staple cavity rows 4510a, 4510b, 4510c, the middle-most row 4516d is configured to overlap with the longitudinal slot 4514, and the last three longitudinal rows 4516e, 4516f, 4516g are configured to overlap respective staple cavity rows 4512a, 4512b, 4512c. As a result, as partially illustrated in FIGS. 45B-45C, based on the position of the surface features 4504 relative to the staple cavities, each surface feature 4504 overlaps with and extends at least partially through a corresponding void. Thus, each void is configured to receive and engage at least one surface feature, to thereby retain the adjunct 4500 to the cartridge 4502 prior to staple deployment. In other embodiments, all or some of the voids can be replaced with a thinned area of material in which the at least on surface feature can penetrate into.

Further, as partially illustrated in FIGS. 45B-45C, for each staple cavity row and corresponding row of repeating unit cells, each staple disposed within a staple cavity (only staples 4506, 4507, 4508 and corresponding staple cavities rows 4510a, 4510b, 4510c are illustrated in FIG. 45B) extends across a respective repeating unit cell such that each staple leg overlaps with a corresponding void positioned on one side of the repeating unit cell. For example, as shown in FIG. 45B, with respect to repeating unit cell 4515a in the first unit cell row 4516a and corresponding staple 4508, the first leg 4508a and the second leg 4508b of the staple 4508 overlap with the first void 4518a and the second void 4518b, respectively, which are on opposing sides of the repeating unit cell 4515b in the second unit cell row 4516b. As further illustrated in FIG. 45C, the staple legs 4507a, 4507b extend at least partially through the voids 4522a, 4522b, respectively, when the adjunct 4500 is positioned on the top surface 4502a of the staple cartridge 4502. This can further retain the adjunct 4500 to the cartridge 4502 prior to staple deployment. Thus, the repeating unit cells of an adjunct can be configured to be positioned between and engage with the first and second staple legs of a corresponding staple.

Figure 46A:
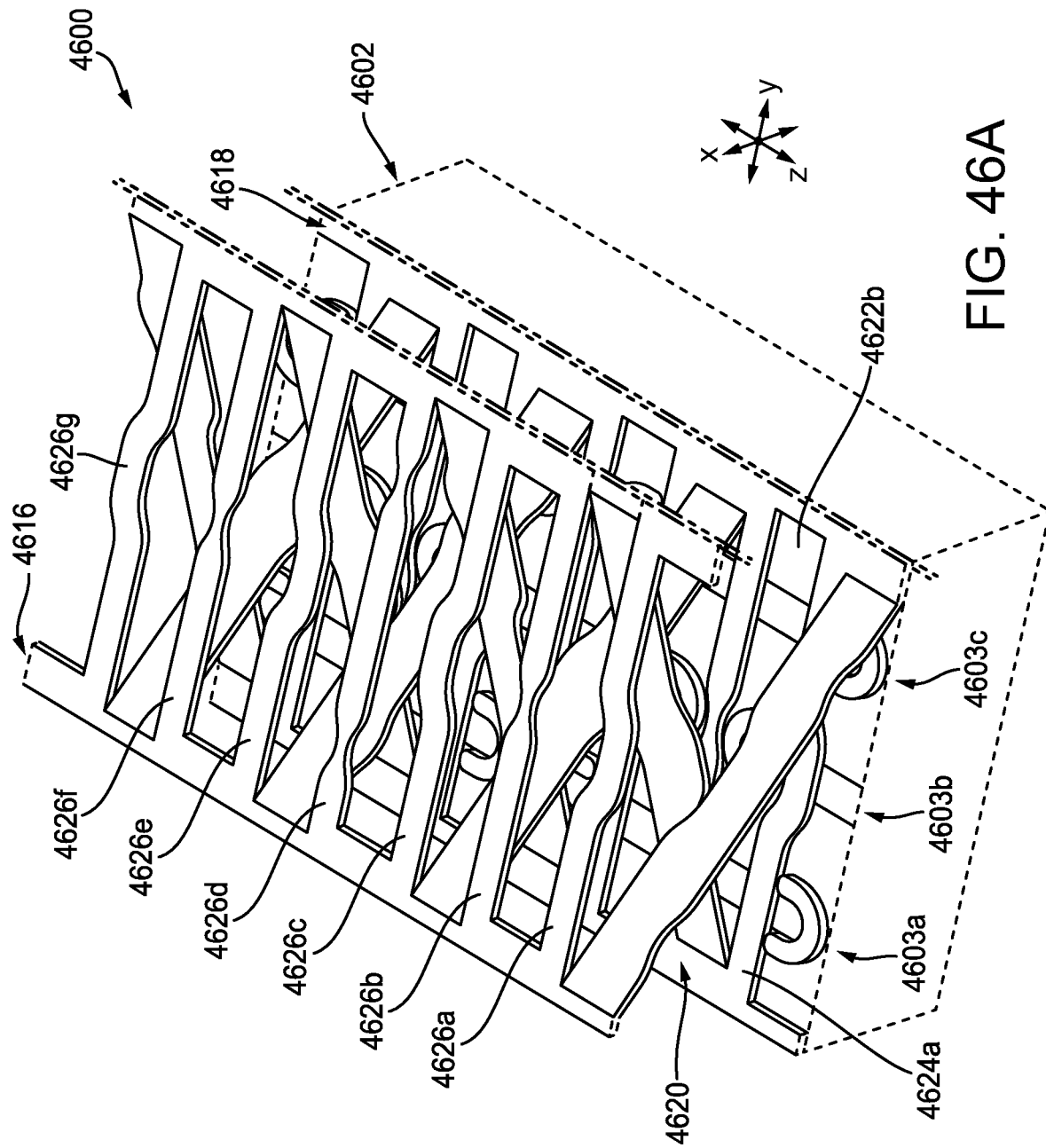
FIG. 46A is a perspective view of another exemplary embodiment of a portion of a stapling assembly having a compressible non-fibrous adjunct releasably retained on a staple cartridge.

FIGS. 46A-46B illustrates another exemplary embodiment of a strut-based adjunct 4600 that can be configured to interact with surface features of a staple cartridge 4602. The staple cartridge 4602 is similar to staple cartridge 3901 in FIG. 39A and therefore common features are not described in detailed herein. Each surface feature has a U-shaped configuration and is positioned about a respective end portion of each staple cavity, and therefore extends along respective longitudinal rows of staple cavities (only three longitudinal rows of staple cavities 4603a, 4603b, 4603c, and therefore three longitudinal rows of surface features are illustrated in FIGS. 46A-46B).

As shown in more detail in FIG. 46B, the longitudinal row of first surface features (only four first surface features 4604a, 4604b, 4604c, 4604d are illustrated) and the longitudinal row of third surface features (only four third surface features 4608a, 4608b, 4608c, 4608d are illustrated) are laterally aligned with each other in the y-direction, and therefore form a set of first lateral rows 4605a, 4605b, 4605c, 4605d, each having respective first and third surface features. The longitudinal row of second surface features (only four second surface features 4606a, 4606b, 4606c, 4606d are illustrated) are laterally offset with respect to the first and second surface features in the z-direction, and therefore forms a set of second lateral rows 4607a, 4607b, 4607c, 4607d, each having a respective second surface feature.

Further, aside from the differences described in detail below, the adjunct 4600 is similar to adjunct 3000 in FIGS. 30A-30B. The adjunct 4600 includes a tissue-contacting layer 4616, a cartridge-contacting layer 4618, and an internal structure 4620 extending therebetween.

As shown in FIG. 46, and in more detail in FIG. 46B, each opening (only eight openings 4622a, 4622b, 4622c, 4622d, 4622e, 4622f, 4622g, 4622h being illustrated) within the cartridge-contacting layer 4618 is configured to receive at least one respective surface feature. As a result, when the adjunct 4600 is positioned on the staple cartridge 4602, the respective surface features extend into and engage respective openings within the cartridge-contacting layer 4618. By way of example, as shown in FIG. 46, the first and third surface features 4604a, 4608a of the first lateral row 4605a extend into the first opening 4622a and engage at least the first cross strut 4624a, whereas the second surface feature 4606a of the second lateral row 4607a extends into a second opening 4622b and engages at least the first cross strut 4624a and opposing cross strut 4624b.

The cross struts (only eight cross struts 4624a, 4624b, 4624c, 4624d, 4624e, 4624f, 4624g are illustrated in FIG. 46B) of the cartridge-contacting layer 4618 can have a variety of configurations. For example, in some embodiments, the width of a cross strut (e.g., in the z-direction) can be generally uniform (e.g., uniform within manufacturing tolerances), whereas in other embodiments, the width of a cross-strut can be non-uniform. In this illustrated embodiment, the width of cross struts 4624a, 4624c, 4624e, 4624g are uniform, whereas the width of remaining cross struts 4624b, 4624d, 4624f are non-uniform. A person skilled in the art will appreciate that the structural configuration of the cross-struts of the cartridge-contacting layer can depend at least upon the structural configuration of the surface features. For example, in this illustrated embodiment, at least a portion of the cross struts include bowing segments to accommodate the U-shaped configuration of the surface features. Depending on the orientation of the U-shaped configuration, some of the bowing segments have a convex-configuration, whereas other bowing segments have a concave-configuration. Further, while the structural configuration of the cross struts 4626a, 4626b, 4626c, 4626d, 4626e, 4626f, 4626g of the tissue-contacting layer 4616 can have a variety of configurations, as shown in FIG. 46A, the cross struts 4626a, 4626b, 4626c, 4626d, 4626e, 4626f, 4626g are structurally similar to the corresponding cross struts 4624a, 4624b, 4624c, 4624d, 4624e, 4624f, 4624g of the cartridge-contacting layer 4618.

Variable Tissue Gap

In some embodiments, it may be desirable to have a variable tissue gap between the adjunct and the anvil to enhance gripping and stabilization of the tissue during stapling and/or cutting tissue. However, the variable tissue gap can adversely affect the ability of the adjunct to apply a generally uniform pressure to the stapled tissue. As such, and as described in more detail below, the adjuncts disclosed herein can be configured to create a variable tissue gap for tissue manipulation, and when stapled to tissue, can further be configured to apply a generally uniform pressure (e.g., a pressure in a range of about 30 kPa to 90 kPa) to the tissue stapled thereto for a predetermined period of time (e.g., for at least 3 days). In certain embodiments, the adjuncts can apply a pressure of at least about 30 kPa for at least three days. In such embodiments, after 3 days, the adjuncts can be configured to apply an effective amount of pressure (e.g., about 30 kPa or less) to the tissue such that the tissue can remain sealed through the tissue's healing cycle (e.g., about 28 days). For example, the adjuncts can be configured to apply a pressure to the stapled tissue, in which the pressure decreases (e.g., a linear decrease) from about 30 kPa to 0 kPa over a predetermined time period from about 3 days to 28 days, respectively.

In general, the adjunct can include a tissue-contacting surface, a cartridge-contacting surface, and an internal structure extending therebetween in which the internal structure includes at least two lattice structures each having a different compressive strength. The at least two lattice structures can vary in structure, shape, or interconnection laterally along its width and/or longitudinally along its length to form a variable tissue gap. In some embodiments, the base geometry of the adjunct can be formed of strut-less based unit cells. In such embodiments, the outer geometry of the adjunct can be formed of strut-based lattice structures. In other embodiments the base geometry can be formed of strut-based unit cells.

Figure 47A:
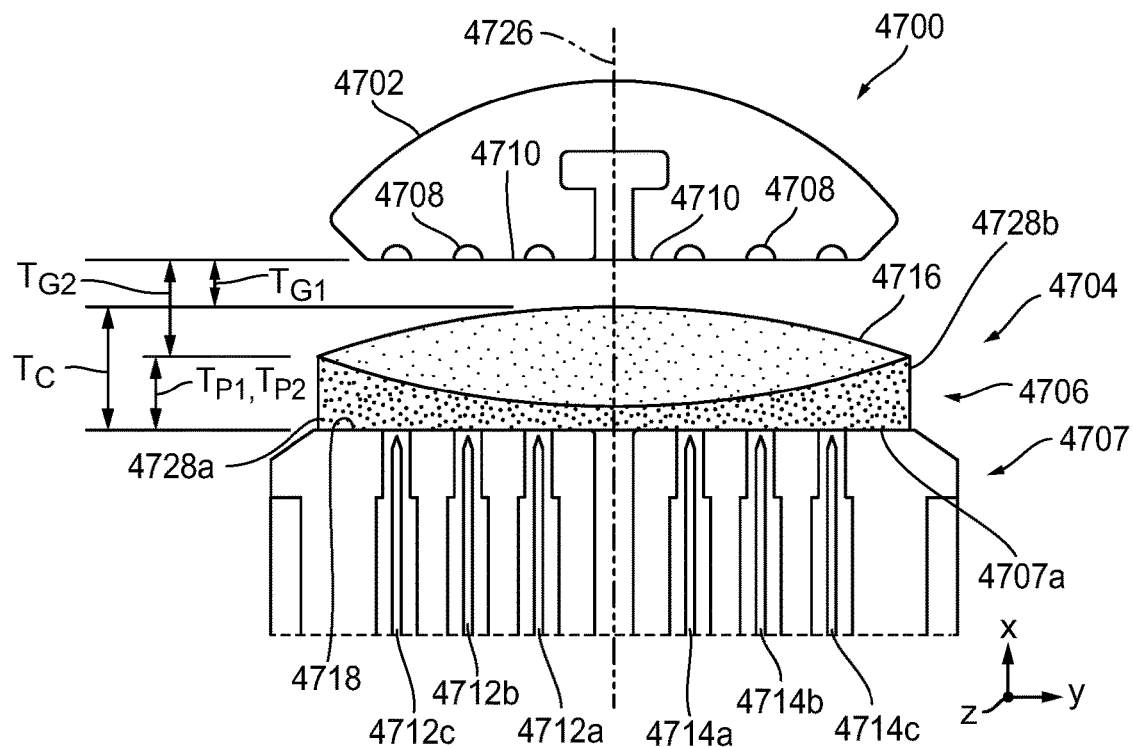
FIG. 47A is a cross-sectional front view of an exemplary embodiment of a surgical end effector having an anvil and a stapling assembly, the stapling assembly having a compressible non-fibrous adjunct releasably retained on a staple cartridge, showing the surgical end effector in a closed positioned without tissue positioned between the anvil and the stapling assembly.
Figure 47B:
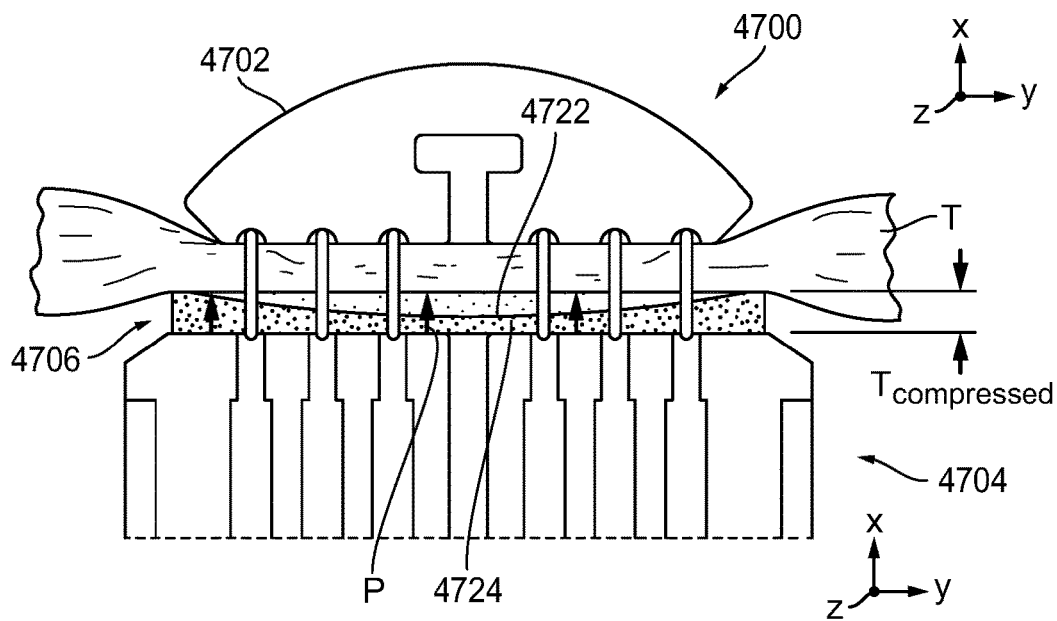
FIG. 47B is a cross-sectional front view of the surgical end effector of FIG. 47A, showing tissue clamped between the anvil and the stapling assembly and stapled to the compressible non-fibrous adjunct.
Figure 47C:
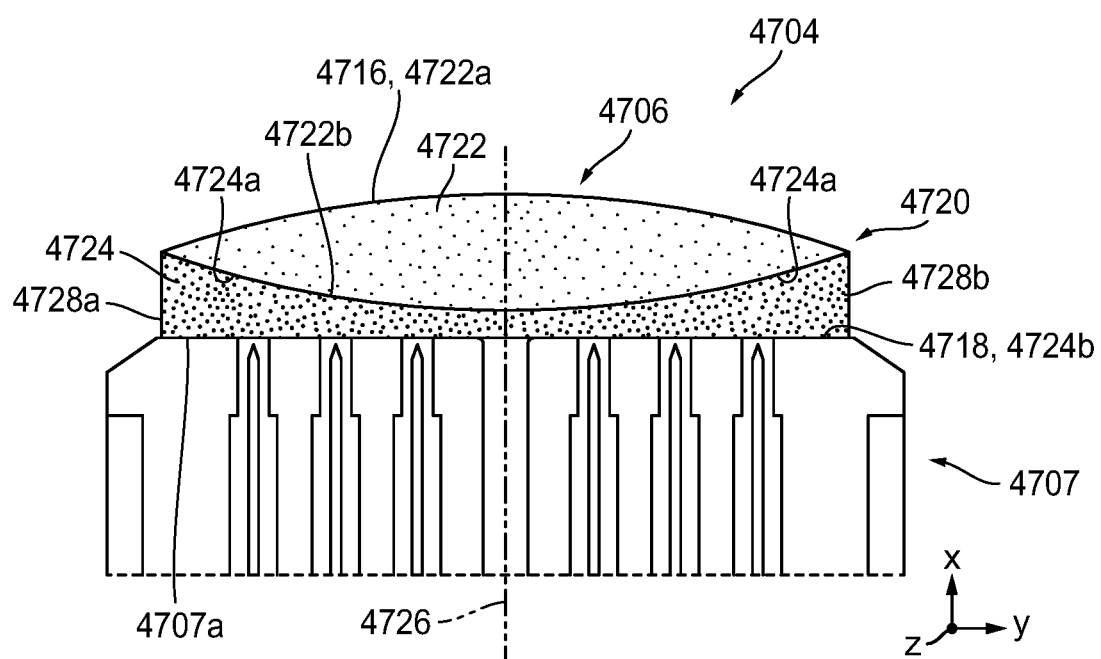
FIG. 47C is a cross-sectional front view of only the stapling assembly of FIG. 47A.

FIGS. 47A-47B illustrate an exemplary embodiment of a surgical end effector 4700 having an anvil 4702 and a stapling assembly 4704. The stapling assembly 4704 includes an adjunct 4706 releasably retained on a top or deck surface 4707a of a staple cartridge 4707 (e.g., the cartridge surface that faces the anvil). The staple cartridge 4707 is similar to cartridge 200 in FIGS. 1-2C, and therefore common features are not described in detail herein. While not illustrated, the anvil 4702 is pivotally coupled to an elongate staple channel, like elongate staple channel 104 in FIG. 1, and the stapling assembly 4704 is positioned within and coupled to elongate staple channel. While the anvil 4702 can have a variety of configurations, as illustrated in FIGS. 47A-47B, the anvil includes a cartridge-facing surface having staple pockets 4708 defined therein with a generally planar tissue-compression surface 4710 (e.g., planar within manufacturing tolerances) extending between the staple pockets 4708 (e.g., extends in the y-direction). FIG. 47A illustrates the surgical end effector 4700, and thus the anvil 4702, in a completely closed position, whereas FIG. 47B illustrates tissue T being clamped between the anvil 4702 and stapling assembly 4704 and being stapled to the adjunct 4706 via staples (only two sets of three staples 4712a, 4712b, 4712c, 4714a, 4714b, 4714c being illustrated). Prior to deployment, in some embodiments, as illustrated in FIGS. 47A and 47C, the staples can be completely disposed within the staple cartridge 4707, whereas in other embodiments, some or all the staples can be partially disposed within the staple cartridge 4707. While the staples 4712a, 4712b, 4712c, 4714a, 4714b, 4714c can have a variety of configurations, in this illustrated embodiment, the staples 4712a, 4712b, 4712c, 4714a, 4714b, 4714c have at least a generally uniform pre-deployed (e.g., unformed) staple height (e.g., nominally identical within manufacturing tolerances). In some embodiments, the staples 4712a, 4712b, 4712c, 4714a, 4714b, 4714c can be generally uniform (e.g., nominally identical within manufacturing tolerances).

As shown in FIG. 47A, and in more detail in FIG. 47C, the adjunct 4706 has a tissue-contacting surface 4716, a cartridge-contacting surface 4718, and an internal structure 4720 extending therebetween. While the internal structure 4720 can have a variety of configurations, in this illustrated embodiments, the internal structure includes two lattice structures 4722, 4724 each having a different compressive strength such that the adjunct 4706, when in a tissue deployed state, is configured to apply a generally uniform pressure to the stapled tissue for a predetermined period of time. In this illustrated embodiment, the first lattice structure 4722 is configured to have a first compressive strength and the second lattice structure 4724 is configured to have a second compressive strength that is greater than the first compressive strength.

Each of the first and second lattice structures 4722, 4724 can be generally formed of unit cells, such as those disclosed herein, e.g., strut-less based unit cells and/or strut-based unit cells. For example, in certain embodiments, one or more unit cells can include at least one triply periodic minimal surface structure, such as those disclosed herein. Alternatively, or in addition, one or more unit cells can be defined by interconnected struts (e.g., planar struts), such as the strut-based unit cells disclosed herein. In certain embodiments, the first and second lattice structures 4722, 4724 can vary in density (e.g., the number of unit cells) and/or shape. As such, aside from general shape and thickness, the specific structural configuration of each of the first and second lattice structures 4722, 4724 is not shown.

The first and second lattice structures 4722, 4724 each extend from a top surface 4722a, 4724a to a bottom surface 4722b, 4724b. Depending on the overall structural configuration of the adjunct, at least a portion of the top surface of at least one lattice structure can serve as a tissue-contacting surface of the adjunct, and at least a portion of the bottom surface of at least one lattice structure can serve as a cartridge-contacting surface of the adjunct. In this illustrated embodiment, the first lattice structure 4722 is positioned on top of the second lattice structure 4724 such that the bottom surface 4722b of the first lattice structure 4722 and the top surface 4724a of the second lattice structure 4724 are in contact. As such, the top surface 4722a of the first lattice structure 4722 therefore forms the tissue-contacting surface 4716 and the bottom surface 4724b of the second lattice structure 4724 therefore forms the cartridge-contacting surface 4718. As a result, the shape of the top surface 4722a of the first lattice structure 4722 can create a tissue gap between the anvil 4702 and the stapling assembly 4704 that is independent of the shape of the top or deck surface 4707a of the staple cartridge 4707.

The top and bottom surfaces 4722a, 4724a, 4724a, 4724b of each lattice structure 4722, 4724 can have a variety of different shapes. In this illustrated embodiment, the top and bottom surfaces 4722a, 4722b of the first lattice structure 4722 each have a convex-shaped configuration. As such, the top surface 4724a of the second lattice structure 4724 has a concave-shaped configuration. Further, since the top or deck surface 4707a of the staple cartridge 4707 has a generally planar configuration (e.g., in the YZ plane), the bottom surface 4724b of the second lattice structure 4724 also has a generally planar configuration (e.g., in the YZ plane). Thus, the resulting overall geometry of the adjunct 4706 creates a curved tissue-contacting surface 4716 relative to the tissue-compression surface 4710 of the anvil 4702, and thus, a variable tissue gap (e.g., two different gap amounts being illustrated as $T_{G1}$, $T_{G2}$) between the anvil 4702 and the stapling assembly 4704.

In this illustrated embodiment, due to the concave-shape of the top surface 4722a of the first lattice structure 4722, the total thickness $T_C$ (e.g., in the x-direction) at the center of the adjunct 4706 (denoted by dotted line 4726, e.g., equidistant from the two opposing terminal lateral-facing edges 4728a, 4728b) is greater than the total thickness $T_{P1}$, $T_{P2}$ (e.g., in the x-direction) at each of the terminal lateral-facing edges 4728a, 4728b of the adjunct 4706 (e.g., the outer longitudinal perimeter of the adjunct 4706 extending in the z-direction). As a result, the overall uncompressed thickness of the adjunct 4706 varies laterally outward along its width relative its center (e.g., ±y-direction), and thus varies laterally relative to the longitudinal axis (e.g., extending in the z-direction) of the adjunct 4706. As such, the uncompressed thickness of the adjunct decreases in the lateral direction while the tissue gap increases. Further, since the two terminal lateral-facing edges 4728a, 4728b are illustrated as being the same thickness, the variation in lateral thickness from the center of the adjunct 4706 to each edge is the same. In other embodiments, the two terminal lateral-facing edges can have different thickness, and thus, the variation in lateral thickness from the center of the adjunct to the respective edges would be different.

As further shown, due to the concave-convex surface relationship between the first and second lattice structures 4722, 4724 and their position and compressive strengths relative to each other, the thickness of each lattice structure (e.g., in the x-direction) also varies laterally outward (e.g., ±y-direction) along their respective lengths (e.g., in the z-direction) relative to their respective centers, which in this embodiment is also the center of the adjunct 4706 (denoted by dotted line 4726). As such, in this illustrated embodiment, the first lattice structure 4722 is thicker than the second lattice structure 4724 at the center of the adjunct and the second lattice structure 4724 is thicker than the first lattice structure 4722 at each of the terminal lateral-facing edges 4728a, 4728b of the adjunct 4706. As a result, the adjunct 4706 is most compressible at its center and least compressible at its terminal lateral-facing edges 4728a, 4728b, and thus, when in a tissue-deployed state, the adjunct 4706 can compress to a generally uniform thickness $T_{compressed}$ (see FIG. 47B). This allows the adjunct 4706 to apply a pressure that is not proportional to its uncompressed variable thickness. Thus when the adjunct is stapled to generally uniform tissue T (e.g., tissue having the same or substantially the same thickness across the width of the adjunct; in the y-direction) with staples 4712a, 4712b, 4712c, 4714a, 4714b, 4714c, the adjunct 4706 can apply a generally uniform pressure P to the stapled tissue T (see FIG. 47B).

Figure 48A:
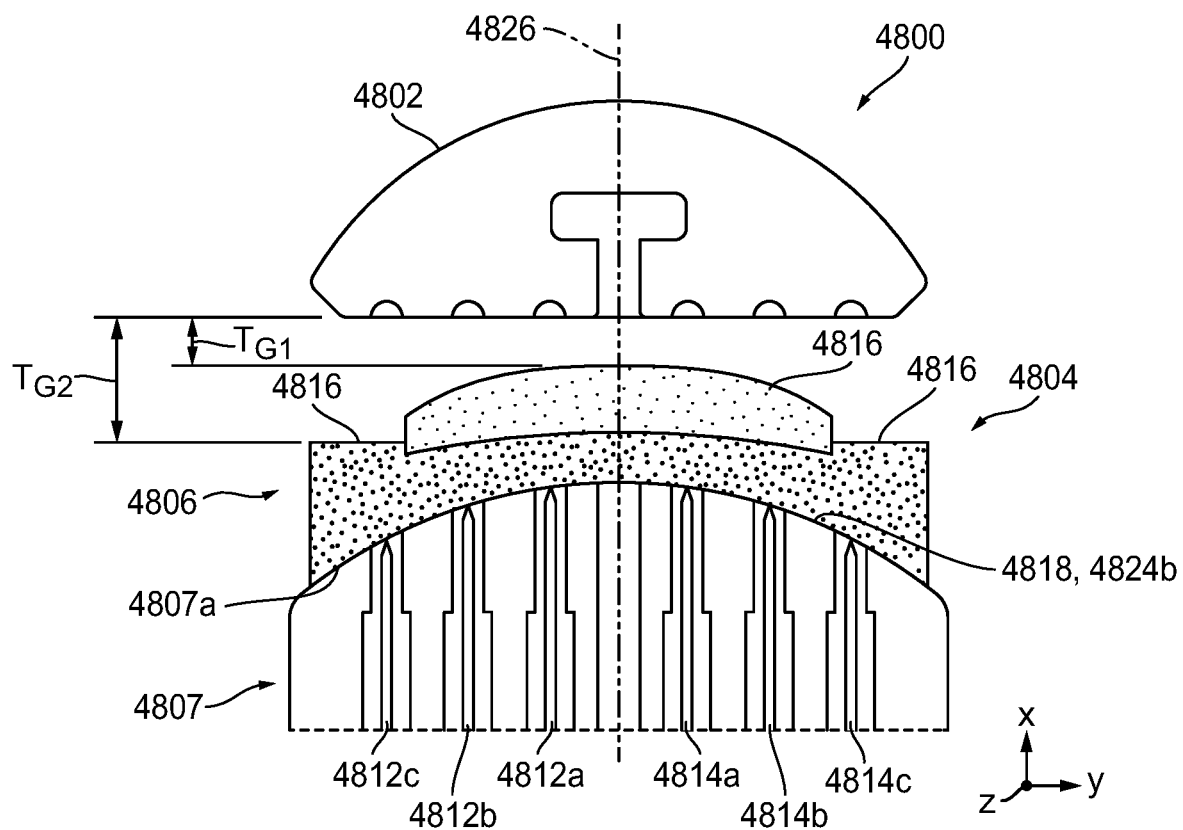
FIG. 48A is a cross-sectional front view of another exemplary embodiment of a surgical end effector having an anvil and a stapling assembly, the stapling assembly having a compressible non-fibrous adjunct releasably retained on a staple cartridge, showing the surgical end effector in a closed positioned without tissue positioned between the anvil and the stapling assembly.
Figure 48B:
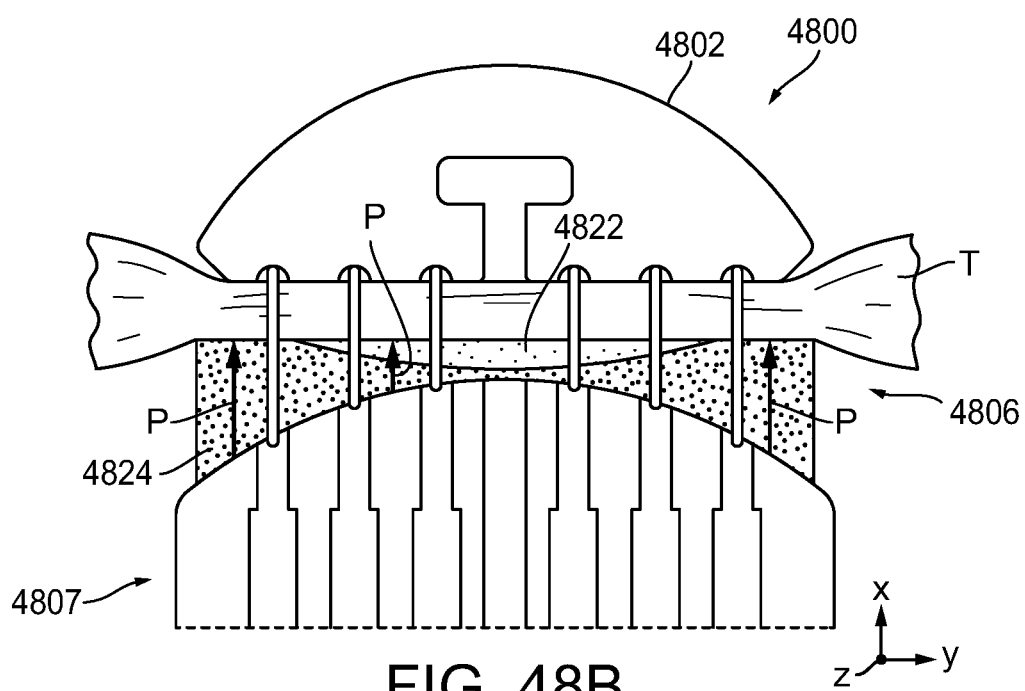
FIG. 48B is a cross-sectional front view of the surgical end effector of FIG. 48A, showing tissue clamped between the anvil and the stapling assembly and stapled to the compressible non-fibrous adjunct.
Figure 48C:
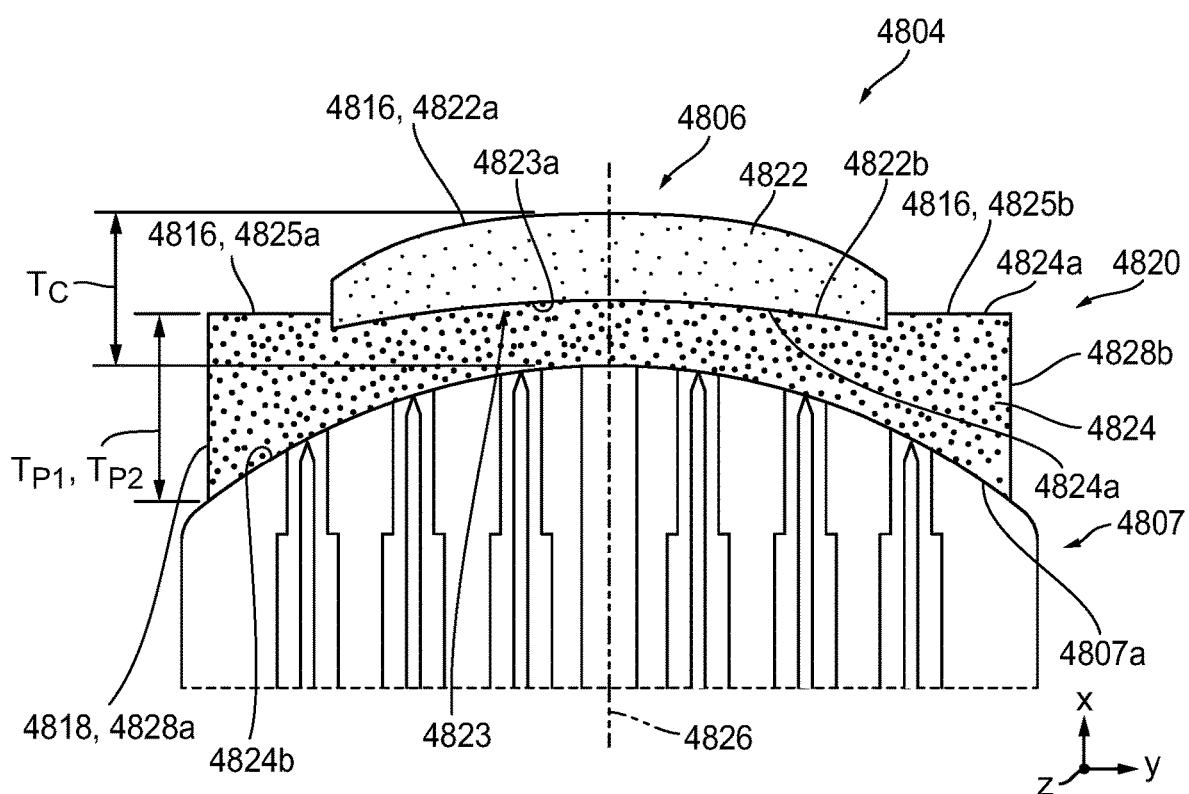
FIG. 48C is a cross-sectional front view of only the stapling assembly of FIG. 48A.

FIGS. 48A-48B illustrate another exemplary embodiment of a surgical end effector 4800 having an anvil 4802 and a stapling assembly 4804. The stapling assembly 4804 includes an adjunct 4806 releasably retained on a top or deck surface 4807a of a staple cartridge 4807 (e.g., the cartridge surface that faces the anvil). Aside from the differences described below, the anvil 4802 is similar to anvil 4702 in FIGS. 47A-47B, and the staple cartridge 4807 is similar to cartridge 200 in FIGS. 1-2C, except that the top or deck surface 4807a is curved, and therefore common features are not described in detail herein. FIG. 48A illustrates the surgical end effector 4800, and thus the anvil 4802, in a completely closed position, whereas FIG. 48B illustrates tissue T being clamped between the anvil 4802 and stapling assembly 4802 and being stapled to the adjunct 4806 via staples (only two sets of three staples 4812a, 4812b, 4812c, 4814a, 4814b, 4814c being illustrated). Prior to deployment, in some embodiments, as illustrated in FIGS. 48A and 48C, the staples can be completely disposed within the staple cartridge 4807, whereas in other embodiments, some or all the staples can be partially disposed within the staple cartridge 4807. While the two sets of staples 4812a, 4812b, 4812c, 4814a, 4814b, 4814c can have a variety of configurations, in this illustrated embodiment, the two sets of staples are same, and thus for each set, the first staples 4812a, 4814a (e.g., inner-most row of staples) have a first height, the second staples 4812b, 4814b (e.g., intermediate row of staples) have a second height that is greater than the first height, and the third staples 4812c, 4814c (e.g., the outer-most row of staples) have a third height that is greater than the second height.

As shown in FIG. 48A, and in more detail in FIG. 48C, the adjunct 4806 has a tissue-contacting surface 4816, a cartridge-contacting surface 4818, and an internal structure 4820 extending therebetween. While the internal structure 4820 can have a variety of configurations, in this illustrated embodiment, the internal structure 4820 includes two lattice structures 4822, 4824 each having a different compressive strength such that the adjunct 4806, when in a tissue deployed state, is configured to apply a generally uniform pressure to the stapled tissue for a predetermined period of time. In this illustrated embodiment, the first lattice structure 4822 is configured to have a first compressive strength and the second lattice structure 4824 is configured to have a second compressive strength that is greater than the first compressive strength.

Each of the first and second lattice structures 4822, 4824 can be generally formed of unit cells, such as those disclosed herein, e.g., strut-less based unit cells and/or strut-based unit cells. For example, in certain embodiments, one or more unit cells can include at least one triply periodic minimal surface structure, such as those disclosed herein. Alternatively, or in addition, one or more unit cells can be defined by interconnected struts (e.g., planar struts), such as the strut-based unit cells disclosed herein. As such, aside from general shape and thickness, the specific structural configuration of each of the first and second lattice structures 4822, 4824 is not shown.

The first and second lattice structures 4822, 4824 each extend from a top surface 4822a, 4824a to a bottom surface 4822b, 4824b. Depending on the overall structural configuration of the adjunct, at least a portion of the top surface of at least one lattice structure can serve as a tissue-contacting surface of the adjunct, and at least a portion of the bottom surface of at least one lattice structure can serve as a cartridge-contacting surface of the adjunct. In this illustrated embodiment, the first lattice structure 4822 is narrower in width (e.g., in the y-direction) compared to the second lattice structure and therefore is positioned only on top of a center region 4823 of the second lattice structure 4824. As such, the entire bottom surface 4822b of the first lattice structure 4822 contacts only a portion of the top surface 4824a of the second lattice structure 4824, e.g., the top surface 4823a of only the center region 4823. As a result, the top surface 4822a of the first lattice structure 4822 and the two exposed portions 4825a, 4825b of the top surface 4824a of the second lattice structure 4824 form the tissue-contacting surface 4816 and the bottom surface 4824b of the second lattice structure 4824 forms the cartridge-contacting surface 4818.

The top and bottom surfaces 4822a, 4824a, 4824a, 4824b of each lattice structure 4822, 4824 can have a variety of different shapes. A person skilled in the art will appreciate that the shape of the top and bottom surfaces can depend at least upon the top or deck surface of the staple cartridge to which the adjunct is to be releasably retained thereto. In this illustrated embodiment, the top and bottom surfaces 4822a, 4822b of the first lattice structure 4822 each have a convex-shaped configuration. As such, the top surface 4823a of the center region 4823 of the second lattice structure 4824 has a convex-shaped configuration, while the two exposed portions 4825a, 4825b of the top surface 4824a of the second lattice structure 4824 each have a generally planar configuration (e.g., extending in the y-direction). Further, since the top or deck surface 4807a of the staple cartridge 4807 has a convex-shaped configuration, the bottom surface 4824b of the second lattice structure 4824 has a concave-shaped configuration.

In this illustrated embodiment, due to the structural interconnection between the first and second lattice structures 4822, 4824 and the resulting shape of the tissue-contacting surface 4816, the total thickness $T_C$ (e.g., in the x-direction) at the center of the adjunct 4806 (denoted by dotted line 4826, e.g., equidistant from the outer-most terminal lateral-facing edges 4828a, 4828b) is less than the total thickness $T_{P1}$, $T_{P2}$ (e.g., in the x-direction) at each of the outer most terminal lateral-facing edges 4828a, 4828b of the adjunct (e.g., the outer longitudinal perimeter of the adjunct 4806 extending in the z-direction). As a result, the overall uncompressed thickness of the adjunct 4806 varies laterally outward along its width relative its center (e.g., ±y-direction). Thus, the overall uncompressed thickness of the adjunct varies laterally relative to the longitudinal axis (e.g., extending in the z-direction) of the adjunct 4806.

As further shown, due to at least the structural relationship between the first and second lattice structures 4822, 4824 and their compressive strengths relative to each other in combination with the curved-configuration of the top surface 4807a of the staple cartridge 4807, the thickness of each lattice (e.g., in the x-direction) also varies laterally outward along their respective lengths relative to their respective centers (e.g., ±y-direction), which in this embodiment, is also the center of the adjunct 4806 (denoted by dotted line 4826). As such, in this illustrated embodiment, the first lattice structure 4822 is thicker than the second lattice structure 4824 at the center of the adjunct 4806. As a result, the adjunct 4806 is most compressible at its center and least compressible at its outer-most terminal lateral-facing edges 4828a, 4828b. This allows the adjunct 4806 to apply a generally uniform pressure despite its variations in its compressed thickness. Thus, when the adjunct is stapled to substantially uniform tissue T (e.g., tissue having the same or substantially the same thickness (e.g., in the x-direction) across the width of the adjunct (e.g., in the y-direction) with staples 4812a, 4812b, 4812c, 4814a, 4814b, 4814c, the adjunct 4806 compresses to a non-uniform compressed thickness while still applying a generally uniform pressure P to the stapled tissue T (see FIG. 48B). As further shown, in this illustrated embodiment, only the second lattice 4824 overlaps with the outer-most row of staples 4812c, 4814c.

Figure 49:
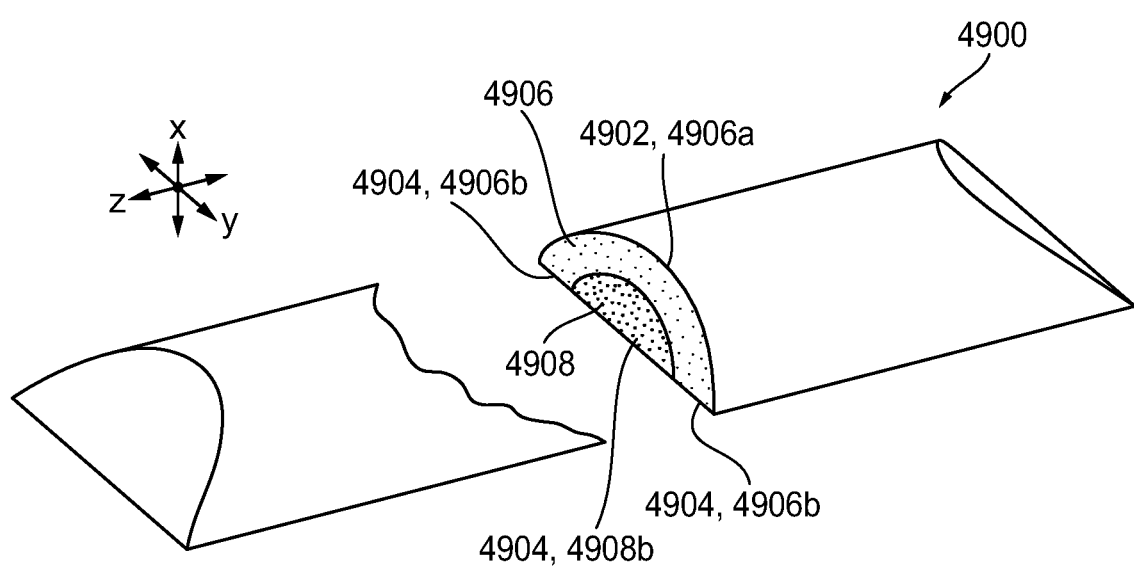
FIG. 49 a perspective view of another exemplary embodiment of a compressible non-fibrous adjunct.

In other embodiments, the second lattice structure can be narrower in width than the first lattice structure. For example, as shown in FIG. 49, the adjunct 4900 includes first and second lattice structures 4906, 4908 having a semi-circular concentric configuration, in which the first lattice structure 4906 envelops the second lattice structure 4908. As a result, the top surface 4906a of the first lattice structure 4906 forms the tissue-contacting surface 4902 of the adjunct 4900 and the bottom surfaces 4906b, 4908b of the first and second lattice structures 4906, 4908 form the cartridge-contacting surface 4904 of adjunct 4900.

As noted above, the adjunct can have two lattice structures that vary in structure, shape, or interconnection longitudinally along the length of the adjunct (e.g., in the z-direction). For example, as illustrated in FIGS. 50A-50B, the adjunct 5002 includes two lattice structures 5004, 5006 that each vary in structure and shape relative to each other and along the length of the adjunct (e.g., extending along the longitudinal axis $L_A$; in the z-direction).

Figure 50A:
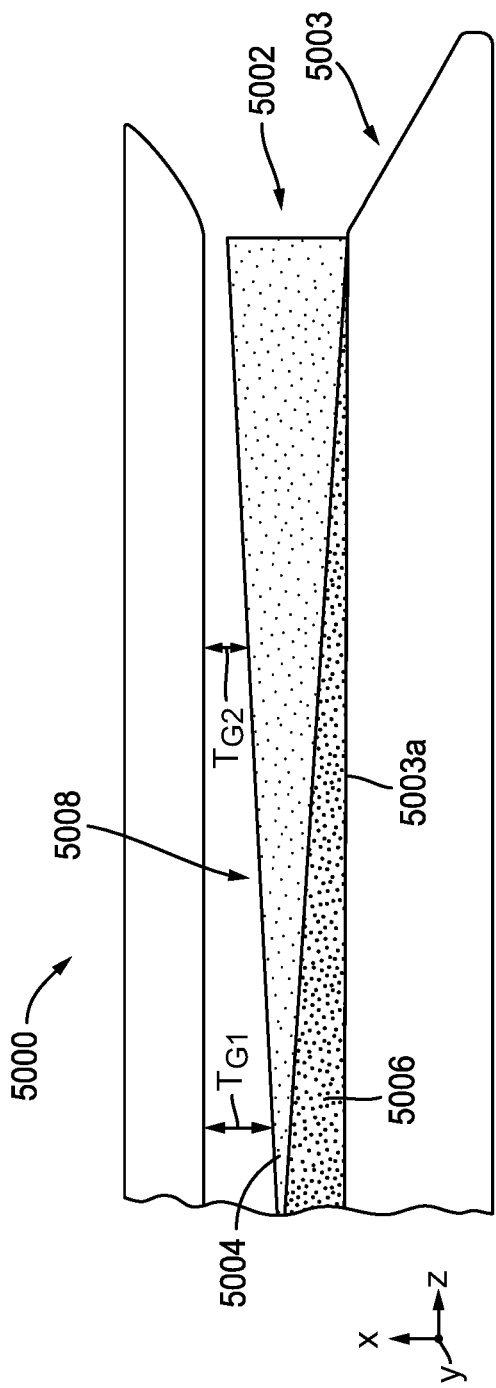
FIG. 50A is a side view of an exemplary embodiment of a surgical end effector having an anvil and a stapling assembly, the stapling assembly having a compressible non-fibrous adjunct releasably retained on a staple cartridge, showing the surgical end effector in a closed positioned without tissue positioned between the anvil and the stapling assembly.
Figure 50B:
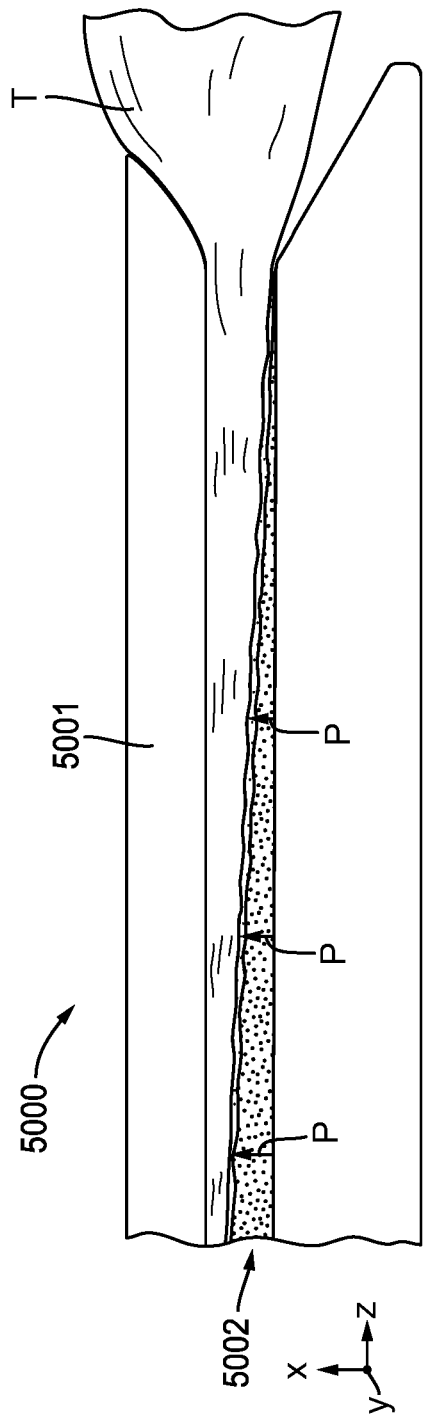
FIG. 50B is a side view of the surgical end effector of FIG. 50A, showing tissue clamped between the anvil and the stapling assembly.
Figure 50C:
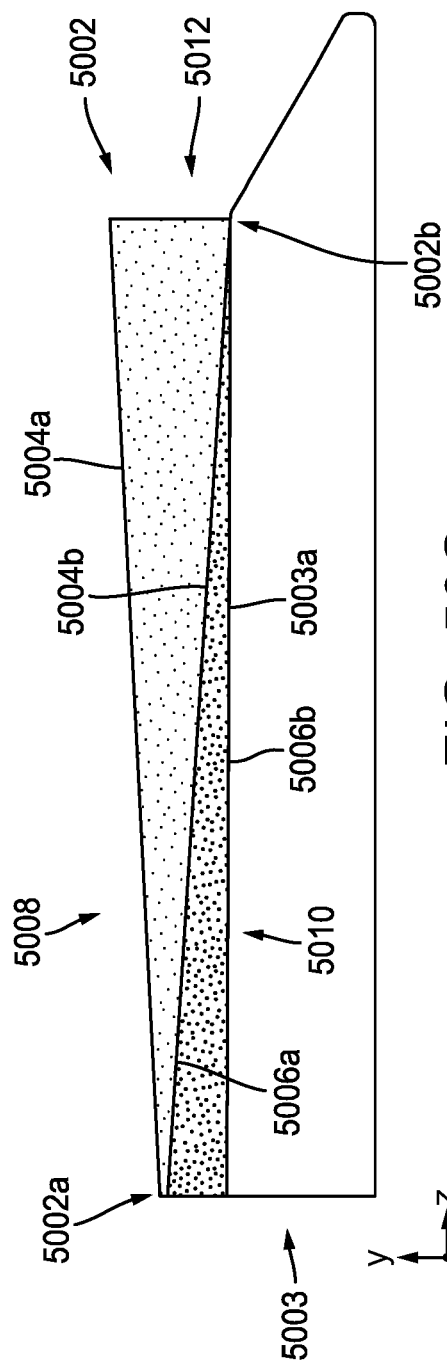
FIG. 50C is side view of only the stapling assembly of FIG. 50A.

FIGS. 50A-50B illustrate an exemplary embodiment of a surgical end effector 5000 that is similar to surgical end effector 5000 except for the adjunct 5002, which has a variable compression strength along its length that extends along the longitudinal axis $L_A$ (e.g., in the z-direction). As shown in FIG. 50A, and in more detail in FIG. 50C, the adjunct 5002 is positioned on a top or deck surface 5003a of a staple cartridge 5003. The staple cartridge 5003 is similar to staple cartridge 4707 in FIGS. 47A-47C with staples 4712a, 4712b, 4712c, 4714a, 4714b, 4714c disposed therein, and therefore common features are not described herein.

The adjunct 5002 has a tissue-contacting surface 5008, a cartridge-contacting surface 5010, and an internal structure 5012 extending therebetween. While the internal structure 5012 can have a variety of configurations, the first and second lattice structures 5004, 5006 each have a different compressive strength such that the adjunct 5002, when in a tissue deployed state, is configured to apply a generally uniform pressure (e.g., a pressure in a range of 30 kPa to 90 kPa) to the tissue stapled thereto for a predetermined period of time (e.g., for at least 3 days). In this illustrated embodiment, the first lattice structure 5004 is configured to have a first compressive strength and the second lattice structure 5006 is configured to have a second compressive strength that is greater than the first compressive strength. Thus, the second lattice structure 5004 is stiffer compared to the first lattice structure 5006. In other embodiments, the first lattice structure can be stiffer than the second lattice structure.

Each of the first and second lattice structures 5004, 5006 can be generally formed of unit cells, such as those disclosed herein, e.g., strut-less based unit cells and/or strut-based unit cells. For example, in certain embodiments, one or more unit cells can include at least one triply periodic minimal surface structure, such as those disclosed herein. Alternatively, or in addition, one or more unit cells can be defined by interconnected struts (e.g., planar struts), such as the strut-based unit cells disclosed herein. In certain embodiments, the first and second lattice structures 5004, 5006 can vary in density (e.g., the number of unit cells) and/or shape. As such, aside from general shape and thickness, the specific structural configuration of each of the first and second lattice structures 5004, 5006 is not shown.

The first and second lattice structures 5004, 5006 each extend from a top surface 5004a, 5006a to a bottom surface 5004b, 5006b. Depending on the overall structural configuration of the adjunct, at least a portion of the top surface of at least one lattice structure can serve as a tissue-contacting surface of the adjunct, and at least a portion of the bottom surface of at least one lattice structure can serve as a cartridge-contacting surface of the adjunct. In this illustrated embodiment, the first lattice structure 5004 is positioned on top of the second lattice structure 5006 such that the bottom surface 5004b of the first lattice structure 5004 and the top surface 5006a of the second lattice structure 5006 are in contact. As such, the top surface 5004a of the first lattice structure 5004 forms the tissue-contacting surface 5008 and the bottom surface 5006b of the second lattice structure 5006 forms the cartridge-contacting surface 5010.

While the first and second lattice structures 5004, 5006 can have a variety of configurations, each lattice structure has an uncompressed thickness (e.g., in the x-direction) that varies along the length of the adjunct (e.g., extending in the z-direction). As shown, the top surface 5004a of the first lattice structure 5004 inclines from the proximal end 5002a to the distal end 5002b of the adjunct 5002. Further, since the top or deck surface 5003a of the staple cartridge 5003 has a generally planar configuration (e.g., in the XZ plane), the bottom surface 5006b of the second lattice structure 5006 also has a generally planar configuration (e.g., in the XZ plane). As a result, a variable tissue gap (e.g., two different gap amounts being illustrated as $T_{G1}$, $T_{G2}$) is created between the anvil 5001 and the adjunct 5002 that is independent of the shape of the top or deck surface 5003a of the staple cartridge 5003.

When the adjunct is stapled to tissue, as illustrated in FIG. 50B, the variations in uncompressed thicknesses of each lattice structure along the length of the adjunct, in combination with the first and second compression strengths and variable tissue gap, can allow the adjunct to apply a generally uniform pressure P to the stapled T (see FIG. 50B).

Consistent Tissue Gap

In some embodiments, it may be desirable to have a consistent tissue gap between the adjunct and the anvil to enhance gripping and stabilization of the tissue during stapling and/or cutting tissue. However, the consistent tissue gap can adversely affect the ability of the adjunct to apply a generally uniform pressure to the stapled tissue. As such, and as described in more detail below, the adjuncts disclosed herein can be configured to create a consistent tissue gap for tissue manipulation, and when stapled to tissue, can further be configured to apply a generally uniform pressure (e.g., a pressure in a range of about 30 kPa to 90 kPa) to the tissue stapled thereto for a predetermined period of time (e.g., for at least 3 days). In certain embodiments, the adjuncts can apply a pressure of at least about 30 kPa for at least three days. In such embodiments, after 3 days, the adjuncts can be configured to apply an effective amount of pressure (e.g., a linear decrease in pressure, e.g., about 30 kPa or less) to the tissue such that the tissue can remain sealed through the tissue's healing cycle (e.g., about 28 days). For example, the adjuncts can be configured to apply a pressure to the stapled tissue, in which the pressure decreases (e.g., a linear decrease) from about 30 kPa to 0 kPa over a predetermined time period from about 3 days to 28 days, respectively.

In some embodiments, the adjunct can be designed with a tissue-contacting surface in which at least a portion is generally planar (e.g., in the y-direction) and an opposing cartridge-contacting surface that is non-planar (e.g., along the width of the adjunct, e.g., in the y-direction). The non-planar surface of the cartridge-contacting surface can vary proportionally along and relative to, e.g., a curved or a stepped top or deck surface of a staple cartridge (e.g., the cartridge surface that faces the anvil) or a stepped tissue-compression surface of an anvil.

In general, the adjunct can include a tissue-contacting surface, a cartridge-contacting surface, and an internal structure extending therebetween. In some embodiments, the adjunct can be formed of at least two lattice structures, with a first lattice structure having a non-planar bottom surface that defines at least a portion of the cartridge-contacting surface, and a second lattice structure (e.g., primary lattice structure) having a top surface with at least a portion that is generally planar and that defines at least a portion of the tissue-contacting surface. In other embodiments, the internal structure can be formed of a single lattice structure formed of repeating unit cells that vary in shape and/or dimension in the lateral direction relative to the longitudinal axis of the adjunct. As a result, the adjunct can have an overall geometry that creates a tissue-contacting surface having planar and non-planar surfaces and a non-planar cartridge-contacting surface that is configured to mate to a curved or stepped top or deck surface of the staple cartridge (e.g., the cartridge surface that faces the anvil). Thus, a generally consistent tissue gap can be created independent of the shape of the top or deck surface of the staple cartridge.

In some embodiments, the dimensions (e.g., wall thickness and/or height) of the repeating unit cells can be varied such that, when the adjunct is stapled to tissue, the adjunct can apply a generally uniform pressure (e.g., a pressure in a range of 30 kPa to 90 kPa) to the stapled tissue for a predetermined period of time (e.g., for at least three days). For example, the repeating unit cells of one longitudinal row can vary relative to the repeating unit cells of an adjacent longitudinal row. Thus, an adjunct can be designed in such a way that, prior to staple deployment, the adjunct can create a consistent tissue gap with the anvil, and when in a tissue-deployed state, can apply a generally uniform pressure (e.g., a pressure in a range of 30 kPa to 90 kPa) to the stapled tissue for a predetermined period of time (e.g., for at least three days).

Figure 51A:
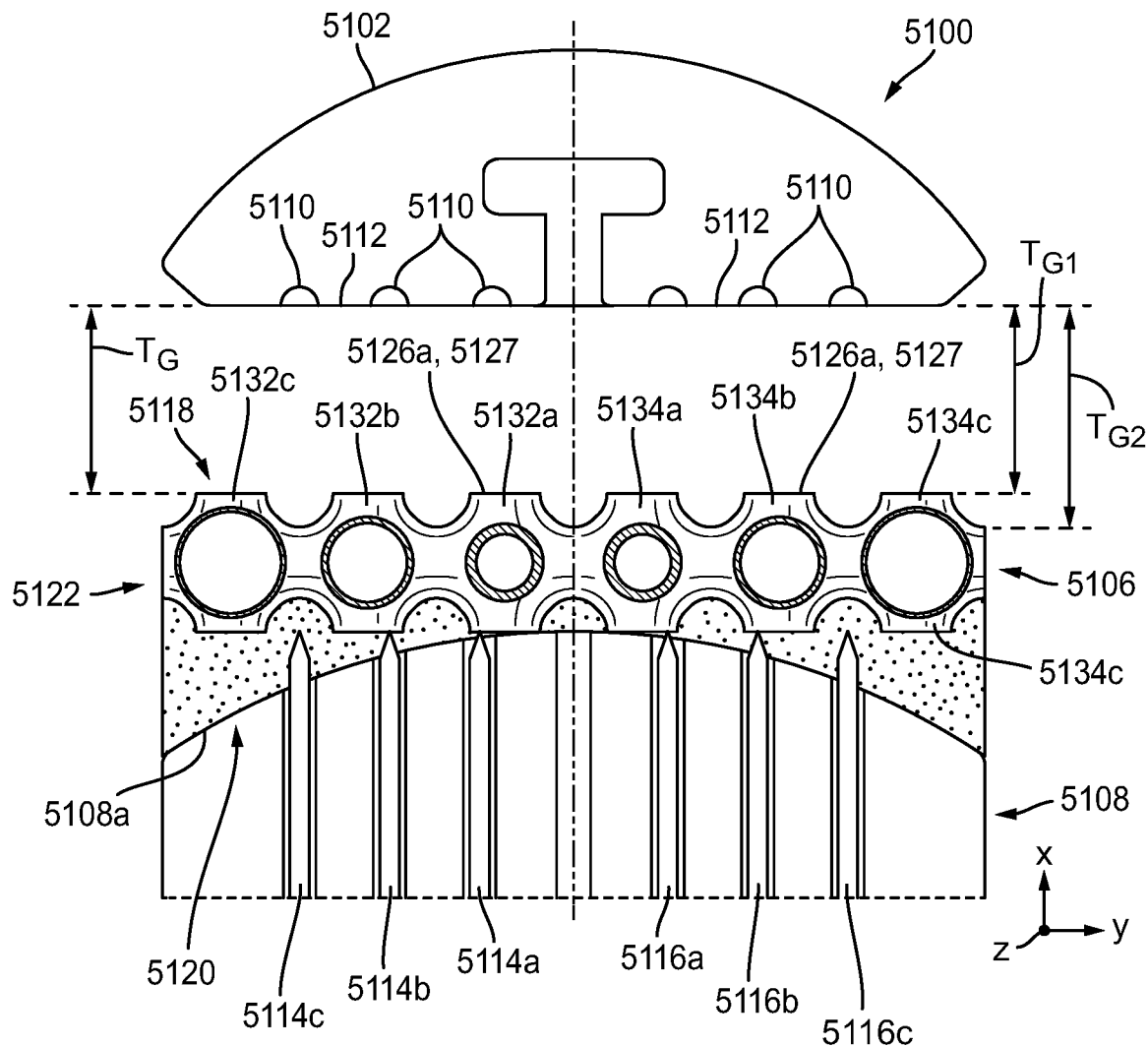
FIG. 51A is a cross-sectional front view of another exemplary embodiment of a surgical end effector having an anvil and a stapling assembly, the stapling assembly having a compressible non-fibrous adjunct releasably retained on a staple cartridge, showing the surgical end effector in a closed positioned without tissue positioned between the anvil and the stapling assembly.

FIG. 51A illustrates an exemplary embodiment of a surgical end effector 5100 having an anvil 5102 and a stapling assembly 5104. The stapling assembly 5104 includes an adjunct 5106 releasably retained on a top or deck surface 5108a of a staple cartridge 5108 (e.g., the cartridge surface that faces the anvil). Aside from the differences described below the staple cartridge 5108 is similar to cartridge 4807 in FIGS. 48A-48C, and therefore common features are not described in detail herein. While not illustrated, the anvil 5102 is pivotally coupled to an elongate staple channel, like elongate staple channel 104 in FIG. 1, and the stapling assembly 5104 is positioned within and coupled to elongate staple channel. While the anvil 5102 can have a variety of configurations, in the embodiment shown in FIG. 51A, the anvil 5102 includes a cartridge-facing surface having staple pockets 5110 defined therein with a generally planar tissue-compression surface 5112 extending between the staple pockets 5110. FIG. 51A illustrates the surgical end effector 5100, and thus the anvil 5102, in a completely closed position, without tissue positioned between the anvil 5102 and the adjunct 5106, and staples disposed within the staple cartridge 5108 (only two sets of three staples 5114a, 5114b, 5114c, 5116a, 5116b, 5116c being illustrated). Prior to deployment, in some embodiments, as illustrated in FIG. 51A, the staples 5114a, 5114b, 5114c, 5116a, 5116b, 5116c can be partially disposed within the staple cartridge 5108, whereas in other embodiments, some or all the staples can be completely disposed within the staple cartridge 5108. While the staples 5114a, 5114a, 5114c, 5116a, 5116b, 5116c can have a variety of configurations, in this illustrated embodiment, the staples 5114a, 5114a, 5114c, 5116a, 5116b, 5116c have at least a generally uniform pre-deployed (e.g., unformed) staple height (e.g., nominally identical within manufacturing tolerances). In some embodiments, the staples 5114a, 5114a, 5114c, 5116a, 5116b, 5116c can be generally uniform (e.g., nominally identical within manufacturing tolerances).

Figure 51B:
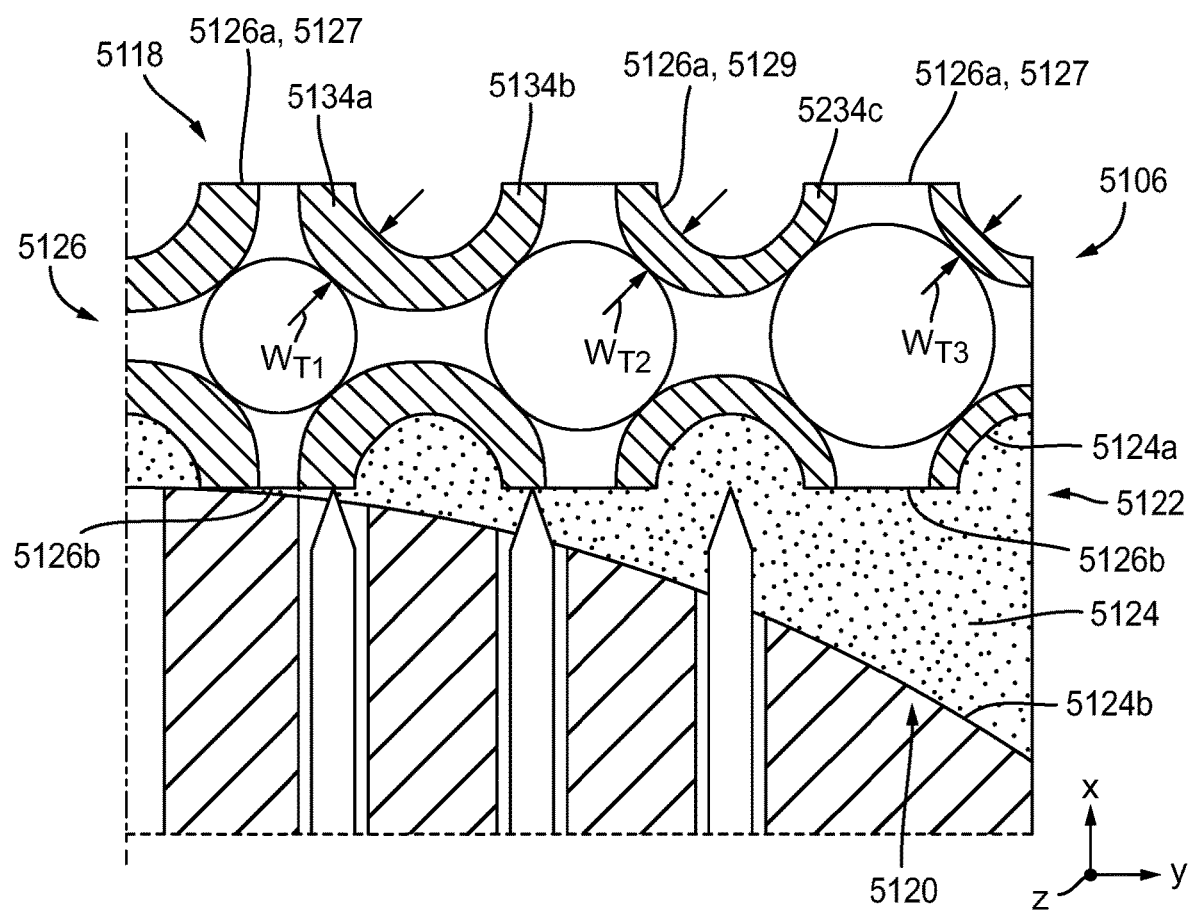
FIG. 51B is a cross-sectional front view of only the compressible non-fibrous adjunct of FIG. 51A.

As shown in FIG. 51A, and in more detail in FIG. 51B, the adjunct 5106 has a tissue-contacting surface 5118, a cartridge-contacting surface 5120, and an internal structure 5122 extending therebetween. While the internal structure 5122 can have a variety of configurations, in this illustrated embodiments, the internal structure 5122 includes two different lattice structures 5124, 5126. The first and second lattice structure 5124, 5126 each extend from a top surface 5124a, 5126a to a bottom surface 5124b, 5126b.

Figure 52A:
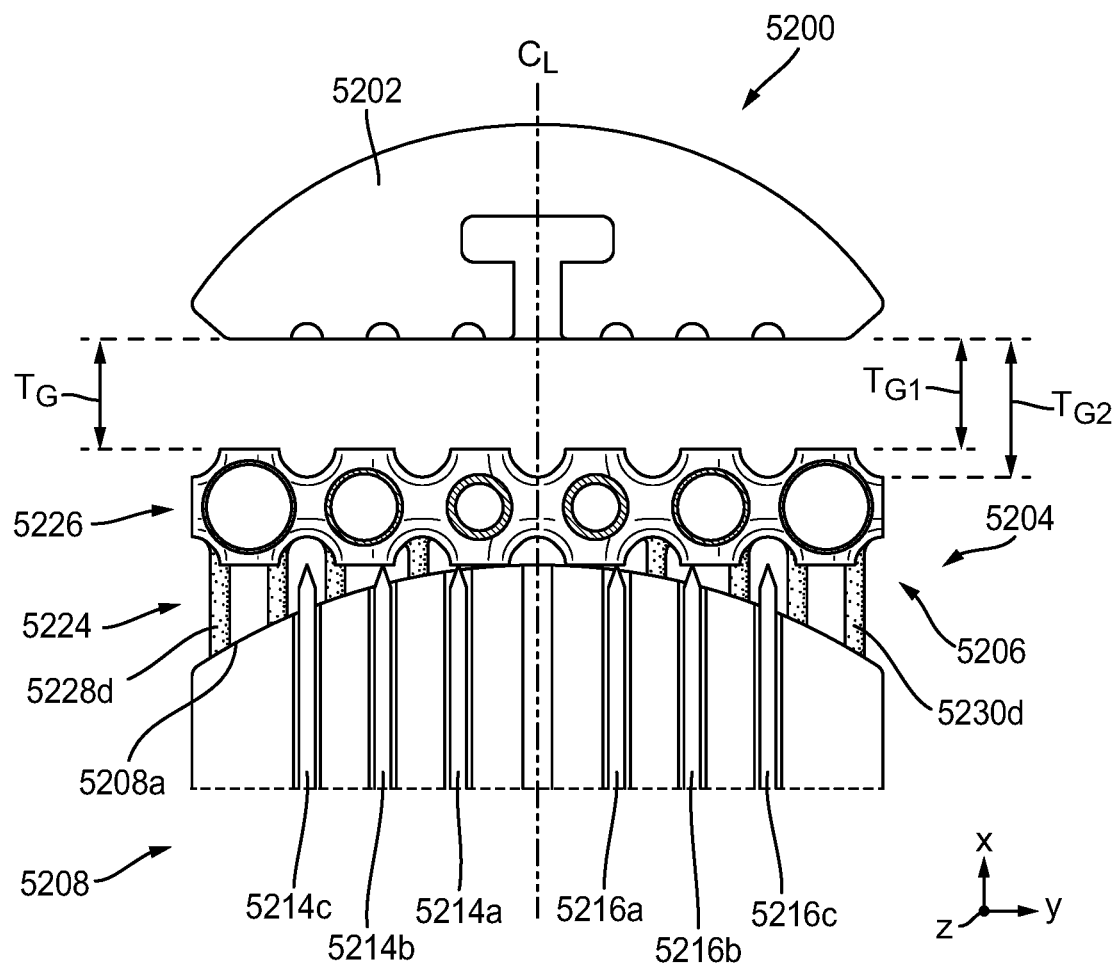
FIG. 52A is a cross-sectional front view of another exemplary embodiment of a surgical end effector having an anvil and a stapling assembly, the stapling assembly having a compressible non-fibrous adjunct releasably retained on a staple cartridge, showing the surgical end effector in a closed positioned without tissue positioned between the anvil and the stapling assembly.
Figure 52B:
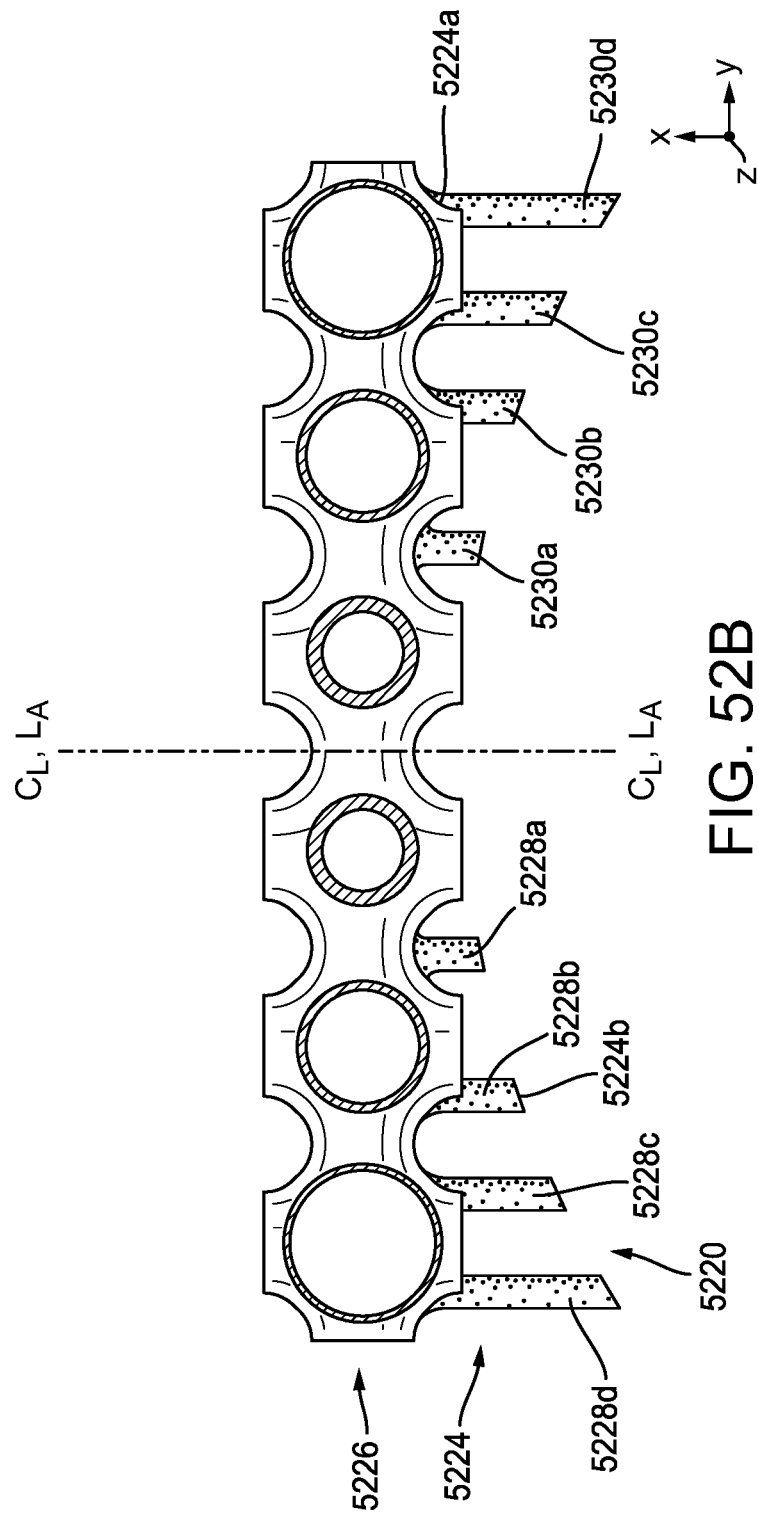
FIG. 52B is a cross-sectional front magnified view of only a portion of the stapling assembly of FIG. 52A.

The first lattice structure 5124 can be generally formed of struts, like struts 5228a, 5228b, 5228c, 5228d, 5230a, 5230b, 5230c, 5230d in FIGS. 52A-52B, or unit cells, such as those disclosed herein, e.g., strut-less based unit cells and/or strut-based unit cells. As such, aside from general overall shape and thickness, the specific structural configuration of the first lattice structure 5124 is not shown.

The first lattice structure 5124 extends between the second lattice 5126 structure and the top or deck surface 5108a of the staple cartridge 5108. As shown, the uncompressed thickness of the first lattice structure 5124 varies laterally relative to the longitudinal axis $L_A$ (e.g., $L_A$ extending in the z-direction) of the adjunct 5106. These lateral variations can be proportionate along the curved top or deck surface 5108a of the staple cartridge 5108 such that the portion of the cartridge-contacting surface 5120 of the adjunct 5106 that is formed by the bottom surface 5124b of the first lattice structure 5124 is complementary in shape to the curved top or deck surface 5108a of the staple cartridge 5108 (e.g., a concave-shaped configuration). As a result, the thickness changes of the first lattice structure 5124 can conform to the changes in the top or deck surface 5108a. Further, this causes the compression ratio of the first lattice structure 5124 to also vary in the lateral direction, which in this illustrated embodiment, increases due to the lateral increase in uncompressed thickness such that the compression behavior of the adjunct 5106 is predominantly driven by the compression properties of the second lattice structure 5126.

The second lattice structure 5126 is formed of interconnected repeating unit cells that are arranged in two sets of three longitudinal arrays, with the first set positioned on one side of the intended cut line of the adjunct and the second set positioned on the second of the intended cut line of the adjunct. For sake of simplicity, only three unit cells from each set 5132a, 5132b, 5132c, 5134a, 5134b, 5134c, are being illustrated. While the repeating unit cells can have a variety of configurations, in this illustrated embodiment, all of the repeating unit cells have generally uniform dimensions (e.g., nominally identical within manufacturing tolerances) and are similar to repeating unit cell 810 in FIGS. 9A-9B, and therefore common features are not described in detail herein. As such, the second lattice structure is similar to adjunct 800 in FIGS. 8A-8F, and therefore common features are not described herein.

As shown, at least a portion of the top surface 5126a is generally planar, and thus includes generally planar surfaces 5127 (e.g., each in the y-direction) with non-planar surfaces 5129 extending therebetween. The top surface 5126a defines the tissue-contacting surface 5118 of the adjunct 5106, and thus the tissue-contacting surface 5118 is formed of planar surfaces 5127 and non-planar surfaces 5129. Since the generally planar surfaces 5127 and non-planar surfaces 5129 of the top surface, and thus of the tissue-contacting surface 5118, alternate along the width of the second lattice structure 5126 (extending in the y-direction), a consistent tissue gap (e.g., alternating between generally uniform tissue gaps and variable tissue gaps) is created between the anvil 5102 and the adjunct 5106. In this illustrated embodiment, each generally uniform tissue gap $T_G$ occurs between the tissue-compression surface 5112 of the anvil 5102 and the generally planar surfaces 5127 of the tissue-contacting surface 5118. The variable tissue gaps (only two variable gaps being illustrated as $T_{G1}$, $T_{G2}$) occur between the tissue-compression surface 5112 of the anvil 5102 and the non-planar surfaces 5129 of the tissue-contacting surface 5118, which extend between the adjacent unit cells of the second lattice structure 5126. A person skilled in the art will appreciate that the length of the generally uniform and variable tissue gaps (extending in the x-direction) can depend at least upon the structural configuration of the tissue-contacting surface, and thus the structural configuration of the second lattice structure.

While the height between the repeating unit cells 5132a, 5132b, 5132c, 5134a, 5134b, 5134c, is generally uniform, the wall thickness can vary, and therefore result in different compression ratios. In this illustrated embodiment, the two sets of three longitudinal arrays are the same, and therefore for each set, the wall thickness $W_T$ from the first repeating unit cell 5132a, 5134a (e.g., the inner-most repeating unit cells) to the third repeating unit cell 5132c, 5134c (e.g., outer-most repeating unit cells) decreases similarly. As such, only the one set of the three longitudinal arrays are illustrated in FIG. 51B. The wall thickness $W_{T1}$ of first repeating unit cell 5132a (not illustrated) is greater than the wall thickness $W_{T2}$ of the second repeating unit cell 5132b (e.g., intermediate repeating unit cells), and the wall thickness $W_{T2}$ of the second repeating cell 5132b is greater than the wall thickness $W_{T3}$ of the third repeating unit cell 5132c, 5134c. As a result, the compression ratio from the first repeating unit cell 5132a, 5134a to the third repeating unit cell 5132c, 5134c increases, and thus the first repeating unit cell 5132a, 5134a will compress the least (e.g., most stiff) and the third repeating unit cell 5132c, 5134c will compress the most (e.g., least stiff). That is, the first compression ratio of the first repeating unit cell 5132a, 5134a is less than each of the second and third compression ratios of the second and third repeating unit cells 5132b, 5134b, 5132c, 5134c, respectively, and the second compression ratio is less than the third compression ratio. These compression ratios, in combination with the laterally varying compression ratio of the first lattice structure 5124, will therefore generate a varying overall compression ratio of the adjunct 5106 such that, when the adjunct is stapled to tissue with generally uniform staples 5114a, 5114b, 5114c, 5116a, 5116b, 5116c (e.g., nominally identical within manufacturing tolerances), the adjunct 5106 is configured to apply a generally uniform pressure to the stapled tissue for a predetermined time period.

In certain embodiments, the first lattice structure can be configured in such a way that it does not overlap with staple rows when the adjunct is releasably retained on a staple cartridge. As such, the first lattice structure will not be captured, or will be minimally captured, by the staples during deployment. As a result, the first lattice structure will not contribute, or will minimally contribute, to the solid height of the adjunct when in a tissue-deployed state. Thus, densification of the adjunct can be delayed.

FIG. 52A illustrates another exemplary embodiment of a surgical end effector 5200 having an anvil 5202 and a stapling assembly 5204. The stapling assembly 5204 includes an adjunct 5206 releasably retained on a top or deck surface 5208a of a staple cartridge 5208 (e.g., the cartridge surface that faces the anvil). Aside from the differences described below, the anvil 5202 and staple cartridge 5208 are similar to anvil 5102 and staple cartridge 5208 in FIGS. 52A-52B, and therefore common features are not described in detail herein.

The adjunct 5204 is similar to adjunct 5104 in FIGS. 51A-51B except that the first lattice structure 5224 is formed of two sets of four longitudinal rows of spaced apart vertical planar struts (e.g., in the x-direction) that extend between the second lattice 5226 structure and the top or deck surface 5208a of the staple cartridge 5208. As shown, the first set is positioned on one side of the intended cut line $C_L$ of the adjunct 5206 and the second set is positioned on the second size of the intended cut line $C_L$ of the adjunct 5206. For sake of simplicity, only four struts from each set 5228a, 5228b, 5228c, 5228d, 5230a, 5230b, 5230c, 5230d are illustrated. While the two sets of struts can have a variety of configurations, in this illustrated embodiment, the two sets of struts are the same, and thus for each set, the first struts 5228a, 5230a (e.g., inner-most row of struts) have a first height, the second struts 5228b, 5228b (e.g., inner-most intermediate row of struts) have a second height that is greater than the first height, the third struts 5228c, 5230c (e.g., outer-most intermediate row of struts) have a third height that is greater than the second height, and the fourth struts 5228d, 5230d (e.g., the outer-most row of struts) have a fourth height that is greater than the second height. As such, the uncompressed thickness (e.g., along the width of the adjunct; in the y-direction) of the first lattice structure 5224 varies laterally relative to the longitudinal axis $L_A$ (e.g., $L_A$ extending in the z-direction) of the adjunct 5206. These lateral variations can be proportionate along the curved top or deck surface 5208a of the staple cartridge 5208 such that the portion of the cartridge-contacting surface 5220 of the adjunct 5206 that is formed by the bottom surface 5224b of the first lattice structure 5224 is complementary in shape to the curved top or deck surface 5208a of the staple cartridge 5208 (e.g., a concave-shaped configuration). Thus, the thickness changes of the first lattice structure 5224 can conform to the changes in the top or deck surface 5208a.

As further shown in FIG. 52A, in an effort to minimize the impact the first lattice structure 5224 can have on the densification of the adjunct 5206, the first lattice structure 5224 can be designed in such a way that it does not overlap with the staples 5214a, 5214a, 5214c, 5216a, 5216b, 5216c. For example, in this illustrated embodiment, none of the struts 5228a, 5228b, 5228c, 5228d, 5230a, 5230b, 5230c, 5230d, overlap with any of the staples 5214a, 5214b, 5214c, 5216a, 5216b, 5216c, and thus, the first lattice structure 5224 will not be captured by the staples during deployment. As a result, when the adjunct 5206 is stapled to tissue, the applied pressure to the stapled tissue by the adjunct 5206 can be completely, or substantially completely, dependent on the compressive properties of the second lattice structure 5226.

Figure 53:
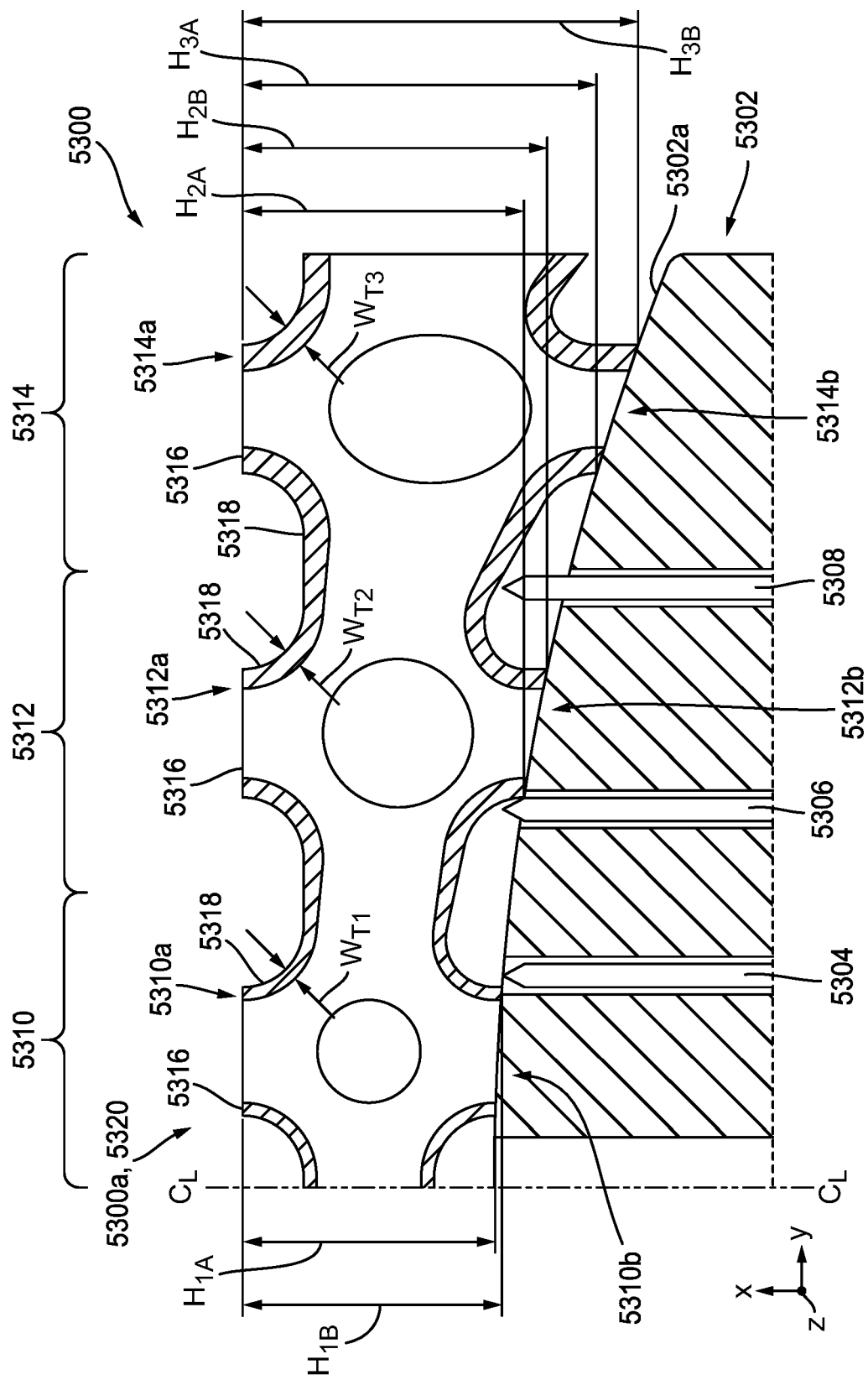
FIG. 53 a cross-sectional view of a portion of another exemplary embodiment of a compressible non-fibrous adjunct releasably retained on a staple cartridge.

In some embodiments, the wall thickness and height of each repeating unit cell can vary among other repeating unit cells. For example, FIG. 53 illustrates another exemplary embodiment of an adjunct 5300 releasably retained on a top or deck surface 5302a of a staple cartridge 5302 (e.g., the cartridge surface that faces the anvil). Aside from the differences described below, the staple cartridge 5302 is similar to staple cartridge 5108 in FIGS. 51A-51B, and therefore common features are not described in detail herein. As shown in FIG. 53, only one half (e.g., the right half) of the adjunct 5300 is illustrated on the staple cartridge 5302 with three rows of staples 5304, 5306, 5308 partially disposed therein, in which the inner-most staple row 5304 has the smallest staple height and the outer-most staple row 5308 has the largest staple height. As noted above, the difference in staple height can be a contributor to the overall compression behavior of the adjunct when the adjunct is stapled to tissue.

While the adjunct 5300 can have a variety of configurations, the adjunct 5300 is formed of interconnected repeating unit cells that are arranged in two sets of three longitudinal arrays, with the first set positioned on one side of the intended cut line $C_L$ of the adjunct 5300 and the second set (not shown) positioned on the second of the intended cut line $C_L$ of the adjunct 5300. Since both sets are the same, only one repeating unit cell 5310, 5312, 5314 of one set of the three longitudinal arrays are illustrated in FIG. 53.

The repeating unit cells 5310, 5312, 5314 can have a variety of configurations. In this illustrated embodiment, the repeating unit cells 5310, 5312, 5314 are similar in overall shape except the wall thickness and height vary among the three repeating unit cells 5310, 5312, 5314. As shown, each repeating cell has a varying height (e.g., in the X-direction) from their respective outer-most top surface 5310a, 5312a, 5314a, which are laterally offset and aligned relative to each other in the y-direction, to their respective outer-most bottom surface 5310b, 5312b, 5314b, and thus for simplicity, the minimum and maximum heights $H_{1A}$, $H_{1B}$ for the repeating unit cell 5310, the minimum and maximum height $H_{2A}$, $H_{2B}$ for the repeating unit cell 5312, and the minimum and maximum heights $H_{3A}$, $H_{3B}$ for the repeating unit cell 5314 is illustrated.

As shown, a portion of the top surface 5300a of the adjunct 5300 is generally planar and thus, includes generally planar surfaces 5316 (e.g., each in the y-direction) with non-planar surfaces 5318 extending therebetween. The top surface 5300a defines the tissue-contacting surface 5320 of the adjunct 5300, and thus the tissue-contacting surface 5320 is formed of planar surfaces 5316 and non-planar surfaces 5318. Since the generally planar surfaces 5316 and non-planar surfaces 5318 of the top surface 5300a, and thus of the tissue-contacting surface 5320, alternate along the width of the adjunct 5300 (extending in the y-direction), a consistent tissue gap (e.g., alternating between generally uniform tissue gaps and variable tissue gaps) is created between the anvil, like anvil 5102 in FIG. 51, and the adjunct 5300. In this illustrated embodiment, each generally uniform tissue gap occurs between the tissue-compression surface, like tissue-compression surface 5112 of anvil 5102 in FIG. 51, and the generally planar surfaces 5316 of the tissue-contacting surface 5320. The variable tissue gaps occur between the tissue-compression surface, like tissue-compression surface 5112 of anvil 5102 in FIG. 51, and the non-planar surfaces 5318 of the tissue-contacting surface 5320, which extend between the adjacent unit cells of the adjunct 5300. A person skilled in the art will appreciate that the length of the generally uniform and variable tissue gaps (extending in the x-direction) can depend at least upon the structural configuration of the tissue-contacting surface, and thus the structural configuration of the adjunct.

Further, the wall thickness and the height between at least two repeating cells can vary, and therefore result in different compression ratios. In this illustrated embodiment, the wall thickness $W_T$ and H from the first repeating unit cell 5310 (e.g., the inner-most repeating unit cells) to the third repeating unit cell 5314 (e.g., outer-most repeating unit cells) increases. That is, the wall thickness $W_{T1}$ and height $H_1$ of first repeating unit cell 5310 is less than the wall thickness $W_{T2}$ and height $H_2$ of the second repeating unit cell 5312 (e.g., intermediate repeating unit cells), and the wall thickness $W_{T2}$ and height $H_2$ of the second repeating cell 5312 is less than the wall thickness $W_{T3}$ and height $H_3$ of the third repeating unit cell 5314. As a result, the compression ratio from the first repeating unit cell 5310 to the third repeating unit cell 5314 decreases. That is, the first compression ratio of the first repeating unit cell 5310 is greater than each of the second and third compression ratios of the second and third repeating unit cells 5312, 5314, respectively, and the second compression ratio is greater than the third compression ratio. These compression ratios will therefore generate a varying overall compression ratio of the adjunct 5300 such that, when the adjunct is stapled to tissue with staples 5304, 5306, 5308 with varying staple lengths (e.g., the inner-most staples 5304 having the least staple height and the outer-most staples 5308 having the greatest height), the adjunct 5300 is configured to apply a generally uniform pressure to the stapled tissue for a predetermined time period.

Figure 54:
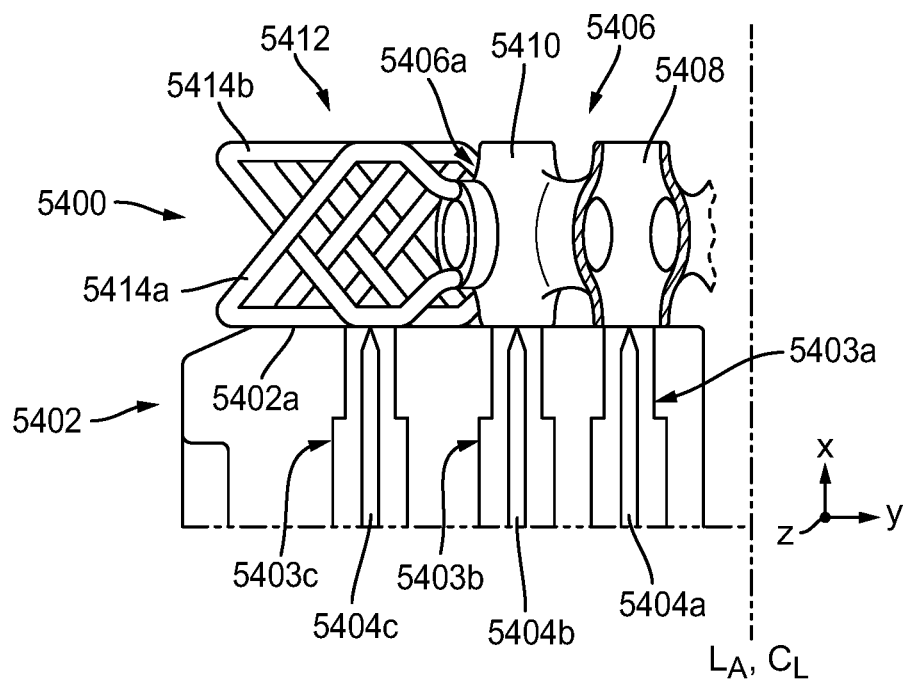
FIG. 54 a cross-sectional view of a portion of another exemplary embodiment of a compressible non-fibrous adjunct releasably retained on a staple cartridge, showing only three staples from three staple rows of the staple cartridge.

As noted above, the adjunct can include a combination of strut-less based unit cells and strut-based unit cells and/or spacer struts. For example, FIG. 54 illustrates an exemplary embodiment of an adjunct 5400 releasably retained on a top or deck surface 5402a of a staple cartridge 5402 (e.g., the cartridge surface that faces the anvil). Aside from the differences described below, the staple cartridge 5402 is similar to staple cartridge 200 in FIGS. 1-2C, and therefore common features are not described in detail herein. As shown in FIG. 54, only one half (e.g., the left half) of the adjunct 5400 is illustrated on the staple cartridge 5402 with three longitudinal rows 5303a, 5303b, 5303c of substantially uniform staples 5404a, 5404b, 5404c disposed therein.

While the adjunct 5400 can have a variety of configurations, as shown the adjunct has an internal lattice structure 5406 formed of two sets of two longitudinal arrays of repeating strut-less based unit cells, with the first set positioned on one side of the intended cut line $C_L$ of the adjunct 5400 and the second set (not shown) positioned on the second of the intended cut line $C_L$ of the adjunct 5400. Since both sets are the same, only one repeating unit cell 5408, 5410 of one set of the two longitudinal arrays is illustrated in FIG. 54. Further, the adjunct 5400 includes first and second outer lattice structures that are structurally similar and are positioned on opposite sides of the internal lattice structure (only the first outer lattice structure 5412 being illustrated). While only the first outer lattice structure 5412 and the first and second repeating unit cells 5408, 5410 of the adjunct 5400 are illustrated, a person skilled in the art will appreciate that the following discussion is also applicable to the second lattice structure and the second set of longitudinal arrays of repeating cells.

The first and second repeating unit cells 5408, 5410 can have a variety of configurations. In this illustrated embodiment, the repeating unit cells 5408, 5410 are generally uniform (e.g., nominally identical within manufacturing tolerances) and are structurally similar to repeating unit cell 810 in FIGS. 9A-9B, and therefore common features are not described in detail herein. As shown, the first and second repeating unit cells 5408, 5410 are oriented similar to the repeating unit cells 4516 in FIGS. 45A-45C, and therefore the internal lattice structure 5406 can have a structurally similar configuration to adjunct 4500 in FIGS. 45A-45C. As a result, the repeating unit cells 5408, 5410 are oriented in a way (e.g., a repeating pattern) that can coincide with the positions of the staples in one or more of the staple rows that the internal lattice structure 5406 overlaps. As further shown, the first outer lattice structure 5412 includes strut-based unit cells (only two unit cells 5414a, 5414b are fully illustrated). While the strut-based unit cells can have a variety of configurations, the first strut-based unit cell 5414a has a triangular configuration and the second strut-based unit cell 5414b has an inverted triangular configuration. As further shown, a portion of the second strut-based unit cell 5414b crosses over the first strut-based unit cell 5414a.

As shown, the lattice structures 5406, 5412 are adjacent to and laterally offset from each other relative to the longitudinal axis $L_A$ of the adjunct 5400 (e.g., $L_A$ extending in the z-direction). That is, the first outer lattice structure 5412 is positioned directly adjacent to a first longitudinal side 5406a of the internal lattice structure 5406. Further, the internal lattice structure 5406 overlaps with the first and second staple rows 5403a, 5303b (e.g., inner-most staple row and intermediate staple row), and thus the first and second staples 5404a, 5404b, respectively, whereas the first outer lattice structure 5412 overlaps with the third staple row 5404c (e.g., the outer-most staple row), and thus the third staples 5404c. In this illustrated embodiment, the first longitudinal array of the first repeating unit cells 5408 and the second longitudinal array of the second repeating unit cells 5410 are staggered relative to each other, and thus oriented in a way (e.g., a repeating pattern) that coincides with the positions of the first and second staples 5404a, 5404b, respectively.

Figure 55:
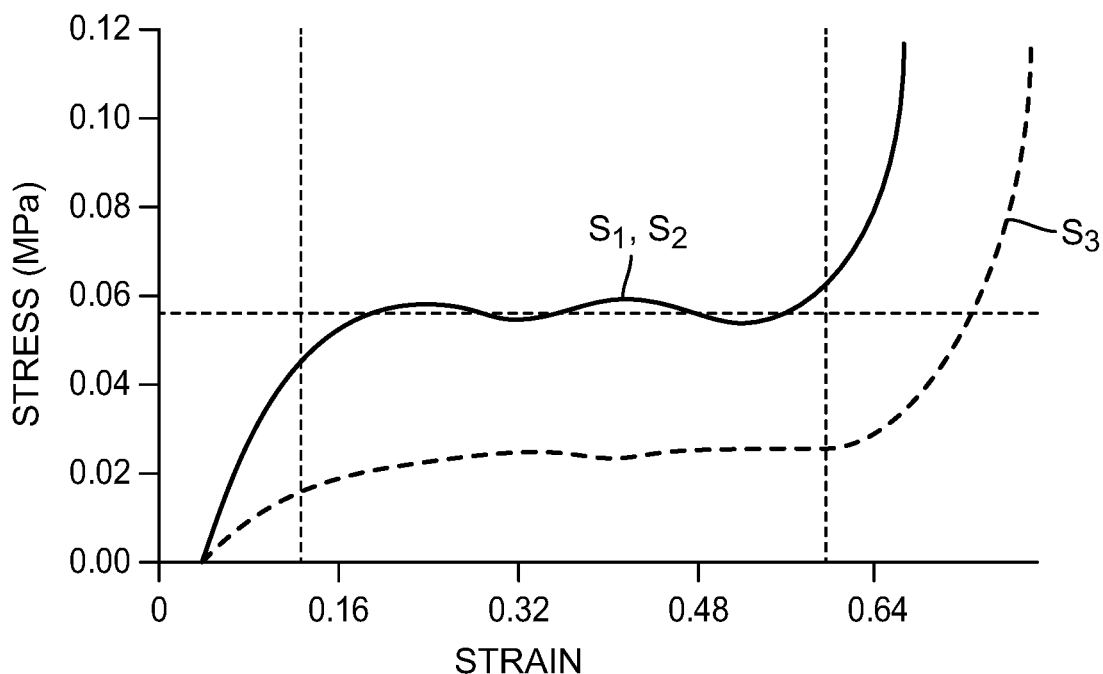

This alignment of the lattice structures 5406, 5412 relative to the first, second, and third staples 5404a, 5404b, 5404c, in combination with the different structural configurations of the lattice structures 5406, 5412, can result in at least two different stress-strain curves when the adjunct is stapled to tissue. Given the orientation of the first and second repeating unit cells relative to the first and second staples, the resulting stress-strain curve of the adjunct at the first and second staples can be the same, or substantially the same. The compressive behavior of adjunct 5300 at each of the first, second, and third staples 5404a, 5404b, 5404c is schematically illustrated in FIG. 55, in which S1 represents the stress-strain curve of the adjunct at the first staples 5404a, S2 represents the stress-strain curve of the adjunct at the second staples 5404b, and S3 represents the stress-strain curve at the third staples 5404c. In this schematic, the stress-strain curves S1, S2 at the first and second staples are illustrated as the same curve. A person skilled in the art will appreciate that the stress-strain curves at each staple can vary.

Adjunct Systems

In general, the adjunct systems described herein can include at least two different adjuncts, in which each adjunct, while under a respective applied stress in a range of about 30 kPa to 90 kPa, is configured to undergo a respective strain in a respective range of strains. In some embodiments, at least two respective ranges of strain can at least partially overlap, whereas in other embodiments, at least two respective ranges do not overlap. In addition, or alternatively, the combination of the respective ranges of strain can result in a combined range from at least 0.1 to 0.9. In other embodiments, the combined range can be of about 0.1 to 0.8, of about 0.1 to 0.7, of about 0.1 to 0.6, of about 0.1 to 0.5, of about 0.1 to 0.4, of about 0.1 to 0.3, of about 0.2 to 0.8, of about 0.2 to 0.7, of about 0.3 to 0.7, of about 0.3 to 0.8, of about 0.3 to 0.9, of about 0.4 to 0.9, of about 0.4 to 0.8, of about 0.4 to 0.7, of about 0.5 to 0.8, or of about 0.5 to 0.9. While the adjunct systems can include at least two different adjuncts, for sake of simplicity, the following description is with respect to an adjunct system having only first and second adjuncts. A person skilled in the art will understand, however, that the following discussion is also applicable to additional adjuncts of an adjunct system.

In some embodiments, the adjunct system can include first and second adjuncts in which, the first adjunct, while under an applied stress in a range of about 30 kPa to 90 kPa, undergoes a strain in a first range, and the second adjunct, while under an applied stress in a range of about 30 kPa to 90 kPa, undergoes a strain in a second range. The stress-strain response of each adjunct depends at least upon the structural configurations and compositional makeup of each adjunct. As such, the first and second adjuncts can be tailored to effect a desired strain response under an applied stress and/or a range of applied stresses. For example, in some embodiments, the first adjunct can be configured such that, while under an applied stress in a range of about 60 kPa to 90 kPa, the first adjunct undergoes a strain in a first range of about 0.2 to 0.5, whereas the second adjunct can be configured such that, while under an applied stress in a range of about 40 kPa to 70 kPa, the second adjunct undergoes a strain in a second range of about 0.3 to 0.7. In another embodiment, the first adjunct can be configured such that, while under an applied stress in a range of about 30 kPa to 90 kPa, the first adjunct undergoes a strain in a first range of about 0.1 to 0.7, whereas the second adjunct can be configured such that, while under an applied stress in a range of about 30 kPa to 90 kPa, the second adjunct undergoes a strain in a second range of about 0.3 to 0.9. In another embodiment, the first adjunct can be configured such that, while under an applied stress in a range of about 30 kPa to 90 kPa, the first adjunct undergoes a strain in a first range of about 0.2 to 0.6, whereas the second adjunct can be configured such that, while under an applied stress in a range of about 30 kPa to 90 kPa, the second adjunct undergoes a strain in a second range of about 0.4 to 0.8. In another embodiment, the first adjunct can be configured such that, while under an applied stress in a range of about 40 kPa to 80 kPa, the first adjunct undergoes a strain in a first range of about 0.1 to 0.7, whereas the second adjunct can be configured such that, while under an applied stress in a range of about 30 kPa to 90 kPa, the second adjunct undergoes a strain in a second range of about 0.2 to 0.8.

The first and second adjuncts can have a variety of structural configurations. For example, the first adjunct can have a configuration similar to any one of the exemplary adjuncts described herein and the second adjunct can have a different configuration than the first adjunct and similar to another one of the exemplary adjuncts described herein. In some embodiments, the first adjunct can be a non-strut based adjunct and the second adjunct can be another non-strut based adjunct or a strut-based adjunct described herein. In other embodiments, the first adjunct can be a strut-based adjunct and the second adjunct can be another strut-based adjunct or a non-strut based adjunct.

In some embodiments, the first adjunct has a first internal structure formed of a first plurality of repeating interconnected unit cells, and the second adjunct has a second internal structure formed of a second plurality of repeating interconnected unit cells. In certain embodiments, the first plurality of repeating interconnected unit cells can be formed of a first material and the second plurality of repeating interconnected unit cells can be formed of a second material that is different than the first material. The first and second materials can be any of the materials described herein and in more detail below. In addition, or alternatively, each unit of the first plurality of repeating interconnected unit cells has a first geometry and each unit of the second plurality of repeating interconnected unit cells has a second geometry that is different than the first geometry.

In some embodiments, each unit cell of at least one of the first plurality of repeating interconnected unit cells and the second plurality of repeating interconnected unit cells is a triply periodic minimal surface structure (e.g., a Schwarz-P structure). In one embodiment, each unit cell of the first plurality of repeating interconnected unit cells is a first triply periodic minimal surface structure, and each unit cell of the second plurality of repeating interconnected unit cells is a second triply periodic minimal surface structure that is different than the first triply periodic minimal surface structure. For example, the first and second triply periodic minimal surface structures can differ in geometry, e.g., shape, size (e.g., height, wall thickness, and the like), or a combination thereof.

In some embodiments, each unit cell of the first plurality of repeating interconnected unit cells can include a first top portion formed from a first plurality of struts defining a first plurality of openings therebetween, a first bottom portion formed from a second plurality of struts defining a second plurality of openings therebetween, and first spacer struts that interconnect the first top portion and the first bottom portion. In such embodiments, each unit cell of the second plurality of repeating interconnected unit cells can be a Schwarz-P structure. In other embodiments, each unit cell of the second plurality of repeating interconnected unit cells can include a second top portion formed from a third plurality of struts defining a third plurality of openings therebetween, a second bottom portion formed from a fourth plurality of struts defining a fourth plurality of openings therebetween, and second spacer struts that interconnect the second top portion and the second bottom portion.

Materials

The adjuncts described herein can be formed of one or more polymers, such as bioabsorbable polymer(s), non-bioabsorbable polymer(s), bioresorbable polymer(s), or any combination thereof. For clarity purposes only, the use of "polymers" herein can be understood to encompass one or more polymers, including one or more macromers. Non-limiting examples of suitable polymers include polylactide (PLA), polycaprolactone (PCL), polyglycolide (PGA), polydioxanone (PDO), polytrimethylene carbonate (PTMC), polyethylene glycol (PEG), polyethylene diglycolate (PEDG), polypropylene fumarate (PPF), poly(ethoxyethylene diglycolate), a poly(ether ester) (PEE), a poly(amino acid), poly(epoxycarbonate), poly(2-oxypropylene carbonate), poly(diol citrates), polymethacrylate anhydrides, and poly(N-isopropylacrylamide), a copolymer of any thereof, or any combination thereof. Non-limiting examples of suitable copolymers include random copolymers such as PLGA-PCL, block copolymers such as poly(lactide-co-glycolide) (PLGA), triblock copolymers such as PLGA-PCL-PLGA or PLGA-PEG-PLGA, or any combination thereof. Additional non-limiting examples of suitable polymers are disclosed in, for example, U.S. Pat. Nos. 9,770,241, 9,873,790, 10,085,745, and 10,149,753; and in U.S. Patent Pub. No. 2017/0355815, each of which is incorporated by reference herein in its entirety.

In some embodiments, the polymers can be formed from a resin. In general, the resins described herein can be suitable for use in additive manufacturing techniques such as bottom-up and top-down stereolithography, (b) produce adjuncts that are bioresorbable, and/or (c) produce adjuncts that are flexible or elastic (e.g., at temperature(s) of about 25° C., of about 37° C., and/or any temperature therebetween).

In some embodiments, the polymer can be formed from a light polymerizable resin that includes oligomer prepolymer(s). The oligomer prepolymer(s) can be linear or branched (e.g., "star" oligomers such as tri-arm oligomers).

Non-limiting examples of suitable end groups for such oligomer prepolymers include acrylate, methacrylate, fumarate, vinyl carbonate, methyl ester, ethyl ester, etc. Non-limiting examples of suitable constituents of exemplary resins that can be used to form polymers, and consequently, the adjuncts provided herein, are listed in Table 2 below. Constituents in each column of Table 2 can be combined with constituents of the other columns in any combination.

block, BAB block, CBC block, BCB block, AB random composition, BC random composition, homopolymer, or any combination thereof, where: A=poly(lactide) (PLA), poly(glycolide) (PGA), poly(lactide-co-glycolide) (PLGA), or polypropylene fumarate (PPF), B=polycaprolactone (PCL), poly(lactide-co-caprolactone) (PLACL), poly(glycolide-co-caprolactone) (PGACL), poly(trimethylene carbonate) (PTMC), or poly(caprolactone-co-lactide)

TABLE 2

Exemplary Resin Compositions

| Backbone Chemistry | Reactive End Group | Oligomer Architecture | Plasticizer | Diluent | Photo-initiator |
|---|---|---|---|---|---|
| PLGA | Methacrylate | Linear | HO-PCL-OH | Mono-vinyl ether | Irgacure® 2959 |
| PCL | Acrylate | Star (branching) | HO-PLGA-PCL-PLGA-OH | DEGMA | Irgacure® TPO |
| PLGA-PCL-PLGA | Vinyl Carbonate | Hyperbranched | | Vinyl acetate | ITX |
| PLGA-PEG-PLGA | Unsaturated Fatty acid methyl ester | Pendant | | n-butyl methacrylate | Irgacure® 819 |
| PLGA-PCL | | Dendritic | | Triacetine | |
| PDO-PCL-PDO | | | | NMP | |
| PGA-PTMC-PGA | | | | DMSO | |
| PLC-PGA | | | | NMP | |
| PGA-PLC-PGA | | | | DMSO | |
| | | | | Divinyl Adipate | |

PLGA = poly(lactide-co-glycolide);
PEG = poly(ethylene glycol);
PCL = polycaprolactone;
PLC = poly(lactide-co-caprolactone);
PDO = Polydioxanone;
PTMC = Poly(trimethylene carbonate);
DEGMA = Di(ethylene glycol) methyl ether methacrylate;
TPO = diphenyl (2,4,6-trimethylbenzoyl) phosphine oxide;
ITX = isopropylthioxanthone;
NMP = N-methyl pyrrolidone;
DMSO = dimethyl sulfoxide.

While various types of resins can be used to form the polymers, in some embodiments, the polymers are formed from a resin that is based on a bioresorbable polyester oligomer (e.g., a methacrylate terminated oligomer with a bioresorbable polyester linkage). For example, the bioresorbable polyester oligomer can be present in an amount from about 5% to 90%, from 5% to 80%, from about 10% to 90%, or from about 10% to 80% by weight of the resin. Unlike conventional resins (e.g., polycaprolactone dimethacrylate based resins and poly(D,L-lactide) dimethacrylate based resins), this resin can form an adjunct having rubber-like elastic behavior at physiological temperatures, short-term retention of mechanical properties (e.g., 1 month or less), and/or long-term full resorption (e.g., over a time period of approximately 4-6 months).

In some embodiments, the oligomer can include a linear oligomer. Alternatively, or in addition, the oligomer can include a branched oligomer (e.g., a star oligomer, such as a tri-arm oligomer).

In some embodiments, the bioresorbable polyester oligomers described herein are bioresorbable oligomers with methacrylate end-groups. Such oligomers typically include biodegradable ester linkages between constituents such as caprolactone, lactide, glycolide trimethylene carbonate, dioxanone and propylene fumarate monomers in an ABA (PCLLA), and C=polydioxanone (PDO). The copolymers can have a molecular weight (Mn) from about 2 kilodaltons to 6 kilodaltons, from about 2 kilodaltons to 10 kilodaltons, from about 2 kilodaltons to 15 kilodaltons, from about 2 kilodaltons to 20 kilodaltons, from about 2 kilodaltons to 50 kilodaltons, from about 5 kilodaltons to 6 kilodaltons, from about 5 kilodaltons to 10 kilodaltons, from about 5 kilodaltons to 15 kilodaltons, from about 5 kilodaltons to 20 kilodaltons, from about 5 kilodaltons to 50 kilodaltons, from about 10 kilodaltons to 15 kilodaltons, from about 10 kilodaltons to 20 kilodaltons, or from about 10 kilodaltons to 50 kilodaltons, in either linear or star structure. Monomers used to produce such oligomers may optionally introduce branches, such as to enhance elasticity, an example being gamma-methyl-epsilon caprolactone and gamma-ethyl-epsilon-caprolactone.

In some embodiments, lactides can include L-Lactides, D-Lactide, or mixtures thereof (e.g., D,L-Lactides). For example, in some embodiments with PLA blocks, L-Lactide can be used for better regularity and higher crystallinity.

In some embodiments, the oligomer can include an ABA block, a BAB block, a CBC block, or a BCB block in linear and/or branched (e.g., star or tri-arm) form.

In some embodiments, A can be: (i) poly(lactide); (ii) poly(glycolide); (iii) poly(lactide-co-glycolide) containing lactide and glycolide in a molar ratio of 90:10 to 55:45 lactide:glycolide (e.g., a lactide rich ratio), 45:55 to 10:90 lactide:glycolide (e.g., a glycolide rich ratio), or 50:50 lactide:glycolide; or any combination thereof. In such embodiments, the oligomer can be in linear and/or branched (e.g., star or tri-arm) form. In some embodiments, a D,L-Lactide mixture can be used for making the PLGA random copolymer.

In some embodiments, B can be: (i) polycaprolactone; (ii) polytrimethylene carbonate; (iii) poly(caprolactone-co-lactide) containing caprolactone and lactide in a molar ratio of 95:5 to 5:95 caprolactone:lactide; or any combination thereof.

In some embodiments, A (PLA, PGA, PLGA, PPF, or any combination thereof) can have a molecular weight (Mn) from about 1 kilodaltons to 4 kilodaltons, from about 1 kilodaltons to 6 kilodaltons, from about 1 kilodaltons to 10 kilodaltons, from about 2 kilodaltons to 4 kilodaltons, from about 2 kilodaltons to 6 kilodaltons, or from about 2 kilodaltons to 10 kilodaltons; and B (PCL, PLACL, PGACL, PTMC, PCLLA, or any combination thereof) can have a molecular weight (Mn) from about 1 kilodaltons to 4 kilodaltons, from about 1 kilodaltons to 6 kilodaltons, from about 1 kilodaltons to 10 kilodaltons, from about 1 kilodaltons to 50 kilodaltons, from about 1.6 kilodaltons to 4 kilodaltons, from about 1.6 kilodaltons to 6 kilodaltons, from about 1.6 kilodaltons to 10 kilodaltons, or from about 1.6 kilodaltons to 50 kilodaltons.

The resin can also include additional constituents, such as additional cross-linking agent(s), non-reactive diluent(s), photoinitiator(s), reactive diluent(s), filler(s), or any combination thereof.

In some embodiments, the resin can include an additional cross-linking agent. For example, the additional cross-linking agent can be present in an amount from about 1% to 5%, from about 1% to 10%, from about 2% to 5%, or from about 2% to 10% by weight of the resin. Any suitable additional cross-linking agents can be used, including bioabsorbable cross-linking agents, non-absorbable cross-linking agents, or any combination thereof. Non-limiting examples of suitable bioabsorbable cross-linking agents include divinyl adipate (DVA), poly(caprolactone)trimethacrylate (PCLDMA, e.g., at a molecular weight MW of about 950 to 2400 daltons), etc. Non-limiting examples of suitable non-absorbable cross-linking agents include trimethylolpropane trimethacrylate (TMPTMA), poly(propylene glycol) dimethacrylate (PPGDMA), poly(ethylene glycol) dimethacrylate (PEGDMA), etc.

In some embodiments, the resin can include a non-reactive diluent. For example, the non-reactive diluent can be present in an amount from about 1% to 70%, from about 1% to 50%, from about 5% to 70%, or from about 5% to 50% by weight of the resin. Non-limiting examples of non-reactive diluents include dimethylformamide, dimethylacetamide, N-methyl pyrrolidone (NMP), dimethyl sulfoxide, cyclic carbonate (e.g., propylene carbonate), diethyl adipate, methyl ether ketone, ethyl alcohol, acetone, or any combination thereof.

In some embodiments, the resin can include a photoinitiator. For example, the photoinitiator can be present in an amount from about 0.1% to 4%, from about 0.1% to 2%, from about 0.2% to 4%, or from about 0.2% to 2% by weight of the resin. Photoinitiators included in the resin can be any suitable photoinitiator. Non-limiting examples of suitable photoinitiators include type I and type II photoinitiators, and UV photoinitiators (e.g., acetophenones (e.g., diethoxyacetophenone), phosphine oxides (e.g., diphenyl(2,4,6-trimethylbenzoyl) phosphine oxide, phenylbis(2,4,6-trimethylbenzoyl), phosphine oxide (PPO), Irgacure® 369,) and the like. Additional exemplary photoinitiators can be found in U.S. Pat. No. 9,453,142, which is incorporated by reference herein in its entirety.

In one embodiment, the resin can include a bioresorbable polyester oligomer that can be present in an amount from about 5% to 90%, from 5% to 80%, from about 10% to 90%, or from about 10% to 80% by weight of the resin; a non-reactive diluent that can be present in an amount from about 1% to 70%, from about 1% to 50%, from about 5% to 70%, or from about 5% to 50% by weight of the resin; and a photoinitiator that can be present in an amount from about 0.1% to 4%, from about 0.1% to 2%, from about 0.2% to 4%, or from about 0.2% to 2% by weight of the resin.

In some embodiments, the resin can include a reactive diluent (including di- and trifunctional reactive diluents). For example, the reactive diluent can be present in an amount from about 1% to 50%, from about 1% to 40%, from about 5% to 50%, or from about 5% to 40% by weight of the resin. Non-limiting examples of reactive diluents include an acrylate, a methacrylate, a styrene, a vinyl amide, a vinyl ether, a vinyl ester, polymers containing any one or more of the foregoing, or any combination thereof (e.g., acrylonitrile, styrene, divinyl benzene, vinyl toluene, methyl acrylate, ethyl acrylate, butyl acrylate, methyl (meth)acrylate, isobornyl acrylate (IBOA), isobornyl methacrylate (IBOMA), an alkyl ether of mono-, di- or triethylene glycol acrylate or methacrylate, a fatty alcohol acrylate or methacrylate such as lauryl (meth)acrylate, and mixtures thereof).

In one embodiment, the resin can include a bioresorbable polyester oligomer that can be present in an amount from about 5% to 90%, from about 5% to 80%, from about 10% to 90%, or from about 10% to 80% by weight of the resin; a non-reactive diluent that is present in an amount from about 1% to 70%, from about 1% to 50%, from about 5% to 70%, or from about 5% to 50% by weight of the resin; a photoinitiator that can be present in an amount from about 0.1% to 4%, from about 0.1% to 2%, from about 0.2% to 4%, or from about 0.2% to 2% by weight of the resin; and a reactive diluent that can be present in an amount from about 1% to 50%, from about 1% to 40%, from about 5% to 50%, or from about 5% to 40% by weight of the resin.

In some embodiments, the resin can include a filler. For example, the filler can be present in an amount from about 1% to 50%, from about 1% to 40%, from about 2% to 50%, or from about 2% to 40% by weight of the resin. Any suitable filler may be used in connection with the present invention, including but not limited to bioresorbable polyester particles, sodium chloride particles, calcium triphosphate particles, sugar particles, and the like.

In one embodiment, the resin can include a bioresorbable polyester oligomer that can be present in an amount from about 5% to 90%, from about 5% to 80%, from about 10% to 90%, or from about 10% to 80% by weight of the resin; a non-reactive diluent that is present in an amount from about 1% to 70%, from about 1% to 50%, from about 5% to 70%, or from about 5% to 50% by weight of the resin; a photoinitiator that can be present in an amount from about 0.1% to 4%, from about 0.1% to 2%, from about 0.2% to 4%, or from about 0.2% to 2% by weight of the resin; a reactive diluent that can be present in an amount from about 1% to 50%, from about 1% to 40%, from about 5% to 50%, or from about 5% to 40% by weight of the resin; and a filler that can be present in an amount from about 1% to 50%, from about 1% to 40%, from about 2% to 50%, or from about 2% to 40% by weight of the resin.

Further, depending upon the particular use of the adjunct, in some embodiments, the resin can have additional constituents. For example, in certain embodiments, the resin can include one or more additional constituents that can be present in an amount from about 0.1% to 10% by weight of the resin, from about 0.1% to 10% by weight of the resin, from about 1% to 20% by weight of the resin, or from about 1% to 10% by weight of the resin. Non-limiting examples of suitable additional constituents include pigments, dyes, diluents, active compounds or pharmaceutical compounds, detectable compounds (e.g., fluorescent, phosphorescent, radioactive), proteins, peptides, nucleic acids (DNA, RNA) such as siRNA, sugars, etc., including any combination thereof.

In some embodiments, the resin can include a non-reactive pigment or dye that absorbs light, particularly UV light. Non-limiting examples of suitable non-reactive pigments or dyes include: (i) titanium dioxide (e.g., present in an amount from about 0.05% to 5%, from about 0.05% to 1%, from about 0.1% to 1%, or from about 0.1% to 5% by weight of the resin), (ii) carbon black (e.g., present in an amount from about 0.05% to 5%, from about 0.05% to 1%, from about 0.1% to 1%, or from about 0.1% to 5% by weight of the resin), and/or (iii) an organic ultraviolet light absorber such as a hydroxybenzophenone, hydroxyphenylbenzotriazole, oxanilide, benzophenone, thioxanthone, hydroxyphenyltriazine, and/or benzotriazole ultraviolet light absorber (e.g., Mayzo BLS1326) (e.g., present in an amount from about 0.001% to 1%, 0.001% to 2%, from about 0.001% to 4%, from about 0.005% to 1%, from about 0.005% to 2%, or from about 0.005% to 4% by weight of the resin). Additional exemplary non-reactive pigments or dyes are disclosed in U.S. Pat. Nos. 3,213,058, 6,916,867, 7,157,586, and 7,695,643, each of which is incorporated by reference herein in its entirety.

In some embodiments, a resin can include: (a) a (meth)acrylate terminated bioresorbable polyester oligomer present in an amount from about 5% to 80%, from about 5% to 90%, from about 10% to 80%, or from about 10% to 90% by weight of the resin; (b) a non-reactive diluent present in an amount from about 1% to 50%, from about 1% to 70%, from about 5% to 50%, or from about 5% to 70% by weight of the resin; and (c) a photoinitiator present in an amount from about 0.1% to 2%, from about 0.1% to 4%, from about 0.2% to 2%, or from about 0.2% to 4% by weight of the resin. In such embodiments, the resin can also include (d) a reactive diluent present in an amount from about 1% to 40%, from about 1% to 50%, from about 5% to 40%, or from about 5% to 50% by weight of the resin, (e) a filler present in an amount from about 1% to 40%, from about 1% to 50%, from about 2% to 40%, or from about 2% to 50% by weight of the resin; (f) additional ingredient(s) (e.g., an active agent, detectable group, pigment or dye, and the like) present in an amount from about 0.1% to 10%, from about 0.1% to 20%, from about 1% to 10%, or from about 1% to 20% by weight of the resin; and/or (g) an additional cross-linking agent (e.g., trimethylolpropane trimethacrylate (TMPTMA)) present in an amount from about 1% to 5%, from about 1% to 10%, from about 2% to 5%, or from about 2% to 10% by weight of the resin.

In some embodiments, a resin can include:

(a) a (meth)acrylate terminated, linear or branched, bioresorbable polyester oligomer of monomers in an ABA block, a BAB block, CBC block, or a BCB block, the oligomer being present in an amount from about 5% to 80%, from about 5% to 90%, from about 10% to 80%, or from about 10% to 90% by weight of the resin, wherein: A is poly(lactide) (PLA), poly(glycolide) (PGA), poly(lactide-co-glycolide) (PLGA), or any combination thereof, with the PLGA containing lactide and glycolide in a molar ratio of either 90:10 to 60:40 lactide:glycolide or 40:60 to 10:90 lactide:glycolide, and A has a molecular weight (Mn) from about 1 kilodaltons to 4 kilodaltons, from about 1 kilodaltons to 10 kilodaltons, from about 2 kilodaltons to 4 kilodaltons, or from about 2 kilodaltons to 10 kilodaltons; B is polycaprolactone (PCL, PTMC, and PCLLA), poly(lactide-co-caprolactone) (PLACL), poly(glycolide-co-caprolactone) (PGACL) or poly(trimethylene carbonate) (PTMC) and has a molecular weight (Mn) from about 1 kilodaltons to 4 kilodaltons, from about 1 kilodaltons to 10 kilodaltons, from about 1.6 kilodaltons to 4 kilodaltons, or from about 1.6 kilodaltons to 10 kilodaltons; and C is polydioxanone (PDO) and has a molecular weight (Mn) from about 1 kilodaltons to 4 kilodaltons, from about 1 kilodaltons to 10 kilodaltons, from about 2 kilodaltons to 4 kilodaltons, or from about 2 kilodaltons to 10 kilodaltons;

(b) propylene carbonate present in an amount from about 1% to 50%, from about 1% to 70%, from about 5% to 50%, or from about 5% to 70% by weight of the resin;

(c) a photoinitiator present in the amount from about 0.1% to 2%, from about 0.1% to 4%, from about 0.2% to 2%, or from about 0.2% to 4% by weight of the resin;

(d) optionally, a reactive diluent present in the amount from about 1% to 40%, from about 1% to 50%, from about 5% to 40%, or from about 5% to 50% by weight of the resin; and (e) optionally, a filler present in the amount from about 1% to 40%, from about 1% to 50%, from about 2% to 40%, or from about 2% to 50% by weight of the resin.

Methods of Manufacturing

The non-fibrous adjuncts described herein can be formed from a matrix that includes at least one fused bioabsorbable polymer, and thus it can be formed using any additive manufacturing process. In some embodiments, the additive manufacturing process can be a continuous liquid interface production (CLIP) which involves curing liquid plastic resin using ultraviolet light. Details of the CLIP process are disclosed, for example, in U.S. Pat. Nos. 9,211,678, 9,205,601, and 9,216,546; U.S. Patent Publication Nos. 2017/0129169, 2016/0288376, 2015/0360419, 2015/0331402, 2017/0129167, 2018/0243976, 2018/0126630, and 2018/0290374; J. Tumbleston et al., *Continuous liquid interface production of 3D Objects*, Science 347, 1349-1352 (2015); and R. Janusziewcz et al., *Layerless fabrication with continuous liquid interface production*, Proc. Natl. Acad. Sci. USA 113, 11703-11708 (2016); each of which is incorporated by reference herein in its entirety. Non-limiting examples of other additive manufacturing apparatuses and methods that can be used to form the non-fibrous adjuncts described herein, and thus a matrix that includes at least one fused bioabsorbable polymer, can include bottom-up and top-down additive manufacturing methods such as those described, for example, in U.S. Pat. Nos. 5,236,637, 5,391,072 5,529,473, 7,438,846, 7,892,474, and 8,110,135 and U.S. Patent Publication Nos. 2013/0292862 and 2013/0295212, each of which is incorporated by reference herein in its entirety, as well as fused deposition modeling (e.g., heating a thermoplastic filament and extruding the melted filament layer by layer), material jetting, 2-photon polymerization, and holographic multi-focus polymerization as understood by a person skilled in the art.

In certain embodiments, after the additive manufacturing process, one or more post-processing steps can be performed. For example, in some embodiments, the one or more post-processing steps can include washing the adjunct (e.g., in an organic solvent such as acetone, isopropanol, a glycol ether such as dipropylene glycol methyl ether or DPM), wiping the adjunct (e.g., with an absorbent material, blowing with a compressed gas or air blade, etc.), centrifugal separation of residual resin, extraction of residual solvents, additional curing such as by flood exposure with ultraviolet light or the like so as to, for example, further react unpolymerized constituents of the adjunct, drying the adjunct (e.g., under a vacuum) to remove extraction solvents therefrom, or any combination thereof, in accordance with known techniques. The one or more post-processing steps can cause the adjunct to shrink, and therefore, in some embodiments, the adjunct can be produced in an enlarged form to offset such shrinkage.

In other embodiments, the non-fibrous adjuncts can be partially or wholly formed using any suitable non-additive manufacturing processes, such as injection molding, foaming, and forming processes as understood by a person skilled in the art.

The stapling assemblies can be manufacturing in a variety of ways. For example, in some embodiments, as discussed above, the non-fibrous adjunct can be releasably attached to the staple cartridge by placing a cartridge-contacting surface of the adjunct against a surface of the cartridge (e.g., an anvil-facing surface, e.g., a top or deck surface) so as to insert at least one attachment feature of the adjunct into at least one surface feature (e.g., a recessed channel) of the cartridge (see e.g., FIGS. 19A-26C, 37A-39B, and 41A-41C). Alternatively or in addition, as discussed above, the non-fibrous adjunct can be configured to receive one or more cartridge projections (e.g., staple pocket projections) and/or staple legs (see e.g., FIGS. 45A-46B). Additional details on the surface features and other exemplary surface features can be found in U.S. Publication No. 2016/0106427, which is incorporated by reference herein in its entirety. Alternative or in addition, as discussed above, the non-fibrous adjunct can include an outer layer that is in the form of an adhesive film that is used to releasably retain the adjunct to the staple cartridge (see e.g., FIG. 40). Additional details on the adhesive film and other attachment methods can be found in U.S. Pat. No. 10,349,939, which is incorporated by reference herein in its entirety.

The adjuncts and methods may be further understood with the following non-limiting examples.

EXAMPLES

Examples 1-3: Preparation of a Difunctional Methacrylate (MA) Terminated Polyester Oligomer Examples 1-3 describe the preparation of a difunctional, methacrylate terminated, polyester oligomer. The midblock is PLGA-PCL-PLGA, the molecular weight is 6 kilodaltons, and PCL is included as 40 wt. % of the total molecular weight (MW). PLGA is a random copolymer of lactide (L) and glycolide (G) with an L:G weight ratio of 1:1.

The molar ratios and masses of each reagent used for a 1 kg batch of HO-PLGA-b-PCL-b-PLGA-OH synthesis as discussed in Examples 1 and 2 are provided in Table 3 below.

TABLE 3

Molar ratios and mass of reagents for Examples 1 and 2

| Reagent | Molecular Weight (g/mol) | Molar Ratio | Density (g/mol) | Mass (g) | Volume (mL) | Moles |
|---|---|---|---|---|---|---|
| Caprolactone (CL) | 114.14 | 22 | 1.03 | 400.0 | 388.4 | 3.50 |
| Diethylene glycol (DEG) | 106.12 | 1 | 1.12 | 16.9 | 15.1 | 0.16 |
| Stannous Octoate (Sn(Oct)) | 405.12 | $2.38 \times 10^{-3}$ | 1.25 | 0.15 | 0.12 | $3.81 \times 10^{-4}$ |
| D,L-Lactide (L) | 144.13 | 14 | — | 321.4 | — | 2.22 |
| Glycolide (G) | 116.07 | 14 | — | 258.8 | — | 2.22 |

Example 1: HO-PCL-OH Synthesis

A round bottom flask was dried in a drying oven overnight and cooled under $N_2$ flow to room temperature. Caprolactone and stannous octoate were added to the round bottom flask via a glass syringe and syringe needle. The reaction flask contents were heated to 130° C. Meanwhile, diethylene glycol was heated to 130° C. Once preheated, the diethylene glycol was added to the reaction flask as an initiator and was allowed to react until complete monomer conversion. Monomer conversion was monitored using $H^1$ NMR. Once complete monomer conversion was reached, the reaction was stopped, and the reaction contents were allowed to cool to room temperature. The HO-PCL-OH was precipitated into cold MeOH from chloroform to obtain a white solid. $H^1$ NMR, DSC, FTIR, and THF GPC were used to characterize HO-PCL-OH.

Example 2: HO-PLGA-b-PCL-b-PLGA-OH Synthesis

HO-PCL-OH as prepared in Example 1 and varying amounts of D,L-lactide and glycolide were added into a round-bottom flask under $N_2$ and heated to 140° C. to melt the reaction contents. After melting, the temperature was reduced to 120° C. and stannous octoate was added. The reaction continued with stirring while monitoring the monomer conversion with $H^1$ NMR and THF GPC. Once the reaction reached the desired molecular weight, the reaction contents were cooled to room temperature, dissolved in chloroform, and precipitated into cold diethyl ether three times. The precipitate was dried under vacuum.

Example 3: MA-PLGA-b-PCL-b-PLGA-MA Synthesis

The molar ratios and masses of each reagent used to synthesize a 1 kg batch of MA-PLGA-b-PCL-b-PLGA-MA are provided in Table 4 below.

TABLE 4

Molar ratios and mass of each reagent for Example 3

| Reagent | Molecular Weight (g/mol) | Molar Ratio | Density (g/mol) | Mass (g) | Volume (mL) | Moles |
|---|---|---|---|---|---|---|
| HO-PLGA-b-PCL-b-PLGA-OH | 6000 | 1 | — | 1000 | — | 0.17 |
| Methacryloyl Chloride (MC) | 104.54 | 3.8 | 1.07 | 66.2 | 61.9 | 0.63 |
| Triethylamine (TEA) | 101.19 | 3.8 | 0.726 | 64.1 | 88.3 | 0.63 |
| Butylated hydroxytoluene (BHT) | 220.35 | ~400 ppm | | 0.45 | | |
| Dichloromethane (DCM) | — | 0.2 g/mL | — | — | 5000 | — |

HO-PLGA-b-PCL-b-PLGA-OH as prepared in Example 2 was dissolved in anhydrous DCM in a round bottom flask under $N_2$. Triethylamine and BHT were added the reaction flask and the reaction flask was cooled to 0° C. in an ice water bath. The reaction flask was equipped with a pressure-equalizing addition funnel that was charged with methacryloyl chloride. Once the reaction flask reached 0° C., methacryloyl chloride was added dropwise over 2 hours. The reaction proceeded for 12 hours at 0° C. and then 24 hours at room temperature. Once complete, the reaction contents were washed with distilled water 2 times to remove the triethylamine hydrochloride salts, washed with saturated $Na_2CO_3$, and then dried over magnesium sulfate. The collected and dried DCM layer was dried with rotary evaporation. The final product was characterized with THF GPC, $H^1$ NMR, FTIR, and DSC.

Examples 4-6: Preparation of a Tri-Arm MA Terminated Polyester Oligomer

Examples 4-6 describe the preparation of a tri-arm, or star shaped, bioresorbable polyester oligomer. Each arm is terminated with methacrylate. Each arm has a molecular weight of 2 kilodaltons and is a block copolymer of a random poly(lactide-co-glycolide) (PLGA) segment and a poly(caprolactone) (PCL) segment with PCL being the core of the oligomer. The PCL is included as 40 wt % of the total molecular weight (MW). The PLGA is a random copolymer of lactide (L) and glycolide (G) with L:G weight ratio of 1:1.

Example 4: PCL-3OH Synthesis

The molar ratios and masses of each reagent used for a 1 kg batch of (PLGA-b-PCL)-3OH synthesis as discussed in Examples 4 and 5 are provided in Table 5 below.

TABLE 5

Example of molar ratios and mass of each reagent for Examples 4 and 5

| Reagent | Molecular Weight (g/mol) | Molar Ratio | Density (g/mol) | Mass (g) | Volume (mL) | Moles |
|---|---|---|---|---|---|---|
| Caprolactone (CL) | 114.14 | 22 | 1.03 | 400.0 | 388.4 | 3.50 |
| Trimethylolpropane (TMP) | 134.07 | 1 | 1.08 | 21.4 | 19.8 | 0.16 |
| Stannous Octoate (Sn(Oct)) | 405.12 | $2.38 \times 10^{-3}$ | 1.25 | 0.15 | 0.12 | $3.81 \times 10^{-4}$ |
| D,L-Lactide (L) | 144.13 | 14 | — | 321.4 | — | 2.22 |
| Glycolide (G) | 116.07 | 14 | — | 258.8 | — | 2.22 |

A round bottom flask was dried in a drying oven overnight and cooled under $N_2$ flow to room temperature. Caprolactone and stannous octoate were added to the round bottom flask via a glass syringe and syringe needle. The reaction flask contents were heated to 130° C. Meanwhile, trimethylolpropane (TMP) was heated to 130° C. Once preheated, TMP was added to the reaction flask as an initiator and was allowed to react until complete monomer conversion. Monomer conversion was monitored using $H^1$ NMR. Once complete monomer conversion was reached, the reaction was stopped, and the reaction contents were allowed to cool to room temperature. The (PCL)-3OH was precipitated into cold MeOH from chloroform to obtain a white solid. $H_1$ NMR, DSC, FTIR, and GPC were used to characterize (PCL)-3OH.

Example 5: (PCL-b-PLGA)-3OH Synthesis (PCL)-3OH as prepared in Example 4 and varying amounts of D,L-lactide and glycolide were added into a round-bottom flask under $N_2$ and heated to 140° C. to melt the reaction contents. After melting, the temperature was reduced to 120° C. and stannous octoate was added. The reaction continued with stirring while monitoring the monomer conversion with $H^1$ NMR and THF GPC. Once the reaction reached the desired molecular weight, the reaction contents were cooled to room temperature, dissolved in chloroform and precipitated into cold diethyl ether three times. The precipitate was dried under vacuum.

Example 6: (PCL-b-PLGA)-3MA Synthesis

The molar ratio and masses of each reagent used to synthesize a 1 kg batch of (PLGA-b-PCL)-3MA are provided in Table 6 below.

TABLE 6

Molar ratios and mass of each reagent for Example 6

| Reagent | Molecular Weight (g/mol) | Molar Ratio | Density (g/mol) | Mass (g) | Volume (mL) | Moles |
|---|---|---|---|---|---|---|
| (PLGA-b-PCL)-3OH | 6000 | 1 | — | 1000 | — | 0.17 |
| Methacryloyl Chloride (MC) | 104.54 | 4.8 | 1.07 | 83.6 | 78.2 | 0.80 |
| Triethylamine (TEA) | 101.19 | 4.8 | 0.726 | 80.9 | 111.5 | 0.63 |

TABLE 6-continued

Molar ratios and mass of each reagent for Example 6

| Reagent | Molecular Weight (g/mol) | Molar Ratio | Density (g/mol) | Mass (g) | Volume (mL) | Moles |
|---|---|---|---|---|---|---|
| Butylated hydroxytoluene (BHT) | 220.35 | ~400 ppm | | 0.47 | | |
| Dichloromethane (DCM) | — | 0.2 g/mL | — | — | 5000 | — |

(PCL-b-PLGA)-3OH as prepared in Example 5 was dissolved in anhydrous DCM in a round bottom flask under $N_2$. Triethylamine (TEA) and BHT were added the reaction flask and the reaction flask was cooled to 0° C. in an ice water bath. The reaction flask was equipped with a pressure-equalizing addition funnel that was charged with methacryloyl chloride. Once the reaction flask reached 0° C., methacryloyl chloride was added dropwise over 2 hours. The reaction proceeded for 12 hours at 0° C. and then 24 hours at room temperature. Once complete, the precipitate was removed via vacuum filtration. The filtrate was collected and DCM was removed with rotary evaporation. The resulting viscous oil was dissolved in THF and precipitated into cold methanol. The precipitate was dissolved in DCM and washed with aqueous HCl (3%, 2 times), saturated aqueous sodium bicarbonate solution, and saturated aqueous sodium chloride, then dried over magnesium sulfate. The magnesium sulfate was filtered off via vacuum filtration, and the filtrate was collected. DCM was removed via rotary evaporation and the solid product was collected and characterized with GPC, $H^1$ NMR, FTIR, and DSC.

Example 7: Difunctional Oligomer Resin Formulation

The following constituents were mixed together in the following weight percent (% by weight of the resin) to provide an exemplary resin for additive manufacturing:

(1) 66.2% of the difunctional oligomer as prepared in Examples 1-3 above;
(2) 3.5% trimethylolpropane triacrylate (TMPTMA) reactive diluent;
(3) 28.4% of N-methyl pyrrolidone (NMP) non-reactive diluent; and
(4) 1.89% of Irgacure® 819 photoinitiator.

Example 8: Tri-arm Oligomer Resin Formulation

The following constituents were mixed together in the following weight percents (% by weight of the resin) to provide an exemplary resin for additive manufacturing:

(1) 68.6% of the tri-arm oligomer as prepared in Examples 4-6 above;
(2) 29.4% of N-methyl pyrrolidone (NMP) non-reactive diluent; and
(3) 1.96% of Irgacure® 819 photoinitiator.

Example 9: Additive Manufacturing and Post-Processing

Five exemplary adjuncts were prepared. The first exemplary adjunct (Adjunct 1) was structurally similar to adjunct 800 in FIGS. 8A-8F, except that the first adjunct was formed of two longitudinal rows of 20 unit cells. The four other exemplary adjuncts were structural similar to adjuncts 3100, 3200, 3300, 3400 as illustrated in FIGS. 31A-31D (Adjunct 2), FIGS. 32A-32D (Adjunct 3), FIGS. 33A-33E (Adjunct 4), and FIGS. 34A-34E (Adjunct 5), respectively. The five adjuncts were prepared by additive manufacturing that was carried out on a Carbon Inc. M1 or M2 apparatus, available from Carbon Inc., 1089 Mills Way, Redwood City Calif., 94063 in accordance with standard techniques. The resin formulation for each adjunct is provided in Table 7 below.

TABLE 7

Exemplary Adjunct Resin Formulations

| Adjunct | Material | ATPE Composition |
|---|---|---|
| 1 | ATPE-5 + 30% NMP + 5% TMPTMA | MA-PLGA-PCL-PLGA-MA, 40% PCL, 60% PLGA, 50:50 L:G, 5650 Da |
| 2 (FIGS. 31A-31D) | ATPE-5 + 30% NMP | MA-PLGA-PCL-PLGA-MA, 40% PCL, 60% PLGA, 50:50 L:G, 5650 Da |
| 3 (FIGS. 32A-32D) | SIL30 | |
| 4 (FIGS. 33A-33E) | ATPE-5 + 30% NMP | MA-PLGA-PCL-PLGA-MA, 40% PCL, 60% PLGA, 50:50 L:G, 5650 Da |
| 5 (FIGS. 34A-34E) | ATPE-5 + 30% NMP | MA-PLGA-PCL-PLGA-MA, 40% PCL, 60% PLGA, 50:50 L:G, 5650 Da |

When the resin contains a non-reactive diluent, the objects can experience a global shrinkage upon washing/extraction by the extent of the non-reactive diluent loading amount. Therefore, a dimensional scaling factor is applied to the part stereolithography (.stl) file or 3D manufacturing format (3MF) file to enlarge the printed adjunct and intentionally account for subsequent shrinkage during post processing steps.

Post processing of each adjunct was carried out as follows: after removing the build platform from the apparatus, excess resin is wiped from flat surfaces around the adjunct, and the platform left on its side to drain for about 10 minutes. The adjunct was carefully removed from the platform. The adjunct was washed in acetone 3 times, for 30 seconds each on an orbital shaker at 280 rpm, followed by 5 minutes of drying between washes. After the third wash, the adjunct was allowed to dry for 30 minutes, and then flood cured for 20 seconds per side, in a PrimeCure™ ultraviolet flood curing apparatus.

Next, residual non-reactive diluent (e.g., N-methyl pyrrolidone or propylene carbonate) was extracted from the adjunct by immersing the adjunct in acetone and shaking at room temperature on an orbital shaker for ~18 hours, with one solvent exchange after 12 hours. The adjunct was then removed from the acetone and vacuum dried overnight at 60° C. The adjunct was then checked for residual solvent using extractions for GCMS and FTIR. If no residual was detected the part was checked for tackiness. If the adjunct remained tacky, it was then flood cured under nitrogen in an LED based flood lamp (such as a PCU LED N2 flood lamp, available from Dreve Group, Unna, Germany).

Example 10: Stress-Strain Analysis of Representative Samples

Figure 56:
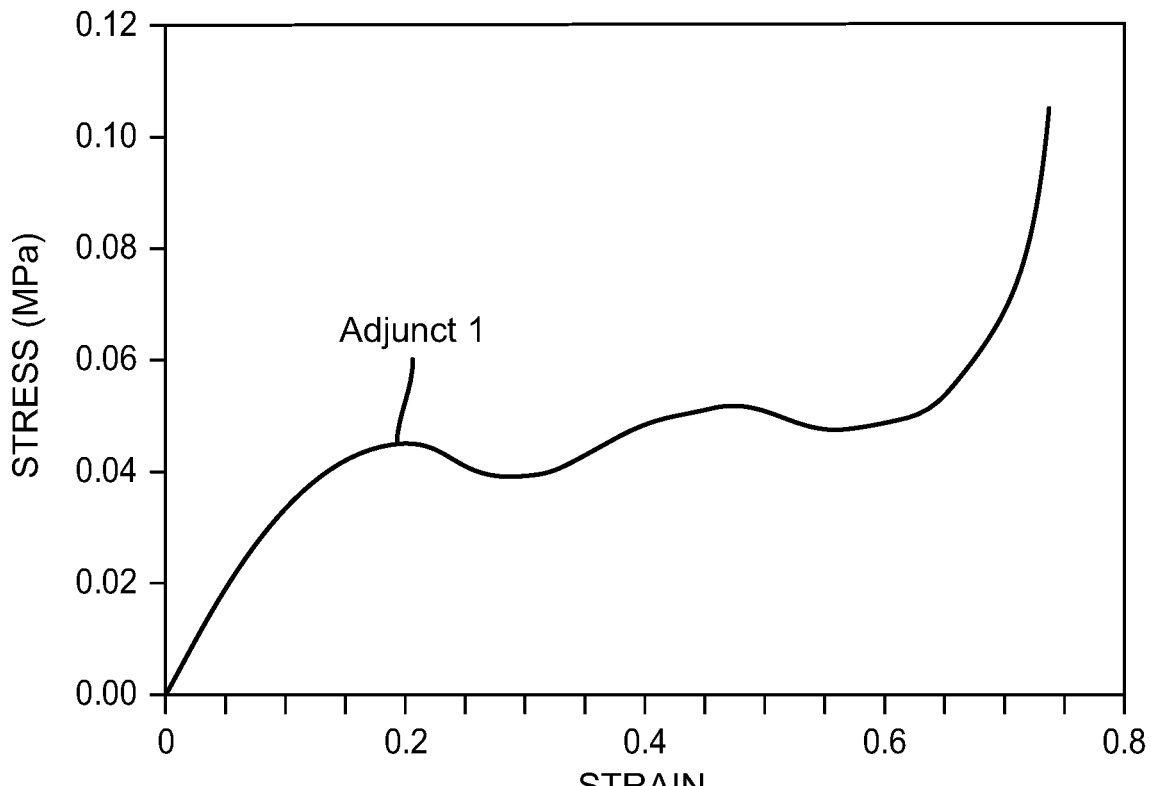
Figure 57:
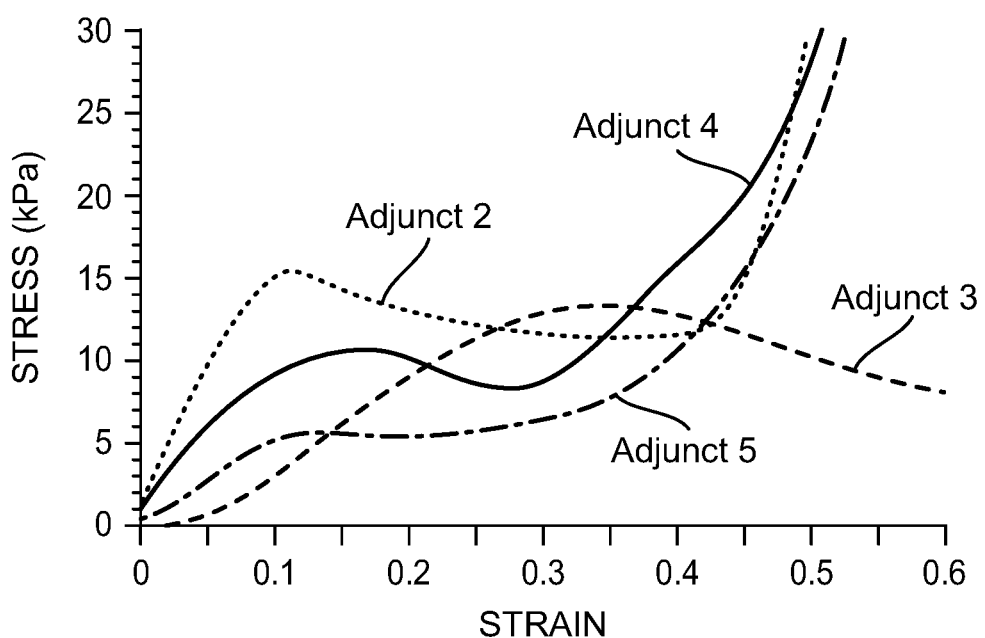

The stress-strain curve for Adjunct 1 of Example 9 is illustrated in FIG. 56, and the stress-strain curves for Adjuncts 2-5 of Example 9 are illustrated in FIG. 57.

The stress-strain curves illustrated in FIGS. 56 and 57 were generated by placing the adjuncts between a pair of 25 millimeter diameter circular stainless steel compression plates on an RSA-G2 solids analyzer (available from TA Instruments, 159 Lukens Drive, New Castle, Del. 19720 USA), lowering the compression plate at 0.1 mm per step until the initial axial force hits between 0.03-0.05 N, equilibrating at a temperature of 37° C. for 120 seconds, and carrying out the compression test (lowering the compression plate at 10 mm/min for 14 seconds until reaching a gap height of 0.7 mm or an overload force of ~17N, whichever occurs first, while recording real-time compression stress) to generate a stress-strain curve for each adjunct. As such, the stress-strain curves were generated by compressing each adjunct from its respective uncompressed height of 3 mm (within manufacturing tolerances) to its respective compressed height. The compressed height and strain for each adjunct under while the adjunct was under an applied stress is provided in Table 8 below. These measurements are based on the actual manufactured adjunct (including any measurement errors of the measurement system, e.g., a bias of 50 μm to the uncompressed height, and/or manufacturing tolerances, e.g., a bias of 100 μm to the uncompressed height).

TABLE 8

Compressed Height and Strain Measurements for Adjuncts 1-5

| | Measurement Condition | Compressed Height (mm) | Strain |
|---|---|---|---|
| Adjunct 1 | Applied stress of 90 kPa | 0.81 | 73 |
| Adjunct 2 | Applied stress of 30 kPa | 1.53 | 49 |
| Adjunct 3 | Applied stress of 9.43 kPa | 1.2 | 60 |
| Adjunct 4 | Applied stress of 30 kPa | 1.5 | 50 |
| Adjunct 5 | Applied stress of 30 kPa | 1.35 | 55 |

As shown in FIG. 56, the adjunct formed of strut-less based unit cells, e.g., adjunct 800 in FIGS. 8A-8F, demonstrated: (i) A unit structure that is sufficiently stable so that, even though the wall thicknesses are approximately 0.2 millimeters, the structures can be successfully printed and post-processed as described above; (ii) the adjunct goes through a broad range of buckling deformation and achieves a stress plateau between about 0.1 strain (about 10% deformation) to about 0.73 strain (73% deformation); and (iii) the adjunct has a bi-stable nature, so the unit structure can be deformed and achieve a new stable form that does not change until additional force is applied, potentially providing the surgeon with tactile feedback of the deformation status of the adjunct.

As shown in FIG. 57, the adjuncts formed of strut-based strut unit cells, e.g., adjunct 3100 in FIGS. 31A-31D, adjunct 3200 in FIGS. 32A-32D, adjunct 3300 in FIGS. 33A-33E, and adjunct FIGS. 34A-34E, exhibited a stress "plateau" within 5 kPa to 20 kPa of stress over 10 to 60 percent of strain. This result is based, at least in part, on the structural configuration of the unit cells. In particular, each unit cell is designed such that the spacer struts (e.g., the struts of the internal structure) fold inward without contacting one another during compression of the adjunct. As a result, densification of the adjunct (e.g., reaching solid height) can be delayed (e.g., occurs at a higher strain).

Example 11: Stress-Strain Analysis of Representative Samples

Six exemplary adjuncts, referred to herein as Sample 1, Sample, 2, Sample 3, Sample 4, Sample 5, and Sample 6, respectively, were prepared in a similar manner as set forth in Example 9, except that the resin formulation for each of Samples 1-6 was: Trifunctional oligomer (methacrylate end groups) with midblock of PCL and endblock of PLGA (85/15 L:G ratio); target molecular weight of 6,000 Daltons. Sample 1 was formed from repeating interconnected Schwarz-P structure unit cells, and Samples 2-5 were formed from respective repeating interconnected modified Schwarz-P structures in which the top and/or bottom of the initial Schwarz-P structure were cropped. Thus, the geometric properties of the repeating unit cells of each Sample were different. A list of geometric unit cell properties for each adjunct is provided in Table 9 below, which are based on theoretical/intended sizes.

TABLE 9

Exemplary Unit Cell Geometric Properties

| Geometry Property | Lower Limit | Upper Limit | Sample | | | | | |
|---|---|---|---|---|---|---|---|---|
| | | | 1 | 2 | 3 | 4 | 5 | 6 |
| Unit Cell Height (mm)* | 2 | 4 | 3.82 | 2.85 | 2.85 | 2.85 | 2.85 | 2.99 |
| Unit Cell Width (mm)* | 2 | 4 | 2.38 | 2.49 | 2.38 | 2.38 | 2.38 | 2.49 |
| Unit Cell Length (mm)* | 2 | 4 | 3.82 | 2.49 | 3.82 | 2.38 | 2.38 | 3.98 |
| Crop Distance from Top (mm) | 0 | 1.5 | 0.00 | 0.00 | 0.00 | 0.00 | 0.42 | 0.20 |
| Crop Distance from Bottom (mm) | 0 | 1.5 | 1.49 | 0.81 | 0.52 | 0.00 | 0.42 | 0.55 |
| Wall Thickness (mm) | 100 | 600 | 157.7 | 166 | 249 | 166 | 182.6 | 315.4 |
| Overall Height (mm)** | 1.8 | 3.5 | 2.32 | 2.04 | 2.32 | 2.85 | 1.99 | 2.24 |

*Using unit cell 810 in FIGS. 9A-9B as a reference, height extends in the x-direction, width extends in the y-direction, and length extends in the z-direction.
** Overall height reflects the uncompressed unit cell height of Sample 1 (no-cropping) and the uncompressed, but cropped height of Samples 2-6.

Figure 58:
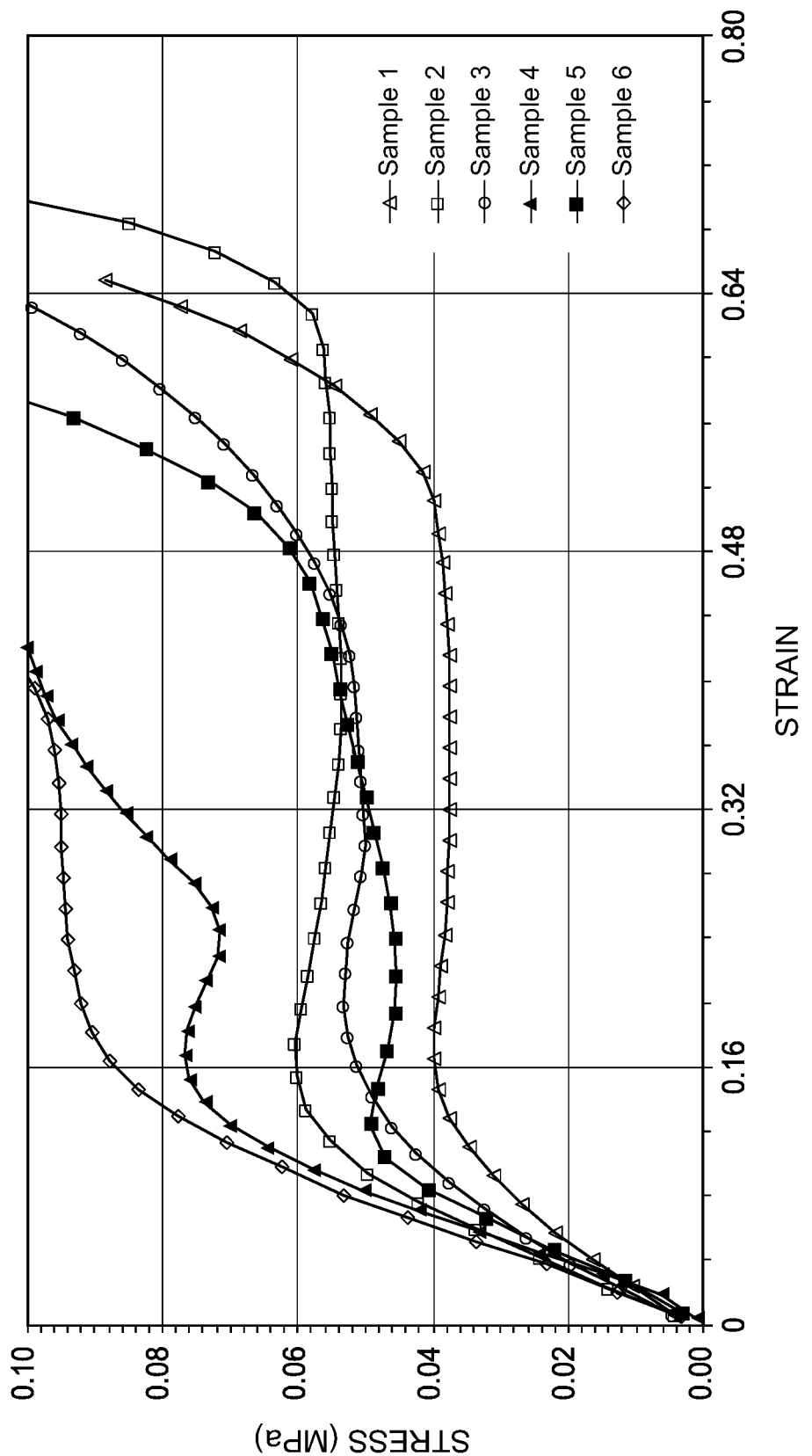

The stress-strain curves of Samples 1-6 were generated in a similar manner as set forth in Example 10, and are illustrated in FIG. 58. As shown, while each unit cell was formed of the same resin, each Sample had a different stress-strain curve. As such, these different stress-strain curves illustrate the relationship between the geometric properties of the unit cells (e.g., height, width, length, and wall thickness) and the stress-strain response of the resulting adjunct when being compressed from respective uncompressed heights (listed as overall height in Table 9 above) to a respective compressed height. Thus, in addition to the composition makeup of a unit cell, the various geometric properties thereof also need to be taken into account, and thus tailored, to effect an adjunct with a desired stress-strain response, such as the stress-strain responses described herein. The compressed height and strain for each sample while the sample was under an applied stress of 90 kPa is provided in Table 10 below. These measurements are based on the actual manufactured adjunct (including any measurement errors of the measurement system, e.g., a bias of 50 μm to the uncompressed height, and/or manufacturing tolerances, e.g., a bias of 100 μm to the uncompressed height).

TABLE 10

Compressed Height and Strain Measurements for Samples 1-6 at 90 kPa

| Measurement at 90 kPa | Sample | | | | | |
|---|---|---|---|---|---|---|
| | 1 | 2 | 3 | 4 | 5 | 6 |
| Compressed Height (mm) | 0.77 | 0.61 | 0.83 | 1.82 | 0.82 | 1.74 |
| Strain | 0.65 | 0.69 | 0.61 | 0.34 | 0.56 | 0.17 |

Examples 12-14: Preparation of a Tri-Arm MA Terminated Polyester Oligomer

Examples 12-14 describe the preparation of a tri-arm, or star shaped, bioresorbable polyester oligomer. Each arm is terminated with methacrylate. Each arm has a molecular weight of 2 kilodaltons and is a block copolymer of poly (L-lactic acid) (PLLA) and poly(caprolactone-r-L-lactic acid) (PCLLA) with PCLLA being the core of the oligomer. The PCLLA is included as 70 wt. % of the total molecular weight (MW) and the CL:L ratio is 60:40.

The molar ratios and masses of each reagent used for a 1 kg batch of (PLLA-b-PCLLA)-3OH synthesis as discussed in Examples 12 and 13 are provided in Table 11 below.

TABLE 11

Example of molar ratios and mass of each reagent for Examples 12 and 13

| Reagent | Molecular Weight (g/mol) | Molar Ratio | Density (g/mol) | Mass (g) | Volume (mL) | Moles |
|---|---|---|---|---|---|---|
| Caprolactone (CL) | 114.14 | 22 | 1.03 | 418 | 405 | 3.66 |
| Trimethylol-propane (TMP) | 134.07 | 1 | 1.08 | 21.4 | 19.8 | 0.16 |
| Stannous Octoate (Sn(Oct)) | 405.12 | 2.38 × $10^{-3}$ | 1.25 | 0.15 | 0.12 | 3.81 × $10^{-4}$ |
| L-Lactide (L) | 144.13 | 24 | — | 576 | — | 3.99 |

Example 12: PCLLA-3OH Synthesis

A round bottom flask was dried in a drying oven overnight and cooled under $N_2$ flow to room temperature. Caprolactone, L-lactide and stannous octoate were added to the round bottom flask. The reaction flask contents were heated to 130° C. Meanwhile, trimethylolpropane (TMP) was heated to 130° C. Once preheated, TMP was added to the reaction flask as an initiator and was allowed to react until complete monomer conversion. Monomer conversion was monitored using $H^1$ NMR. Once complete monomer conversion was reached, the reaction was stopped, and the reaction contents were allowed to cool to room temperature. The (PCLLA)-3OH was precipitated into cold MeOH from chloroform to obtain a white solid. $H^1$ NMR, DSC, FTIR, and THF GPC were used to characterize (PCLLA)-3OH.

Example 13: (PLLA-b-PCLLA)-3OH Synthesis (PCLLA)-3OH as prepared in Example 12 and L-lactide were added into a round-bottom flask under $N_2$ and heated to 140° C. to melt the reaction contents. After melting, the temperature was reduced to 120° C. and stannous octoate was added. The reaction continued with stirring while monitoring the monomer conversion with $H^1$ NMR and THF GPC. Once the reaction reached the desired molecular weight, the reaction contents were cooled to room temperature, dissolved in chloroform and precipitated into cold diethyl ether three times. The precipitate was dried under vacuum.

Example 14: (PLLA-b-PCLLA)-3MA Synthesis

The molar ratios and masses of each reagent used to synthesize a 1 kg batch of (PLLA-b-PCLLA)-3MA are provided in Table 12 below.

TABLE 12

Molar ratios and mass of each reagent for Example 14.

| Reagent | Molecular Weight (g/mol) | Molar Ratio | Density (g/mol) | Mass (g) | Volume (mL) | Moles |
|---|---|---|---|---|---|---|
| (PLLA-b-PCLLA)-3OH | 6000 | 1 | — | 1000 | — | 0.17 |
| Methacrylol Chloride (MC) | 104.54 | 4.8 | 1.07 | 83.6 | 78.2 | 0.80 |
| Triethylamine (TEA) | 101.19 | 4.8 | 0.726 | 80.9 | 111.5 | 0.63 |
| Butylated hydroxytoluene (BHT) | 220.35 | ~400 ppm | — | 0.47 | — | — |
| Dichloromethane (DCM) | — | — | 0.2 g/mL | — | 5000 | — |

(PLLA-b-PCLLA)-3OH as prepared in Example 13 was dissolved in anhydrous DCM in a round bottom flask under $N_2$. Triethylamine (TEA) and a 400 ppm BHT were added the reaction flask and the reaction flask was cooled to 0° C. in an ice water bath. The reaction flask was equipped with a pressure-equalizing addition funnel that was charged with methacrylol chloride. Once the reaction flask reached 0° C., methacrylol chloride was added dropwise over 2 hours. The reaction proceeded for 12 hours at 0° C. and then 24 hours at room temperature. Once complete, the precipitate was removed via vacuum filtration. The filtrate was collected and DCM was removed with rotary evaporation. The resulting viscous oil was dissolved in THF and precipitated into cold methanol. The precipitate was dissolved in DCM and washed with aqueous HCL (3%, 2 times), saturated aqueous sodium bicarbonate solution, and saturated aqueous sodium chloride, and then dried over magnesium sulfate. The magnesium sulfate was filtered off via vacuum filtration, and the filtrate was collected. DCM was removed via rotary evaporation and the solid product was collected and characterized with THF GPC, H' NMR, FTIR, and DSC.

Example 15: Difunctional Oligomer Resin Formulation

The following constituents were mixed together in the following weight percent (% by weight of the resin) to provide an exemplary light polymerizable resin for additive manufacturing:

(1) 58.82% of the difunctional oligomer prepared in Examples 12-13 above;
(2) 39.22% propylene carbonate (PC) non-reactive diluent; and
(3) 1.96% of Irgacure® 819 photoinitiator.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning/replacement, and reassembly. Use of such techniques, and the resulting reconditioned instrument, are all within the scope of the present application.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is only to the extent that the incorporated material does not conflict with existing definitions, statements, or other disclosure material set forth in this document. As such the disclosure as explicitly set forth herein supersedes any conflicting material incorporated herein by reference.

What is claimed is:
1. A surgical end effector for use with a surgical stapler, comprising:
 a cartridge and an anvil movable relative to the cartridge between open and closed positions, the cartridge having a plurality of staples disposed therein, the plurality of staples being configured to be deployed into tissue; and
 a non-fibrous adjunct formed of at least one fused bioabsorbable polymer and configured to be releasably retained on the cartridge such that the adjunct can be attached to tissue by the plurality of staples in the cartridge, the adjunct having a first end, a second end, and a longitudinal axis extending therebetween, the adjunct comprising,
  a cartridge-contacting surface,
  a tissue-contacting surface that is opposite the cartridge-contacting surface, wherein at least a portion of the tissue-contacting surface is curved, and
  an internal structure extending between the cartridge-contacting surface and the tissue-contacting surface, the internal structure being formed of a first lattice and a second lattice that is interposed between the first lattice and the cartridge, the first lattice having a first compressive strength and the second lattice having a second compressive strength that is greater than the first compressive strength, wherein at least one of the first lattice and the second lattice comprise a plurality of unit cells, and wherein each unit cell is a triply periodic minimal surface structure;

wherein the adjunct has an uncompressed thickness that at least partially varies in a lateral direction relative to the longitudinal axis of the adjunct to thereby create a variable tissue gap between the anvil and the adjunct when the adjunct is releasably retained on the cartridge and the anvil is in a closed position without tissue therebetween, and wherein, the adjunct, when in a tissue deployed state, applies a generally uniform pressure to the tissue stapled thereto for a predetermined period of time.

2. The surgical end effector of claim 1, wherein, when in a tissue deployed state, the adjunct has a compressed generally uniform thickness.

3. The surgical end effector of claim 1, wherein, when in a tissue deployed state, the adjunct has a compressed thickness that at least partially varies in the lateral direction.

4. The surgical end effector of claim 1, wherein the adjunct is configured to be releasably retained on a surface of the cartridge that faces the anvil, and wherein the surface of the cartridge is planar and the plurality of staples are generally uniform.

5. The surgical end effector of claim 1, wherein the adjunct is configured to be releasably retained on a surface of the cartridge that faces the anvil, wherein the surface is non-planar and the plurality of staples includes a first plurality of staples having a first height and a second plurality of staples having a second height that is greater than the first undeformed height.

6. The surgical end effector of claim 5, wherein the plurality of staples are arranged in a plurality of staples rows, wherein the plurality of staples rows includes an inner-most staple row of the first plurality of staples and an outer-most staple row of the second plurality of staples.

7. The surgical end effector of claim 6, wherein the outer-most staple row overlaps with only the second lattice.

8. The surgical end effector of claim 6, wherein the plurality of staples includes a third plurality of staples having a third height that is between the first and second heights, and wherein the plurality of staple rows includes an intermediate staple row of the third plurality of staples that is positioned between the inner-most staple row and the outer-most staple row.

9. The surgical end effector of claim 1, wherein the adjunct has a first thickness measured at a center of the adjunct and a second thickness measured at a terminal lateral-facing edge of the adjunct, and wherein the second thickness is less than the first thickness.

10. The surgical end effector of claim 9, wherein the center of the adjunct has a first stiffness and the terminal lateral-facing edge of the adjunct has a second stiffness that is greater than the first stiffness.

11. The surgical end effector of claim 9, wherein the uncompressed thickness of the adjunct decreases in the lateral direction from the first thickness to the second thickness while the tissue gap increases in the same direction.

12. The surgical end effector of claim 1, wherein the first lattice extends from a first top surface to a first bottom surface, and wherein the top surface defines at least a portion of the tissue-contacting surface of the adjunct.

13. The surgical end effector of claim 12, wherein the first top surface has a convex configuration.

14. The surgical end effector of claim 12, wherein the second lattice extends from a second top surface to a second bottom surface, and wherein the second top surface defines at least a portion of the tissue-contacting surface of the adjunct.

15. The surgical end effector of claim 14, wherein the second top surface has a concave configuration.

16. The surgical end effector of claim 1, wherein the first lattice comprises the plurality of unit cells, and wherein the second lattice comprises another plurality of unit cells and each unit cell of the another plurality of unit cells is a triply periodic minimal surface structure or defined by a plurality of planar interconnected struts.

17. The surgical end effector of claim 1, wherein the second lattice comprises the plurality of unit cells, and wherein the first lattice comprises another plurality of unit cells and each unit cell of the another plurality of unit cells is defined by a plurality of planar interconnected struts.

18. A surgical end effector for use with a surgical stapler, comprising:
a cartridge and an anvil movable relative to the cartridge between open and closed positions, the cartridge having a plurality of staples disposed therein, the plurality of staples being configured to be deployed into tissue; and
a non-fibrous adjunct formed of at least one fused bioabsorbable polymer and configured to be releasably retained on at least a portion of the top surface of the cartridge such that the adjunct can be attached to tissue by the plurality of staples in the cartridge, the adjunct having a cartridge-contacting surface and a tissue-contacting surface that is opposite the cartridge-contacting surface, the adjunct comprising,
a first lattice structure having first compressive strength, the first lattice extending from a first top surface and a first bottom surface that opposes the first top surface, wherein the first bottom surface defines the cartridge-contacting surface;
a second lattice structure disposed on at least the first top surface of the first lattice structure, the second lattice structure having a second compressive strength that is less than the first compressive strength, the second lattice extending from a second top surface and a second bottom surface that is opposite the second top surface, wherein the second top surface defines at least a portion of the tissue-contacting surface;
wherein at least one of the first lattice structure and the second lattice structure comprise a plurality of unit cells, and wherein each unit cell is a triply periodic minimal surface structure; and
wherein the adjunct has proximal and distal ends and a longitudinal axis extending therebetween, and wherein the adjunct has a variable compression strength along a length that extends along the longitudinal axis such that the adjunct, when in a tissue deployed state, applies a generally uniform pressure to the tissue stapled thereto for a predetermined period of time.

19. The surgical end effector of claim 18, wherein the adjunct has an uncompressed thickness that at least partially varies along the length of the adjunct to thereby create a variable tissue gap between the anvil and the adjunct when the adjunct is releasably retained on the cartridge and the anvil is in a closed position without tissue therebetween.

20. The surgical end effector of claim 18, wherein the first lattice structure and the second lattice structure differ from each other in at least one of unit cells, density, and shape.

21. The surgical end effector of claim 18, wherein the first lattice structure has an uncompressed thickness that at least partially varies along the length of the adjunct.

22. The surgical end effector of claim 18, wherein the second lattice structure has an uncompressed thickness that at least partially varies along the length of the adjunct.

23. The surgical end effector of claim 18, wherein the first lattice structure comprises the plurality of unit cells, and wherein the second lattice structure comprises another plurality of unit cells and each unit cell of the another plurality of unit cells is a triply periodic minimal surface structure or defined by a plurality of interconnected struts interconnected.

24. The surgical end effector of claim 18, wherein the second lattice structure comprises the plurality of unit cells, and wherein the first lattice structure comprises another plurality of unit cells and each unit cell is defined by a plurality of interconnected struts.

* * * * *